(12) United States Patent
Zaplin et al.

(10) Patent No.: US 9,351,507 B2
(45) Date of Patent: May 31, 2016

(54) METHOD OF PREPARING FOOD USING RICE OIL

(71) Applicants: Ella Zaplin, Wagga Wagga (AU); Sadequr Rahman, Nicholls (AU); Zhongyi Li, Kaleen (AU); Qing Liu, Girralang (AU); Surinder Pal Singh, Downer (AU); Robert Charles de Feyter, Monash (AU)

(72) Inventors: Ella Zaplin, Wagga Wagga (AU); Sadequr Rahman, Nicholls (AU); Zhongyi Li, Kaleen (AU); Qing Liu, Girralang (AU); Surinder Pal Singh, Downer (AU); Robert Charles de Feyter, Monash (AU)

(73) Assignee: COMMONWEALTH SCIENTIFIC AND INDUSTRIAL RESEARCH ORGANISATION, Campbell (AU)

( * ) Notice: Subject to any disclaimer, the term of this patent is extended or adjusted under 35 U.S.C. 154(b) by 187 days.

(21) Appl. No.: 14/021,173

(22) Filed: Sep. 9, 2013

(65) Prior Publication Data

US 2014/0120225 A1    May 1, 2014

Related U.S. Application Data

(62) Division of application No. 12/309,276, filed as application No. PCT/AU2007/000977 on Jul. 13, 2007.

(30) Foreign Application Priority Data

Jul. 14, 2006  (AU) ................. 2006903810

(51) Int. Cl.
| | |
|---|---|
| C12N 15/82 | (2006.01) |
| A23L 1/01 | (2006.01) |
| A23D 9/00 | (2006.01) |
| C11B 1/10 | (2006.01) |

(52) U.S. Cl.
CPC ............. *A23L 1/0107* (2013.01); *A23D 9/00* (2013.01); *C11B 1/10* (2013.01); *C12N 15/8218* (2013.01); *C12N 15/8247* (2013.01)

(58) Field of Classification Search
None
See application file for complete search history.

(56) References Cited

U.S. PATENT DOCUMENTS

| | | | |
|---|---|---|---|
| 4,948,811 A | 8/1990 | Spinner et al. | |
| 5,500,361 A | 3/1996 | Kinney et al. | |
| 6,100,077 A | 8/2000 | Sturley et al. | |
| 6,344,548 B1 | 2/2002 | Farese et al. | |
| 6,432,684 B1 | 8/2002 | Mukerji et al. | |
| 6,998,516 B2 | 2/2006 | Brar et al. | |
| 7,001,771 B1 | 2/2006 | Morell et al. | |
| 7,045,326 B2 | 5/2006 | Cases et al. | |
| 7,109,392 B1 | 9/2006 | Broglie et al. | |
| 7,135,617 B2 | 11/2006 | Lardizabal et al. | |
| 7,244,599 B2 | 7/2007 | Tanner et al. | |
| 7,417,176 B2 | 8/2008 | Lardizabal et al. | |
| 7,521,593 B2 | 4/2009 | Regina et al. | |
| 7,589,253 B2 | 9/2009 | Green et al. | |
| 7,619,105 B2 | 11/2009 | Green et al. | |
| 7,667,114 B2 | 2/2010 | Morell et al. | |
| 7,700,139 B2 | 4/2010 | Bird et al. | |
| 7,700,826 B2 | 4/2010 | Morell et al. | |
| 7,741,532 B2 | 6/2010 | Lardizabal et al. | |
| 7,790,955 B2 | 9/2010 | Li et al. | |
| 7,807,849 B2 | 10/2010 | Singh et al. | |
| 7,812,221 B2 | 10/2010 | Morell et al. | |
| 7,834,248 B2 | 11/2010 | Green et al. | |
| 7,834,250 B2 | 11/2010 | Singh et al. | |
| 7,888,499 B2 | 2/2011 | Morell et al. | |
| 7,892,803 B2 | 2/2011 | Tanner et al. | |
| 7,919,132 B2 | 4/2011 | Regina et al. | |
| 7,932,438 B2 | 4/2011 | Singh et al. | |
| 7,932,440 B2 | 4/2011 | Reid et al. | |
| 7,993,686 B2 | 8/2011 | Bird et al. | |
| 8,049,069 B2 | 11/2011 | Wu et al. | |
| 8,071,341 B2 | 12/2011 | Singh et al. | |
| 8,106,226 B2 | 1/2012 | Singh et al. | |
| 8,115,087 B2 | 2/2012 | Regina et al. | |
| 8,158,392 B1 | 4/2012 | Singh et al. | |
| 8,178,759 B2 | 5/2012 | Morell et al. | |
| 8,188,336 B2 | 5/2012 | Li et al. | |
| 8,269,082 B2 | 9/2012 | Millar et al. | |
| 8,288,572 B2 | 10/2012 | Singh et al. | |
| 8,501,262 B2 | 8/2013 | Bird et al. | |
| 8,530,724 B2 | 9/2013 | Whitelaw et al. | |
| 8,535,917 B2 | 9/2013 | Singh et al. | |
| 8,716,555 B2 | 5/2014 | Liu et al. | |
| 8,735,111 B2 | 5/2014 | Vanhercke et al. | |
| 8,809,026 B2 | 8/2014 | Vanhercke et al. | |
| 8,921,652 B2 | 12/2014 | Liu et al. | |
| 9,057,075 B2 | 6/2015 | Liu et al. | |

(Continued)

FOREIGN PATENT DOCUMENTS

| | | |
|---|---|---|
| EP | 1806398 | 7/2007 |
| EP | 1837397 | 9/2007 |

(Continued)

OTHER PUBLICATIONS

Greenwell et al. (2010) "Placing microalgae on the biofuels priority list: a review of the technological challenges" J. R. Soc. Interface 7:703-726.

(Continued)

*Primary Examiner* — Elizabeth McElwain
(74) *Attorney, Agent, or Firm* — John P. White; Gary J. Gershik; Cooper & Dunham LLP

(57) ABSTRACT

The present invention relates to methods of preparing food using rice oil which has increased levels of oleic acid and decreased palmitic and linoleic acids, for increased stability to oxidation and health benefits.

7 Claims, 38 Drawing Sheets

(56) References Cited

U.S. PATENT DOCUMENTS

Figure 1:
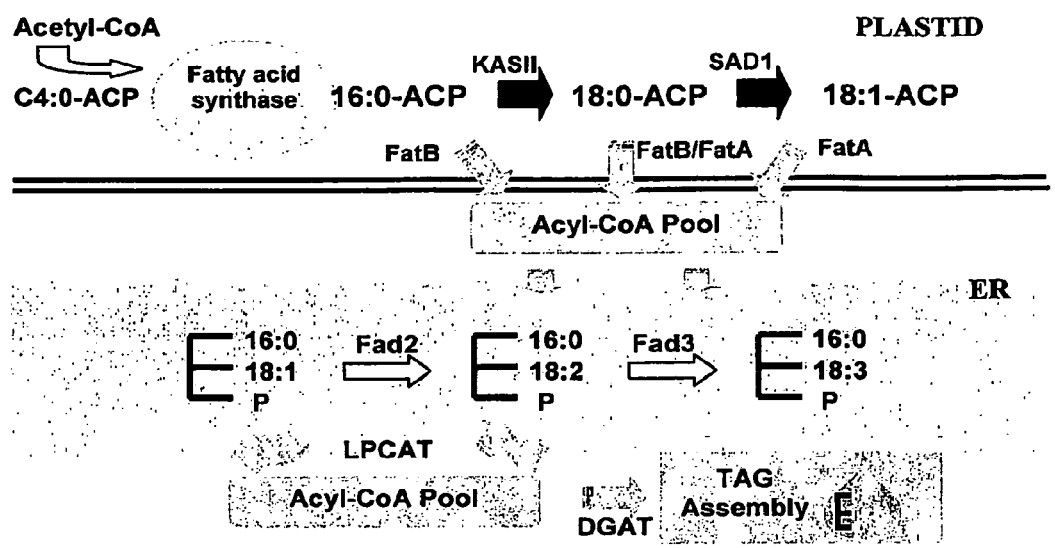

| | | | |
|---|---|---|---|
| 2002/0104124 | A1 | 8/2002 | Green et al. |
| 2004/0221335 | A1 | 11/2004 | Shewmaker et al. |
| 2005/0106697 | A1 | 5/2005 | Cases et al. |
| 2005/0262588 | A1 | 11/2005 | Dehesh et al. |
| 2006/0053512 | A1 | 3/2006 | Bao et al. |
| 2006/0094088 | A1 | 5/2006 | Picataggio et al. |
| 2006/0206963 | A1 | 9/2006 | Voelker et al. |
| 2008/0268539 | A1 | 10/2008 | Singh et al. |
| 2008/0311580 | A1 | 12/2008 | Abrahams et al. |
| 2009/0061492 | A1 | 3/2009 | Benning et al. |
| 2009/0308041 | A1 | 12/2009 | Whitelaw et al. |
| 2010/0184130 | A1 | 7/2010 | Koprowski et al. |
| 2010/0221400 | A1 | 9/2010 | Chapman et al. |
| 2011/0015415 | A1 | 1/2011 | Singh et al. |
| 2011/0045127 | A1 | 2/2011 | Ral et al. |
| 2011/0054198 | A1 | 3/2011 | Singh et al. |
| 2011/0190521 | A1 | 8/2011 | Damcevski et al. |
| 2011/0201065 | A1 | 8/2011 | Singh et al. |
| 2011/0218348 | A1 | 9/2011 | Zhou et al. |
| 2011/0223311 | A1 | 9/2011 | Liu et al. |
| 2011/0229623 | A1 | 9/2011 | Liu et al. |
| 2011/0281818 | A1 | 11/2011 | Jenkins et al. |
| 2011/0314725 | A1 | 12/2011 | Petrie et al. |
| 2012/0016144 | A1 | 1/2012 | Petrie et al. |
| 2012/0041218 | A1 | 2/2012 | Singh et al. |
| 2012/0114770 | A1 | 5/2012 | Regina et al. |
| 2012/0129805 | A1 | 5/2012 | Li et al. |
| 2012/0208198 | A1 | 8/2012 | Bogs et al. |
| 2013/0115362 | A1 | 5/2013 | Regina et al. |
| 2013/0164798 | A1 | 6/2013 | Vanhercke et al. |
| 2013/0247451 | A1 | 9/2013 | Vanhercke et al. |
| 2014/0256006 | A1 | 9/2014 | Vanhercke et al. |
| 2015/0176017 | A1 | 6/2015 | Liu et al. |

FOREIGN PATENT DOCUMENTS

| | | |
|---|---|---|
| EP | 1944375 | 7/2008 |
| WO | WO 98/55631 | 12/1998 |
| WO | WO 99/49050 | 9/1999 |
| WO | WO 99/67268 | 12/1999 |
| WO | WO 99/67403 | 12/1999 |
| WO | WO 00/01713 | 1/2000 |
| WO | WO 00/11176 | 3/2000 |
| WO | WO 00/32756 | 6/2000 |
| WO | WO 00/32793 | 6/2000 |
| WO | WO 00/36114 | 6/2000 |
| WO | WO 00/60095 | 10/2000 |
| WO | WO 00/66750 | 10/2000 |
| WO | WO 00/66749 | 11/2000 |
| WO | WO 03/078639 | 9/2003 |
| WO | WO 03/080802 | 10/2003 |
| WO | WO 04/001001 | 12/2003 |
| WO | WO 2004/011671 | 2/2004 |
| WO | WO 2005/003322 | 1/2005 |
| WO | WO 2005/063988 | 7/2005 |
| WO | WO 2005/103253 | 11/2005 |
| WO | WO 2007/103738 | 9/2007 |
| WO | WO 2008/025068 | 6/2008 |
| WO | WO 2008/130248 | 10/2008 |
| WO | WO 2008/157226 | 12/2008 |
| WO | WO 2008/157827 | 12/2008 |
| WO | WO 2009/027335 | 3/2009 |
| WO | WO 2009/129582 | 10/2009 |
| WO | WO 2009/143397 | 11/2009 |
| WO | WO 2010/009499 | 1/2010 |
| WO | WO 2010/009500 | 1/2010 |
| WO | WO 2010/057246 | 5/2010 |
| WO | WO 2012/000026 | 1/2012 |

OTHER PUBLICATIONS

Hutchins et al., (1968) "A New Process for the Selective Hydrogenation Cyclopropenoids in Cottonseed Oil" Journal of American Oil Chemists Society 45: 397-399.

Jain et al., (2000) "Enhancement of seed oil content by expression of glycerol-3-phosphate acyltransferase genes" Biochemical Society Transactions 28(6): 958-961.

Jako et al., Seed-Specific Over-Expression of an Arabidopsis cDNA Encoding a Diacylglycerol Acyltransferase Enhances Seed Oil Content and Seed Weight. Plant Physiology, 2001, 126:861-874.

James et al (2010) "Disruption of the Arabidopsis CGI-58 homologue produces Chanarin-Dorfman-like lipid droplet accumulation in plants," 107(41):17832-17838 and supporting information pp. 1-3.

Kargiotidou et al., (2008) "Low temperature and light regulate delta 12 fatty acid desaturases (FAD2) at a transcriptional level in cotton (Gossypium hirsutum)" Journal of Experimental Botany 2008 59(8): 2043-2056.

Karmakar et al. (2010) "Properties of various plants and animals feedstocks for biodiesel production" Bioresource Technology 101:7201-7210.

Kelly et al. (2012) "Suppression of the Sugar-DEPENDENT1 triacylglycerol lipase family during seed development enhances oil yield in oilseed rape (Brassica napus L.)" Plant Biotechnology Journal, pp. 1-7.

Kelly et al., (2011) "Seed Storage Oil Mobilization Is Important But Not Essential for Germination or Seedling Establishment in Arabidopsis" Plant Physiology, vol. 157, pp. 866-875.

Kozeil et al. (1996) "Optimizing expression of transgenes with an emphasis on post-transcriptional events." Plant Molecular Biology, 32:393-405.

Lardizabal et al. (2001) "DGAT2 Is a New Diacylglycerol Acyltransferase Gene Family" J. Biol. Chem. 276:38862-38869.

Lardizabal et al. (2008) "Expression of Umbelopsis ramanniana DGAT2A in Seed Increases Oil in Soybean" Plant Physiol. 148: 89-96.

Liu et al. (2010) "Producing biodiesel from high free fatty acids waste cooking oil assisted by radio frequency heating" Fuel 89:2735-2740.

Liu et al., Genetic modification of cotton seed oil using inverted-repeat gene-silencing techniques. Biochemical Society Transations, 2000, 28(6):927-929.

Liu et al., (1999) "Cloning and Sequence Analysis of a Novel Member (Accession No. Y10112) of the Microsomal w-6 Fatty Acid Desaturase Family from Cotton" Plant Physiol. (PGR 99-063) 120:339.

Lu et al., (2011) "New frontiers in oilseed biotechnology: meeting the global demand for vegetable oils for food, feed, biofuel, and industrial applications" Current Opinion in Biotechnology, 22:252-259.

Maher and Bressler (2007) "Pyrolysis of triglyceride materials for the production of renewable fuels and chemicals" Bioresource Technology 98:2351-2368.

O'Brien, (2002) Cottonseed Oil. In: F.D. Gunstone (Ed.) Vegetable Oils in Food Technology: Composition, Properties and Uses. Blackwell Publishing, Oxford, pp. 203-223.

Okuley et al. Arabidopsis FAD2 Gene Encodes the Enzyme that is Essential for Polyunsaturated Lipid Synthesis. Plant Cell, 1994, 6:147-158.

Parthibane et al. (2012) "Oleosin Is a Bifunctional Enzyme That Has Both Monoacylglycerol Acyltransferase and Phospholipase Activities" J. Biol. Chem. 287:1946-19541.

Perez-Vich et al. (1998) "Determination of Seed Oil Content and Fatty Acid Composition in Sunflower Through the Analysis of Intact Seeds, Husked Seeds, Meal and Oil by Near-Infrared Reflectance Spectroscopy" JAOCS 75:547-555.

Petrie et al. (2012) "Recruiting a New Substrate for Triacylglycerol Synthesis in Plants: The Monoacylglycerol Acyltransferase Pathway" PLoS ONE 7:e35214.

Pirtle et al., (2001) "Molecular cloning and functional expression of the gene for a cotton v-12 fatty acid desaturase (FAD2)" Biochim. Biophys, Acta 1522: 122-129.

Pokharkar et al., (2008) "Synthesis and Characterizationof Fatty Acid Methyl Ester by In-Situ Transesterification in Capparis Deciduas Seed" Leonardo Electronic Journal of Practices and Technologies 13:12-18.

Rajasekharan et al., (2006) "Monoacylglycerol as an intermediate in triacylglycerol biosynthesis in plants" International Symposium on Plant Lipids, Abstract.

(56) References Cited

OTHER PUBLICATIONS

Roston et al., (2012) "TGD1, -2, and -3 Proteins Involved in Lipid Trafficking Form ATP-binding Cassette (ABC) Transporter with Multiple Substrate-binding Proteins" The Journal of Biological Chemistry vol. 287, No. 25, pp. 21406-21415.
Sanjaya et al. (2011) "Increasing the energy density of vegetative tissues by diverting carbon from starch to oil biosynthesis in transgenic Arabidopsis" Plant Biotech. J. 9:874-883.
Sanjaya et al (2013) "Altered Lipid Composition and Enhanced Nutritional Value of Arabidopsis Leaves following Introduction of an Algal Diacylglycerol Acyltransferase 2" Plant Cell, 1-17.
Semwal et al. (2011) "Biodiesel production using heterogeneous catalysts" Bioresource Technology 102:2151-2161.
Sheikh et al (2002) "Fatty Acids Composition in Germinating Cotton Seedlings Affected by High Temperature Stress" Pakistan Journal of Applied Sciences 2:1 p. 97-99.
Shenstone and Vickery, (1961) "Occurrence of Cyclo-Propene Acids in Some Plants of the Order Malvales" Nature 190: 68-169.
Shiina et al. (1997) "Identification of Promoter Elements Involved in Cytosolic Ca2+-Mediated Photoregulation of Maize cab-ml Expression" Plant Physiol. 115:477-483.
Singh et al. (2012) "Accumulating Triacylglycerol in leaves via the Monoacylglycerol Acyltransferase Pathway" 20th International Symposium on Plant Lipids.
Smith et al. (2000) "Total silencing by intron-spliced hairpin RNAs" Nature 407:319-320.
Slocombe et al (2009) "Oil accumulation in leaves directed by modification of fatty acid breakdown and lipid synthesis pathways" Plant Biotechnology Journal, 7, 694-703.
Srinivasan et al. (2007) "Heterologous expression of the BABY BOOM AP2/ERF transcription factor enhances the regeneration capacity of tobacco (Nicotiana tabacum L.)" Planta 225:341-51.
Stalberg et al., (1993) "Deletion Analysis of a 2S Seed Storage Protein Promoter of Brassica napes in Transgenic Tobacco," Plant Molecular Biology, 23(4): 671-683.
Takeyama, H., et al., (1997) "Expression of the Eicosapentaenoic Acid Synthesis Gene Cluster From *Shewanella* sp. in a Transgenic Marine Cyanobacterium, *Synechococcus* sp.," Microbiology, 143(Pt 8): 2725-2731.
To et al., (2012) "WRINKLED Transcription Factors Orchestrate Tissue-Specific Regulation of Fatty Acid Biosynthesis in Arabidopsis" The Plant Cell, vol. 24: 5007-5023.
Vanhercke et al. (2012) "Maximizing lipid accumulation in vegetative plant tissues" 8th International Symposium on Biocatalysis and Agricultural Biotechnology.
Vanhercke et al. (2013) "Synergistic effect of WRI1 and DGAT1 coexpression on triacylglycerol biosynthesis in plants" FEBS Letters 587:364-369.
Vanhercke et al (2013) "Metabolic engineering of biomass for high energy density: oilseed-like triacylglycerol yields from plant leaves" Plant Biotechnol. J., doi: 10.1111/pbi.12131.
Weselake et al. (2009) "Increasing the flow of carbon into seed oil" Biotechnology Advances 27:866-878.
Wood et al. (2009) "A leaf-based assay using interchangeable design principles to rapidly assemble multistep recombinant pathways" Plant Biotech. J. 7: 914-924.
Wu et al. (1994) "A Mutant Arabidopsis Deficient in the Elongation of Palmitic Acid" Plant Physiol. 106: 143-150.
Wu et al. (1997) "Low-Temperature Damage and Subsequent Mutant Arabidopsis Exposed to Recovery of fabl 20C'" Plant Physiol, 113: 347-356.
Xu et al., (2008) "Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content" Plant Biotechnology Journal 6, pp. 799-818.
Xu et al., (2008) "Lipid Trafficking between the Endoplasmic Reticulum and the Plastid in Arabidopsis Requires the Extraplastidic TGD4 Protein" The Plant Cell, vol. 20: 2190-2204.
Xu et al., (2005) "Mutation of the TGD1 Chloroplast Envelope Protein Affects Phosphatidate Metabolism in Arabidopsis" The Plant Cell, vol. 17, 3094-3110.
Xu et al., (2010) "Lipid Transport Mediated by Arabidopsis TGD Proteins is Unidirectional from the Endoplasmic Reticulum to the Plastid" Plant Cell Physiol, 51(6): 1019-1028.
Yang et al. (2010) "A distinct type of glycerol-3-phosphate acyltransferase with sn-2 preference and phosphatase activity producing 2-monoacylglycerol" PNAS 107:12040-12045.
Yang & Ohlrogge (2009) "Turnover of Fatty Acids during Natural Senescence of Arabidopsis, Bracnypodium, and Switchgrass and in Arabidopsis b-Oxidation Mutants" Plant Physiology, 150, 1981-1989.
Yen et al., Identification of a gene encoding MGAT1, a monoacylglycerol acyltransferase. PNAS, 2002, 99(13):8512-8517.
Liu et al., (2005) GenBank Accession No. AY574036.
Liu et al., (2005) GenBank Accession No. AY574037.
Liu et al., (2005) GenBank Accession No. AY574038.
Sasaki et al., (2002) GenBank Accession No. BAC45173.1.
Sasaki et al., (2002) GenBank Accession No. BAC45170.1.
Feb. 21, 2014 Office Action, issued in connection with Canadian Patent Application No. 2,693,630.
Aug. 21, 2014 Response, filed in connection with Canadian Patent Application No. 2,693,630.
Nov. 15, 2013 Office Action, issued in connection with Australian Patent Application No. 2007272316.
Dec. 6, 2013 Response, filed in connection with Australian Patent Application No. 2007272316.
International Preliminary Report on Patentability issued on Jan. 14, 2009 in connection with PCT International Patent Application No. PCT/AU2007/000977.
International Search Report issued on Sep. 8, 2009 in Connection with International Application No. PCT/AU2009/000929.
Written Opinion of the International Search Authority, issued on Sep. 8, 2009 in Connection with International Application No. PCT/AU2009/000929.
International Search Report issued on Sep. 8, 2009 by the International Searching Authority (ISA/US) in connection with International Application No. PCT/AU2006/000930.
Written Opinion issued on Aug. 18, 2009 by the International Searching Authority (ISA/US) in connection with International Application No. PCT/AU2006/000930.
Dec. 9, 2013 Response, filed in connection with U.S. Appl. No. 13/011,779.
Dec. 20, 2013 Notice of Allowance, including Examiner Interview Summary, issued in connection with U.S. Appl. No. 13/011,773.
Apr. 16, 2013 Chinese Notice of Rejection, issued in connection with Chinese Patent Application No. 200780033971.4, including English Language Translation.
Aug. 1, 2013 Request for Re-Examination, filed in connection with Chinese Patent Application No. 200780033971.4.
May 16, 2013 Response to Japanese Office Action, filed in connection with Japanese Patent Application No. 2009-519744.
English Language Translation of May 21, 2013 Second Japanese Office Action, issued in connection with Japanese Patent Application No. 2009-519744.
Aug. 27, 2013 Response to European Examination Report, filed in connection with European Patent Application No. 07763775.9.
Oct. 9, 2013 European Examination Report, issued in connection with European Patent Application No. 07763775.9.
Andrianov et al. (2010) "Tobacco as a production platform for biofuel: overexpression of Arabidopsis DGAT and LEC2 genes increases accumulation and shifts the composition of lipids in green biomass" Plant Biotech. J. 8:277-287.
Aghoram, K., Wilson, R.F., Burton, J.W., Dewey, R.E. 2006. A mutation in a 3-keto-acyl-acp synthase ii gene is associated with elevated palmitic acid levels in soybean seeds. Crop Sci. 46:2453-2459.
Alemanno et al. (2008) "Characterization of leafy cotyledonl-like during embryogenesis in Theobroma cacao L." Planta 227:853-866.
Alonso et al. (2010) "Catalytic conversion of biomass to biofuels" Green Chem. 12:1493-1513.

(56) References Cited

OTHER PUBLICATIONS

Awai et al., (2006) "A phosphatidic acid-binding protein of the chloroplast inner envelope membrane involved in lipid trafficking" PNAS 103(28):10817-22.
Bao and Ohlrogge, Supply of Fatty Acid is One Limiting Factor in the Accumulation of Triacylglycerol in Developing Embryos. Plant Physiology, 1999, 120:1057-1062.
Barthole et al. (2011) "Controlling lipid accumulation in cereal grains" Plant Sci. 105-186:33-39.
Benning, (2008) "A role for lipid trafficking in chloroplast biogenesis" Progress in Lipid Research 47, 381-389.
Benning, (2009) "Mechanisms of Lipid Transport Involved in Organelle Biogenesis in Plant Cells" Annu. Rev. Cell Dev. Biol. 25:71-91.
Bligh and Dyer (1959) "A Rapid Method of Total Lipid Extraction and Purification" Canadian Journal of Biochemistry and Physiology 37:911-917.
Bouvier-Nave et al. (2000) "Expression in yeast and tobacco of plant cDNAs encoding acyl CoA:diacylglycerol acyltransferase" European Journal of Biochemistry/FEBS 267:85-96.
Broun et al. (1998) "A bifunctional oleate 12-hydroxylase: desaturase from Lesquerella fenleri." The Pant Journal, 13(2): 201-210.
Burgal et al., (2008) "Metabolic engineering of hydroxy fatty acid production in plants: RcDGAT2 drives dramatic increases in ricinoleate levels in seed oil" Plant Biotechnology Journal 6(8):819-831.
Cases et al., Identification of a gene encoding an acyl CoA:diacylglycerol acyltransferase, a key enzyme in triacylglycerol synthesis, PNAS (1998) 95:13018-13023.
Cases et al., Cloning of DGAT2, a second mammalian diacylglycerol acyltransferase, and related family members, J. Biol. Chem. (2001) 276(42):38870-38876.
Cao et al., Properties of the Mouse Intestinal Acyl-CoA:Monoacylglycerol Acyltransferase, MGAT2. The Journal of Biological Chemistry, 2003, 278(28)25657-25669.
Cernac and Benning (2004) "WRINKLED1 encodes an AP2/EREB domain protein involved in the control of storage compound biosynthesis in Arabidopsis" Plant J. 40:575-585.
Chappell et al (1998) "Vegetable Oil Production: Industry Profile" Preliminary Final Report, EPA contract 68-D4-0099, TRU Project # 7018-54, 1-1-5-26.
Cheng et al., Identification of Acyl Coenzyme A:Monoacylglycerol Acyltransferase 3, an Intestinal Specific Enzyme Implicated in Dietary Fat Absorption. The Journal of Biological Chemistry, 2403, 278(126):13611-13614.
Cherry, (1983) "Cottonseed Oil" J. Am. Oil Chem. Soc. 60: 360-367.
Dowd et al., (2004) "Gene Expression Profile Changes in Cotton Root and Hypocotyl Tissues in Response to Infection with *Fusarium oxysporum f.* sp. vasinfectum" Molecular Plant-Microbe Interactions. 17: 654-667.
Dulermo and Nicaud (2011) "Involvement of the G3P shuttle and (β-oxidation pathway in the control of TAG synthesis and lipid accumulation in Yarrowia lipolytica" Metab. Eng. 13:482-491.
Durrett et al. (2008) "Plant triacylglycerols as feedstocks for the production of biofuels" Plant J. 54 : 593-607.
Eastmond, (2006) "SUGAR-DEPENDENT1 Encodes a Patatin Domain Triacylglycerol Lipase That Initiates Storage Oil Breakdown in Germinating Arabidopsis Seeds" The Plant Cell, vol. 18, 665-675.
Endalew et al. (2011) "Inorganic heterogeneous catalysts for biodiesel production from vegetable oils" Biomass and Bioenergy 35:3787-3809.
Folch et al., (1957) "A Simple Method for the Isolation and Purification of total Lipides From Animal Tissues" J. Biol. Chem. 226: 497.
Fuller et al., (1966) "A Gas Chromatographic Method for Continuous Accelerated Study of O2 Uptake in Fats" JAOCS. 43:477-478.
Ghosal et al. (2007) "*Sacchromyces cerevisiae* phospholipid: diacylglycerol acyl transferase (PDAT) devoid of its membrane anchor region is a soluble and active enzyme retaining its substrate specificities" Biochimica et Biophysica Acta 1771:1457-1463.

Gong and Jiang (2011) "Biodiesel production with microalgae as feedstock: from strains to biodiesel" Biotechnol. Lett. 33:1269-1284.
International Search Report issued by the International Searching Authority (ISA/AU) on Oct. 25, 2007 in connection with International Application No. PCT/AU2007/000977.
Third Office Action which issued on Nov. 16, 2011 in connection with Chinese Patent Application No. 200780033971.4, including English language translation.
Response filed to the third Office Action filed on Apr. 5, 2012 in connection with Chinese Patent Application No. 200780033971.4, including English language the claims.
Fourth Office Action which issued on Aug. 3, 2012 in connection with Chinese Patent Application No. 200780033971.4, including English language translation.
Examination Report which issued on Jun. 8, 2012 in connection with Australian Patent Application No. 2007272316.
English language translation of First Office Action which issued on Oct. 16, 2012 in connection with Japanese Patent Application No. 2009-519744.
English translation of Office Action issued Aug. 27, 2010 in connection with corresponding Chinese Patent Application No. 200780033971.4.
Response to First Office Action filed with the Chinese Patent Office on Jan. 11, 2011 in connection with Chinese Patent Application No. 200780033971.4, and an English Translation of the Claims.
Response to Second Office Action and English Translation of Claims, filed with the Chinese Patent Office on Aug. 3, 2011 in connection with Chinese Patent Application No. 200780033971.4, and an English Translation of the Claims.
European Examination Report issued Jun. 8, 2010 by the European Patent Office in connection with European Patent Application No. 07763775.9.
Response to European Examination Report, filed with the European Patent Office in Connection on Dec. 16, 2010 in connection with European Patent Application No. 07763775.9.
European Examination Report issued Apr. 1, 2011 by the European Patent Office in connection with European Patent Application No. 07763775.9.
Response to European Examination Report, filed with the European Patent Office in Connection on Oct. 3, 2011 in connection with European Patent Application No. 07763775.9
Supplementary European Search Report issued Feb. 23, 2010 in connection with corresponding European Patent Application No. 07763775.9.
Feb. 6, 2012 European Examination Report issued in connection with European Patent Application No. 07763775.9
Dec. 4, 2012 Request for Further Processing and Response to Feb. 6, 2012 European Examination Report filed in connection with European Patent Application No. 07763775.9.
Dec. 18, 2012 Response to Aug. 3, 2012 Chinese Office Action filed in connection with Chinese Patent Application No. 200780033971.4.
File History of U.S. Patent Publication No. 2011-0314725, Petrie et al., published Dec. 29, 2011 (U.S. Appl. No. 13/171,032, filed Jun. 28, 2011).
File History of U.S. Patent Publication No. 2011-0223311, Liu et al., published Sep. 15, 2011 (U.S. Appl. No. 13/011,773, filed Jan. 21, 2011).
File History for U.S. Patent Publication No. 2009-0308041, Whitelaw et al., Dec. 17, 2009 (U.S. Appl. No. 12/309,276, filed Jul. 6, 2009).
File History of U.S. Patent Publication No. 2011-0229623, Liu et al., Sep. 22, 2011 (U.S. Appl. No. 13/011,779, filed Jan. 21, 2011).
Feb. 20, 2013 Examination Report issued in connection with European Patent Application No. 07763775.9.
Jan. 9, 2013 Office Action issued in connection with U.S. Appl. No. 13/011,773.
Feb. 11, 2013 Response filed in connection with U.S. Appl. No. 13/011,773.
Apr. 9, 2013 Office Action issued in connection with U.S. Appl. No. 13/011,773.
Dec. 6, 2012 Office Action issued in connection with U.S. Appl. No. 13/011,779.

(56) References Cited

OTHER PUBLICATIONS

Jan. 4, 2013 Response filed in connection with U.S. Appl. No. 13/011,779.
Mar. 13, 2013 Office Action issued in connection with U.S. Appl. No. 13/011,779.
U.S. Appl. No. 13/001,779, Liu et al., filed Jan. 21, 2011.
U.S. Appl. No. 12/989,405, Zhou et al., filed May 16, 2011.
U.S. Appl. No. 13/129,940, Petrie et al., filed May 18, 2011.
U.S. Appl. No. 13/011,773, Liu et al., filed Jan. 21, 2011.
U.S. Appl. No. 13/243,747, Singh et al., filed Sep. 23, 2011.
U.S. Appl. No. 13/171,032, Petrie et al., filed Jun. 28, 2011.
Abdullah et al., (1983) Efficient Plant Regeneration from Rice Protoplasts Through Somatic Embryogenesis. Biotechnology, 4:1087-1090.
Agarwal et al. (2003) "Cottonseed Oil Quality, Utilization and Processing" CICR Technical Bulletin No. 25, pp. 1-16.
Almeida and Allshire, (2005) RNA silencing and genome regulation. Trends in Cell Biology, 15:251-258.
Akagi et al. (1995) Nucleotide Sequence of a Stearoyl-Acel carrier Protein Desaturase cDNA from Developing Seeds of Rice. Plant Physiol. 108, 845-846.
Anal et al. (2003) Improvement of rice (Oryza sativa L.) seed oil quality through introduction of a soybean microsomal omega-3 fatty acid desaturase gene. Plant Cell Rep. 21,988-992.
Ascherio and Willett (1997) Health effects of trans fatty acids. Am. J. Clin, Nutr. 66: 1006S-1010S.
Bäumlein, H., et al., (1991) "A Novel Seed Protein Gene From *Vicia faba* Is Developmentally Regulated in Transgenic Tobacco and Arabidopsis Plants," Molecular and General Genetics, 225(3): 459-467.
Bligh and Dyer, (1959) Orange-red Flesh in Cod and Haddock. J. Fish. Res. Bd. Canada, 16(4):449-452.
Boggs et al. (1964) Relation of Hexanal in Vapor Above Stored Potato Granules to Subjective Flavor Extimates. J. Food Sci. 29:487-489.
Bonanome and Grundy (1988) Effect of Dietary Stearic Acid on Plasma Cholesterol and Lipoprotein Levels. N. Engl. Med. 318: 1244-1248.
Brandt et al., (1985) Primary Structure of a B1 Hordein Gene from Barley. Carlsberg Res. Commun., 50:333-345.
Broun et al., (1998) a bifunctional oleate 12-hydroxylase: desaturase from *Lesquerella fendleri*. The Plant Journal, 13(2):201-210.
Buhr et al. (2002) Ribozyme termination of RNA transcripts down-regulate seed fatty acid genes in transgenic soybean. Plant J. 30: 155-163.
Champagne et al. (1995) Stabilization of Brown Rice Products Using Ethanol Vapors as an Antioxidant Delivery System. Cereal Chem 72:255-258.
Chang et al., (1978) Chemical Reactions Involved in the Deep-Fat Frying of Foods. Journal of American Oil Chemists' Society, 55:718-727.
Chapman et al. (2001) Transgenic Cotton Plants with Increased Seed Oleic Acid Content. Journal of American Chemists' Chemistry; vol. 78 No. 9, 941-947.
Choudhury et al. (1980) Lipids in Developing and Mature Rice Grain. Phytochemistry 19: 1063-1069.
Cicero et al. (2001) Rice bran oil and [gamma]-oryzanol in the treatment of hyperlipoproteinaemias and other conditions. Phytotherapy Research; vol. 15 No. 4, 277-289.
Clapp et al., (1993) The 16-Kilodalton N-Terminal Fragment of Human Prolactin is a Potent Inhibitor of Angiogenesis. Endocrinology, 133(3):1292-1299.
Colot et al., (1987) Localization of sequences in wheat endosperm protein genes which confer tissue-specific expression in tobacco. The EMBO Journal, 6(12):3559-3564.
Comai et al., (2004) Efficient discovery of DNA polymorphisms in natural populations by Ecotilling. The Plant Journal, 37:778-786.
Domergue et al., (2005) In vivo characterization of the first acyl-CoA Δ6-desaturase from a member of the plant kingdom, the microalga Ostreococcus tauri. Biochem J. 389, 483-490.

Dougherty et al. (1995) Effects of diets containing high or low amounts of stearic acid on plasma lipoprotein fractions and fecal fatty acid excretion of men. Am. J. Clin. Nutr. 61:1120-1128.
Dubois et al. (2007) Fatty acid profiles of 80 vegetable oils with regard to their nutritional potential. European Journal of Lipid Science Technology 109(7):710-732.
Goffman et al. (2003) Genetic Diversity for Lipid Content and Fatty Acid Profile in Rice Bran. Journal of the American Oil Chemists' Society 80:485-490.
Ha (2005) Bioactive components in rice bran oil improve lipid profiles in rats fed on high-cholesterol diet. Nutrition research 25, 597-606.
Haseloff and Gerlach, (1988) Simple RNA enzymes with new and highly specific endoribonuclease activities. Nature, 334:585-591.
Henikoff et al., (2004) TILLING. Traditional Mutagenesis Meets Functional Genomics. Plant Physiology, 135:630-636.
Hu et al. (1997) Dietary Fat Intake and the Rist of Coronary Heart Disease in Women. N. Engl. J. Med. 337:1491-1499.
Jennings and Akoh (2000) Lipase-Catalyzed Modification of Rice Bran Oil to Incorporate Capric Acid. Journal of Agricultural and Food Chemistry, 48:4439-4443.
Jones et al. (1995) Palmitoyl-Acyl Carrier Protein (ACP) Thioesterase and the Evolutionary Origin of Plant Acyl-ACP Thioesterases. Plant Cell 7: 359-371.
Klahre et al. (2002) High molecular weight RNAs and small interfering RNAs induce systemic posttranscriptional gene silencing in plants. PNAS 99(18): 11981-11986.
Kinney (1996) Development of Genetically Engineered Soybean Oils for Food Applications. J. Food Lipids 3: 273-292.
Kozeil et al., (1996) Optimizing expression of transgenes with an emphasis on post-transcriptional events. Plant Molecular Biology, 32:393-405.
Kodama et al. (1997) Structure, chromosomal location and expression of a rice gene encoding the microsome ω-3 fatty acid desaturase. Plant Molecular Biology 33:493-502.
Kohno-Murase et al. (2006) Production of trans-10, cis-12 conjugated linoleic acid in rice. Transgenic Research 15:95-100.
Langridge et al., (2001) Trends in genetic and genome analysis in wheat: a review. Aust. J. Agric. Res., 52:1043-1077.
Lee, M., et al., (1998) Identification of Non-Heme Diiron Proteins That Catalyze Triple Bond and Epoxy Group Formation. Science, 280(5365): 915-918.
Lemieux B., (2000) High Throughput Single Nucleotide Polymorphism Genotyping Technology. Current Genomics, 1:301-311.
Leonard et al. (1997) Cuphea wrightii thioesterases have unexpected broad specificities on saturated fatty acids. Plant Molecular Biology, vol. 34, Issue 4: 669-679.
Li et al., (1997) Comparison of promoters and selectable marker genes for use in Indica rice transformation. Molecular Breeding, 3:1-14.
Liu et al. (1999) Molecular cloning and expression of a cDNA encoding a microsomal ω-6 fatty acid desaturase from cotton (Gossypium hirsutum) Aust. J. Plant Physiol. 26:101-106.
Liu et al. (2002) High-Oleic and High-Stearic Cottonseed Oils: Nutritionally Improved Cooking Oils Developed Using Gene Silencing. J. Am. Coll. Nutr. 21: 205S-211S.
Liu et al. (2002) High-Stearic and High-Oleic Cottonseed Oils Produced by Hairpin RNA-Mediated Post-Transcriptional Gene Silencing. Plant Physiol. 129: 1732-1743.
Lu et al., (1993) High Efficiency Retroviral Mediated Gene Transduction into Single Isolated Immature and Replatable $CD34^{3+}$ Hematopoietic Stem/Progenitor Cells from Human Umbilical Cord Blood. J. Exp. Med., 178:2089-2096.
Mensink and Katan (1990) Effect of Dietary Trans Fatty Acids on High-Density and Low-Density Lipoprotein Cholesterol Levels in Healthy Subjects. N. Engl. J. Med. 323: 439-445.
Miquel et al. (1992) Arabidopsis mutants deficient in polyunsaturated fatty acid synthesis: Biochemical and genetic characterization of a plant oleoyl-phosphatidylcholine desaturase. Journal of Biological Chemistry; vol. 267 No. 3, 1502-1509.

(56) References Cited

OTHER PUBLICATIONS

Mikkilineni and Rocheford (2003) Sequence variation and genomic organization of fatty acid desaturase-2 (fad2) and fatty acid desaturase-6 (fad6) cDNAs in maize. Theor. Applied Genetics, 106, 1326-1332.
Millar and Waterhouse, (2005) Plant and animal microRNAs: similarities and differences. Funot Integr Genomics, 5:129-135.
Moghadasian and Frohlich (1999) Effects of Dietary Phytosterols on Cholesterol Metabolism and Atherosclerosis: Clinical and Experimental Evidence. Am. J. Med. 107: 588-94.
Morrison (1988) Lipids in Cereal Starches: A Review. J Cereal Sci. 8:1-15.
Most et al. (2005) Rice bran oil, not fiber, lowers cholesterol in humans. Am J Clin Nutr 81:64-8.
Needleman and Wunsch, (1970) A General Method Applicable to the Search of Similarities in the Amino Acid Sequence of Two Proteins. J. Mol. Biol., 48:443-453.
Nielsen et al. (2004) Formation of Volatile Compounds in Model Experiments with Crude Leek (*Allium ampeloprasum* Var. *Lancelot*) Enzyme Extract and Linoleic Acid or Linolenic Acid. Journal of Agricultural and Food Chemistry 52:2315-2321.
Noakes and Clifton (1998) Oil blends containing partially hydrogenated or interesterified fats: differential effects on plasma lipids. Am. J. Clin. Nutr. 98: 242-247.
O'Brien (2005) "Cottonseed Oil" Bailey's Industrial Oil and Fat Products, 6th Edition, edited by Fereidoon Shahidi.
Ohlrogge and Jaworski (1997) Regulation of Fatty Acid Synthesis. Annu Rev Plant Physiol Plant Mol Biol. 48:109-136.
Pasquinelli et al., (2005) MicroRNAs: a developing story. Current Opinion in Genetics & Development, 15:200-205.
Perriman et al., (1992) Extended target-site specificity for a hammerhead ribozyme. Gene, 113:157-163.
Pirtle et al. (1999) Characterization of a Palmitoyl-Acyl Carrier Protein Thioesterase (FatB1) in Cotton. Plant Cell Physiology 40:2 p. 155-163.
Radcliffe et al. (1997) Serum Lipids in Rats Fed Diets Containing Rice Bran Oil or High-Linolenic Acid Safflower Oil. Biochemical Archives 13:87-95.
Resurreccion et al (1979) Nutrient Content and Distribution in Milling Fractions of Rice Grain. Journal of the Science of Food and Agriculture, 30: 475-481.
Roche and Gibney (2000) Effect of long-chain n-3 polyunsaturated fatty acids on fasting and postprandial triacylglycerol metabolism. Am. J. Clin. Nutr. 71: 232S-237S.
Rukmini and Raghuram (1991) Nutritional and Biochemical Aspects of the Hypolipidemic Review. Journal of the American College of Nutrition 10(6):593-601.
Senior I.J., (1998) Uses of Plant Gene Silencing. Biotechnology & Genetic Engineering Reviews, Ed. Tombs, M.P., 15:79-119.
Slade and Knauf, (2005) TILLING moves beyond functional genomics into crop improvement. Transgenic Research, 14:109-115.
Smith et al., (2000) Total silencing by intron-spliced hairpin RNAs. Nature, 407:319-320.
Shin et al. (1986) Correlation Between Oxidative Deterioration of Unsaturated Lipid and n-Hexanal during Storage of Brown Rice. J. Food Sci. 51:460-463.
Shippy et al., (1999) The Hairpin Ribozyme. Molecular Biotechnology, 12:117-129.
Sivaraman et al. (2004) Development of high oleic and low linoleic acid transgenics in a zero erucic acid Brassica juncea L. (Indian mustard) line by antisense suppression of the fad2 gene. Molecular Breeding, Kluwer Academic Publishers, DO; vol. 13 No. 1, 365-375.
St Angelo et al. (1980) Identification of Lipoxygenase-Linoleate Decomposition Products by Direct Gas Chromatography-Mass Spectrometry. J Lipids 1:45-49.
Stoutjesdijk et al., (2000) High-oleic acid Australian Brassica napus and B. juncea varieties produced by co-suppression of endogenous Δ12-desaturases. Biochem. Soc. Trans. 28: 938-940.
Stoutjesdijk et al. (2002) hpRNA-mediated targeting of the Arabidopsis FAD2 gene gives highly efficient and stable silencing.
Plant Physiology, American Society of Plant Physiologists, Rockville, MD, US; vol. 129, 1723-31.
Suzuki et al. (1999) Volatile Components in Stored Rice [Oryza sativa (L.)] of Varieties with and without Lipoxygenase-3 in Seeds. J. Agric. Food Chem. 47: 1119-1124.
Taira et al. (1989) Fatty Acid Composition of Indica-Types and Japonica-Types of Rice Bran and Milled Rice. Journal of the American Oil Chemists' Society; vol. 66 No. 9, 1326-1329.
Taira et al. (1988) Fatty Acid Composition of Indica Sinica Javanica and Japonica Groups of Nonglutinous Brown Rice. Journal of Agricultural and Food Chemistry; vol. 36 No. 1, 45-47.
Taira et al. (1986) Lipid Content and Fatty-Acid Composition of Indica and Japonica Types of Nonglutinous Brown Rice. Journal of Agriculture and Food Chemistry; vol. 34 No. 3, 542-545.
Thelen and Ohlrogge (2002) Metabolic Engineering of Fatty Acid Biosynthesis in Plants. Metabolic Engineering 4: 12-21.
Theriault et al. (1999) Tocotrienol: A Review of its Therapeutic Potential. Clin. Biochem. 32: 309-19.
Tholstrup et al. (1994) Fat high in stearic acid favorably affects blood lipids and factor VII coagulant activity in comparison with fats high in palmitic acid or high in myristic and lauric acids. Am. J. Clin. Nutr. 59: 371-377.
Toriyama et al., (1986) Haploid and diploid plant regeneration from protoplasts of anther callus in rice. Theor Appl Genet, 73:16-19.
Trautwein, E.A., (2001) n-3 Fatty Acids—Physiological and Technical Aspects for Their Use in Food. European Journal of Lipid Science and Technology, 103(1): 45-55.
Tsugita et al (1983) Cooking Flavor and Texture of Rice Stored under Different Conditions. Agricultural and Biological Chemistry 47: 543-549.
Tsuzuki et al (2004) Oxidation Rate of Conjugated Linoleic Acid and Conjugated Linolenic Acid is Slowed by Triacylglycerol Esterification and α-Tocopherol. Lipids 39:475-480.
Valvekens, D., et al., (1988) Agrobacterium tumefaciens-Mediated Transformation of Arabidopsis thaliana Root Explants by Using Kanamycin Selection. Proceedings of the National Academy of Sciences of the United States of America, 85(15) 5536-5540.
van de Loo, F. J., Braun, P., Turner, S., & Somerville, C. (Jul. 1995). An oleate 12-hydroxylase from Ricinus communis L. is a fatty acyl desaturase homolog. Proc. Natl. Acad. Sci. USA, 92, 6743-6747.
Voelker et al. (1996) Genetic engineering of a quantitative trait: metabolic and genetic parameters influencing the accumulation of laurate in rapeseed. Plant J. 9: 229-241.
Wagner et al., (1992) Coupling of adenovirus to transferring-polylysine/DNA complexes greatly enhances receptor-mediated gene delivery and expression of transfected genes. Proc. Natl. Acad. Sci USA, 89:6099-6103.
Wang et al., (1998) Improved Vectors for *Agrobacterium tumefaciens*-Mediated Transformation of Monocot Plants. Acta Hort, 461:401-407.
Waterhouse, (1998) Virus resistance and gene silencing in plants can be induced by simultaneous expression of sense and antisense RNA. Proc. Natl. Acad. Sci. USA, 95:13959-13964.
Whitelaw, E. S., Li, Z., Singh, S., Liu, Q., Upadhyaya, N., Morell, M., . . . Rahman, S. (Sep. 2004). Investigation of lipid synthesis in the rice grain: [m]odification of fatty acids in rice bran oil. In C. K. Black, J. F. Panozzo, & G. J. Rebetzke (Eds.), *Cereals 2004: Proceedings of the 54th Australian Cereal Chemistry Conference and 11th Wheat Breeders Assembly*, Sep. 21-24, 2004, Canberra ACT, North Melbourne VIC: Cereal Chemistry Division, Royal Australian Chemical Institute, AU (pp. 418-420).
Whitelaw et al. (1986) A Rice FATB Insertional Mutant Exhibits Improved Growth and Reduced Photoinhibition at High Temperatures. Proceedings of the 55th Australian Cereal Chemistry Conference, 55th Australian Cereal Chemistry Conference, Jul. 3-7, 2008, Sydney Australia, Jul. 3, 2005, pates 101-104.
Williams et al. (1999) Impaired Endothelial Function Following a Meal Rich in Used Cooking Fat. J. Am. Coll. Cardiol. 33:1050-1055.
Yasumatsu et al. (1966) Studies on Cereals Part V Stale Flavor of Stored Rice. Agric. Biol. Chem. 30:483-486.
Zhou et al. (2002) Ageing of Stored Rice: Changes in Chemical and Physical Attributes. Journal of Cereal Science 35:65-78.

(56) References Cited

OTHER PUBLICATIONS

Zock et al. (1994) Impace of myristic acid versus palmitic acid on serum lipid and piloprotein levels in healthy women and men. Arterioscler Thromb. 14: 567-575.
Connolly et al. (1998) GenBank Accession No. AC004236, NCBI, pp. 1-11.
Sharma et al., (2003) GenBank Accesion No. AC108870, NCBI, pp. 1-27.
Kim et al., (1999) GenBank Accesion No. AF213480, NCBI, p. 1.
Liu et al. (1997) EMBL Nucleotide Sequence Database as X97016.
Sasaki et al., (2001) GenBank Accession No. AP004047, NCBI, pp. 1-36.
Sasaki et al., (1999) GenBank Accession No. AP000399, NCBI, pp. 1-33.
Sasaki et al., (2001) Genbank Accession No. AP004236, NCBI, pp. 1-37.
Sasaki et al., (2002) GenBank Accession No. AP005168, NCBI, pp. 1-31.
Sasaki et al., (2002) GenBank Accession No. AP005291, NCBI, pp. 1-38.
Sasaki et al. (2002) GenBank Accession No. BAC45170.1.
Sasaki et al. (2002) GenBank Accession No. BAC45173.1.
Jul. 1, 2011 Office Action, issued in connection with U.S. Appl. No. 12/309,276, internationally filed Jul. 13, 2007.
Sep. 1, 2011 Response, filed in connection with U.S. Appl. No. 12/309,276, internationally filed Jul. 13, 2007.
Nov. 4, 2011 Office Communication, issued in connection with U.S. Appl. No. 12/309,276, internationally filed Jul. 13, 2007.
Dec. 5, 2011 Response, filed in connection with U.S. Appl. No. 12/309,276, internationally filed Jul. 13, 2007.
Jan. 12, 2012 Office Action, issued in connection with U.S. Appl. No. 12/309,276, internationally filed Jul. 13, 2007.
Feb. 6, 2012 Petition, filed in connection with U.S. Appl. No. 12/309,276, internationally filed Jul. 13, 2007.
Mar. 26, 2012 Decision on Petition, issued in connection with U.S. Appl. No. 12/309,276, internationally filed Jul. 13, 2007.
Aug. 3, 2012 Office Action, issued in connection with U.S. Appl. No. 12/309,276, internationally filed Jul. 13, 2007.
Dec. 3, 2012 Response, filed in connection with U.S. Appl. No. 12/309,276, internationally filed Jul. 13, 2007.
Jan. 17, 2013 Final Office Action, issued in connection with U.S. Appl. No. 12/309,276, internationally filed Jul. 13, 2007.
Apr. 17, 2013 Response, filed in connection with U.S. Appl. No, 12/309,276, internationally filed Jul. 13, 2007.
May 6, 2013 Notice of Allowance, issued in connection with U.S. Appl. No. 12/309,276, internationally filed Jul. 13, 2007.
Jul. 5, 2013 Notice, issued in connection with U.S. Appl. No. 12/309,276, internationally filed Jul. 13, 2007.
Jul. 29, 2013 Response to Notice, filed in connection with U.S. Appl. No. 12/309,276, internationally filed Jul. 13, 2007.
Jul. 31, 2013 Declaration, filed in connection with Chinese Patent Application No. 200780033971.4.
Aug. 1, 2013 Response, filed in connection with Chinese Patent Application No. 200780033971.4, including English Language of pending claims.
English Language Translation of Apr. 16, 2013 Grounds of Rejection, issued in connection with Chinese Patent Application No. 200780033971.4.
English Language translation of May 21, 2013 Office Action, issued in connection with Japanese Patent Application No. 2009-519744.
Apr. 16, 2013 Response, filed in connection with Japanese Patent Application No. 2009-519744.
Aug. 27, 2013 Response, filed in connection with European Patent Application No. 07763775.9.
Aug. 8, 2013 Response, filed in connection with U.S. Appl. No. 13/011,773.
Jul. 15, 2013 Response, filed in connection with U.S. Appl. No. 13/011,779.
Aug. 8, 2013 Final Office Action, issued in connection with U.S. Appl. No. 13/011,779.
Sheikh et al (2002) Fatty Acids Composition in Germinating Cotton Seedlings Affected by High Temperature Stress. Pakistan Journal of Applied Sciences 2(1):97-99.
Sep. 9, 2015 Response to Examination Report, filed in connection with Canadian Patent Application No. 2,693,630.
Dec. 2, 2014 Fifth Chinese Office Action, issued in connection with Chinese Patent Application No. 200780033971.4, including English Language Translation.
Mar. 20, 2015 Response to Jan. 14, 2015 Communication, filed in connection with European Patent Application No. EP 07763775.9.
Sep. 25, 2015 Summons to Oral Proceedings, issued in connection with European Patent Application No. EP 07763775.9.
Jan. 28, 2016 Response to the Summons to Oral Proceedings, filed in connection with European Patent Application No. 07763775.9.
Feb. 23, 2016 Proposed Amendments, filed in connection with European Patent Application No. 07763775.9.
Jan. 12, 2016 Office Action, issued in connection with Japanese Patent Application No. 2013-240977, including English Language Translation.
Mar. 17, 2016 Decision, issued in connection with European Patent Application No. 07763755.9.

```
proteinFATB2        MAGSLAASAFFPGPGSSPAASARSSKNAAVTGELPENLSVRGIVAKPNPPPAAMQVKA...
proteinFATB3    1   MAGSLAASAFFPGPGSSPAASARSSKNAAVTGELPENLSVCGIVAKPNPPPAAMQVKA...
proteinFATB1        MAGSLAASAFFPVPGSSPAASARSSKN..TTGELPENLSVRGIVAKPNFSPGAMQVKA...
proteinFATB4        MAGSIAASAFLPG...SPAAAPPKS....VLGERPDSLDVRGLAAKPGSSSSAALRAGK proteinFATB2        ...QAQTLPKVNGTKVNLKTVKPD.MEETVPYSAPKTFYNQLPDWSMLLAAITTIFLAAEK
proteinFATB3    61  ...QAQTLPKVNGTKVNLKTVKPD.MEETVPHSAPKTFYNQLPDWSMLLAAITTIFLAAEK
proteinFATB1        ...QAQALPKVNGTKVNLKTTSPD.KEDIIPYTAPKTFYNQLPDWSMLLAAVTTIFLAAEK
proteinFATB4        TRTHAAIPKVNGGSSALADPEHDTMSSSSSAAPRTFYNQLPDWSMLLAAITTIFLAAEK proteinFATB2        QWTLLDWKPKKPDMLVDTFGFGRIIQDGMVFRQNFMIRSYEIGADRTASIETLMNHLQET
proteinFATB3    121 QWTLLDWKPKKPDMLVDTFGFGRIIQDGMVFRQNEMIRSYEIGADRTASIETLMNHLQET
proteinFATB1        QWTLLDWKPKPDMLADTFGFGRIIQDGLVFRQNFLIRSYEIGADRTASIETLMNHLQET
proteinFATB4        QWTLLDWKPKRPDMLTDTFGFGRMIHEGLMFRQNFSIRSYEIGADRTASIETLMNHLQET proteinFATB2        ALNHVRTAGLLGDGFGATPEMSKRNLIWVVSKIQLLVEQYPAWGDTVQVDTWVAAAGKNG
proteinFATB3    181 ALNHVRTAGLLGDGFGATPEMSKRNLIWVVSKIQLLVEQYPAWGDMVQVDTWVAAAGKNG
proteinFATB1        ALNHVKTAGLLGDGFGATPEMSKRNLIWVVSKIQLLVERYPSWGDMVQVDTWVAAAGKNG
proteinFATB4        ALNHVKSAGLLGDGFGSTPEMSKRDLFWVVSQMQAIVERYPCWGDTVEVDTWVGAHGKNG proteinFATB2        MRRDWHVRDYNSGRTILRATSVWVMMHKKTRRLSRMPDEVRAEIGPYFNDRSAITEEQSE
proteinFATB3    241 MRRDWHVRDYNSGRTILRATSVWVMMHKKTRRLSRMPDEVRAEIGPYFNDRSAITEEQSE
proteinFATB1        MRRDWHVRDYNSGQTILRATSVWVMMQNKNTRRLSRMPDEVRAEIGPYFNGRSAISEEQGE
proteinFATB4        MRRDWHIRDSVTGETILRATSKWVMMHLTRRLARIPDEVRTEIEPYFFEHASIVDEDNQ
```

Fig. 2A

```
              301       311       321       331       341       351
proteinFATB2  KLAKTGNKVGDDATEQFIRKGLIPRWGDLDVNQHVNNVKYIGWILESAPISVLEKHELAS
proteinFATB3  KLA*---------------------------------------------------------
proteinFATB1  KLPKPGTTFDGAATKQFTRKGLTPKWSDLDVNQHVNNVKYIGWILESAPISILEKHELAS
proteinFATB4  KLPKLPD.IEGANVAKYVRTGLTPRWADLDINQHVNNVKYIGWILESAPISILEKHELAS 361       371       381       391       401       411
proteinFATB2  MTLDYRKECGRDSVLQSLTTVSGECTSIGADKQASAIQCDHLLQLESGADIVKAHTEWRP
proteinFATB3  ------------------------------------------------------------
proteinFATB1  MTLDYRKECGRDSVLQSLTAVSGECDDGNTE...SSIQCDHLLQLESGADIVKAHTEWRP
proteinFATB4  IVLDYKRECGRDSVLQSHTTVTDC...NKHSGQTTLHCEHLLSLESGPTIVKARTMWRP 421       431
proteinFATB2  KRSHAAAENA*---
proteinFATB3  ---------------
proteinFATB1  KRAQGEGNMGFFPAESA*
proteinFATB4  KGTRPQESSIIPSSS*---
```

Fig. 2B

```
LOC_Os02g4  CCATATGTGCAGCATAAAAGGCAAATCAGCCCTGTTTGACATGGCTCCAATGCTTAAATT
LOC_Os11g4  ------------------------------------------------------------
LOC_Os06g0  ------------------------------------------------------------
LOC_Os06g3  ------------------------------------------------------------

1981      1991      2001      2011      2021      2031
LOC_Os02g4  CTTTAGAGAAAAAACAGACTTTGTAGATTAAATCAAAGTGGCATAATCTTTTTATTTTGA
LOC_Os11g4  ------------------------------------------------------------
LOC_Os06g0  ------------------------------------------------------------
LOC_Os06g3  ------------------------------------------------------------

2041      2051      2061      2071      2081      2091
LOC_Os02g4  TAAAAATATTAGAAAATATCATACCCTAATATTCTTAGCATAGTACTCCATTCATCTCAC
LOC_Os11g4  ------------------------------------------------------------
LOC_Os06g0  ------------------------------------------------------------
LOC_Os06g3  ------------------------------------------------------------

2101      2111      2121      2131      2141      2151
LOC_Os02g4  TTATTAAGGTACGATCAAACTTGGCATAGTCTTCAAAGGCTGTGTTCTTTCCCCCATTTT
LOC_Os11g4  ------------------------------------------------------------
LOC_Os06g0  ------------------------------------------------------------
LOC_Os06g3  ------------------------------------------------------------

2161      2171      2181      2191      2201      2211
LOC_Os02g4  CCTAACCCATCTATCTCGTTTTCCGCGCACACATTTTTCAAACTGCTAAACGGTGTGATT
LOC_Os11g4  ------------------------------------------------------------
LOC_Os06g0  ------------------------------------------------------------
LOC_Os06g3  ------------------------------------------------------------

2221      2231      2241      2251      2261      2271
LOC_Os02g4  TATGCAAAAACTTCTATATGAAAGTTGTTTAAAAAAATCATATTAATCCATTTTTTAAAA
LOC_Os11g4  ------------------------------------------------------------
LOC_Os06g0  ------------------------------------------------------------
LOC_Os06g3  ------------------------------------------------------------

2281      2291      2301      2311      2321      2331
LOC_Os02g4  AAATCAGTTAATACTTAATTAATCATGCAATAAAACGAACTTCATTTTGCGTGCTGGGGA
LOC_Os11g4  ------------------------------------------------------------
LOC_Os06g0  ------------------------------------------------------------
LOC_Os06g3  ------------------------------------------------------------

2341      2351      2361      2371      2381      2391
LOC_Os02g4  GGAGGGGCTCCCAACCCCTCCTCCGAACACAGCCAAAAGCTACTTTTGGACTTTAAATTT
LOC_Os11g4  ------------------------------------------------------------
LOC_Os06g0  ------------------------------------------------------------
LOC_Os06g3  ------------------------------------------------------------

2401      2411      2421      2431      2441      2451
LOC_Os02g4  GTCATATATTATAATGTTTCTAGTAACAAAACCATAGTCATATGAAAGTAAATTTAAATG
LOC_Os11g4  ------------------------------------------------------------
LOC_Os06g0  ------------------------------------------------------------
LOC_Os06g3  ------------------------------------------------------------

2461      2471      2481      2491      2501      2511
LOC_Os02g4  ATAATCCAATGATATTATTTTCATCAAATAGAATTTAATTTATAATAAACTATTTATTGA
LOC_Os11g4  ------------------------------------------------------------
LOC_Os06g0  ------------------------------------------------------------
LOC_Os06g3  ------------------------------------------------------------

2521      2531      2541      2551      2561      2571
LOC_Os02g4  TAAAATATTCAGAGAGTTGAATATTAAAATACCTGTGTGCCTTAGTGAGTGGGCCAAATT
LOC_Os11g4  ------------------------------------------------------------
LOC_Os06g0  ------------------------------------------------------------
LOC_Os06g3  ------------------------------------------------------------
```

Fig. 4A

```
              2581       2591       2601       2611       2621       2631
LOC_Os02g4    AATTAATGGAGTAGTAACAGCTTTAACCAAAGAAATTTCAACAATTTCCCAAGCTAGAAA
LOC_Os11g4    ------------------------------------------------------------
LOC_Os06g0    ------------------------------------------------------------
LOC_Os06g3    ------------------------------------------------------------

2641       2651       2661       2671       2681       2691
LOC_Os02g4    AAACCCAACTCCAAAATAAACTTGAGTTAGAACTGTGTTAAGCACCTAAATTGTAATACC
LOC_Os11g4    ------------------------------------------------------------
LOC_Os06g0    ------------------------------------------------------------
LOC_Os06g3    ------------------------------------------------------------

2701       2711       2721       2731       2741       2751
LOC_Os02g4    TGTTACTCTCTCGTTCTCATTCTATATTTGTCCTAAGTTAAATATATCTACCTTTTTTTA
LOC_Os11g4    ------------------------------------------------------------
LOC_Os06g0    ------------------------------------------------------------
LOC_Os06g3    ------------------------------------------------------------

2761       2771       2781       2791       2801       2811
LOC_Os02g4    TCTGTCCTAAGTTAACTATGTGTATGTCTATCTTTTCTACTACTCCCTCCGTTTCAGGTT
LOC_Os11g4    ------------------------------------------------------------
LOC_Os06g0    ------------------------------------------------------------
LOC_Os06g3    ------------------------------------------------------------

2821       2831       2841       2851       2861       2871
LOC_Os02g4    ATAAGACGTTTTGACTTTGGTCAAAGTCAAACTGCTTTAAGTTTGACTAAGTTTGTAGAA
LOC_Os11g4    ------------------------------------------------------------
LOC_Os06g0    ------------------------------------------------------------
LOC_Os06g3    ------------------------------------------------------------

2881       2891       2901       2911       2921       2931
LOC_Os02g4    AAAATAATAACATTTTCAACCCAAGACAAATTTATTATGAAAATATGTTCAATTATTGAT
LOC_Os11g4    ------------------------------------------------------------
LOC_Os06g0    ------------------------------------------------------------
LOC_Os06g3    ------------------------------------------------------------

2941       2951       2961       2971       2981       2991
LOC_Os02g4    TTAATGAAACTAAATTTGGTATTATAAATATTATTATATTTATATATAAACTTAGTTAAAT
LOC_Os11g4    ------------------------------------------------------------
LOC_Os06g0    ------------------------------------------------------------
LOC_Os06g3    ------------------------------------------------------------

3001       3011       3021       3031       3041       3051
LOC_Os02g4    TTAAAGTAGTTTAAGTTTGATCAAAGTCAAAATGTTTTATAACCTGAAATGGAGGGAGTA
LOC_Os11g4    ------------------------------------------------------------
LOC_Os06g0    ------------------------------------------------------------
LOC_Os06g3    ------------------------------------------------------------

3061       3071       3081       3091       3101       3111
LOC_Os02g4    AGTAATTTGAAACGAAGAGAGCAGACAAATAATAAACTAGTAAAGCCTGTGACTTGGGTT
LOC_Os11g4    ------------------------------------------------------------
LOC_Os06g0    ------------------------------------------------------------
LOC_Os06g3    ------------------------------------------------------------

3121       3131       3141       3151       3161       3171
LOC_Os02g4    CTAGTCATTGATCGTGTACATGTAGGTCTTGTTTAGATCCCAAAAAATTTTAGCCAAAAC
LOC_Os11g4    ------------------------------------------------------------
LOC_Os06g0    ------------------------------------------------------------
LOC_Os06g3    ------------------------------------------------------------

3181       3191       3201       3211       3221       3231
LOC_Os02g4    CTCACATCAAATATTTGGACACATGCACCCCTACCAGTGTGTGGAGGCATTGCATACACG
LOC_Os11g4    ------------------------------------------------------------
LOC_Os06g0    ------------------------------------------------------------
LOC_Os06g3    ------------------------------------------------------------
```

Fig. 4B

```
                3241       3251       3261       3271       3281       3291
LOC_Os02g4      AAACATGGAAAAGGAATCAACTTGAGAGGTTAGACCTGCTAGCTCTACTAGGTCTGGATG
LOC_Os11g4      ------------------------------------------------------------
LOC_Os06g0      ------------------------------------------------------------
LOC_Os06g3      ------------------------------------------------------------

3301       3311       3321       3331       3341       3351
LOC_Os02g4      GTCATGCATTTTTTTTTGAAAAAAACCACGCTGCAAGCTCGACAGCCTCAACCTCAATGG
LOC_Os11g4      ------------------------------------------------------------
LOC_Os06g0      ------------------------------------------------------------
LOC_Os06g3      ------------------------------------------------------------

3361       3371       3381       3391       3401       3411
LOC_Os02g4      CAACCATGACAATAATATGCATGACAATGGTGTAGGAGAAAAGACACGTCGATAACCAAA
LOC_Os11g4      ------------------------------------------------------------
LOC_Os06g0      ------------------------------------------------------------
LOC_Os06g3      ------------------------------------------------------------

3421       3431       3441       3451       3461       3471
LOC_Os02g4      GGGCGCGGCTGCGCATACAAAGGCGGAGAGAAGGAACGATGGTGGCTCAAAAAGAAAGAG
LOC_Os11g4      ------------------------------------------------------------
LOC_Os06g0      ------------------------------------------------------------
LOC_Os06g3      ------------------------------------------------------------

3481       3491       3501       3511       3521       3531
LOC_Os02g4      CGTCGGTGGCAGTGGTGCGTGGAGCGACACTAAAGTTAGTGGTTGCTGATGGTCTCACAC
LOC_Os11g4      ------------------------------------------------------------
LOC_Os06g0      ------------------------------------------------------------
LOC_Os06g3      ------------------------------------------------------------

3541       3551       3561       3571       3581       3591
LOC_Os02g4      AATCCCTAATCGAAATATTTATTTTTTTTCACTTAGTATTGCTGATCCGTGGGCCACCAG
LOC_Os11g4      ------------------------------------------------------------
LOC_Os06g0      ----------------------------------------------------CGCGTCGTG
LOC_Os06g3      ------------------------------------------------------------

3601       3611       3621       3631       3641       3651
LOC_Os02g4      CCAATCATAAAGAAAAATGTTGAGATAAAAGGTGGAGTATCTTCCCCTTCCTTCCCTTTT
LOC_Os11g4      ------------------------------------------------------------
LOC_Os06g0      TGAGTTGGCGAGCCCGAGGAGCGGAGGCGGCCACAAGTCTAATCCGCGTCGTCTGCGCGT
LOC_Os06g3      ------------------------------------------------------------

3661       3671       3681       3691       3701       3711
LOC_Os02g4      TGACTCGAAAAAAAAAAGCGTCGGTGGCGGCCGTGCGTGTAACAACACTAAAGTTAGTGG
LOC_Os11g4      ------------------------------------------------------------
LOC_Os06g0      TCGTGGGCGAGGAGGAGAAAGAAGAGGAGGAAGAGAGGGAAGGGGGCTTGA--TTTGATT
LOC_Os06g3      ------------------------------------------------------------

3721       3731       3741       3751       3761       3771
LOC_Os02g4      TTGCTGGTGGTCTGACACAATCCCTAATCAAGTTTGATAATAATAATAATTTATTTCCTC
LOC_Os11g4      ------------------------------------------------------------
LOC_Os06g0      TGGGCGCGTCTCGTGGAGTATCCGGTGAGTTCTTGGCGATCTGGCGAGGCGAGTGATGAG
LOC_Os06g3      ------------------------------------------------------------

3781       3791       3801       3811       3821       3831
LOC_Os02g4      TTATTAGTATTGCTGATGCGTGGGCCACCAATCAATCGTAAAGAAAAAAAAATGTTGAGAT
LOC_Os11g4      ------------------------------------------------------------
LOC_Os06g0      TGATTCCTGCTGCTGCTGGGGGATTTTGGCGTGATTTTCGTTGGTTGCATTTTGTTTCTT
LOC_Os06g3      ------------------------------------------------------------

3841       3851       3861       3871       3881       3891
LOC_Os02g4      AAAAGGTGGGGGTATCTTCTCCTTCTCTTTTTTTTGGCTAAAATAAAAGTGGTTTCTGG
LOC_Os11g4      ------------------------------------------------------------
LOC_Os06g0      TTTTTTTGTATCGATTTGTTGGAGCT-TTATTCGGTAGATCTGGTCGATTCCATGGTGAG
LOC_Os06g3      ------------------------------------------------------------
```

Fig. 4C

```
                 3901       3911       3921       3931       3941       3951
LOC_Os02g4   TAGTCTGACACAATCTCTAATCGAAATATTTATTTTTTTCTCTTAGTATTGCTGATACGT
LOC_Os11g4   ------------------------------------------------------------
LOC_Os06g0   TTGTATCGGCGCCGGAGTGATAGCTGATTCTGTTTTTTTGTGTGATTTTTTTTTTGTTTT
LOC_Os06g3   ---------------GCGATGCGAGCCTGTGTTGACAGCGGAGAA-AGCAGTGTAATCC 3961       3971       3981       3991       4001       4011
LOC_Os02g4   GGGCCACCAGCCAATAATAAAGAAAAAAAATGTTAGAGATAAAAGGCGGAGAGTATCTTC
LOC_Os11g4   ------------------------------------------------------------
LOC_Os06g0   GGAAATAGGGTTTGTGTCGAATTGAGGGCATTTTTTTTCCTTAGGCAATGCAGGAT-TTC
LOC_Os06g3   GGTCCCGCCACCGCAGCCGCCTCCACCTCTCTTCCCGGCGCCAATGGCCGCGTCGT-GAA 4021       4031       4041       4051       4061       4071
LOC_Os02g4   CCCTTCCTTTTTTTGGCGTAAATGAAAGAAAAGAGAAAATCTCCCGTCGTCTCCTTCCT
LOC_Os11g4   --------------------------------AGAGGAGAAATTCTCCCGTCGTCTCCTTCCT
LOC_Os06g0   GTTTTGTATGTTTTTGCGTGGAATGGATATGAACAGACCTCGAACAAATGGAAGAAT--T
LOC_Os06g3   GCGCAGCAGCAGCAGCAGCGGAGACAGCGGCAGAAGCTTTGCCTAAGGTCGGTTTGC 4081       4091       4101       4111       4121       4131
LOC_Os02g4   TGCGCCAAGAAAGACGAGCCGCGGCTCAACACCGGAGGGGAGGGGCGC--CGATCTCCAT
LOC_Os11g4   TGCGCCAAGAAAGACGAGCCGCGGCTCAACAGCGGAGTGGAGGGGCGC--CGATCTCCAT
LOC_Os06g0   TGTATTTTGTATGATGGATTGCAATGCGATACTTGTTTGGGGCGTGATTCGATTGAAAT
LOC_Os06g3   CTCCCCGCCTCCGCCGCATTCCGGTTGGAGTTTTGTCCGTGTTCGTCGG-CGGTTTCT-T 4141       4151       4161       4171       4181       4191
LOC_Os02g4   CGCCAAGGAGAGCAGAGCAGGGGAGGGGA------TCCTGGT-GAGCCTCCTCTTCCTGAT
LOC_Os11g4   CGCCGAGGAGAGCAGAGCAGGGGAGGGGAGGGGATCCTGGT-GAGCCTCCTCTTCCTGAT
LOC_Os06g0   AAATGAA-ATATTAGAGTTATTTTGGGAT------TCCTGTTTGCTGCGCCTTTTTTTTA
LOC_Os06g3   GGCTGGCCGGAT--GAATTGTTGTGGGGAGGGG-GAGGGGGAGGGGCTC-TCTCACGCAC 4201       4211       4221       4231       4241       4251
LOC_Os02g4   TCATCTCTCTCCCATT--CTAGCTTCGGGGGACT--ACTTTTGCCTGGAATTTGCTCGCG
LOC_Os11g4   TCACCTCTCTCTCCCATT--CTAGCTTCGGGGGACT--ACTTTTGCCTCGAATTTGCT----
LOC_Os06g0   GCATTTCT-TGATATGAACAAGAGAAGAAAGGGCTGAATTTTTTTCTTAGCTTTGGAGGCA
LOC_Os06g3   TCGCTGCT-GGATTTCGGTTAGGTTTCGCGGCTGGGGGAATCGCGGGGGAATTCAGGATC 4261       4271       4281       4291       4301       4311
LOC_Os02g4   TTCGTTCGTGCGTTCGTTCGT--TAACCCTAGCTTCTTCTCTTCTAGATCTGGAGGAAGC
LOC_Os11g4   --------TGCGTTCGTTCGT--TAACCCTAGCTTCTTCTCTTCTAGATCTGGAGGAAGC
LOC_Os06g0   TTTACTGTCCCAGTATTTTCTCCTACCGGAAGCAGAATATTTTGTTTGATTGGAGGGTTG
LOC_Os06g3   TT---TGTTTTGTTAGTTCTTCTTTCGGGCGGGGTTGGATCTCGAGTAATCTGCGTCGTG 4321       4331       4341       4351       4361       4371
LOC_Os02g4   TCTTCCTCCTCCCTTAATT-------------TCAGAGCCTT---AATACAAGTAGTAACAG
LOC_Os11g4   TCTTCCTCCTCCCTTAATT-------------TCAGAGCCTT---AATACAAGTAGTAACAG
LOC_Os06g0   CCTCCCTTTGCCAAATTGAATCAAATGTTCTCGGATGTTTTAAAATTTCCGTGGACTCTT
LOC_Os06g3   TTATTTGCCGCGAGATT-------------TGGGTGTTTT---TTTTCTTCTCCGCAT 4381       4391       4401       4411       4421       4431
LOC_Os02g4   TTTAACCTCCCCCC------ATGTCCCAAGTTGGATCCGCCCCTGCGAGTTCCGATATTGG
LOC_Os11g4   TTTAACCCCCCCCCCCCCCCCATGTCCCAAGTTGGATCCGCCCCTGCGAGTTCCGATATTGG
LOC_Os06g0   TTTGCCCCAGGGGAGACCGCTTTTAGCAGCTGGATCCCGTGTTTTCATTTCAAGTTCTTG
LOC_Os06g3   CTTCTCTCTCGTT------CCTTCGTCTGTACGGTCTAGTGGTGGTCTACGGGCTACGGC 4441       4451       4461       4471       4481       4491
LOC_Os02g4   GTCCTCCCAATTCTCAATGCCATTTTGTTCATCGGGGGGCATATGGTTCATTTTTGCCTG
LOC_Os11g4   GTCCTCCCAATTCTCAATGCCATTTTGTTCATCGGGGGGCATATGGTTCATTTT-GCCTG
LOC_Os06g0   TT--TTCCTAGTCTCCATATATTTCTGATTGTTAACTCGTATTCTCTACCTCAC-ATATG
LOC_Os06g3   CGTGGTAAAAGTTTCTCTAGATTTTTGGTC-TCGTTTTTTTCTTTATTTTAGGCGGCTTG 4501       4511       4521       4531       4541       4551
LOC_Os02g4   CATTGATTCAAATGTGGTTTCGAATCGTTTGTGAAAT-TC-GCGGGTGTACTTGTTTATG
LOC_Os11g4   CATTGATTCAAATGTGGTTTCGAATCGTTTGGGAAAT-TC-GCGGGTGTACTTGTTTATG
LOC_Os06g0   CAAAATCACACTTGCGTCGTTCTGTAATTAGTTAGAT-TCTGCAAGAAAAATCCGGAATT
LOC_Os06g3   CTTTGCTTCGCCTGCTTTGACGTTTGACCAGCGGTTTATCCTCGATTATTCTTCCTCGTG
```

Fig. 4D

```
                4561       4571       4581       4591       4601       4611
LOC_Os02g4      ATACATGAGGCCTTTTTTC-CCCCATGAGGAGGCAAACTTTTTAGTGGGTGGATCCACTA
LOC_Os11g4      ATATATGAGGCCTTTTTTTTCCCCATGAGGAGGCAAACTTTTTAGTGGGTGGATCCACTA
LOC_Os06g0      TTCAAGCATGCTAGTAGTTTTAAATTGATG--CCATGTTTTTTAGACAATGT------TA
LOC_Os06g3      AGTCGTGA-GCAAGCTATG---ATTTGCAG--CTAATGATTTTTGTGCTTGGATTAGATA 4621       4631       4641       4651       4661       4671
LOC_Os02g4      GTTCATGC--CTCA--ATT--TTTTTTCTCCTCTTTTAAGTTTTCCAAAGAGCTACATTG
LOC_Os11g4      GTTCATGC--CTCA--ATT--TTTTTCTCCTCTTTTAAGTTTTCCAAAGAGCTACATTG
LOC_Os06g0      ATTGATGC--CATATGACT--ATAGGACACATTATATTGCGTTTCTGAATA--TACCACC
LOC_Os06g3      AAAGATGCTTCTCACTCTTCGTTTGTTTCCATTTTCTGGAATTTGTGATTTCCTGG--TG 4681       4691       4701       4711       4721       4731
LOC_Os02g4      TTGTAAAGTGTCTGATACAATTGATTGTTTATTCAGGTTAGCGCTTTTGGCGTG--TGAT
LOC_Os11g4      TTGTAAAGTGTCTAATACAATTGATTGTTTATTCAGGTTAGCGCTTTTGGCGTG--TGAT
LOC_Os06g0      TCATGAAACTCATAATTTTGTTGATTAATTGTTCAGGTTGCCCCTTCTAGTGTG--TAAC
LOC_Os06g3      ATGATAATGTTGTGCTCGTGTTGATTCAG-GTTGGGATCCTCCCTATTCGCGCGCGTCTT 4741       4751       4761       4771       4781       4791
LOC_Os02g4      TGATTTCTAAACGAATTTTGGGCCGTGAGGGGAAGTTCAATCATGGCAGGGTCTCTTGCC
LOC_Os11g4      TGATTTCTAAACGAATTTTGGGCCGTGAAGGGAAGTTCAATCATGGCAGGGTCTCTTGCC
LOC_Os06g0      T------TGGAGCAAATTTGGACCCTGAGACGCAAATCAGTCATGGCTGGTTCTCTTGCG
LOC_Os06g3      TGATTTGGCGCGTAAAGTTG-----TAATCCGTACTCCGG--ATGGCCGGCTCAATCGCC 4801       4811       4821       4831       4841       4851
LOC_Os02g4      GCCTCAGCATTCTTCCCAGGTCCAGGCTCATCTCCTGCAGCATCAGCTAGAAGCTCCAAG
LOC_Os11g4      GCCTCAGCATTCTTCCCAGGTCCAGGCTCATCTCCTGCAGCATCAGCTAGAAGCTCCAAG
LOC_Os06g0      GCGTCTGCATTCTTCCCTGTCCCAGGGGTCTTCCCCTGCAGCTTCGGCTAGAAGCTCTAAG
LOC_Os06g3      GCCTCGGCGTTCTTGCCGG------GGTCGCCGGCGGCCGCGCCGCCCAAGAGCG-----

4861       4871       4881       4891       4901       4911
LOC_Os02g4      AATGCTGCTGTTACCGGCGAATTGCCGGAGAATTTGAGTGTCTGTGGCATTGTCGCAAAG
LOC_Os11g4      AATGCTGCTGTTACCGGCGAATTGCCGGAGAATTTGAGTGTCCGTGGCATTGTCGCAAAG
LOC_Os06g0      AACACA------ACCGGTGAATTGCCAGAGAATTTGAGTGTCCGCGGGAATCGTCGCGAAG
LOC_Os06g3      --TCCTG--------GGCGAGCGCCCGGACAGCCTGGACGTCCGCGGCATCGCCGCGAAG 4921       4931       4941       4951       4961       4971
LOC_Os02g4      CCTAACCCACCTCCTGCAGCC---------ATGCAAGTAAAGGCACAGGCTCAAACCC--
LOC_Os11g4      CCTAACCCACCTCCTGCAGCC---------ATGCAAGTAAAGGCACAGGCTCAAACCC--
LOC_Os06g0      CCTAATCCGTCTCCAGGGGCC---------ATGCAAGTCAAGGCGCAGGCGCAAGCCC--
LOC_Os06g3      CCGGGGCTCCTCGTCGTCGGCCGCCGCCCTGAGGGCCGGCAAGACGCGCACCCACGCCGCC 4981       4991       5001       5011       5021       5031
LOC_Os02g4      -TTCCCAAGGTTAATGGTACGAAGGTTAACCTCAAGACGGTCGAAGCCTGACATGGAGGAA
LOC_Os11g4      -TTCCAAGGTTAATGGTACGAAGGTTAACCTCAAGACGGTCGAAGCCTGACATGGAGGAA
LOC_Os06g0      -TTCCTAAGGTTAATGGAACCAAGGTTAACCTGAAGACTACAAGCCCAGACAAGGAGGAT
LOC_Os06g3      ATCCCCAAGGTGAACGGCGGCAGTTCGGCGCTGGCGGATCCGGAGCACGACACG-ATGTC 5041       5051       5061       5071       5081       5091
LOC_Os02g4      ACGGTGC----CTCACAGTGCTCCAAAGACGTTCTATAACCAACTGCCGGATTGGAGCAT
LOC_Os11g4      ACGGTGC----CTTACAGTGCTCCAAAGACGTTCTATAACCAACTGCCGGATTGGAGCAT
LOC_Os06g0      ATAATAC----CGTACACTGCTCCGAAGACATTCTATAACCAATTGCCAGACTGGAGCAT
LOC_Os06g3      CTCCTCCTCCTCCTCCGCGGCCGCCGAGGACGTTCTACAACCAGCTCCCCGACTGGAGCAT 5101       5111       5121       5131       5141       5151
LOC_Os02g4      GCTTCTTGCGGCTATTACAACCATCTTCCTCGCCGCAGAGAAGCAGTGGACACTGCTTGA
LOC_Os11g4      GCTTCTTGCGGCTATTACAACCATCTTCCTTGCCGCAGAGAAGCAGTGGACACTGCTTGA
LOC_Os06g0      GCTTCTTGCAGCTGTCACGACCATTTTCCTGGCAGCTGAGAAGCAGTGGACTCTGCTTGA
LOC_Os06g3      GCTCCTCGCAGCCATCACGACCATCTTCTTGGCCGCGGAGAAGCAGTGGACGCTGCTGGA 5161       5171       5181       5191       5201       5211
LOC_Os02g4      TTGGAAGCCGAAGAAACCTGACATGCTTGTTGACACATTTGGCTTTGGTAGGATCATCCA
LOC_Os11g4      TTGGAAGCCAAAGAAACCTGACATGCTTGTTGACACATTTGGCTTTGGTAGGATTATCCA
LOC_Os06g0      CTGGAAGCCGAAGAAGCCTGACATGCTGGCTGACACATTCGGCTTTGGTAGGATCATCCA
LOC_Os06g3      CTGGAAGCCGAAGCGGCCCGACATGCTCACCGACACGTTCGGTTTCGGCAGGATGATACA
```

Fig. 4E

```
                 5221       5231       5241       5251       5261       5271
LOC_Os02g4  GGACGGTATGGTGTTTAGGCAGAACTTCATGATTCGGTCCTACGAGATTGGCGCTGATCG
LOC_Os11g4  GGACGGTATGGTGTTTAGGCAGAACTTCATGATTCGGTCCTACGAGATTGGTGCTGATCG
LOC_Os06g0  AGACGGGCTGGTGTTTAGGCAAAACTTCTTGATTCGGTCCTACGAGATTGGTGCTGATCG
LOC_Os06g3  TGAGGGGCTCATGTTCAGGCAGAACTTCTCGATTAGGTCCTATGAGATCGGGGCCGATAG 5281       5291       5301       5311       5321       5331
LOC_Os02g4  TACAGCTTCTATAGAGACATTGATGAATCATTTTACAGGTAAGTGGTTGCAC--ATTCTGT
LOC_Os11g4  TACAGCTTCTATAGAGACATTGATGAATCATTTTACAGGTAAGTGGTTGCAC--ATTCTGT
LOC_Os06g0  TACAGCTTCTATTGAGACATTAATGAATCATTTTACAGGTGATACAATGGAGCTATGCTGC
LOC_Os06g3  GACGGCGTCTATAGAAACGCTGATGAACCATTTGCAGGTGAAATATTGTGAATTTTCAGG 5341       5351       5361       5371       5381       5391
LOC_Os02g4  TTTTAGTTTCATTTCTCATTTCAGCATTTTGTTATAGATTCGTATGTCTCTTTCAAGCTG
LOC_Os11g4  TTTTAGTTTTATTTCTCATTTCAGCATTTTGTTATAGATTCATATGTCTCTTTCAAGCTG
LOC_Os06g0  TTTAGCTTTTCTTCCGTATTTTTCACTATTGGTAC--AT---TATGTTCGTGGCATACTA
LOC_Os06g3  CGTCGGATTGCTCGGGC-----TGGGCATCAGAAC--ATTGAAATGTTTTTGGT------

5401       5411       5421       5431       5441       5451
LOC_Os02g4  GCAATTATTTAAAATTTTGCAGGAAACGGCTCTTAACCATGTAAGGACTGCTGGTCTTCT
LOC_Os11g4  GCAATTATTTAAAATTTTTGCAGGAAACAGCTCTTAACCATGTGAGGACTGCTGGTCTTCT
LOC_Os06g0  ACTGTAATTTGAAGCTTTGCAGGAAACAGCTCTGAACCATGTGAAAACTGCTGGTCTCTT
LOC_Os06g3  ----T---TTGA-----TGCAGGAAACCGCACTGAATCATGTGAAGAGCGCTGGGCTGCT 5461       5471       5481       5491       5501       5511
LOC_Os02g4  TGGAGATGGTTTTGGGGCTACACCGGAGATGAGCAAACGGAACTTGATATGGGTTGTCAG
LOC_Os11g4  TGGAGATGGTTTTGGGGCTACACCGGAGATGAGCAAACGGAACTTGATATGGTTGTCAG
LOC_Os06g0  AGGTGATGGTTTTGGTGCTACGCCGGAGATGAGCAAACGGAACTTAATATGGGTTGTCAG
LOC_Os06g3  AGGAGATGGTTTTGGCTCAACGCCAGAGATGAGTAAACGAGACTTGTTCTGGGTTGTCAG 5521       5531       5541       5551       5561       5571
LOC_Os02g4  CAAAATCCAGCTTCTTGTTGAGCAATACCCCGCATGGTACTTTTT-TGCAAACCTTTGCT
LOC_Os11g4  CAAAATCCAGCTTCTTGTTGAGCAATACCCCGCATGGTAGTTCTT-TGCAAACCTTTGCT
LOC_Os06g0  CAAAATTCAGCTTCTTGTTGAGCGATACCCATCATGGTACTTTTTCTGCAATCCA----CT
LOC_Os06g3  CCAAATGCAGGCAATCGTTGAGCGTTATCCGTGCTGGTA-----TAATACTATAAT---TT 5581       5591       5601       5611       5621       5631
LOC_Os02g4  CCTCTTGATATATGTATCTTTGGTTTCTTTCTATCAAT--TCCTTACTCTAAGTTGTCAT
LOC_Os11g4  CCTCTTAATATATGTATCTTTGGTTGCTTTCTATCAAT--TCCTTACCGTAAGTTTTCAT
LOC_Os06g0  ACTCTCCACATCATTTTCTTGGATGGCAAAACTTCTCT--TTTTACTCTTAATTCATAAC
LOC_Os06g3  -CACATATCAGCATGTTCTTGGTTTTGTTTTCTTACATAGTTTGAGCTCCAAATAGGGTG 5641       5651       5661       5671       5681       5691
LOC_Os02g4  TTAATTTTCACATTTTAAATTACTTCATATTTGTTTTGCTTCTTTTTACAGATATCGTTTT
LOC_Os11g4  TT--TTGTCACATTTTAAATTACTTCATATTTGTTTTGCTTCTTTTTACAGATATCGTTTT
LOC_Os06g0  AT--TTCTTTCATTCTTAATGGAGTACTTTTGTCCCCGGTGCATTTAGTGTCACAATTTA
LOC_Os06g3  TTGCTTTTCTGCTTTCGTGTTACATGACAATT---AGGAGGCACATAGATGTATGGTTGG 5701       5711       5721       5731       5741       5751
LOC_Os02g4  ATGTACTACTTTACAGCTGTGTGTCCCTTTGCATATTTGTTTTTATTTGTTAAAGAAGAT
LOC_Os11g4  ATGTACTACTTTATAGCTGTGTGTCCTTGGCATATTTGTTTCTATTTGTTTAAAGAAGAT
LOC_Os06g0  ATG------TTTACA--TG---GTACGGGAAAGATTTATCACTCAATATCCACGGTGTAA
LOC_Os06g3  CTGTC--ACAGTACG--TTACTGTAGTTATAGTAGCTATCA-TCTTGCTTCACAGCAG--

5761       5771       5781       5791       5801       5811
LOC_Os02g4  TCTTACACAAGCAACAGTAGTATTTAGCTCAATATTTACTTTAACATGGTTTATCATATT
LOC_Os11g4  TCTTACTCAGGCAACAGTAGTATTTAGCTCAATATTTACTTTAACATGTTTATCATAAT
LOC_Os06g0  TGTTTT-----------TAGC---TAAACTCAATATCCACGGTGTAATGTTTTTAGCTAAA
LOC_Os06g3  TCATGG-------AATAACAGG-TTTAGGTAAATGGA---GTTTTCAAGTTGTTGGCAAT 5821       5831       5841       5851       5861       5871
LOC_Os02g4  GTTGTGTGGATCTCTGGTCTGATTTCTCCATACACTGGTTGGTTGATGAAAATCAAGTGA
LOC_Os11g4  GTTGTGTGGATCTCTGGTCTGATTTCTCCATATACTGGTTGGTTGATGAAAATCAAGTGA
LOC_Os06g0  CTTGTCTTCAGTCCTTTTTTCCTTTTTCCCTATGTTTGTGTGCTG-TGGCATTCGA-TGG
LOC_Os06g3  GAA-TATGAAAAA-------GATTTTCCCAAGT----GTTTGT--ATCAATTTTAAATGG
```

Fig. 4F

```
              5881      5891      5901      5911      5921      5931
LOC_Os02g4    ATCTTTTACTTGCTCGTAAATTTCGCTGCTGCAGGTTTGCAAGAATATGGGTTGAAGTTT
LOC_Os11g4    ATCTTTTACTTGGTCGTATATTTCGCTGCTGCTGGTTTGCAAGAATATGGGTTGAAATTT
LOC_Os06g0    ATC----------------AT--CG------------------AGACTCTGAGTAGACGTA-
LOC_Os06g3    ATG----------------AGCAACT-------------C-CCATCTCTTAACTGT- 5941      5951      5961      5971      5981      5991
LOC_Os02g4    TTATACTGCTATAGAAGGCCATGTTTTCTTTGATTTCCCGTGATAGG-CCTCATGTTTT
LOC_Os11g4    TT--ACTGCTATAGAAGGCCATGTTTTCTTTGATTTCCCGTGATAGG-CCTCATGTTTA
LOC_Os06g0    -G----------AT---------TCTTGCATTCCTTATGCGACATGAG-GCACATGTT--
LOC_Os06g3    ---------------------TTTTGCTATCGGCATTAAATATTTGTGCAACTGGT--

6001      6011      6021      6031      6041      6051
LOC_Os02g4    GGAGGTTCTGTTATTCCTCCTTGGTTGACTAAGAAATGTGTAGTAATATCAGCTCCAGTT
LOC_Os11g4    GGAGGTGCTGTTATTCCTCCTCATTGGTTGACTAAGAAATGTGTAGTAATATCAGCTCCAGTT
LOC_Os06g0    CGAG----TGTTTATCACCCT------AC--ATGAAA--------ACCTTTCCCTACTAAG
LOC_Os06g3    AGACTTTCAGTAAACGATGAT--G---ATGCAGAAGCCT-------CCTGTGCTCTTAAT 6061      6071      6081      6091      6101      6111
LOC_Os02g4    TTGTTGGATCAAGGATAGATTTTGTGGCAAACTAAATTTTCCAATTAGGAAGAAATGAAT
LOC_Os11g4    TTGTTGGATCAAGGATAGAGTTTGTGGCAAACTAAATTTTCCAATTAGGAAGAAATGAAT
LOC_Os06g0    TTGCTGCTTCTA--------TTG---------------TTCTGCAGATAT-AAGCAAT--AT
LOC_Os06g3    ATTATTGATCATG--------TATC---------ATATTTCTGTGAG-ATGTTAT--AA 6121      6131      6141      6151      6161      6171
LOC_Os02g4    ATATTCCTACTTAAGTGGG-AGGAGCATGCACTTTGTTTCCAATTGTCGAGCCCTGATTA
LOC_Os11g4    ATATTCCTACTTAAGTGGGAGGAGCATGCACTTTGTTTCCAATTGTCGAGCCCTGATTA
LOC_Os06g0    TTTTGCCTATTT--TT---------CCTGTGCTTTGA--AC--TTCTCGTAG---GTTCA
LOC_Os06g3    TTGTTCGTGTTT--GTT---ACCTGAAAGTGCCATGTTGCCAATAATTAACTTCTTATCT 6181      6191      6201      6211      6221      6231
LOC_Os02g4    TAACACAAACTATCAAGTTATTTCTTTGCATTTAGAAACAGGATTTGCATCTTGGGTAAT
LOC_Os11g4    TAACACAAACTATCAAGTTATTTCTTTGCATTTAGAAACAGGATTTGCATCTTGAGTAAT
LOC_Os06g0    TGGCCCA------CAA--------CCT-----TTAG---CAGGGCATAGTGCCTTGA-----
LOC_Os06g3    GTGTGCAGGGGTGATA-------CTGTCGAAGTAGATACATGGGTTGGTGCTCATG----

6241      6251      6261      6271      6281      6291
LOC_Os02g4    CCTCATTAAAGACATAATCTAGCTTTAGTACATGCAACATAAAAGTTATGATGCCCCAAG
LOC_Os11g4    CCTCATTAAAGACATAATCTAGCTTTAGTACATGCAACATAAAAGTTCTGATGCCCCAAG
LOC_Os06g0    -------------AATGGAG---TATTACACTCAA--AA---------G-----------
LOC_Os06g3    ----------GTAAAAATGGAA------TGCGCAGAGACT---------------------

6301      6311      6321      6331      6341      6351
LCC_Os02g4    GCCTTTTTGGTACAGCACTGTAAGTCTGTAGCTCTCCTTGCTCTATGTTGTCCTCAAAAG
LOC_Os11g4    GCCTTTTTGGTACAGCACTGTAAGTCTGTAGCTATCCTTGCTCTATGTTGTCCTCAAAAG
LOC_Os06g0    ----------CATA--ACAATAACA-TGTA--TTGCCTTG---TATGAT------------
LOC_Os06g3    ---------GGCATAT--AC-GTGATTCTGTAACAGGCCATACAATATTGA-----------

6361      6371      6381      6391      6401      6411
LOC_Os02g4    ACACAACATCAGTTAAAA--------GAACAGTAATCTCTCCTTTAGACGTCAATTATTA
LOC_Os11g4    ACACAACATCAGTTAAAAACAAAGAAGAACAGTAATCTCTCCTTTAGACGTCAGTTATTA
LOC_Os06g0    ----AAGATGAGTGATAG----------------ATCT-----TTTGAAATCATTTACT-
LOC_Os06g3    AGGCTACAAG-GTTTGAAT------------TATTGTCACTCTCATAAAT-ACTGATGA 6421      6431      6441      6451      6461      6471
LOC_Os02g4    GTGGAGTAGTAATTTAGATCCAAGAGCAACTTCATTTGTTACGCCTTATTCATTGCCCAA
LOC_Os11g4    GTGGAGTAGTAATTTAGATCCAAGAGCAACTTCATTTGTTACGCCTTATTCATTGCCCAA
LOC_Os06g0    ---GAGGAAAACGTTTGTTT--------ATTTGACAAG--ACAATGTATTGATGAACTAG
LOC_Os06g3    T--CATGAAAACTGTATTAGCATCTGCTATTCAACTTCCTAC-CCATCTTATT--ACCAC 6481      6491      6501      6511      6521      6531
LOC_Os02g4    AGCTGCCTCATTAAATGATGTCTTCTCTGTGCTTCCTTGGATCTTGAATTATGCTGAGTG
LOC_Os11g4    AGCTGCCTCATTAAATGATGTCTTCTCTGTGCTTCCTTGGATCTTGAATTATGTTGAGTG
LOC_Os06g0    AACTGCTCTATTAAGTGGTATCTGCCCTGTCTCCTT---TCGTACAAATTGTTGC---
LOC_Os06g3    TGTTTGCATATGAAGTC-TAGAAGTTCTGTTTCTTCTG--AACATATATAAGCTGCCT-
```

Fig. 4G

```
             6541      6551       6561      6571      6581      6591
LOC_Os02g4   GGAATGCCAGAACGGGCATGTACTTACGTTTTCCAGCGATAAGCTCCGTTTTAAAAATAA
LOC_Os11g4   GGAATGCCAGAACGGGCATGTACTTTCGTTTTCCAGCGATAAGCTCCGTTTTAAAAATAA
LOC_Os06g0   ---ACCCCTGTTCATGTTACTTCTCACTTTTCACCATGGCAGGCAT-GTTTAGAAAATCA
LOC_Os06g3   ----TACAGCAACATGAAGCTACCTATTTGTCCTAATTGTTTGCTCAATGTGCA--GTAA 6601      6611      6621      6631      6641      6651
LOC_Os02g4   ATTAGCAAGTGATTTATTTGCATTTATAAACAAAAATTTACCACTCGGGTAGTTCATATT
LOC_Os11g4   ATTAGCAAGTGATTTATTTACATTTACAAACAAAAATTTACCACTCGGGTAGTTCACATT
LOC_Os06g0   TT--------TGATTT-T------------ACAGGGCATTACCA----------------
LOC_Os06g3   AT--------GGGTTATG---------ATGCACAAGCTTACAAGGAGGCTAGCA------

6661      6671      6681      6691      6701      6711
LOC_Os02g4   AAAGTTATTGTCTAGCTTTATTACAAGCAGCATGAAAGTTACGATACCCCAAGGCCTGAG
LOC_Os11g4   AAAATTATTGTCTAGCTTTATTACAAGCAACATGAAAATTTCGATACCCCAAGGCCTGAG
LOC_Os06g0   --------TGTGACCCCTTAATA--ACTAACA--AATAT------------------AT
LOC_Os06g3   ------A--GAATTCCTGATGAAGTACGTACTGAAATAGAGCCATAC-------------T 6721      6731      6741      6751      6761      6771
LOC_Os02g4   TTTGGCAGCACT-TAACTCTGTTGCCCTGTTTTGTCTTGAAAAGTATAACATCACTTAGC
LOC_Os11g4   TTTGGCAGCACTATAACTCTGTTGCCCTGTTTTGTCTTGAAAAGTATAATATCACTTAAC
LOC_Os06g0   TTTGGGTCCACC--AAATCTGTGG---TGGATGGAAAGGGAAATTA-ATAAACAC--AAA
LOC_Os06g3   TTTTTGAGCATGCTTCTATTGTAGA--TGAAGCAACCAGAAACTTCCAAAACTGCCAGA 6781      6791      6801      6811      6821      6831
LOC_Os02g4   AGGACAATGCTCTCCCGAAAACATAACTGATTAGTGGATAGAGGGAG-AGGTTTAG----
LOC_Os11g4   AGGACAATGCTCTCCCGAAAACATAACTGATTAGTGGATAGAGAGAG-TGGTTTAGGTGG
LOC_Os06g0   TGGAAAATTCTTCATTGTGAA----ACGTGATAAG---------GACAA-ATTTTGTG----
LOC_Os06g3   TATTGAAGGTGCTAATGTAGCCAAATATGTCCGGACAGGCCTGACTGTAAGTTTTG----

6841      6851      6861      6871      6881      6891
LOC_Os02g4   ------------------------------------------------------------
LOC_Os11g4   TGTTTGGATCCGGGGACTAAATTTTAGTTCATGTCACATCGGATGTTTGGACACTAATTA
LOC_Os06g0   ------------------------------------------------------------
LOC_Os06g3   ------------------------------------------------------------

6901      6911      6921      6931      6941      6951
LOC_Os02g4   ----------------------------TCCCAATAGATAATTGACTGGTTACT
LOC_Os11g4   GAAATATTAAACATAGACTAATAATAAAATTTAGTCCCAATAGATAATTGACTGGTTACT
LOC_Os06g0   -------------------------------AATAAATAA--------------
LOC_Os06g3   -------------------------------TGGAATTATACAAGATTACAGTT---

6961      6971      6981      6991      7001      7011
LOC_Os02g4   TCATATTCATTGCCCAGAGCTGCCTCATTAAATGTT--CTGTCCTGTGCTTTCTTGGATC
LOC_Os11g4   TCATATTCATTGCCCAGAGCTGCCTCATTAAATGTTGTCTGTTCTGTGCTTTCTTGGATC
LOC_Os06g0   ----AGTAA-------------C---AAAAAATGG---CTAGTATTTGCCTAC-------
LOC_Os06g3   TACAAGTAT----------------ACAAAATGT----GCATGTTTTTCTTTCAT-----

7021      7031      7041      7051      7061      7071
LOC_Os02g4   TTGAATTAAAAGACGTCTGTACAGGGTACCACACCTCAAGGGATCACAATTCAGAAAGTT
LOC_Os11g4   TTGAATTAAAAGACGTCTGTACAGGGTACCACACCTCAAGGGATCACAATTCAGAAAGTT
LOC_Os06g0   ----ATATAGAGT----------------ACACCTCAAGAGATCA--------GAAAAGT
LOC_Os06g3   -TTTTTACATCTTCTTCTGTCTCATAATGCAGCCACGATGGGCCGACCTTGATATCAATC 7081      7091      7101      7111      7121      7131
LOC_Os02g4   TCCCT-TTATTGGGCTGCAGTAAAT-GATTCCATCGTGTAGAAAAGAACAAAAGCAATTA
LOC_Os11g4   TCCCT-TTATTGGTCTGCAGTAAAT-GATTCCATCGTATAGAAAAGAACAAAAGCAATTA
LOC_Os06g0   TGCCT-TTATTG--ATGGAGTAATT-GAATTAGTAGT--------A-------AGCAATAA
LOC_Os06g3   AGCATGTTAATAACGTTAAATACATAGGGTGGATCCTAGAGGTAAAAAAAGTTCCCCT--

7141      7151      7161      7171      7181      7191
LOC_Os02g4   ATGCTGTGCCATATCATGGGAGAAGCTAAGGACCGATCTAGAACAGTGAACTTTTGTTG-
LOC_Os11g4   ATGCTGTGCCATATCATGGGAGAAGCTAAGGACCCATCTAGAACAGTGAACTTTTGTTG-
LOC_Os06g0   ATTCTGTGG-ACCT-AGGGGACATCC-------CTGATCTAGATC-----GAGTTTTGAT--
LOC_Os06g3   ATTATGTTCATCTTTATTGCCCTTGCTAA---CACCTCTTGCCTAGATGATTCTTGAGGG
```

Fig. 4H

```
              7201       7211       7221       7231       7241       7251
LOC_Os02g4    AACAGCATCTGTCAGTTTAAATTTCTAGGTGGTCATCATTCATCAAATAAGTGGTGCTAG
LOC_Os11g4    AACAGCATCTGTCAGTTTAAAAATCTAGGTGGTCATCATTCATCAAATAAGTGGTGCTAG
LOC_Os06g0    ---CTCATGCTACA-TTTAATCTTCCATGTCAGCAACTTTCA-----------GTAC---
LOC_Os06g3    AAAAAAATGCTTC--T-TGAAGTTCAGTATGTT--ACTTTCAGAAAAAAT---ATCCATT 7261       7271       7281       7291       7301       7311
LOC_Os02g4    TACTACTATT-CACACGTTATGTTTAAATCCTCTTGTCAACTGTGTCAACAAGTGGTTGA
LOC_Os11g4    TGCTACTATTGCACACGTTATGTTTAAATCCTCTTGTCAACTGTGTCAACAAGTGGTTGA
LOC_Os06g0    --CTGCTATT---------AAATT----TCCCCTGTTCTTCTG-----ACGATTGATGCA
LOC_Os06g3    TGTTTTTATT---------TACTGTAAACACTCCATGGAGTTGCTGTTAGGCATCTTTGT 7321       7331       7341       7351       7361       7371
LOC_Os02g4    AAACTTCTTTTTTGGGGTTTTGAGTTAGAAAAATGGAAGTGCAATTTCAAACTGTTTTTT
LOC_Os11g4    AAACTTCTTTTTGGGGGTTTTGAGTTATAAAAATGGAGGTGCAATTTCAAATTGTTTTTT
LOC_Os06g0    --A------TTT-TAAGTTTATGAGA-AGGAAAACGGTCTGCTGTTTTTGAATTCTGAATG
LOC_Os06g3    CGC-----GGTATTCATTATTAAGT-TGTCACATGGTGGAGCA-T----AACTTTGTGT- 7381       7391       7401       7411       7421       7431
LOC_Os02g4    TAGTTCAGATACAATTGCCGATGTCTTTCTGTGGATCAAAAAGAATGACAGATGTATTGT
LOC_Os11g4    TAGTTCAGATACAATTGCCGACGTCTTTCTGTGGATCAAAAA-AATGACAGATGTATTGT
LOC_Os06g0    TAGTTTACA--CAATT---------TCTCATAGGCTGAAAT----T--T-----TG--GT
LOC_Os06g3    TGCTTTACTTGCCTTT-----T---TCTCTTTGGGCATACA--------------TTTAGT 7441       7451       7461       7471       7481       7491
LOC_Os02g4    ACCAACCTGCTATGGTTTTAGGGGAGATATGGTTCAAGTTGACACATGGGTCGCTGCTGC
LOC_Os11g4    ACCAACCTGCTATGGTTTTAGGGGAGATACGGTTCAAGTTGACACATGGGTTGCTGCTGC
LOC_Os06g0    TGCAA------AT--TTTTAGGGGAGATATGGTCCAAGTTGACACATGGGTAGCTGCTGC
LOC_Os06g3    ACTA-----------TTGATGGTGCTACATAATTCAAAGAGATTCATTTATCTCGCTATA 7501       7511       7521       7531       7541       7551
LOC_Os02g4    TGGCAAAAATGGCATGCGTCGAGACTGGCATGTTCGTGACTACAACTCTGGCCGAACAAT
LOC_Os11g4    TGGCAAAAATGGCATGCGTCGAGACTGGCATGTTCGTGACTACAACTCTGGCCGAACAAT
LOC_Os06g0    TGGCAAAAATGGCATGCGTCGAGATTGGCATGTTCGGGACTACAACTCTGGTCAAACAAT
LOC_Os06g3    TTTCCCATATGTTATGTTCCAAGAA-------TTTGGGAATA-AACAGT--------AAT 7561       7571       7581       7591       7601       7611
LOC_Os02g4    CTTGAGAGCTACAAGGTTTGGGCTTCAACTGTATTCTATTGCAAGAATCATCTGTATCAT
LOC_Os11g4    CTTGAGAGCTACAAGGTTTGGGCTTCAACTTTATTCTATTGCAAGAATCATCTGTATCGT
LOC_Os06g0    CTTGAGGGCTACAAGGTTTGTGTTTA-----T---CGTTTGCA--------TTTGTTGCAT
LOC_Os06g3    CAGAAGAG-TACTGGATTTGTAGGTA--CTTTAT-TTTTTGTG-------TGTGTGT-GT 7621       7631       7641       7651       7661       7671
LOC_Os02g4    TTTTTTTGTGAGGACATCCAATCTTGGTATTTCTGCTTGGTCACATCATTGATAATCACT
LOC_Os11g4    TTTCTTTTATGAGGATATCCAATCTTGGTATTTCTGCTTGATCACATCATTGATAATTGCT
LOC_Os06g0    TTCTTTTGT------TTC--ATGCTG-TTTACCAGCATGTTTTATTCCTTTTCGATTGCT
LOC_Os06g3    GGGGGGGGGGGGGGGGCTCAGATCATG-CCTATGATTAGGCATTACTGTAGGAGTTTAGAT 7681       7691       7701       7711       7721       7731
LOC_Os02g4    AATTGTGCTCCTTTTCCAATCCATTTGTTGCAGTGTTTGGGTGATGATGCACAAGAAAAC
LOC_Os11g4    AATTGTGCTCCTTTTCCAATCC-TTTCTTGCAGTGTTTGGGTGATGATGCACAAGAAAAC
LOC_Os06g0    AATTGT--TCCTCT-------C-TTGTTTGCAGTGTTTGGGTGATGATGAATAAGAACAC
LOC_Os06g3    AAACTTGGTCAAGG---------TCCCAAAAGGGTGTGCCTATGGTTCTACAAGTGTCC 7741       7751       7761       7771       7781       7791
LOC_Os02g4    TAGAAGACTTTCAAAAATGCCAGATGAAGTTAGAGCTGAAATAGGCCCATATTTCAATGA
LOC_Os11g4    TAGAAGACTTTCAAAAATGCCAGATGAAGTTAGAGCTGAAATAGGCCCATATTTCAATGA
LOC_Os06g0    TAGAAGACTTTCAAAAATGCCAGATGAAGTTAGAGCTGAAATAGGCCCGTATTTCAATGG
LOC_Os06g3    -ACCTAACTTT--A---TCCTCAAGCACGCAACCACTTTATCTGGCAGCTTTGTACTCTTT 7801       7811       7821       7831       7841       7851
LOC_Os02g4    CCGTTCAGCTATAACAGAGG-AGCAGAGTGAAAAGTTAGCCTAGACAGGAAATAAAGTTG
LOC_Os11g4    CCGTTCAGCTATAACAGAGG-AGCAGAGTGAAAAGTTAGCCAAGACAGGAAATAAAGTTG
LOC_Os06g0    CCGTTCTGCTATATCAGAGG-AGCAGGGTGAAAAGTTGCCTAAGCCAGGGACCACATTTG
LOC_Os06g3    CA----AGCTATACGAAAAATATCTGTTGCACTAGTTGGAGAAGTAATG---TATCCTAG
```

Fig. 4I

```
              7861      7871      7881      7891      7901      7911
LOC_Os02g4    GTGATGATGCTACAGAGCAATTCATAAGAAAGGGGCTCAC--TGTAAGTCAGCTAGACAT
LOC_Os11g4    GTGATGATGCTACAGAGCAATTCATAAGAAAGGGGCTCAC--TGTAAGTCAGCTAGACAT
LOC_Os06g0    ATGGCGCTGCTACCAAACAATTCACAAGAAAAGGGCTTAC--TGTAAGTCAGTTA-ATAT
LOC_Os06g3    CAGATTTTACTACATTAGGTTGGTCACCTACGTACCTAACCCTGTACGCTTGTTG-CTTC 7921      7931      7941      7951      7961      7971
LOC_Os02g4    GGTTACATACTGAATTATCATTATGCCTCAACTGCTATCATTTATCTAAGAAAAACAGTA
LOC_Os11g4    AGTTACATACTAAATTATCATTATGCCTCAACTGCAATCATTTATCTAAGAAAAATAGTA
LOC_Os06g0    TGCTTGTTACCG-----TCATT-------------CATTTTGCTGG-------------
LOC_Os06g3    CGATAAAGAGCTTGGCTGGAATA----CTTATATG----CAATTTGATCACAAG-------

7981      7991      8001      8011      8021      8031
LOC_Os02g4    ATAATTGATCTCACCCCTCATTTATTTTAAATGATATTTGATGGACTCTTGTTTACTGCA
LOC_Os11g4    ATATTTGATCTCACCCCTCATTTATTTTAAATGATCTTTGATGGACTCTTGTTTACTGCA
LOC_Os06g0    ----TGGTTCTCATGCATAAAATTTCTCA---------TGAGGGATCCTTTGTTCATGT-
LOC_Os06g3    ----TCATTCACTTAATTCAATTTTTTTAGAG-----TGATCAACACCTGCATATAAT- 8041      8051      8061      8071      8081      8091
LOC_Os02g4    ACAGCCTAGATGGGGTGACCTCGATGTCAATCAGCA-TGTGAACAATGTTAAATATATTG
LOC_Os11g4    ACAGCCTAGATGGGGTGACCTCGATGTCAATCAGCA-TGTGAACAATGTTAAATATATTG
LOC_Os06g0    -CAGCCGAAGTGGAGTGACCTTGATGTCAACCAGCA-TGTGAACAATGTGAAGTATATTG
LOC_Os06g3    ---GCATATTTG------CCTGGTTGACAATCTGCCGTGTGTA---TGTG---TGTTTTG 8101      8111      8121      8131      8141      8151
LOC_Os02g4    GGTGGATCCTTGAGGTGGTTATTCTTGTCCCTTATATTCATTGTTTAGAGAA--AAATAA
LOC_Os11g4    GGTGGATCCTTGAGGTGGTTATTCTTGTCCCTTTTATTCATTGTTTAGAGAA--AAATAA
LOC_Os06g0    GTTGGATACTTGAGGTAAC--TTCTTTTTCCTT-------TTCTCTATCCGA--ACATGC
LOC_Os06g3    GAAGAAGGGGAGGGGTAGT----CATGTATGTAT------TTATCCAGTGGACCACATAA 8161      8171      8181      8191      8201      8211
LOC_Os02g4    TTTGGCTTTATCCTTTTATATGGTACTTCCTTTGTTTCACAATGTAAGTCATTTTAGCAT
LOC_Os11g4    TTTGGCTTTATCCTTTTATATGGTG-----------------------------------
LOC_Os06g0    TATCTCTAGATCAGAAAAGAGAGTG-----------------------------------
LOC_Os06g3    TGAGGAAAAAGAAATTGTTCAGGTG-----------------------------------

8221      8231      8241      8251      8261      8271
LOC_Os02g4    TTCCCATATTTATATTTATGCTAATGAATCTAAATAGATATATGTCTAGATTCATTGG
LOC_Os11g4    ------------------------------------------------------------
LOC_Os06g0    ------------------------------------------------------------
LOC_Os06g3    ------------------------------------------ACCTG---------

8281      8291      8301      8311      8321      8331
LOC_Os02g4    CATCAATATGAATGTGAGAAATGCTAAAATGACTTACATTATGAAACGGAGGGAGTAGTT
LOC_Os11g4    ----------------------------------------------G------TT
LOC_Os06g0    ------------------------------------------------------------
LOC_Os06g3    ---CAACCT---------AGA----------------------------------TG 8341      8351      8361      8371      8381      8391
LOC_Os02g4    GTTAGGGAACCATTTTATGTAGTACTTGCAATTATTTTCTAGAGATTCTGATCTGACCAT
LOC_Os11g4    GTTAGGGAACCATTTTATGTAGTACTTGCAATTATTTTCTAGAGATTCTGATCTGACCAT
LOC_Os06g0    -------TCTGATCGTAATTAGTA-----ACCTAGTTCCTAG------TCATATGCCAAG
LOC_Os06g3    GGCCCAAAACAACCCAAAATATTAGG-GAAATTAACACTTCAGG-----CATTTCCTAAC 8401      8411      8421      8431      8441      8451
LOC_Os02g4    CTGTATTGTTGATATTGTCATTAGTCTTACATCTGGTCAGTCAGAAGGCTTTCAAACATG
LOC_Os11g4    CTGTATTGTTGATATTGTCATTAGTCTTACATCTGGTCAGTCAGAAGGCTTTCAAACATG
LOC_Os06g0    CTGTA------------AAA-ACACTTGCA-CTGTATATTCAAAAGCTATTCAAA-----
LOC_Os06g3    ATACA------------GAAATATTTATTAC--CAACATGCGCACATGTTGCTTAAC----

8461      8471      8481      8491      8501      8511
LOC_Os02g4    TTTCTGAGTTCTTTCTAATTTTTTCCCC-CAGAGTGCTCCAATTTCAGTACTGGAGAAGC
LOC_Os11g4    TTTTTGAGTTCTTTCTAATTTTTTCCCC-CAGAGTGCTCCAATTTCAGTACTGGAGAAGC
LOC_Os06g0    TTTCTGAGTACGTTTTGTTTTTTTTCCTCAGAGTGCTCCAATTTCGATACTGGAGAAGC
LOC_Os06g3    ---CCTACCTTTTTGTCCTTTTTTCCCCTCAGAGCGCACCAATCTCCATTCTGGAGAAAC
```

Fig. 4J

```
            8521      8531      8541      8551      8561      8571
LOC_Os02g4  ATGAGCTTGCAAGCATGACCCTGGATTACAGGAAGGAGTGTGGCCGAGACAGCGTGCTGC
LOC_Os11g4  ATGAGCTTGCAAGCATGACCCTGGATTACAGGAAGGAGTGTGGTCGAGACAGCGTGCTGC
LOC_Os06g0  ACGAGCTTGCAAGCATGACCTTGGATTACAGGAAGGAGTGTGGCCGTGACAGTGTGCTTC
LOC_Os06g3  ATGAGCTGGCAAGTATTGTCCTGGATTACAAGGGGAGTGTGGCCGAGACAGCGTGCTGC 8581      8591      8601      8611      8621      8631
LOC_Os02g4  AATCACTTACCACCGTGTCAGGGGAATGCACCAGCATTGGCGCCGACAAGCAGGCTTCTG
LOC_Os11g4  AATCACTTACCACCGTGTCAGGGGAATGCACCAGCATTGGCGCCGACAAGCAGGCTTCTG
LOC_Os06g0  AGTCGCTTACCGCTGTTTCAGGTGAATGCGA------TGATGGCAACA--CAGAATCCT-
LOC_Os06g3  AATCACACACTACCGTGTACACTGACTGCAACA----AGCACTCTGGA--CAAACCACT- 8641      8651      8661      8671      8681      8691
LOC_Os02g4  CCATCCAGTGCGACCATCTTGTGAAG-----------GCTGACATTGTGAAGGCACACA
LOC_Os11g4  CCATCCAGTGCGACCATCTTCTTCAGCTTGAGTCAGGAGCTGATATTGTGAAGGCACACA
LOC_Os06g0  CCATCCAGTGTGACCATCTGCTTCAGCTGGAGTCCGGAGCAGACATTGTGAAGGCTCACA
LOC_Os06g3  --TTGCACTGTGAGCATTTGCTGAGCCTGGAATCAGGACCTACCATCGTCAAGGCCAGGA 8701      8711      8721      8731      8741      8751
LOC_Os02g4  CAGAGTGGCGACCAAAGCGATCGCATGCAGCAGCTGAGAACGCG-----TAAACAAACAA
LOC_Os11g4  CAGAGTGGCGACCAAAGCGATCGCACGCAGCAGCTGAGAACGCG-----TAAACAAACAA
LOC_Os06g0  CAGAGTGGCGACCGAAGCGAGCTCAGGGCG-AGGGGAACATGGGCT--TTTTCCCAGCTG
LOC_Os06g3  CCATGTGGAGGCCAAAAGGAAC-CAGGGCCCAAGAGAGTATCATTCCGTCTTCGTCGTGA 8761      8771      8781      8791      8801      8811
LOC_Os02g4  ACCGACGAAAATCTGTGGTAGGGAGAATATCAAACTTCCCTTGCCTCTGTTGCCCTGAAG
LOC_Os11g4  ACCGACGAAAATCTGTGGGAGGGAGAATATCAAACTTCCCTTGCCTCTGTTGCCCTGAAG
LOC_Os06g0  AGAGTGCATGAGCGCT--TCTGTAGTTTATCCGGCAAG--TAACCTCT-TTGA---GAAG
LOC_Os06g3  AGCGCGTAAAATCTTTCATGTGTTGATTTT----GGTAGCAACAACTTGGTTAAAC-CAAG 8821      8831      8841      8851      8861      8871
LOC_Os02g4  CTGATCTTGA-AGTGTGAGTTGTATTCTGTAAAAAATTAGTAGTTTCCATAGTGTGAGGT
LOC_Os11g4  CTTATCTTGA-AGTGTGAGTTGTATTCTGTAAAAAATTAGTAGTTTCCATAGTGTGAGGT
LOC_Os06g0  TGCAGATTCT-AACTTGGCTAGCAACACAGGACAAATGATTGTTGGTGGGAAATTTGGCA
LOC_Os06g3  GACAAGTGGACAACAACTTGTGTTCTCTATGGAAAGGCAAAACCTGGATGAACATAACGA 8881      8891      8901      8911      8921      8931
LOC_Os02g4  TGGAGGGGAGGTGTTGGTGCTTGCCTACTGTACCTGCT-ACATCT-ATTATTTCTTGATT
LOC_Os11g4  TGGAGGGGAGGTGTTGGTGCTTGCCTACTGTACCTGCT-ACATCT-ATTATTTCTTGATT
LOC_Os06g0  TGCCGAGCCTGGGTTTTGTGATGCACACAGCACACATTCAGATTTGAAGATTGAGAGATG
LOC_Os06g3  CGGGGACGTAAGTTATTTACAGACAAAATGTATGGATT------TGGAGGAGTTCAAAAGA 8941      8951      8961      8971      8981      8991
LOC_Os02g4  CTTTGTTCGCTTTTTTTTTTCTTTTTTGTTTTTAACCCCTGTGGAGATAAGA-CAGGT--
LOC_Os11g4  CTTTGTTCGCTTTTTTTTTTCTTTTTTGTTTTTAACCCCTGTGGAGATAAGA-CAGGT--
LOC_Os06g0  CTTCTTATTGGCAGCTTGTTCAGAAAGATGACTAAGCGGTTTGG-GATAAAATCAGCTGA
LOC_Os06g3  GG--GGGGGGGGGGGGGGGCAAGATGGAGGTAAAA------TGCAGAAAAGA-CAGAAGG 9001      9011      9021      9031      9041      9051
LOC_Os02g4  TTTGAAGTGTGGAAGAGGTTGTTTCAATCGTCTAATTGATTCAACTATTCAGCAAGTAAA
LOC_Os11g4  TTTGAAGTGTGGAAGAGGTTGTTTCAATCGTCTAATTGATTCAACTATTCAGCAAGTAAA
LOC_Os06g0  TTGGGAAACATTAGCAGGATGATAAGCATGACTGGTGGTACCAATGAAAAGGGTTGAAAT
LOC_Os06g3  CGTATTGTGCATGATTTGTTGTTTCAGCTTTTCCTTCTATTTTTCCTTTCCTTAGCAAAG 9061      9071      9081      9091      9101      9111
LOC_Os02g4  CTGCTCCATGGAA-ATTT------------------------------------------
LOC_Os11g4  CTGCTCCATGGAA-TTTCATCGTTTGGTTGGAGCCTGAG---------------------
LOC_Os06g0  CCTTTGCATTGTTCATTTGTTGTGGAGCAAGAGTGGCCGCAGTTGCTTATCACACAGGAT
LOC_Os06g3  ATATTCAATTACACAGATGG-GTGTTGTAAGTATTGAAATTGTAGCTACTGCTGTACAAT 9121      9131      9141      9151      9161      9171
LOC_Os02g4  ------------------------------------------------------------
LOC_Os11g4  ------------------------------------------------------------
LOC_Os06g0  GATG-GAGGTGTTTGTGTGAAGCTTATTGCTGAAGCTGGATTGTTTTTGACCTGTGTTTC
LOC_Os06g3  GGGAAGTGAAATGCTTCTCATGCATGTTTCTGTCTGGGCTATGTCTATATTATGAGCCCT
```

Fig. 4K

```
           9181      9191      9201      9211      9221      9231
LOC_Os02g4  ------------------------------------------------------------
LOC_Os11g4  ------------------------------------------------------------
LOC_Os06g0  TAAAAGAAAAGGGAAAAGAAGAAGCTGTGGATTGAGGCCGGAGCAGCAGAGATATTACAA
LOC_Os06g3  CGAAAGCAGATTGCCTGGTCCGAATTGTTTGAAATTTTAAGTTT----------------

9241      9251      9261      9271      9281      9291
LOC_Os02g4  ------------------------------------------------------------
LOC_Os11g4  ------------------------------------------------------------
LOC_Os06g0  TCGACATAGATAAATAAGATGTAATACTAATTTAGCCCAGGTGGTTTGTGTGGAGATG
LOC_Os06g3  ------------------------------------------------------------

9301      9311      9321      9331      9341      9351
LOC_Os02g4  ------------------------------------------------------------
LOC_Os11g4  ------------------------------------------------------------
LOC_Os06g0  CAATCCATTGTAGTAACAGCCTAACTTGTACATTCTTGCCATCTTTTTCTTATTAATTGA
LOC_Os06g3  ------------------------------------------------------------

9361      9371      9381      9391      9401      9411
LOC_Os02g4  ------------------------------------------------------------
LOC_Os11g4  ------------------------------------------------------------
LOC_Os06g0  ATGAATGAATCGCAGACCTCCTGCGTTTTCATCAATAATTGAAATGACTTCTGCTTCATC
LOC_Os06g3  ------------------------------------------------------------

9421      9431      9441
LOC_Os02g4  ----------------------------
LOC_Os11g4  ----------------------------
LOC_Os06g0  AAGAATTGAATGAATTGTCTGTCTG
LOC_Os06g3  ----------------------------
```

Fig. 4L

```
   1 ..ATGGCTGGTTCTCTTGCGGCGTCTGCATTCTTCCCTGTCCCAGGGTCT  48
     ||||||||||||||||||||||||||||||||||||||||||||||||
1151 TCATGGCTGGTTCTCTTGCGGCGTCTGCATTCTTCCCTGTCCCAGGGTCT 1200

49 TCCCCTGCAGCTTCGGCTAGAAGCTCTAAGAACACAACCGGTGAATTGCC  98
     ||||||||||||||||||||||||||||||||||||||||||||||||||
1201 TCCCCTGCAGCTTCGGCTAGAAGCTCTAAGAACACAACCGGTGAATTGCC 1250

99 AGAGAATTTGAGTGTCCGCGGAATCGTCGCGAAGCCTAATCCGTCTCCAG 148
     ||||||||||||||||||||||||||||||||||||||||||||||||||
1251 AGAGAATTTGAGTGTCCGCGGAATCGTCGCGAAGCCTAATCCGTCTCCAG 1300

149 GGGCCATGCAAGTCAAGGCGCAGGCGCAAGCCCTTCCTAAGGTTAATGGA 198
     ||||||||||||||||||||||||||||||||||||||||||||||||||
1301 GGGCCATGCAAGTCAAGGCGCAGGCGCAAGCCCTTCCTAAGGTTAATGGA 1350

199 ACCAAGGTTAACCTGAAGACTACAAGCCCAGACAAGGAGGATATAATACC 248
     ||||||||||||||||||||||||||||||||||||||||||||||||||
1351 ACCAAGGTTAACCTGAAGACTACAAGCCCAGACAAGGAGGATATAATACC 1400

249 GTACACTGCTCCGAAGACATTCTATAACCAATTGCCAGACTGGAGCATGC 298
     ||||||||||||||||||||||||||||||||||||||||||||||||||
1401 GTACACTGCTCCGAAGACATTCTATAACCAATTGCCAGACTGGAGCATGC 1450

299 TTCTTGCAGCTGTCACGACCATTTTCCTGGCAGCTGAGAAGCAGTGGACT 348
     ||||||||||||||||||||||||||||||||||||||||||||||||||
1451 TTCTTGCAGCTGTCACGACCATTTTCCTGGCAGCTGAGAAGCAGTGGACT 1500

349 CTGCTTGACTGGAAGCCGAAGAAGCCTGACATGCTGGCTGACACATTCGG 398
     ||||||||||||||||||||||||||||||||||||||||||||||||||
1501 CTGCTTGACTGGAAGCCGAAGAAGCCTGACATGCTGGCTGACACATTCGG 1550

399 CTTTGGTAGGATCATCCAAGACGGGCTGGTGTTTAGGCAAAACTTCTTGA 448
     ||||||||||||||||||||||||||||||||||||||||||||||||||
1551 CTTTGGTAGGATCATCCAAGACGGGCTGGTGTTTAGGCAAAACTTCTTGA 1600

449 TTCGGTCCTACGAGATTGGTGCTGATCGTACAGCTTCTATTGAGACATTA 498
     ||||||||||||||||||||||||||||||||||||||||||||||||||
1601 TTCGGTCCTACGAGATTGGTGCTGATCGTACAGCTTCTATTGAGACATTA 1650

499 ATGAATCATTTA...................................... 510
     ||||||||||||
1651 ATGAATCATTTACAGGTGATACAATGGAGCTATGCTGCTTTAGCTTTTCT 1700
```

Fig. 5A

```
 511 ...........CAGGAAACAGCTCTGAACCATGTGAAAACTGCTGGTCT 548
             ||||||||||||||||||||||||||||||||||||||
1751 TTTGAAGCTTTGCAGGAAACAGCTCTGAACCATGTGAAAACTGCTGGTCT 1800

549 CTTAGGTGATGGTTTTGGTGCTACGCCGGAGATGAGCAAACGGAACTTAA 598
     ||||||||||||||||||||||||||||||||||||||||||||||||||
1801 CTTAGGTGATGGTTTTGGTGCTACGCCGGAGATGAGCAAACGGAACTTAA 1850

599 TATGGGTTGTCAGCAAAATTCAGCTTCTTGTTGAGCGATACCCATCAT.. 646
     |||||||||||||||||||||||||||||||||||||||||||||||
1851 TATGGGTTGTCAGCAAAATTCAGCTTCTTGTTGAGCGATACCCATCATGG 1900

647 ................................GGGGAGATATGGT 659
                                     |||||||||||||
3101 ATTTCTCATAGGCTGAAATTTTGGTTGCAAATTTTTAGGGGAGATATGGT 3150

660 CCAAGTTGACACATGGGTAGCTGCTGCTGGCAAAAATGGCATGCGTCGAG 709
     ||||||||||||||||||||||||||||||||||||||||||||||||||
3151 CCAAGTTGACACATGGGTAGCTGCTGCTGGCAAAAATGGCATGCGTCGAG 3200

710 ATTGGCATGTTCGGGACTACAACTCTGGTCAAACAATCTTGAGGGCTACA 759
     ||||||||||||||||||||||||||||||||||||||||||||||||||
3201 ATTGGCATGTTCGGGACTACAACTCTGGTCAAACAATCTTGAGGGCTACA 3250

760 ....AGTGTTTGGGTGATGATGAATAAGAACACTAGAAGACTTTCAAAAA 805
         ||||||||||||||||||||||||||||||||||||||||||||||
3351 TTGCAGTGTTTGGGTGATGATGAATAAGAACACTAGAAGACTTTCAAAAA 3400

806 TGCCAGATGAAGTTAGAGCTGAAATAGGCCCGTATTTCAATGGCCGTTCT 855
     ||||||||||||||||||||||||||||||||||||||||||||||||||
3401 TGCCAGATGAAGTTAGAGCTGAAATAGGCCCGTATTTCAATGGCCGTTCT 3450

856 GCTATATCAGAGGAGCAGGGTGAAAAGTTGCCTAAGCCAGGGACCACATT 905
     ||||||||||||||||||||||||||||||||||||||||||||||||||
3451 GCTATATCAGAGGAGCAGGGTGAAAAGTTGCCTAAGCCAGGGACCACATT 3500

906 TGATGGCGCTGCTACCAAACAATTCACAAGAAAAGGGCTTACT....... 948
     |||||||||||||||||||||||||||||||||||||||||||
3501 TGATGGCGCTGCTACCAAACAATTCACAAGAAAAGGGCTTACTGTAAGTC 3550
```

Fig. 5B

```
 949 ..............................CCGAAGTGGAGTGA  962
                                   ||||||||||||||
3601 TAAAATTTCTCATGAGGGATCCTTTGTTCATGTCAGCCGAAGTGGAGTGA 3650

963 CCTTGATGTCAACCAGCATGTGAACAATGTGAAGTATATTGGTTGGATAC 1012
     ||||||||||||||||||||||||||||||||||||||||||||||||||
3651 CCTTGATGTCAACCAGCATGTGAACAATGTGAAGTATATTGGTTGGATAC 3700

1013 TTG............................................... 1015
     |||
3701 TTGAGGTAACTTCTTTTTCCTTTTCTCTATCCGAACATGCTATCTCTAGA 3750

1016 .........................AGAGTGCTCCAATTTCGATACT 1037
                              |||||||||||||||||||||||
3851 TCTGAGTACGTTTTGTTTTTTTTCCTCAGAGTGCTCCAATTTCGATACT 3900

1038 GGAGAAGCACGAGCTTGCAAGCATGACCTTGGATTACAGGAAGGAGTGTG 1087
     |||||||||||||||||||||||||||||||||||||||||||||||||
3901 GGAGAAGCACGAGCTTGCAAGCATGACCTTGGATTACAGGAAGGAGTGTG 3950

1088 GCCGTGACAGTGTGCTTCAGTCGCTTACCGCTGTTTCAGGTGAATGCGAT 1137
     |||||||||||||||||||||||||||||||||||||||||||||||||
3951 GCCGTGACAGTGTGCTTCAGTCGCTTACCGCTGTTTCAGGTGAATGCGAT 4000

1138 GATGGCAACACAGAATCCTCCATCCAGTGTGACCATCTGCTTCAGCTGGA 1187
     |||||||||||||||||||||||||||||||||||||||||||||||||
4001 GATGGCAACACAGAATCCTCCATCCAGTGTGACCATCTGCTTCAGCTGGA 4050

1188 GTCCGGAGCAGACATTGTGAAGGCTCACACAGAGTGGCGACCGAAGCGAG 1237
     |||||||||||||||||||||||||||||||||||||||||||||||||
4051 GTCCGGAGCAGACATTGTGAAGGCTCACACAGAGTGGCGACCGAAGCGAG 4100

1238 CTCAGGGCGAGGGGAACATGGGCTTTTTCCCAGCTGAGAGTGCATGA... 1284
     ||||||||||||||||||||||||||||||||||||||||||||||||
4101 CTCAGGGCGAGGGGAACATGGGCTTTTTCCCAGCTGAGAGTGCATGAGCG 4150
```

```
proteinF_1    MGAGGRMTEKEREEQQKLLGRAGNGAAVQRSPTDKPFTLGQIKKAIPPHCFQRSVIKSF
proteinF_3    ------------------------------MQRSPVDKPFTLGDIKKAIPPHCFHRSVIKSF
proteinF_2    MGTSSRPTTVKEGKKLEAPRRAGSHAAVKRSPVDKPFTLGDIRKAIPPHCFHRSVIKSF
proteinF_4    ------------------------------MAGGRRWGGWREQEPPRRAGSSAAVQRFHRSVIKSF 61         71         81         91        101        111
proteinF_1    SYVVHDLVTVAALLYFALVMIPVLPSGMEFAAMPLYWIAQGCVLTGVWVIAHECGHHAFS
proteinF_3    SYLLHDLAIAAGLLYFALVGIPALPSILRLVAMPLYWAAQGSVLTGVWVIGHECGHHAFS
proteinF_2    SYLLHDLAIAAGLLYFALVVIPALPGVLRLVAWPFYWAAQGCFLFGVWIIAHECGHHAFS
proteinF_4    SYLLRDVAIAAGLLNFALVGIFVLPAGVLRPRRLAVLLGRAGLLPVRGVDHRARVRAPR 121        131        141        151        161        171
proteinF_1    DYSVLDDIVGLVLHSSLIVPYFSWKYSHRRHHSNTGSLERDEVFVPKQKSAMAWYTPYVY
proteinF_3    DYLLDNLVGLVLHSALLTPFFSWKYSHRRHHANTGSMEKDEVYVAKKKSALPWYTPYVF
proteinF_2    GHALLDDTLGLVLHSWLLAPYFSWKYTHQRHHSNTSSQERDEVFVPRFKSDLPWYSPYVY
proteinF_4    APRRHPRSGPALVASGTILLVEIQPPAAPLQHQLTGAARGVRPQVQVRSAVELPVRVQVQ 181        191        201        211        221        231
proteinF_1    H--NPIGRLVHIFVQLTLGWPLYLAFNVSGRPYPRFA-CHFDPYGPIYNDRERVQIFISD
proteinF_3    G--NPVGRLIVYIALQLTLAWPLYLAFNLSGQPYPRLVTCHYDPYSPLFSDQERVQVLVSD
proteinF_2    KYNNPVARLILLVVQLTVGWPMYLVFNTWGRQYPREA-SHFDPSGPIYKGRERVFIAISD
proteinF_4    Q--RPVARLILLGMQLTVGWPMYLVFNTWGRWYPRFA-SHFDPSGAIYMRRERVFIAISD
```

Fig. 7A

```
              241         251         261         271         281         291
proteinF_1    VGVVSAGLALFKLSSAFGFWNVVRVYGVPLLIVNAMLVLITYLQHTHPALPHYDSSEWDW
proteinF_3    AAILAVLLALHRLTAAYGLWWVRVYGVPVMIVGALFVLITYLHHTHRALPHYDSSEWEW
proteinF_2    IGMLAVSLALYRLAEGYGFWWVVRVYGVPLLVVNAMLVVVTYLHETHRAIPHYDSSEWDW
proteinF_4    IGMLAVSLAL--------------------------------------------------

301         311         321         331         341         351
proteinF_1    LRGALATVDRDYGILNKVFHNITDTHVABHLFSTMPHYHAMEATKAIRPILGEYYQFDPT
proteinF_3    LRGSLATVDRDYGVLNRVLHNVTDTHVLBHLFPSMPHYHAMEATRAARPVLGEYIKFDRI
proteinF_2    LRGALATVDRDYSFLNRVFHNITDTHVRHHLFPTIPHYHAVEATKAIRPILGEYYQFDPT
proteinF_4    ------------------------------------------------------------

361         371         381
proteinF_1    PVAKATWREAKECIYVEPEDNKGVTWYNNKF
proteinF_3    PIIEATWREAKECMYVEPRERDGIYWYNNKF
proteinF_2    PIVKAIWREAKECIYIQSEDHKGVFWYSNKF
proteinF_4    ----------------------------------
```

```
cdsFAD20_2       ATGGGTACCAGCAGCCGGCCGACGACGGTGAAGGAGGAAGAAACTAGAGGCGCCCCGC
cdsFAD20_4       ------------------------------------------------------------
cdsFAD20_1       ATGGGTGCCGGCGGCGCAGGATGACGGCAGGAGCGGGAGGAGCAGCAGAAGCTGCTCGGC
cdsFAD20_3       ------------------------------------------------------------

61         71         81         91        101        111
cdsFAD20_2       CGTGCCGCGGCCAGCCATGCAGCCGTGAAGCGCTCCGGTGGACA--AGCCGCCGTTCACGC
cdsFAD20_4       ---ATGGGGGCGACGGCGGTGGGGCGGATGCG-TGAACAGGAGCGCC--TCCCCG
cdsFAD20_1       CGCGCCGGCAATGGCGCGGGCCGTGCAGCGGTCGCGACGGACA--AGCCGCCGTTCACGC
cdsFAD20_3       ------------------------ATGCAGCGGCTCACCGGTGGACA--AACCGCCGTTCACGC 121        131        141        151        161        171
cdsFAD20_2       TGGGCGACATCAGAAAGGCCATCCCACCGACTGCTTCCACCGCTCCGTGATCAAGTCAT
cdsFAD20_4       TGC-CGGCAGCAGTGCAGCCGT------GCAGCGTTCCACCGCTCCGTGATGATCAAGTCAT
cdsFAD20_1       TGGGCCAGATCAAGAGGCCATCCCGCCTCACTGCTTCCAGCGCTCGGTGATGATCAAGTCCT
cdsFAD20_3       TGGGGACATAAAGAAGGACCATCCCCGACTGCTTCCACCGCTCCGTGATCAAGTCAT 181        191        201        211        221        231
cdsFAD20_2       TCTCCTACCTGCTCCACGACCTTGCCATTGCCCGGCCCTCCCTCTACTTTGCTCTGGTCG
cdsFAD20_4       TCTCCTACCTGCTCCGTGACGTAGCCATTGCCGGGGCCTCCCTCGACTTTGCGCTGGTCG
cdsFAD20_1       TCTCCTACGTGGTCCATGACCTCGTGATCGTCGCCGGCGCTGCTCTACTTCGCGCTGGTCA
cdsFAD20_3       TCTCCTACCTGCTCCACGACCTTGCCATCGCCGCCGCTGGCCTCTCCTCTACTTGCTCTGGTCG 241        251        261        271        281        291
cdsFAD20_2       TCATCCCTGCCCCTGCCC----AGGGTCTC---CGCCTCGTCGCCTGGCCGTTCTACTGG
cdsFAD20_4       GCATCCCTGCCCTCCCTGCCAGGCGTCCTCCGGCCGCCTCGTGCCGGCCGTTCTACTGG
cdsFAD20_1       TGATCCCCGTGCTGCC----GAGCGGGATG----GAGTTCGCGGCATGGCCGCCTACTGG
cdsFAD20_3       GCATCCCTGCCCCTCCC----AAGCATCCTC---CGCCTCGTCGCCTGGCCGCTCTACTGG
```

Fig. 10A

```
              301         311         321         331         341         351
cdsFAD20_2    GCCGCGCCAGGGGTGCTCCTGTTCGGGGTGGATCATCGGCACGAGTGCGGGCACCAC
cdsFAD20_4    GCCGCGCCAGGGGCTGCTTCGTTCGTCGTGGATCATCGCGCACGAGTGCGGGCACCAC
cdsFAD20_1    ATCGCGCCAGGGCTGCGTGCTCACCCGCCGTGGGTCATCCGCACGAGTGCGGCCACCAT
cdsFAD20_3    GCCGCGCCAGGGCAGTGTACTCACCGGCGTGTGGGTCATCGGGCACGAGTGTGGCCACCAC 361         371         381         391         401         411
cdsFAD20_2    GCGTTCTCGGGCCACGCACTCCTCGACGACACCCTCGGCTCCTCGCACTCATGGCTC
cdsFAD20_4    GCG---------------CTCCAAGACGACACCCTCGGTCTGTCGCCTCGCACTTGTGGCTT
cdsFAD20_1    GCCTTCTCCCGACTACTCGGTGCTCGACGACATCGTCGGCCTCGTGCTCGACTCGCTG
cdsFAD20_3    GCCTTCTCGGACTACTTGCTCCTCGACAACCTCGTGGGCCTTAGTCGTCTCCACTCGGCGCTT 421         431         441         451         461         471
cdsFAD20_2    CTAGCGCCATACTCTCGTGGAAATACACCCACCAACGGCACCACTCCAACACCAGCTCA
cdsFAD20_4    CTGGCACCATACTCTCGTGGAAATACACCCAGCCGCACCACTCCAACACCAGCTCA
cdsFAD20_1    CTCGTCCCCTACTTCTCGTGGAAGTACAGCCACCACCACCACTCCACCACCGGGTCG
cdsFAD20_3    CTCACGGCCCTTCTCTCGTGGAAGTACAGCCACCACCGGCACCACCGGGCTCC 481         491         501         511         521         531
cdsFAD20_2    CAGGAGCGGACGAGGTGTTCGTCCCAGTTCAAGTTCCGTCCGACCTGCCGTGTACTCCCA
cdsFAD20_4    CAGGAGGCGGACGAGGTGTTCGTCCCCAGTTCAAGTTCCGATCTGCCGTGGAACTCCCG
cdsFAD20_1    CTGGAGCGCCGACGAGGTGTTCGTCCCGAAGCAGAAGTCGGCCGATGGCGTGCTGTACCCCG
cdsFAD20_3    ATGGAGAAAGACGAGGTGTACGTCGGAGGAAGAAGAAGTCCGCGCTGCCGTGGTACACCCCG 541         551         561         571         581         591
cdsFAD20_2    TACGTGTACAAGTACAACAAC--CCCGTCGCTCGGCTGCTCCTCGTCGTCGTGCAGCTCA
cdsFAD20_4    TACGTGTACAAGTACAACAACGGCCCCGTCGCCGTCCTACTGCTCCTCGGCATGCAGCTCA
cdsFAD20_1    TACGTGTAC------CACAAC--CCGATCGGCCCCGTGGTGCACATCTTCGTGCAGCTCA
cdsFAD20_3    TACGTGTTC-------GGCAAC--CCCGTCGGGCGGCCTGGTGTACATCGCCCTGAGCTCA
```

Fig. 10B

```
cdsFAD20_2        601 CCGTCGGGTGGCCGATGTATTTGGTGTTCAACACCTGGGTCGCCAGTACCCAAGGTTCG
cdsFAD20_4            CTGTCGGGTGGCCGATGTATTTGGTGTTCAACACCTGGGTCGCCGCTGTACCCGCGGTTCG
cdsFAD20_1            CCCTCGGGTGGCCGCTGTACCTGGCGTTCAACGTGTCCGGCCGCCCTACCCGCGCTTCG
cdsFAD20_3            CCCTCGCGTGGCCACTCTACCTGCCGTTCAACCTGTCCGGGCAGCCGTACCCACGCCTCG cdsFAD20_2        661 ---CCAGCCACTTCGATCCCTCTGGGCCATCTACAAGGGGCGGGAGCCGCGTCTTCATCG
cdsFAD20_4            ---CCAGCCACTTCGATCCCTCCGGAGCCATCTACATGAGGCGGAGCGCGTCTTCATCG
cdsFAD20_1            ---CGTGCCACTTCGACCCCTACGGCCGATCTACAACGACCGGGAGCGCGTCCAGATCT
cdsFAD20_3            TCACCTGCCACTACGACCCCTACAGCCCGCTGTTCAGCGACCAGGAGCGCGTCCAAGTCC cdsFAD20_2        721 CCATCTCGGACATCGGCATGCTGGCGTCCGCCGTGTCGCGCGTGTACAGGCTTGCGGAGGGTT
cdsFAD20_4            CCATCTCGGACATCGGCATGCTGGCCGTGTCGCTCGCGCTGTAA------------
cdsFAD20_1            TCATCTCCGACGTCGGCGTCGTGTCCGGGGCTCGCCCTGTTCAAGCTCGTCGTCGGCGT
cdsFAD20_3            TCGTCTCCGACGCCGGGCCCATCTGGCCGTGCTGCTGCGCCTGCACAGGCTGACGGCGCGT cdsFAD20_2        781 ACGGGTTTTGGTGGTGGCCGTCTACGGCCGTGCCGCTGCTTGTCGTCAACGCGTGGC
cdsFAD20_4            
cdsFAD20_1            TCGGGTTCTGGTGGTGGGTGCCGCTCTACGGCGTCTACGGGCTGCTGATCGTGAACGCGTGGC
cdsFAD20_3            ACGGGCTCTGGGTGGGTGCCGCGTGCACGGGCTGTACGGCGCTGGCGGTGGCGGTGT cdsFAD20_2        841 TTGTGCTCATCGTCACGTACCTGCATCACACTCACCGGGACATCCCACACTACGACTCCAGCG
cdsFAD20_4            
cdsFAD20_1            TGGTGCTCATCACGTACCTGCAGCACACCACACCCCGGCGCTGCCGCACTACGACTCGAGCG
cdsFAD20_3            TCGTGCTCATCACGTACCTGCACCACTGACCACCACCGGGCTCCCGACCTACGACTCCAGCG
```

Fig. 10C

```
        901         911         921         931         941         951
cdsFAD20_2  AGTGGGACTGGTTGCGCGGGGGCCTCGGCCACCGTGGACGGCGACTACAGCTTCCTTAACC
cdsFAD20_4  ------------------------------------------------------------
cdsFAD20_1  AGTGGGACTGGCTCCGCGGCGCCGCTGGCCACCGTGGACCGGCGACTACGGCCATCCTCAACA
cdsFAD20_3  AGTGGGAGTGGCTGCCTGCCTCCGCCGCCACCGTCGCCACCCGTCGACCCGACTACGGCGTCCTCAACC 961         971         981         991        1001        1011
cdsFAD20_2  GAGTGTTTCACAACATCACGGACACACACGTCGTGCACCACCTGTTCCCTACCATCCCGC
cdsFAD20_4  ------------------------------------------------------------
cdsFAD20_1  AGGTGTTCACACATCACGGACACGACGCACGTCGCGCACCACCTCTTCTCCACCATGCGC
cdsFAD20_3  GCGTGCTGACAACGTCACGGACCACCACCTCCTCCACCACCTCTTCCCCAGCATGCCAC 1021        1031        1041        1051        1061        1071
cdsFAD20_2  ACTACCACGCTGTGGAGGGACCAAGGCGATCCGCCCTATCCTCGGCGAGTACTACCAGT
cdsFAD20_4  ------------------------------------------------------------
cdsFAD20_1  ACTACCACGCCATGGAGGCCACTAAGGCGATCCGCCCCATCCTCGGCGAGTACTACCAGT
cdsFAD20_3  ACTACCACGCCATGAGGAGGCCACCAGGCGACGGAGGCCGTCCTCGGTGAGTACTACAAGT 1081        1091        1101        1111        1121        1131
cdsFAD20_2  TCGATCCCACACCCATCGTCAAGGCGATATGGCGGCGTAAGGAGGTGCATCTACATCC
cdsFAD20_4  ------------------------------------------------------------
cdsFAD20_1  TCGACCCGACGCCCGTCGCCAAGGCGACATGGCGCGAGGCCAAGGAGTGCATCTACGTCG
cdsFAD20_3  TTGACCGGCACGCCCATCATCGAGGCAACATGGGCGTGAGGCCAAGGAGTGCATGTACGTTG 1141        1151        1161        1171        1181
cdsFAD20_2  AGTCCGAGGACCACAAGGGCGTCTTCTGGTACAGCAACAAGTTCTAG
cdsFAD20_4  -----------------------------------------------
cdsFAD20_1  AGCCTGAGGACAACAAGGGCGTCTTCTGGTACACACAAGTCTAA
cdsFAD20_3  AGCCCAGGAGGAGCGCGATGGTATCTACTGGTACACAACAACAAGTTTAG
```

Fig. 10D

SEQUENCE LISTING

```
<160> NUMBER OF SEQ ID NOS: 83

<210> SEQ ID NO 1
<211> LENGTH: 425
<212> TYPE: PRT
<213> ORGANISM: Oryza sativa

<400> SEQUENCE: 1

Met Ala Gly Ser Leu Ala Ala Ser Ala Phe Phe Pro Gly Pro Gly Ser
1               5                   10                  15

Ser Pro Ala Ala Ser Ala Arg Ser Lys Asn Ala Ala Val Thr Gly
            20                  25                  30

Glu Leu Pro Glu Asn Leu Ser Val Arg Gly Ile Val Ala Lys Pro Asn
        35                  40                  45

Pro Pro Ala Ala Met Gln Val Lys Ala Gln Ala Gln Thr Leu Pro
    50                  55                  60

Lys Val Asn Gly Thr Lys Val Asn Leu Lys Thr Val Lys Pro Asp Met
65                  70                  75                  80

Glu Glu Thr Val Pro Tyr Ser Ala Pro Lys Thr Phe Tyr Asn Gln Leu
                85                  90                  95

Pro Asp Trp Ser Met Leu Leu Ala Ala Ile Thr Thr Ile Phe Leu Ala
            100                 105                 110

Ala Glu Lys Gln Trp Thr Leu Leu Asp Trp Lys Pro Lys Lys Pro Asp
        115                 120                 125

Met Leu Val Asp Thr Phe Gly Phe Gly Arg Ile Ile Gln Asp Gly Met
    130                 135                 140

Val Phe Arg Gln Asn Phe Met Ile Arg Ser Tyr Glu Ile Gly Ala Asp
145                 150                 155                 160

Arg Thr Ala Ser Ile Glu Thr Leu Met Asn His Leu Gln Glu Thr Ala
                165                 170                 175

Leu Asn His Val Arg Thr Ala Gly Leu Leu Gly Asp Gly Phe Gly Ala
            180                 185                 190

Thr Pro Glu Met Ser Lys Arg Asn Leu Ile Trp Val Val Ser Lys Ile
        195                 200                 205

Gln Leu Leu Val Glu Gln Tyr Pro Ala Trp Gly Asp Thr Val Gln Val
    210                 215                 220

Asp Thr Trp Val Ala Ala Gly Lys Asn Gly Met Arg Arg Asp Trp
225                 230                 235                 240

His Val Arg Asp Tyr Asn Ser Gly Arg Thr Ile Leu Arg Ala Thr Ser
                245                 250                 255

Val Trp Val Met Met His Lys Lys Thr Arg Arg Leu Ser Lys Met Pro
            260                 265                 270

Asp Glu Val Arg Ala Glu Ile Gly Pro Tyr Phe Asn Asp Arg Ser Ala
        275                 280                 285

Ile Thr Glu Glu Gln Ser Glu Lys Leu Ala Lys Thr Gly Asn Lys Val
    290                 295                 300

Gly Asp Asp Ala Thr Glu Gln Phe Ile Arg Lys Gly Leu Thr Pro Arg
305                 310                 315                 320
```

```
Trp Gly Asp Leu Asp Val Asn Gln His Val Asn Asn Val Lys Tyr Ile
                325                 330                 335
Gly Trp Ile Leu Glu Ser Ala Pro Ile Ser Val Leu Glu Lys His Glu
            340                 345                 350
Leu Ala Ser Met Thr Leu Asp Tyr Arg Lys Glu Cys Gly Arg Asp Ser
            355                 360                 365
Val Leu Gln Ser Leu Thr Thr Val Ser Gly Glu Cys Thr Ser Ile Gly
        370                 375                 380
Ala Asp Lys Gln Ala Ser Ala Ile Gln Cys Asp His Leu Leu Gln Leu
385                 390                 395                 400
Glu Ser Gly Ala Asp Ile Val Lys Ala His Thr Glu Trp Arg Pro Lys
                405                 410                 415
Arg Ser His Ala Ala Ala Glu Asn Ala
            420                 425

<210> SEQ ID NO 2
<211> LENGTH: 298
<212> TYPE: PRT
<213> ORGANISM: Oryza sativa

<400> SEQUENCE: 2

Met Ala Gly Ser Leu Ala Ala Ser Ala Phe Phe Pro Gly Pro Gly Ser
1               5                   10                  15
Ser Pro Ala Ala Ser Ala Arg Ser Ser Lys Asn Ala Ala Val Thr Gly
            20                  25                  30
Glu Leu Pro Glu Asn Leu Ser Val Cys Gly Ile Val Ala Lys Pro Asn
        35                  40                  45
Pro Pro Pro Ala Ala Met Gln Val Lys Ala Gln Ala Gln Thr Leu Pro
    50                  55                  60
Lys Val Asn Gly Thr Lys Val Asn Leu Lys Thr Val Lys Pro Asp Met
65                  70                  75                  80
Glu Glu Thr Val Pro His Ser Ala Pro Lys Thr Phe Tyr Asn Gln Leu
                85                  90                  95
Pro Asp Trp Ser Met Leu Leu Ala Ala Ile Thr Thr Ile Phe Leu Ala
            100                 105                 110
Ala Glu Lys Gln Trp Thr Leu Leu Asp Trp Lys Pro Lys Lys Pro Asp
        115                 120                 125
Met Leu Val Asp Thr Phe Gly Phe Gly Arg Ile Ile Gln Asp Gly Met
    130                 135                 140
Val Phe Arg Gln Asn Phe Met Ile Arg Ser Tyr Glu Ile Gly Ala Asp
145                 150                 155                 160
Arg Thr Ala Ser Ile Glu Thr Leu Met Asn His Leu Gln Glu Thr Ala
                165                 170                 175
Leu Asn His Val Arg Thr Ala Gly Leu Leu Gly Asp Gly Phe Gly Ala
            180                 185                 190
Thr Pro Glu Met Ser Lys Arg Asn Leu Ile Trp Val Val Ser Lys Ile
        195                 200                 205
Gln Leu Leu Val Glu Gln Tyr Pro Ala Trp Gly Asp Met Val Gln Val
    210                 215                 220
Asp Thr Trp Val Ala Ala Gly Lys Asn Gly Met Arg Arg Asp Trp
225                 230                 235                 240
His Val Arg Asp Tyr Asn Ser Gly Arg Thr Ile Leu Arg Ala Thr Ser
                245                 250                 255
Val Trp Val Met Met His Lys Lys Thr Arg Arg Leu Ser Lys Met Pro
            260                 265                 270
```

Asp Glu Val Arg Ala Glu Ile Gly Pro Tyr Phe Asn Asp Arg Ser Ala
            275                 280                 285

Ile Thr Glu Glu Gln Ser Glu Lys Leu Ala
            290                 295

<210> SEQ ID NO 3
<211> LENGTH: 427
<212> TYPE: PRT
<213> ORGANISM: Oryza sativa

<400> SEQUENCE: 3

Met Ala Gly Ser Leu Ala Ala Ser Ala Phe Phe Pro Val Pro Gly Ser
1               5                   10                  15

Ser Pro Ala Ala Ser Ala Arg Ser Ser Lys Asn Thr Thr Gly Glu Leu
            20                  25                  30

Pro Glu Asn Leu Ser Val Arg Gly Ile Val Ala Lys Pro Asn Pro Ser
        35                  40                  45

Pro Gly Ala Met Gln Val Lys Ala Gln Ala Gln Ala Leu Pro Lys Val
    50                  55                  60

Asn Gly Thr Lys Val Asn Leu Lys Thr Thr Ser Pro Asp Lys Glu Asp
65                  70                  75                  80

Ile Ile Pro Tyr Thr Ala Pro Lys Thr Phe Tyr Asn Gln Leu Pro Asp
                85                  90                  95

Trp Ser Met Leu Leu Ala Ala Val Thr Thr Ile Phe Leu Ala Ala Glu
            100                 105                 110

Lys Gln Trp Thr Leu Leu Asp Trp Lys Pro Lys Lys Pro Asp Met Leu
        115                 120                 125

Ala Asp Thr Phe Gly Phe Gly Arg Ile Ile Gln Asp Gly Leu Val Phe
    130                 135                 140

Arg Gln Asn Phe Leu Ile Arg Ser Tyr Glu Ile Gly Ala Asp Arg Thr
145                 150                 155                 160

Ala Ser Ile Glu Thr Leu Met Asn His Leu Gln Glu Thr Ala Leu Asn
                165                 170                 175

His Val Lys Thr Ala Gly Leu Leu Gly Asp Gly Phe Gly Ala Thr Pro
            180                 185                 190

Glu Met Ser Lys Arg Asn Leu Ile Trp Val Val Ser Lys Ile Gln Leu
        195                 200                 205

Leu Val Glu Arg Tyr Pro Ser Trp Gly Asp Met Val Gln Val Asp Thr
    210                 215                 220

Trp Val Ala Ala Gly Lys Asn Gly Met Arg Arg Asp Trp His Val
225                 230                 235                 240

Arg Asp Tyr Asn Ser Gly Gln Thr Ile Leu Arg Ala Thr Ser Val Trp
                245                 250                 255

Val Met Met Asn Lys Asn Thr Arg Arg Leu Ser Lys Met Pro Asp Glu
            260                 265                 270

Val Arg Ala Glu Ile Gly Pro Tyr Phe Asn Gly Arg Ser Ala Ile Ser
        275                 280                 285

Glu Glu Gln Gly Glu Lys Leu Pro Lys Pro Gly Thr Thr Phe Asp Gly
    290                 295                 300

Ala Ala Thr Lys Gln Phe Thr Arg Lys Gly Leu Thr Pro Lys Trp Ser
305                 310                 315                 320

Asp Leu Asp Val Asn Gln His Val Asn Asn Val Lys Tyr Ile Gly Trp
                325                 330                 335

Ile Leu Glu Ser Ala Pro Ile Ser Ile Leu Glu Lys His Glu Leu Ala
            340                 345                 350

```
Ser Met Thr Leu Asp Tyr Arg Lys Glu Cys Gly Arg Asp Ser Val Leu
            355                 360                 365

Gln Ser Leu Thr Ala Val Ser Gly Glu Cys Asp Asp Gly Asn Thr Glu
    370                 375                 380

Ser Ser Ile Gln Cys Asp His Leu Leu Gln Leu Glu Ser Gly Ala Asp
385                 390                 395                 400

Ile Val Lys Ala His Thr Glu Trp Arg Pro Lys Arg Ala Gln Gly Glu
                405                 410                 415

Gly Asn Met Gly Phe Phe Pro Ala Glu Ser Ala
            420                 425

<210> SEQ ID NO 4
<211> LENGTH: 423
<212> TYPE: PRT
<213> ORGANISM: Oryza sativa

<400> SEQUENCE: 4

Met Ala Gly Ser Ile Ala Ala Ser Ala Phe Leu Pro Gly Ser Pro Ala
1               5                   10                  15

Ala Ala Pro Pro Lys Ser Val Leu Gly Glu Arg Pro Asp Ser Leu Asp
            20                  25                  30

Val Arg Gly Ile Ala Ala Lys Pro Gly Ser Ser Ser Ala Ala Ala
        35                  40                  45

Leu Arg Ala Gly Lys Thr Arg Thr His Ala Ala Ile Pro Lys Val Asn
    50                  55                  60

Gly Gly Ser Ser Ala Leu Ala Asp Pro Glu His Asp Thr Met Ser Ser
65                  70                  75                  80

Ser Ser Ser Ser Ala Ala Pro Arg Thr Phe Tyr Asn Gln Leu Pro Asp
                85                  90                  95

Trp Ser Met Leu Leu Ala Ala Ile Thr Thr Ile Phe Leu Ala Ala Glu
            100                 105                 110

Lys Gln Trp Thr Leu Leu Asp Trp Lys Pro Lys Arg Pro Asp Met Leu
        115                 120                 125

Thr Asp Thr Phe Gly Phe Gly Arg Met Ile His Glu Gly Leu Met Phe
    130                 135                 140

Arg Gln Asn Phe Ser Ile Arg Ser Tyr Glu Ile Gly Ala Asp Arg Thr
145                 150                 155                 160

Ala Ser Ile Glu Thr Leu Met Asn His Leu Gln Glu Thr Ala Leu Asn
                165                 170                 175

His Val Lys Ser Ala Gly Leu Leu Gly Asp Gly Phe Gly Ser Thr Pro
            180                 185                 190

Glu Met Ser Lys Arg Asp Leu Phe Trp Val Val Ser Gln Met Gln Ala
        195                 200                 205

Ile Val Glu Arg Tyr Pro Cys Trp Gly Asp Thr Val Glu Val Asp Thr
    210                 215                 220

Trp Val Gly Ala His Gly Lys Asn Gly Met Arg Arg Asp Trp His Ile
225                 230                 235                 240

Arg Asp Ser Val Thr Gly His Thr Ile Leu Lys Ala Thr Ser Lys Trp
                245                 250                 255

Val Met Met His Lys Leu Thr Arg Arg Leu Ala Arg Ile Pro Asp Glu
            260                 265                 270

Val Arg Thr Glu Ile Glu Pro Tyr Phe Phe Glu His Ala Ser Ile Val
        275                 280                 285

Asp Glu Asp Asn Gln Lys Leu Pro Lys Leu Pro Asp Ile Glu Gly Ala
    290                 295                 300
```

```
Asn Val Ala Lys Tyr Val Arg Thr Gly Leu Thr Pro Arg Trp Ala Asp
305                 310                 315                 320
Leu Asp Ile Asn Gln His Val Asn Val Lys Tyr Ile Gly Trp Ile
            325                 330                 335
Leu Glu Ser Ala Pro Ile Ser Ile Leu Glu Lys His Glu Leu Ala Ser
                340                 345                 350
Ile Val Leu Asp Tyr Lys Arg Glu Cys Gly Arg Asp Ser Val Leu Gln
            355                 360                 365
Ser His Thr Thr Val Tyr Thr Asp Cys Asn Lys His Ser Gly Gln Thr
        370                 375                 380
Thr Leu His Cys Glu His Leu Leu Ser Leu Glu Ser Gly Pro Thr Ile
385                 390                 395                 400
Val Lys Ala Arg Thr Met Trp Arg Pro Lys Gly Thr Arg Pro Gln Glu
                405                 410                 415
Ser Ile Ile Pro Ser Ser Ser
            420

<210> SEQ ID NO 5
<211> LENGTH: 6943
<212> TYPE: DNA
<213> ORGANISM: Oryza sativa

<400> SEQUENCE: 5
ccatatgtgc agcataaaag gcaaatcagc cctgtttgac atggctccaa tgcttaaatt      60
ctttagagaa aaaacagact ttgtagatta aatcaaagtg gcataatctt tttatttga     120
taaaaatatt agaaaatatc ataccctaat attcttagca tagtactcca ttcatctcac    180
ttattaaggt acgatcaaac ttggcatagt cttcaaaggc tgtgttcttt cccccatttt    240
cctaacccat ctatctcgtt ttccgcgcac acatttttca aactgctaaa cggtgtgatt    300
tatgcaaaaa cttctatatg aaagttgttt aaaaaaatca tattaatcca ttttttaaaa    360
aaatcagtta atacttaatt aatcatgcaa taaaacgaac ttcattttgc gtgctgggga    420
ggagggctc ccaaccctc ctccgaacac agccaaaagc tactttttgga ctttaaattt    480
gtcatatatt ataatgtttc tagtaacaaa accatagtca tatgaaagta aatttaaatg    540
ataatccaat gatattattt tcatcaaata gaatttaatt tataataaac tatttattga    600
taaaatattc agagagttga atattaaaat acctgtgtgc cttagtgagt gggccaaatt    660
aattaatgga gtagtaacag ctttaaccaa agaaatttca acaatttccc aagctagaaa    720
aaacccaact ccaaaataaa cttgagttag aactgtgtta agcacctaaa ttgtaatacc    780
tgttactctc tcgttctcat tctatatttg tcctaagtta aatatatcta cctttttta    840
tctgtcctaa gttaactatg tgtatgtcta tcttttctac tactccctcc gtttcaggtt    900
ataagacgtt ttgactttgg tcaaagtcaa actgctttaa gtttgactaa gtttgtagaa    960
aaaataataa cattttcaac ccaagacaaa tttattatga aaatatgttc aattattgat   1020
ttaatgaaac taatttggta ttataaatat tattatattt atatataaac ttagttaaat   1080
ttaaagtagt ttaagtttga tcaaagtcaa atgttttat aacctgaaat ggagggagta   1140
agtaatttga aacgaagaga gcagacaaat aataaactag taaagcctgt gacttgggtt   1200
ctagtcattg atcgtgtaca tgtaggtctt gtttagatcc caaaaattt tagccaaaac   1260
ctcacatcaa atatttggac acatgcaccc ctaccagtgt gtggaggcat tgcatacacg   1320
aaacatggaa aaggaatcaa cttgagaggt tagacctgct agctctacta ggtctggatg   1380
gtcatgcatt ttttttgaa aaaaaccacg ctgcaagctc gacagcctca acctcaatgg   1440
```

```
caaccatgac aataatatgc atgacaatgg tgtaggagaa aagacacgtc gataaccaaa    1500
gggcgcggct gcgcatacaa aggcggagag aaggaacgat ggtggctcaa aaagaaagag    1560
cgtcggtggc agtggtgcgt ggagcgacac taaagttagt ggttgctgat ggtctcacac    1620
aatccctaat cgaaatattt attttttttc acttagtatt gctgatccgt gggccaccag    1680
ccaatcataa agaaaaatgt tgagataaaa ggtggagtat cttcccttc cttccctttt    1740 tgactcgaaa aaaaaaagcg tcggtggcgg ccgtgcgtgt aacaacacta aagttagtgg    1800
ttgctggtgg tctgacacaa tccctaatca agtttgataa taataataat ttatttcctc    1860
ttattagtat tgctgatgcg tgggccacca atcaatcgta agaaaaaaaa atgttgagat    1920
aaaaggtggg ggtatcttct ccttctcttt ttttttggct aaaataaaag tggtttctgg    1980
tagtctgaca caatctctaa tcgaaatatt tattttttc tcttagtatt gctgatacgt    2040
gggccaccag ccaataataa agaaaaaaaa tgttagagat aaaaggcgga gagtatcttc    2100
cccttccttt ttttttggcgt aaatgaaaga aaagagaaaa tctcccgtcg tctccttcct    2160
tgcgccaaga aagacgagcc gcggctcaac accggagggg aggggcgccg atctccatcg    2220
ccaaggagag cagagcaggg gagggatcc tggtgagcct cctcttcctg attcatctct    2280
ctcccattct agcttcgggg gactactttt gcctggaatt tgctcgcgtt cgttcgtgcg    2340
ttcgttcgtt aaccctagct tcttctcttc tagatctgga ggaagctctt ctcctcctta    2400
atttcagagc cttaatacaa gtagtaacag tttaacctcc cccatgtccc aagttggatc    2460
cgcccctgcg agttccgata ttgggtcctc ccaattctca atgccatttt gttcatcggg    2520
gggcatatgt ttcatttttg cctgcattga ttcaaatgtg gtttcgaatc gtttgtgaaa    2580
ttcgcgggtg tacttgttta tgatacatga ggcctttttt cccccatgag gaggcaaact    2640
ttttagtggg tggatccact agttcatgcc tcaattttt ttctcctctt ttaagttttc    2700
caaagagcta cattgttgta aagtgtctga tacaattgat tgtttattca ggttagcgct    2760
tttggcgtgt gattgatttc taaacgaatt ttgggccgtg aggggaagtt caatcatggc    2820
agggtctctt gccgcctcag cattcttccc aggtccaggc tcatctcctg cagcatcagc    2880
tagaagctcc aagaatgctg ctgttaccgg cgaattgccg gagaatttga gtgtctgtgg    2940
cattgtcgca aagcctaacc cacctcctgc agccatgcaa gtaaaggcac aggctcaaac    3000
ccttcccaag gttaatggta cgaaggttaa cctcaagacg tgaagcctg acatggagga    3060 aacggtgcct cacagtgctc caaagacgtt ctataaccaa ctgccggatt ggagcatgct    3120
tcttgcggct attacaacca tcttcctcgc cgcagagaag cagtggacac tgcttgattg    3180
gaagccgaag aaacctgaca tgcttgttga cacatttggc tttggtagga tcatccagga    3240
cggtatggtg tttaggcaga acttcatgat tcggtcctac gagattggcg ctgatcgtac    3300
agcttctata gagacattga tgaatcattt acaggtaagt ggttgcacat tctgttttta    3360
gtttcatttc tcatttcagc attttgttat agattcgtat gtctctttca agctggcaat    3420
tatttaaaat tttgcaggaa acggctctta accatgtaag gactgctggt cttcttggag    3480
atggttttgg ggctacaccg gagatgagca acggaactt gatatgggtt gtcagcaaaa    3540
tccagcttct tgttgagcaa taccccgcat ggtactttt tgcaaacctt tgctcctctt    3600
gatatatgta tctttggttt cttctatca attccttact ctaagttgtc atttaatttt    3660
cacattttaa attacttcat atttgttttg cttcttttac agatatcgtt ttatgtacta    3720
ctttacagct gtgtgtcctt tgcatatttg ttttatttg tttaagaag attcttacac    3780 aagcaacagt agtatttagc tcaatattta ctttaacatg gtttatcata ttgttgtgtg    3840
```

```
gatctctggt ctgatttctc catacactgg ttggttgatg aaaatcaagt gaatctttta    3900
cttgctcgta aatttcgctg ctgcaggttt gcaagaatat gggttgaagt ttttatactg    3960
ctatagaagg ccatgttttt ctttgatttc ccgtgatagg cctcatgttt tggaggttct    4020
gttattcctc cttggttgac taagaaatgt gtagtaatat cagctccagt tttgttggat    4080
caaggataga ttttgtggca aactaaattt tccaattagg aagaaatgaa tatattccta    4140
cttaagtggg aggagcatgc actttgtttc caattgtcga gccctgatta aacacaaac    4200 tatcaagtta tttctttgca tttagaaaca ggatttgcat cttgggtaat cctcattaaa    4260
gacataatct agctttagta catgcaacat aaaagttatg atgccccaag gcctttttgg    4320
tacagcactg taagtctgta gctctccttg ctctatgttg tcctcaaaag acacaacatc    4380
agttaaaaga acagtaatct ctcctttaga cgtcaattat tagtggagta gtaatttaga    4440
tccaagagca acttcatttg ttacgcctta ttcattgccc aaagctgcct cattaaatga    4500
tgtcttctct gtgcttcctt ggatcttgaa ttatgctgag tgggaatgcc agaacgggca    4560
tgtacttacg ttttccagcg ataagctccg ttttaaaaat aaattagcaa gtgatttatt    4620
tgcatttata aacaaaaatt taccactcgg gtagttcata ttaaagttat tgtctagctt    4680
tattacaagc agcatgaaag ttacgatacc ccaaggcctg agtttggcag cacttaactc    4740
tgttgccctg ttttgtcttg aaaagtataa catcacttag caggacaatg ctctcccgaa    4800
aacataactg attagtggat agagggagag gtttagtccc aatagataat tgactggtta    4860
cttcatattc attgcccaga gctgcctcat taaatgttct gtcctgtgct ttcttggatc    4920
ttgaattaaa agacgtctgt acagggtacc acacctcaag ggatcacaat tcagaaagtt    4980 tcccttatt gggctgcagt aaatgattcc atcgtgtaga aaagaacaaa agcaattaat    5040
gctgtgccat atcatgggag aagctaagga ccgatctaga acagtgaact tttgttgaac    5100
agcatctgtc agtttaaatt tctaggtggt catcattcat caaataagtg gtgctagtac    5160
tactattcac acgttatgtt taaatcctct tgtcaactgt gtcaacaagt ggttgaaaac    5220 ttctttttg gggttttgag ttagaaaaat ggaagtgcaa tttcaaactg ttttttagt    5280 tcagatacaa ttgccgatgt ctttctgtgg atcaaaaaga atgacagatg tattgtacca    5340
acctgctatg gttttagggg agatatggtt caagttgaca catgggtcgc tgctgctggc    5400
aaaaatggca tgcgtcgaga ctggcatgtt cgtgactaca actctggccg aacaatcttg    5460
agagctacaa ggtttgggct tcaactgtat tctattgcaa gaatcatctg tatcattttt    5520
tttgtgagga catccaatct tggtatttct gcttggtcac atcattgata atcactaatt    5580
gtgctccttt tccaatccat tgttgcagt gtttgggtga tgatgcacaa gaaaactaga    5640
agactttcaa aaatgccaga tgaagttaga gctgaaatag gcccatattt caatgaccgt    5700
tcagctataa cagaggagca gagtgaaaag ttagcctaga caggaaataa agttggtgat    5760
gatgctacag agcaattcat aagaaagggg ctcactgtaa gtcagctaga catggttaca    5820
tactgaatta tcattatgcc tcaactgcta tcatttatct aagaaaaaca gtaataattg    5880
atctcacccc tcatttattt taaatgatat ttgatggact cttgtttact gcaacagcct    5940
agatggggtg acctcgatgt caatcagcat gtgaacaatg ttaaatatat tgggtggatc    6000
cttgaggtgg ttattcttgt cccttatatt cattgtttag agaaaaataa tttggcttta    6060 tcctttttata tggtacttcc tttgtttcac aatgtaagtc attttagcat ttcccatatt    6120
tatatttatg ctaatgaatc taaatagata tatgtgtcta gattcattgg catcaatatg    6180
aatgtgagaa atgctaaaat gacttacatt atgaaacgga gggagtagtt gttagggaac    6240
```

-continued

| | |
|---|---|
| cattttatgt agtacttgca attattttct agagattctg atctgaccat ctgtattgtt | 6300 |
| gatattgtca ttagtcttac atctggtcag tcagaaggct ttcaaacatg tttctgagtt | 6360 |
| ctttctaatt ttttccccca gagtgctcca atttcagtac tggagaagca tgagcttgca | 6420 |
| agcatgaccc tggattacag gaaggagtgt ggccgagaca gcgtgctgca atcacttacc | 6480 |
| accgtgtcag gggaatgcac cagcattggc gccgacaagc aggcttctgc catccagtgc | 6540 |
| gaccatcttg tgaaggctga cattgtgaag gcacacacag agtggcgacc aaagcgatcg | 6600 |
| catgcagcag ctgagaacgc gtaaacaaac aaaccgacga aaatctgtgg tagggagaat | 6660 |
| atcaaacttc ccttgcctct gttgccctga agctgatctt gaagtgtgag ttgtattctg | 6720 |
| taaaaaatta gtagtttcca tagtgtgagg ttggagggga ggtgttggtg cttgcctact | 6780 |
| gtacctgcta catctattat ttcttgattc tttgttcgct ttttttttc tttttttgttt | 6840 |
| ttaacccctg tggagataag acaggttttg aagtgtggaa gaggttgttt caatcgtcta | 6900 |
| attgattcaa ctattcagca agtaaactgc tccatggaaa ttt | 6943 |

<210> SEQ ID NO 6
<211> LENGTH: 4799
<212> TYPE: DNA
<213> ORGANISM: Oryza sativa

<400> SEQUENCE: 6

| | |
|---|---|
| agaggagaaa ttctcccgtc gtctccttcc ttgcgccaag aaagacgagc cgcggctcaa | 60 |
| cagcggagtg gaggggcgcc gatctccatc gccgaggaga gcagagcagg ggaggggagg | 120 |
| ggatcctggt gagcctcctc ttcctgattc acctctctct cattctagct tcggggggact | 180 |
| acttttgcct cgaatttgct tgcgttcgtt cgttaaccct agcttcttct cttctagatc | 240 |
| tggaggaagc tcttctcctc cttaatttca gagccttaat acaagtagta acagtttaac | 300 |
| cccccccccc cccatgtccc aagttggatc cgccctgcg agttccgata ttgggtcctc | 360 |
| ccaattctca atgccatttt gttcatcggg gggcatatgg ttcattttgc ctgcattgat | 420 |
| tcaaatgtgg tttcgaatcg tttgggaaat tcgcgggtgt acttgtttat gatatatgag | 480 |
| gccttttttt tccccatgag gaggcaaact ttttagtggg tggatccact agttcatgcc | 540 |
| tcaatttttt ttctcctctt ttaagttttc caaagagcta cattgttgta aagtgtctaa | 600 |
| tacaattgat tgtttattca ggttagcgct tttggcgtgt gattgatttc taaacgaatt | 660 |
| ttgggccgtg aagggaagtt caatcatggc agggtctctt gccgcctcag cattcttccc | 720 |
| aggtccaggc tcatctcctg cagcatcagc tagaagctcc aagaatgctg ctgttaccgg | 780 |
| cgaattgccg gagaatttga gtgtccgtgg cattgtcgca aagcctaacc cacctcctgc | 840 |
| agccatgcaa gtaaaggcac aggctcaaac ccttcccaag gttaatggta cgaaggttaa | 900 |
| cctcaagacg gtgaagcctg acatggagga aacggtgcct acagtgctc caaagacgtt | 960 |
| ctataaccaa ctgccggatt ggagcatgct tcttgcggct attacaacca tcttccttgc | 1020 |
| cgcagagaag cagtggacac tgcttgattg gaagccaaag aaacctgaca tgcttgttga | 1080 |
| cacatttggc tttggtagga ttatccagga cggtatggtg tttaggcaga acttcatgat | 1140 |
| tcggtcctac gagattggtg ctgatcgtac agcttctata gagacattga tgaatcattt | 1200 |
| acaggtaagt ggttgcacat tctgttttta gttttatttc tcatttcagc attttgttat | 1260 |
| agattcatat gtctctttca agctggcaat tatttaaaat tttgcaggaa acagctctta | 1320 |
| accatgtgag gactgctggt cttccttgag atggttttgg ggctacaccg gagatgagca | 1380 |
| aacggaactt gatatgggtt gtcagcaaaa tccagcttct tgttgagcaa taccccgcat | 1440 |

```
ggtacttctt tgcaaacctt tgctcctctt aatatatgta tctttggttg ctttctatca    1500
attccttacc gtaagttttc attttttgtca cattttaaat tacttcatat ttgttttgct    1560
tcttttacag atatcgtttt atgtactact ttatagctgt gtgtccttgg catatttgtt    1620
tctatttgtt taaagaagat tcttactcag gcaacagtag tatttagctc aatatttact    1680
ttaacatggt ttatcataat gttgtgtgga tctctggtct gatttctcca tatactggtt    1740
ggttgatgaa atcaagtga atcttttact tggtcgtata tttcgctgct gctggtttgc    1800
aagaatatgg gttgaaattt ttactgctat agaaggccat gttttctctt gatttcccgt    1860
gataggcctc atgtttagga ggtgctgtta ttcctcattg gttgactaag aaatgtgtag    1920
taatatcagc tccagttttg ttggatcaag gatagagttt gtggcaaact aaattttcca    1980
attaggaaga aatgaatata ttcctactta agtggggagg agcatgcact ttgtttccaa    2040 tgtcgagcc ctgattataa cacaaactat caagttattt ctttgcattt agaaacagga    2100
tttgcatctt gagtaatcct cattaaagac ataatctagc tttagtacat gcaacataaa    2160
agttctgatg ccccaaggcc ttttggtac agcactgtaa gtctgtagct atccttgctc    2220
tatgttgtcc tcaaaagaca caacatcagt taaaaacaaa gaagaacagt aatctctcct    2280
ttagacgtca gttattagtg gagtagtaat ttagatccaa gagcaacttc atttgttacg    2340
ccttattcat tgcccaaagc tgcctcatta aatgatgtct tctctgtgct tccttggatc    2400
ttgaattatg ttgagtggga atgccagaac gggcatgtac tttcgttttc cagcgataag    2460
ctccgtttta aaataaatt agcaagtgat ttatttacat ttacaaacaa aaatttacca    2520
ctcgggtagt tcacattaaa attattgtct agctttatta caagcaacat gaaaatttcg    2580
ataccccaag gcctgagttt ggcagcacta taactctgtt gccctgtttt gtcttgaaaa    2640
gtataatatc acttaacagg acaatgctct cccgaaaaca taactgatta gtggatagag    2700
agagtggttt aggtggtgtt tggatccggg gactaaattt tagttcatgt cacatcggat    2760
gtttggacac taattagaaa tattaaacat agactaataa taaaatttag tcccaataga    2820
taattgactg gttacttcat attcattgcc cagagctgcc tcattaaatg ttgtctgttc    2880 tgtgcttttct tggatcttga attaaaagac gtctgtacag ggtaccacac tcaagggat    2940 cacaattcag aaagtttccc tttattggtc tgcagtaaat gattccatcg tatagaaaag    3000
aacaaaagca attaatgctg tgccatatca tgggagaagc taaggaccca tctagaacag    3060
tgaacttttg ttgaacagca tctgtcagtt taaaaatcta ggtggtcatc attcatcaaa    3120
taagtggtgc tagtgctact attgcacacg ttatgtttaa atcctcttgt caactgtgtc    3180
aacaagtggt tgaaaacttc ttttggggg ttttgagtta taaaaatgga ggtgcaattt    3240
caaattgttt ttttagttca gatacaattg ccgacgtctt tctgtggatc aaaaaaatga    3300
cagatgtatt gtaccaacct gctatggttt taggggagat acggttcaag ttgacacatg    3360
ggttgctgct gctggcaaaa atggcatgcg tcgagactgg catgttcgtg actacaactc    3420
tggccgaaca atcttgagag ctacaaggtt tgggcttcaa ctttattcta ttgcaagaat    3480
catctgtatc gttttttta tgaggatatc caatcttggt atttctgctt gatcacatca    3540
ttgataattg ctaattgtgc tccttttcca atcctttctt gcagtgtttg ggtgatgatg    3600
cacaagaaaa ctagaagact ttcaaaaatg ccagatgaag ttagagctga aataggccca    3660
tatttcaatg accgttcagc tataacagag gagcagagtg aaaagttagc caagacagga    3720
aataaagttg gtgatgatgc tacagagcaa ttcataagaa aggggctcac tgtaagtcag    3780
ctagacatag ttacatacta aattatcatt atgcctcaac tgcaatcatt tatctaagaa    3840
```

```
aaatagtaat atttgatctc acccctcatt tattttaaat gatctttgat ggactcttgt   3900
ttactgcaac agcctagatg gggtgacctc gatgtcaatc agcatgtgaa caatgttaaa   3960
tatattgggt ggatccttga ggtggttatt cttgtccctt ttattcattg tttagagaaa   4020
aataatttgg ctttatcctt ttatatggtg gttgttaggg aaccatttta tgtagtactt   4080
gcaattattt tctagagatt ctgatctgac catctgtatt gttgatattg tcattagtct   4140
tacatctggt cagtcagaag gctttcaaac atgttttttga gttctttcta attttttccc   4200
ccagagtgct ccaatttcag tactggagaa gcatgagctt gcaagcatga ccctggatta   4260
caggaaggag tgtggtcgag acagcgtgct gcaatcactt accaccgtgt caggggaatg   4320
caccagcatt ggcgccgaca agcaggcttc tgccatccag tgcgaccatc ttcttcagct   4380
tgagtcagga gctgatattg tgaaggcaca cacagagtgg cgaccaaagc gatcgcacgc   4440
agcagctgag aacgcgtaaa caaacaaacc gacgaaaatc tgtgggaggg agaatatcaa   4500
acttcccttg cctctgttgc cctgaagctt atcttgaagt gtgagttgta ttctgtaaaa   4560
aattagtagt ttccatagtg tgaggttgga ggggaggtgt tggtgcttgc ctactgtacc   4620
tgctacatct attatttctt gattctttgt tcgcttttttt ttttcttttt tgttttttaac  4680
ccctgtggag ataagacagg ttttgaagtg tggaagaggt tgtttcaatc gtctaattga   4740
ttcaactatt cagcaagtaa actgctccat ggaatttcat cgtttggttg gagcctgag    4799
```

<210> SEQ ID NO 7
<211> LENGTH: 4753
<212> TYPE: DNA
<213> ORGANISM: Oryza sativa

<400> SEQUENCE: 7

```
cgcgtcgtgt gagttggcga gcccgaggag cggaggcggc cacaagtcta atccgcgtcg     60
tctgcgcgtt cgtgggcgag gaggagaaag aagaggagga agagagggaa gggggcttga    120
tttgatttgg gcgcgtctcg tggagtatcc ggtgagttct ggcgatctg gcgaggcgag     180
tgatgagtga ttcctgctgc tgctggggga ttttggcgtg attttcgttg gttgcatttt    240
gtttcttttt ttttgtatcg atttgttgga gctttattcg gtagatctgg tcgattccat    300
ggtgagttgt atcggcgccg gagtgatagc tgattctgtt ttttttgtgtg attttttttt     360
tgttttggaa atagggtttg tgtcgaattg agggcatttt ttttccttag gcaatgcagg    420
atttcgtttt gtatgttttt gcgtggaatg gatatgaaca gacctcgaac aaatggaaga   480
atttgtatttt tgtatgatgg attgcaatgc gatacttgtt ttggggcgtg attcgattga    540
aataaatgaa atattagagt tattttggga ttcctgtttg ctgcgccttt tttttagca    600
tttcttgata tgaacaagag aagaagggct gaattttttt cttagctttg gaggcattta   660
ctgtcccagt attttctcct accggaagca gaatattttg tttgattgga gggttgcctc   720
cctttgccaa attgaatcaa atgttctcgg atgttttaaa atttccgtgg actcttttttg    780
ccccagggga gaccgctttt agcagctgga tcccgtgttt tcatttcaag ttcttgtttt    840
cctagtctcc atatatttct gattgttaac tcgtattctc tacctcacat atgcaaaatc   900
acacttgcgt cgttctgtaa ttagttagat tctgcaagaa aaatccggaa ttttcaagca   960
tgctagtagt tttaaattga tgccatgttt tttagacaat gttaattgat gccatatgac   1020
tataggacac attatattgc gtttctgaat ataccacctc atgaaactca taattttgtt   1080
gattaattgt tcaggttgcc ccttctagtg tgtaacttgg agcaaatttg gaccctgaga   1140
cgcaaatcag tcatggctgg ttctcttgcg gcgtctgcat tcttccctgt cccagggtct   1200
```

```
tcccctgcag cttcggctag aagctctaag aacacaaccg gtgaattgcc agagaatttg   1260
agtgtccgcg gaatcgtcgc gaagcctaat ccgtctccag gggccatgca agtcaaggcg   1320
caggcgcaag ccccttcctaa ggttaatgga accaaggtta acctgaagac tacaagccca   1380
gacaaggagg atataatacc gtacactgct ccgaagacat tctataacca attgccagac   1440
tggagcatgc ttcttgcagc tgtcacgacc attttcctgg cagctgagaa gcagtggact   1500
ctgcttgact ggaagccgaa gaagcctgac atgctggctg acacattcgg ctttggtagg   1560
atcatccaag acgggctggt gtttaggcaa aacttcttga ttcggtccta cgagattggt   1620
gctgatcgta cagcttctat tgagacatta atgaatcatt tacaggtgat acaatggagc   1680
tatgctgctt tagcttttct tccgtatttt tcactattgg tacattatgt tcgtggcata   1740
ctaactgtaa tttgaagctt tgcaggaaac agctctgaac catgtgaaaa ctgctggtct   1800
cttaggtgat ggttttggtg ctacgccgga gatgagcaaa cggaacttaa tatgggttgt   1860
cagcaaaatt cagcttcttg ttgagcgata cccatcatgg tactttttct gcaatccact   1920
actctccaca tcattttctt ggatggcaaa acttctcttt ttactcttaa ttcataacat   1980
ttctttcatt cttaatggag tacttttgtc cccggtgcat ttagtgtcac aatttaatgt   2040
ttacatggta cgggaaagat ttatcactca atatccacgg tgtaatgttt ttagctaaac   2100
tcaatatcca cggtgtaatg ttttttagcta aacttgtctt cagtcctttt ttcctttttc   2160
cctatgtttg tgtgctgtgg cattcgatgg atcatcgaga ctctgagtag acgtagattc   2220
ttgcattcct tatgcgacat gaggcacatg ttcgagtgtt tatcacccta catgaaaacc   2280
tttccctact aagttgctgc ttctattgtt ctgcagatat aagcaatatt ttgcctatt   2340 tttcctgtgc tttgaacttc tcgtaggttc atggcccaca accttagca ggcatagtgc   2400 cttgaaatgg agtattacac tcaaaagcat aacaataaca tgtattgcct tgtatgataa   2460
gatgagtgat agatcttttg aaatcattta ctgaggaaaa cgtttgttta tttgacaaga   2520
caatgtattg atgaactaga actgctctat taagtggtat ctgccctgtg tctccttcg   2580 tacaaattgt tgcacccctg ttcatgttac ttctcacttt tcaccatggc aggcatgttt   2640
agaaaatcat ttgattttac agggcattac catgtgaccc cttaataact aacaaatata   2700
ttttgggtcc accaaatctg tggtggatgg aaagggaaat taataaacac aaatggaaaa   2760
ttcttcattg tgaaacgtga taaggacaaa ttttgtgaat aaataaagta acaaaaaatg   2820
gctagtattt gcctacatat agagtacacc tcaagagatc agaaaagttg cctttattga   2880
tggagtaatt gaattagtag taagcaataa attctgtgga cctaggggac atccctgatc   2940
tagatcgagt tttgatctca tgctacattt aatcttccat gtcagcaact ttcagtacct   3000
gctattaaat ttcccctgtt cttctgacga ttgatgcaat tttaagttta tgagaaggaa   3060
aacggtctgc tgtttttgaa ttctgaatgt agtttacaca atttctcata ggctgaaatt   3120
ttggttgcaa atttttaggg gagatatggt ccaagttgac acatgggtag ctgctgctgg   3180
caaaaatggc atgcgtcgag attggcatgt tcgggactac aactctggtc aaacaatctt   3240
gagggctaca aggtttgtgt ttatcgtttg catttgttgc atttcttttg tttcatgctg   3300
tttaccagca tgttttattc cttttcgatt gctaattgtt cctctcttgt ttgcagtgtt   3360
tgggtgatga tgaataagaa cactagaaga ctttcaaaaa tgccagatga agttagagct   3420
gaaataggcc cgtatttcaa tggccgttct gctatatcag aggagcaggg tgaaaagttg   3480
cctaagccag ggaccacatt tgtgcttgtt accgtcattc attttgctgg tggttctcat   3540
gcataaaatt tctcatgagg gatccttttgt tcatgtcagc cgaagtggag tgaccttgat   3600
```

| | |
|---|---:|
| gtcaaccagc atgtgaacaa tgtgaagtat attggttgga tacttgaggt aacttctttt | 3660 |
| tccttttctc tatccgaaca tgctatctct agatcagaaa agagagtgtc tgatcgtaat | 3720 |
| tagtaaccta gttcctagtc atatgccaag ctgtaaaaac acttgcactg tatattcaaa | 3780 |
| agctattcaa atttctgagt acgttttgtt ttttttttcct cagagtgctc caatttcgat | 3840 |
| actggagaag cacgagcttg caagcatgac cttggattac aggaaggagt gtggccgtga | 3900 |
| cagtgtgctt cagtcgctta ccgctgtttc aggtgaatgc gatgatggca acacagaatc | 3960 |
| ctccatccag tgtgaccatc tgcttcagct ggagtccgga gcagacattg tgaaggctca | 4020 |
| cacagagtgg cgaccgaagc gagctcaggg cgaggggaac atgggctttt cccagctga | 4080 |
| gagtgcatga gcgcttctgt agtttatccg gcaagtaacc tctttgagaa gtgcagattc | 4140 |
| taacttggct agcaacacag gacaaatgat tgttggtggg aaatttggca tgccgagcct | 4200 |
| gggttttgtg atgcacacag cacacattca gatttgaaga ttgagagatg cttcttattg | 4260 |
| gcagcttgtt cagaaagatg actaagcggt ttgggataaa atcagctgat tgggaaacat | 4320 |
| tagcaggatg ataagcatga ctggtggtac caatgaaaag ggttgaaatc ctttgcattg | 4380 |
| ttcatttgtt gtggagcaag agtggccgca gttgcttatc acacaggatg atggaggtgt | 4440 |
| ttgtgtgaag cttattgctg aagctggatt gttttgacc tgtgtttcta aaagaaaagg | 4500 |
| gaaaagaaga agctgtggat tgaggccgga gcagcagaga tattacaatc gacatagata | 4560 |
| aataagatgt aatactaatt tagcccaggt ggttgtgtg tggagatgca atccattgta | 4620 |
| gtaacagcct aacttgtaca ttcttgccat ctttttctta ttaattgaat gaatgaatcg | 4680 |
| cagacctcct gcgttttcat caataattga aatgacttct gcttcatcaa gaattgaatg | 4740 |
| aattgtctgt ctg | 4753 |

<210> SEQ ID NO 8
<211> LENGTH: 4441
<212> TYPE: DNA
<213> ORGANISM: Oryza sativa

<400> SEQUENCE: 8

| | |
|---|---:|
| gcgatgcgag cctgtgttga cagcggagaa agcagtgtaa tccggtcccg ccaccgcagc | 60 |
| cgcctccacc tctcttcccg cgccaatggg ccgcgtcgtg aagcgcagca gcagcagcag | 120 |
| cagcggagac agcggcagaa gctttgccta aggtcggttt gcctcccgc ctccgccgca | 180 |
| ttccggttgg agttttgtcc gtgttcgtcg gcggtttctt ggctggccgg atgaattgtt | 240 |
| gtggggaggg ggaggggag gggctctctc acgcactcgc tgctggattt cggttaggtt | 300 |
| tcgcggctgg gggaatcgcg ggggaattca ggatctttgt tttgttagtt cttctttcgg | 360 |
| gcggggttgg atctcgagta atctgcgtcg tgttatttgc cgcgagattt gggtgttttt | 420 |
| tttcttctct ccgcatcttc tctctcgttc cttcgtctgt acggtctagt ggtggtctac | 480 |
| gggctacggc cgtggtaaaa gtttctctag attttggtc tcgttttttt ctttattta | 540 |
| ggcggcttgc tttgcttcgc ctgctttgac gtttgaccag cggtttatcc tcgattattc | 600 |
| ttcctcgtga gtcgtgagca agctatgatt tgcagctaat gattttgtg cttggattag | 660 |
| ataaaagatg cttctcactc ttcgtttgtt tccattttct ggaatttgtg atttcctggt | 720 |
| gatgataatg ttgtgctcgt gttgattcag gttgggatcc tccctattcg cgcgcgtctt | 780 |
| tgatttggcg cgtaaagttg taatccgtac tccggatggc cggctcaatc gccgcctcgg | 840 |
| cgttcttgcc ggggtcgccg gcggccgcgc cgcccaagag cgtcctgggc gagcgcccgg | 900 |
| acagcctgga cgtccgcggc atcgccgcga agccgggctc ctcgtcgtcg gccgccgccc | 960 |

```
tgagggccgg caagacgcgc acccacgccg ccatccccaa ggtgaacggc ggcagttcgg   1020
cgctggcgga tccggagcac gacacgatgt cctcctcctc ctcctccgcg gcgccgagga   1080
cgttctacaa ccagctcccc gactggagca tgctcctcgc agccatcacg accatcttct   1140
tggccgcgga gaagcagtgg acgctgctgg actggaagcc gaagcggccc gacatgctca   1200
ccgacacgtt cggtttcggc aggatgatac atgaggggct catgttcagg cagaacttct   1260
cgattaggtc ctatgagatc ggggccgata ggacggcgtc tatagaaacg ctgatgaacc   1320
atttgcaggt gaaatattgt gaattttcag gcgtcggatt gctcgggctg gcatcagaa    1380 cattgaaatg ttttttggttt tgatgcagga aaccgcactg aatcatgtga agagcgctgg   1440
gctgctagga gatggttttg gctcaacgcc agagatgagt aaacgagact tgttctgggt   1500
tgtcagccaa atgcaggcaa tcgttgagcg ttatccgtgc tggtataata ctataatttc   1560
acatatcagc atgttcttgg ttttgttttc ttacatagtt tgagctccaa atagggtgtt   1620
gcttttctgc tttcgtgtta catgacaatt aggaggcaca tagatgtatg gttggctgtc   1680
acagtacgtt actgtagtta tagtagctat catcttgctt cacagcagtc atggaataac   1740
aggtttaggt aaatggagtt ttcaagttgt ttggcaatga atatgaaaaa gattttccca   1800
agtgtttgta tcaattttaa atggatgagc aactcccatc tcttaactgt ttttgctatc   1860
ggcattaaat atttgtgcaa ctggtagact ttcagtaaac gatgatgatg cagaagcctc   1920
ctgtgctctt aatattattg atcatgtatc atattttctg tgagatgtta taattgttcg   1980
tgtttgttac ctgaaagtgc catgttgcca ataattaact tcttatctgt gtgcaggggt   2040
gatactgtcg aagtagatac atgggttggt gctcatggta aaaatggaat gcgcagagac   2100
tggcatatac gtgattctgt aacaggccat acaatattga aggctacaag gtttgaatta   2160
ttgtcactct cataaatact gatgatcatg aaaactgtat tagcatctgc tattcaactt   2220
cctacccatc ttattaccac tgtttgcata tgaagtctag aagttctgtt tcttctgaac   2280
atattataag ctgccttaca gcaacatgaa gctacctatt tgtcctaatt gtttgctcaa   2340
tgtgcagtaa atgggttatg atgcacaagc ttacaaggag gctagcaaga attcctgatg   2400
aagtacgtac tgaaatagag ccatactttt ttgagcatgc ttctattgta gatgaagaca   2460
accagaaact tccaaaactg ccagatattg aaggtgctaa tgtagccaaa tatgtccgga   2520
caggcctgac tgtaagtttt gtggaattat acaagattac agtttacaag tatacaaaat   2580
gtgcatgttt ttctttcatt ttttacatct tcttctgtct cataatgcag ccacgatggg   2640
ccgaccttga tatcaatcag catgttaata acgttaaata catagggtgg atcctagagg   2700
taaaaaaagt tcccctatta tgttcatctt tattgccctt gctaacacct cttgcctaga   2760
tgattcttga gggaaaaaaa tgcttcttga agttcagtat gttactttca gaaaaaatat   2820
ccatttgttt ttatttactg taaacactcc atggagttgc tgttaggcat ctttgtcgcg   2880
gtattcatta ttaagttgtc acatggtgga gcataacttt tgtgttgcttt acttgccttt   2940 ttctctttgg gcatacattt agtactattg atggtgctac ataattcaaa gagattcatt   3000
tatctcgcta tatttcccat atgttatgtt ccaagaattt gggaataaac agtaatcaga   3060
agagtactgg atttgtaggt actttatttt ttgtgtgtgt gtgtggggggg gggggggggc   3120 tcagatcatg cctatgatta ggcattactg taggagttta gataaacttg gtcaaggtcc   3180
caaaagggtg tgcctatggt tctacaagtg tccacctaac tttatcctca agcacgcaac   3240
cacttatctg gcagctttgt actctttcaa gctatacgaa aaatatcgtg tgcactagtt   3300
ggagaagtaa tgtatcctag cagattttac tacattaggt tggtcaccta cgtacctaac   3360
```

| | |
|---|---|
| cctgtacgct tgttgcttcc gataaagagc ttggctggaa tacttatatg caatttgatc | 3420 |
| acaagtcatt cacttaattc aattttttt agagtgatca acacctgcat ataatgcata | 3480 |
| tttgcctggt tgacaatctg ccgtgtgtat gtgtgttttg gaagaagggg aggggtagtc | 3540 |
| atgtatgtat ttatccagtg gaccacataa tgaggaaaaa gaaattgttc aggtgacctg | 3600 |
| caacctagat gggcccaaaa caacccaaaa tattagggaa attaacactt caggcatttc | 3660 |
| ctaacataca gaatatttta ttaccaacat gcgcacatgt tgcttaaccc tacctttttg | 3720 |
| tccttttttc ccctcagagc gcaccaatct ccattctgga gaaacatgag ctggcaagta | 3780 |
| ttgtcctgga ttacaagagg gagtgtggcc gagacagcgt gctgcaatca cacactaccg | 3840 |
| tgtacactga ctgcaacaag cactctggac aaaccacttt gcactgtgag catttgctga | 3900 |
| gcctggaatc aggacctacc atcgtcaagg ccaggaccat gtggaggcca aaaggaacca | 3960 |
| ggccccaaga gagtatcatt ccgtcttcgt cgtgaagcgc gtaaaatctt tcatgtgttg | 4020 |
| attttggtag caacaacttg gttaaaccaa ggacaagtgg acaacaactt gtgttctcta | 4080 |
| tggaaaggca aaacctggat gaacataacg acggggacga agttattta cagacaaaat | 4140 |
| gtatggattt ggaggagttc aaaagagggg gggggggggg gggcaagat ggaggtaaaa | 4200 |
| tgcagaaaag acagaaggcg tattgtgcat gatttgttgt ttcagctttt ccttctattt | 4260 |
| ttcctttcct tagcaaagat attcaattac acagatgggt gttgtaagta ttgaaattgt | 4320 |
| agctactgct gtacaatggg aagtgaaatg cttctcatgc atgtttctgt ctgggctatg | 4380 |
| tctatattat gagccctcga aagcagattg cctggtccga attgtttgaa attttaagtt | 4440 |
| t | 4441 |

<210> SEQ ID NO 9
<211> LENGTH: 1284
<212> TYPE: DNA
<213> ORGANISM: Oryza sativa

<400> SEQUENCE: 9

| | |
|---|---|
| atggctggtt ctcttgcggc gtctgcattc ttccctgtcc cagggtcttc ccctgcagct | 60 |
| tcggctagaa gctctaagaa cacaaccggt gaattgccag agaatttgag tgtccgcgga | 120 |
| atcgtcgcga agcctaatcc gtctccaggg gccatgcaag tcaaggcgca ggcgcaagcc | 180 |
| cttcctaagg ttaatggaac caaggttaac ctgaagacta aagcccagaa caaggaggat | 240 |
| ataataccgt acactgctcc gaagacattc tataaccaat gccagactg gagcatgctt | 300 |
| cttgcagctg tcacgaccat tttcctggca gctgagaagc agtggactct gcttgactgg | 360 |
| aagccgaaga agcctgacat gctggctgac acattcggct ttggtaggat catccaagac | 420 |
| gggctggtgt ttaggcaaaa cttcttgatt cggtcctacg agattggtgc tgatcgtaca | 480 |
| gcttctattg agacattaat gaatcattta caggaaacag ctctgaacca tgtgaaaact | 540 |
| gctggtctct taggtgatgg ttttggtgct acgccgaga tgagcaaacg gaacttaata | 600 |
| tgggttgtca gcaaaattca gcttcttgtt gagcgatacc catcatgggg agatatggtc | 660 |
| caagttgaca catgggtagc tgctgctggc aaaaatggca tgcgtcgaga ttggcatgtt | 720 |
| cgggactaca actctggtca aacaatcttg agggctacaa gtgtttgggt gatgatgaat | 780 |
| aagaacacta gaagactttc aaaaatgcca gatgaagtta gagctgaaat aggcccgtat | 840 |
| ttcaatggcc gttctgctat atcagaggag cagggtgaaa agttgcctaa gccagggacc | 900 |
| acatttgatg gcgctgctac caaacaattc acaagaaaag gcttactcc gaagtggagt | 960 |
| gaccttgatg tcaaccagca tgtgaacaat gtgaagtata ttggttggat acttgagagt | 1020 |

| | |
|---|---:|
| gctccaattt cgatactgga gaagcacgag cttgcaagca tgaccttgga ttacaggaag | 1080 |
| gagtgtggcc gtgacagtgt gcttcagtcg cttaccgctg tttcaggtga atgcgatgat | 1140 |
| ggcaacacag aatcctccat ccagtgtgac catctgcttc agctggagtc cggagcagac | 1200 |
| attgtgaagg ctcacacaga gtggcgaccg aagcgagctc agggcgaggg gaacatgggc | 1260 |
| tttttcccag ctgagagtgc atga | 1284 |

```
<210> SEQ ID NO 10
<211> LENGTH: 1500
<212> TYPE: DNA
<213> ORGANISM: Oryza sativa

<400> SEQUENCE: 10
```

| | |
|---|---:|
| tcatggctgg ttctcttgcg gcgtctgcat tcttccctgt cccagggtct tccctgcag | 60 |
| cttcggctag aagctctaag aacacaaccg gtgaattgcc agagaatttg agtgtccgcg | 120 |
| gaatcgtcgc gaagcctaat ccgtctccag gggccatgca agtcaaggcg caggcgcaag | 180 |
| cccttcctaa ggttaatgga accaaggtta acctgaagac tacaagccca gacaaggagg | 240 |
| atataatacc gtacactgct ccgaagacat tctataacca attgccagac tggagcatgc | 300 |
| ttcttgcagc tgtcacgacc attttcctgg cagctgagaa gcagtggact ctgcttgact | 360 |
| ggaagccgaa gaagcctgac atgctggctg acacattcgg ctttggtagg atcatccaag | 420 |
| acgggctggt gtttaggcaa aacttcttga ttcggtccta cgagattggt gctgatcgta | 480 |
| cagcttctat tgagacatta atgaatcatt acaggtgat acaatggagc tatgctgctt | 540 |
| tagctttttct tttgaagctt tgcaggaaac agctctgaac catgtgaaaa ctgctggtct | 600 |
| cttaggtgat ggttttggtg ctacgccgga gatgagcaaa cggaacttaa tatgggttgt | 660 |
| cagcaaaatt cagcttcttg ttgagcgata cccatcatgg atttctcata ggctgaaatt | 720 |
| ttggttgcaa atttttaggg gagatatggt ccaagttgac acatgggtag ctgctgctgg | 780 |
| caaaaatggc atgcgtcgag attggcatgt tcgggactac aactctggtc aaacaatctt | 840 |
| gagggctaca ttgcagtgtt tgggtgatga tgaataagaa cactagaaga cttttcaaaaa | 900 |
| tgccagatga agttagagct gaaataggcc cgtatttcaa tggccgttct gctatatcag | 960 |
| aggagcaggg tgaaaagttg cctaagccag ggaccacatt tgatggcgct gctaccaaac | 1020 |
| aattcacaag aaaagggctt actgtaagtc taaaatttct catgagggat cctttgttca | 1080 |
| tgtcagccga agtggagtga ccttgatgtc aaccagcatg tgaacaatgt gaagtatatt | 1140 |
| ggttggatac ttgaggtaac ttctttttcc ttttctctat ccgaacatgc tatctctaga | 1200 |
| tctgagtacg ttttgttttt ttttcctcag agtgctccaa tttcgatact ggagaagcac | 1260 |
| gagcttgcaa gcatgacctt ggattacagg aaggagtgtg gccgtgacag tgtgcttcag | 1320 |
| tcgcttaccg ctgtttcagg tgaatgcgat gatggcaaca cagaatcctc catccagtgt | 1380 |
| gaccatctgc ttcagctgga gtccggagca gacattgtga aggctcacac agagtggcga | 1440 |
| ccgaagcgag ctcagggcga ggggaacatg ggcttttttcc cagctgagag tgcatgagcg | 1500 |

```
<210> SEQ ID NO 11
<211> LENGTH: 1278
<212> TYPE: DNA
<213> ORGANISM: Oryza sativa

<400> SEQUENCE: 11
```

| | |
|---|---:|
| atggcagggt ctcttgccgc ctcagcattc ttcccaggtc caggctcatc tcctgcagca | 60 |
| tcagctagaa gctccaagaa tgctgctgtt accggcgaat tgccggagaa tttgagtgtc | 120 |

```
cgtggcattg tcgcaaagcc taacccacct cctgcagcca tgcaagtaaa ggcacaggct      180
caaacccttc ccaaggttaa tggtacgaag gttaacctca agacggtgaa gcctgacatg      240
gaggaaacgg tgccttacag tgctccaaag acgttctata accaactgcc ggattggagc      300
atgcttcttg cggctattac aaccatcttc cttgccgcag agaagcagtg gacactgctt      360
gattggaagc caaagaaacc tgacatgctt gttgacacat ttggctttgg taggattatc      420
caggacggta tggtgtttag gcagaacttc atgattcggt cctacgagat tggtgctgat      480
cgtacagctt ctatagagac attgatgaat catttacagg aaacagctct taaccatgtg      540
aggactgctg gtcttcttgg agatggtttt ggggctacac cggagatgag caaacggaac      600
ttgatatggg ttgtcagcaa aatccagctt cttgttgagc aataccccgc atggggagat      660
acggttcaag ttgacacatg ggttgctgct gctggcaaaa atggcatgcg tcgagactgg      720
catgttcgtg actacaactc tggccgaaca atcttgagag ctacaagtgt ttgggtgatg      780
atgcacaaga aaactagaag actttcaaaa atgccagatg aagttagagc tgaaataggc      840
ccatatttca atgaccgttc agctataaca gaggagcaga gtgaaaagtt agccaagaca      900
ggaaataaag ttggtgatga tgctacagag caattcataa gaaagggggct cactcctaga      960 tggggtgacc tcgatgtcaa tcagcatgtg aacaatgtta aatatattgg gtggatcctt     1020
gagagtgctc caatttcagt actggagaag catgagcttg caagcatgac cctggattac     1080
aggaaggagt gtggtcgaga cagcgtgctg caatcactta ccaccgtgtc aggggaatgc     1140
accagcattg gcgccgacaa gcaggcttct gccatccagt gcgaccatct tcttcagctt     1200
gagtcaggag ctgatattgt gaaggcacac acagagtggc gaccaaagcg atcgcacgca     1260
gcagctgaga acgcgtaa                                                   1278

<210> SEQ ID NO 12
<211> LENGTH: 897
<212> TYPE: DNA
<213> ORGANISM: Oryza sativa

<400> SEQUENCE: 12
atggcagggt ctcttgccgc ctcagcattc ttcccaggtc caggctcatc tcctgcagca       60
tcagctagaa gctccaagaa tgctgctgtt accggcgaat gccggagaa tttgagtgtc      120 tgtggcattg tcgcaaagcc taacccacct cctgcagcca tgcaagtaaa ggcacaggct      180
caaacccttc ccaaggttaa tggtacgaag gttaacctca agacggtgaa gcctgacatg      240
gaggaaacgg tgcctcacag tgctccaaag acgttctata accaactgcc ggattggagc      300
atgcttcttg cggctattac aaccatcttc ctcgccgcag agaagcagtg gacactgctt      360
gattggaagc cgaagaaacc tgacatgctt gttgacacat ttggctttgg taggatcatc      420
caggacggta tggtgtttag gcagaacttc atgattcggt cctacgagat tggcgctgat      480
cgtacagctt ctatagagac attgatgaat catttacagg aaacggctct taaccatgta      540
aggactgctg gtcttcttgg agatggtttt ggggctacac cggagatgag caaacggaac      600
ttgatatggg ttgtcagcaa aatccagctt cttgttgagc aataccccgc atggggagat      660
atggttcaag ttgacacatg ggtcgctgct gctggcaaaa atggcatgcg tcgagactgg      720
catgttcgtg actacaactc tggccgaaca atcttgagag ctacaagtgt ttgggtgatg      780
atgcacaaga aaactagaag actttcaaaa atgccagatg aagttagagc tgaaataggc      840
ccatatttca atgaccgttc agctataaca gaggagcaga gtgaaaagtt agcctag        897
```

<210> SEQ ID NO 13
<211> LENGTH: 1284
<212> TYPE: DNA
<213> ORGANISM: Oryza sativa

<400> SEQUENCE: 13

| | | | | | |
|---|---|---|---|---|---|
| atggctggtt | ctcttgcggc | gtctgcattc | ttccctgtcc | cagggtcttc | ccctgcagct | 60 |
| tcggctagaa | gctctaagaa | cacaaccggt | gaattgccag | agaatttgag | tgtccgcgga | 120 |
| atcgtcgcga | agcctaatcc | gtctccaggg | gccatgcaag | tcaaggcgca | ggcgcaagcc | 180 |
| cttcctaagg | ttaatggaac | caaggttaac | ctgaagacta | caagcccaga | caaggaggat | 240 |
| ataataccgt | cactgctcc | gaagacattc | tataaccaat | tgccagactg | gagcatgctt | 300 |
| cttgcagctg | tcacgaccat | tttcctggca | gctgagaagc | agtggactct | gcttgactgg | 360 |
| aagccgaaga | gcctgacat | gctggctgac | acattcggct | tggtaggat | catccaagac | 420 |
| gggctggtgt | ttaggcaaaa | cttcttgatt | cggtcctacg | agattggtgc | tgatcgtaca | 480 |
| gcttctattg | agacattaat | gaatcattta | caggaaacag | ctctgaacca | tgtgaaaact | 540 |
| gctggtctct | taggtgatgg | ttttggtgct | acgccggaga | tgagcaaacg | gaacttaata | 600 |
| tgggttgtca | gcaaaattca | gcttcttgtt | gagcgatacc | catcatgggg | agatatggtc | 660 |
| caagttgaca | catgggtagc | tgctgctggc | aaaaatggca | tgcgtcgaga | ttggcatgtt | 720 |
| cgggactaca | actctggtca | aacaatcttg | agggctacaa | gtgtttgggt | gatgatgaat | 780 |
| aagaacacta | gaagactttc | aaaaatgcca | gatgaagtta | gagctgaaat | aggcccgtat | 840 |
| ttcaatggcc | gttctgctat | atcagaggag | cagggtgaaa | agttgcctaa | gccagggacc | 900 |
| acatttgatg | gcgctgctac | caaacaattc | acaagaaaag | ggcttactcc | gaagtggagt | 960 |
| gaccttgatg | tcaaccagca | tgtgaacaat | gtgaagtata | ttggttggat | acttgagagt | 1020 |
| gctccaattt | cgatactgga | gaagcacgag | cttgcaagca | tgaccttgga | ttacaggaag | 1080 |
| gagtgtggcc | gtgacagtgt | gcttcagtcg | cttaccgctg | tttcaggtga | atgcgatgat | 1140 |
| ggcaacacag | aatcctccat | ccagtgtgac | catctgcttc | agctggagtc | cggagcagac | 1200 |
| attgtgaagg | ctcacacaga | gtggcgaccg | aagcgagctc | agggcgaggg | gaacatgggc | 1260 |
| tttttcccag | ctgagagtgc | atga | | | | 1284 |

<210> SEQ ID NO 14
<211> LENGTH: 1272
<212> TYPE: DNA
<213> ORGANISM: Oryza sativa

<400> SEQUENCE: 14

| | | | | | |
|---|---|---|---|---|---|
| atggccggct | caatcgccgc | ctcggcgttc | ttgccggggt | cgccggcggc | cgcgccgccc | 60 |
| aagagcgtcc | tgggcgagcg | cccggacagc | ctggacgtcc | gcggcatcgc | cgcgaagccg | 120 |
| ggctcctcgt | cgtcggccgc | cgccctgagg | gccggcaaga | cgcgcaccca | cgccgccatc | 180 |
| cccaaggtga | acggcggcag | ttcggcgctg | gcggatccgg | agcacgacac | gatgtcctcc | 240 |
| tcctcctcct | ccgcggcgcc | gaggacgttc | tacaaccagc | tccccgactg | gagcatgctc | 300 |
| ctcgcagcca | tcacgaccat | cttccttggcc | gcggagaagc | agtggacgct | gctggactgg | 360 |
| aagccgaagc | ggcccgacat | gctcaccgac | acgttcggtt | tcggcaggat | gatacatgag | 420 |
| gggctcatgt | tcaggcagaa | cttctcgatt | aggtcctatg | agatcggggc | cgataggacg | 480 |
| gcgtctatag | aaacgctgat | gaaccatttg | caggaaaccg | cactgaatca | tgtgaagagc | 540 |
| gctgggctgc | taggagatgg | ttttggctca | acgccagaga | tgagtaaacg | agacttgttc | 600 |

-continued

```
tgggttgtca gccaaatgca ggcaatcgtt gagcgttatc cgtgctgggg tgatactgtc    660
gaagtagata catgggttgg tgctcatggt aaaaatggaa tgcgcagaga ctggcatata    720
cgtgattctg taacaggcca tacaatattg aaggctacaa gtaaatgggt tatgatgcac    780
aagcttacaa ggaggctagc aagaattcct gatgaagtac gtactgaaat agagccatac    840
ttttttgagc atgcttctat tgtagatgaa acaaccaga aacttccaaa actgccagat    900
attgaaggtg ctaatgtagc caaatatgtc cggacaggcc tgactccacg atgggccgac    960
cttgatatca atcagcatgt taataacgtt aaatacatag ggtggatcct agagagcgca   1020
ccaatctcca ttctggagaa acatgagctg gcaagtattg tcctggatta caagagggag   1080
tgtggccgag acagcgtgct gcaatcacac actaccgtgt acactgactg caacaagcac   1140
tctggacaaa ccactttgca ctgtgagcat ttgctgagcc tggaatcagg acctaccatc   1200
gtcaaggcca ggaccatgtg gaggccaaaa ggaaccaggc cccaagagag tatcattccg   1260
tcttcgtcgt ga                                                       1272
```

<210> SEQ ID NO 15
<211> LENGTH: 388
<212> TYPE: PRT
<213> ORGANISM: Oryza sativa

<400> SEQUENCE: 15

```
Met Gly Ala Gly Gly Arg Met Thr Glu Lys Glu Arg Glu Gln Gln
1               5                   10                  15

Lys Leu Leu Gly Arg Ala Gly Asn Gly Ala Ala Val Gln Arg Ser Pro
            20                  25                  30

Thr Asp Lys Pro Pro Phe Thr Leu Gly Gln Ile Lys Lys Ala Ile Pro
        35                  40                  45

Pro His Cys Phe Gln Arg Ser Val Ile Lys Ser Phe Ser Tyr Val Val
    50                  55                  60

His Asp Leu Val Ile Val Ala Ala Leu Leu Tyr Phe Ala Leu Val Met
65                  70                  75                  80

Ile Pro Val Leu Pro Ser Gly Met Glu Phe Ala Ala Trp Pro Leu Tyr
                85                  90                  95

Trp Ile Ala Gln Gly Cys Val Leu Thr Gly Val Trp Val Ile Ala His
            100                 105                 110

Glu Cys Gly His His Ala Phe Ser Asp Tyr Ser Val Leu Asp Asp Ile
        115                 120                 125

Val Gly Leu Val Leu His Ser Ser Leu Leu Val Pro Tyr Phe Ser Trp
    130                 135                 140

Lys Tyr Ser His Arg Arg His His Ser Asn Thr Gly Ser Leu Glu Arg
145                 150                 155                 160

Asp Glu Val Phe Val Pro Lys Gln Lys Ser Ala Met Ala Trp Tyr Thr
                165                 170                 175

Pro Tyr Val Tyr His Asn Pro Ile Gly Arg Leu Val His Ile Phe Val
            180                 185                 190

Gln Leu Thr Leu Gly Trp Pro Leu Tyr Leu Ala Phe Asn Val Ser Gly
        195                 200                 205

Arg Pro Tyr Pro Arg Phe Ala Cys His Phe Asp Pro Tyr Gly Pro Ile
    210                 215                 220

Tyr Asn Asp Arg Glu Arg Val Gln Ile Phe Ile Ser Asp Val Gly Val
225                 230                 235                 240

Val Ser Ala Gly Leu Ala Leu Phe Lys Leu Ser Ser Ala Phe Gly Phe
                245                 250                 255
```

```
Trp Trp Val Val Arg Val Tyr Gly Val Pro Leu Leu Ile Val Asn Ala
            260                 265                 270

Trp Leu Val Leu Ile Thr Tyr Leu Gln His Thr His Pro Ala Leu Pro
        275                 280                 285

His Tyr Asp Ser Ser Glu Trp Asp Trp Leu Arg Gly Ala Leu Ala Thr
    290                 295                 300

Val Asp Arg Asp Tyr Gly Ile Leu Asn Lys Val Phe His Asn Ile Thr
305                 310                 315                 320

Asp Thr His Val Ala His His Leu Phe Ser Thr Met Pro His Tyr His
            325                 330                 335

Ala Met Glu Ala Thr Lys Ala Ile Arg Pro Ile Leu Gly Glu Tyr Tyr
            340                 345                 350

Gln Phe Asp Pro Thr Pro Val Ala Lys Ala Thr Trp Arg Glu Ala Lys
        355                 360                 365

Glu Cys Ile Tyr Val Glu Pro Glu Asp Asn Lys Gly Val Phe Trp Tyr
    370                 375                 380

Asn Asn Lys Phe
385

<210> SEQ ID NO 16
<211> LENGTH: 362
<212> TYPE: PRT
<213> ORGANISM: Oryza sativa

<400> SEQUENCE: 16

Met Gln Arg Ser Pro Val Asp Lys Pro Pro Phe Thr Leu Gly Asp Ile
1               5                   10                  15

Lys Lys Ala Ile Pro Pro His Cys Phe His Arg Ser Val Ile Lys Ser
            20                  25                  30

Phe Ser Tyr Leu Leu His Asp Leu Ala Ile Ala Ala Gly Leu Leu Tyr
        35                  40                  45

Phe Ala Leu Val Gly Ile Pro Ala Leu Pro Ser Ile Leu Arg Leu Val
    50                  55                  60

Ala Trp Pro Leu Tyr Trp Ala Ala Gln Gly Ser Val Leu Thr Gly Val
65                  70                  75                  80

Trp Val Ile Gly His Glu Cys Gly His His Ala Phe Ser Asp Tyr Leu
                85                  90                  95

Leu Leu Asp Asn Leu Val Gly Leu Val Leu His Ser Ala Leu Leu Thr
            100                 105                 110

Pro Phe Phe Ser Trp Lys Tyr Ser His Arg Arg His His Ala Asn Thr
        115                 120                 125

Gly Ser Met Glu Lys Asp Glu Val Tyr Val Ala Lys Lys Lys Ser Ala
    130                 135                 140

Leu Pro Trp Tyr Thr Pro Tyr Val Phe Gly Asn Pro Val Gly Arg Leu
145                 150                 155                 160

Val Tyr Ile Ala Leu Gln Leu Thr Leu Ala Trp Pro Leu Tyr Leu Ala
                165                 170                 175

Phe Asn Leu Ser Gly Gln Pro Tyr Pro Arg Leu Val Thr Cys His Tyr
            180                 185                 190

Asp Pro Tyr Ser Pro Leu Phe Ser Asp Gln Glu Arg Val Gln Val Leu
        195                 200                 205

Val Ser Asp Ala Ala Ile Leu Ala Val Leu Ala Leu His Arg Leu
    210                 215                 220

Thr Ala Ala Tyr Gly Leu Trp Trp Val Val Arg Val Tyr Gly Val Pro
225                 230                 235                 240
```

```
Val Met Ile Val Gly Ala Leu Phe Val Leu Ile Thr Tyr Leu His His
            245                 250                 255

Thr His Arg Ala Leu Pro His Tyr Asp Ser Ser Glu Trp Glu Trp Leu
        260                 265                 270

Arg Gly Ser Leu Ala Thr Val Asp Arg Asp Tyr Gly Val Leu Asn Arg
            275                 280                 285

Val Leu His Asn Val Thr Asp Thr His Val Leu His Leu Phe Pro
        290                 295                 300

Ser Met Pro His Tyr His Ala Met Glu Ala Thr Arg Ala Ala Arg Pro
305                 310                 315                 320

Val Leu Gly Glu Tyr Tyr Lys Phe Asp Arg Thr Pro Ile Ile Glu Ala
            325                 330                 335

Thr Trp Arg Glu Ala Lys Glu Cys Met Tyr Val Glu Pro Arg Glu Arg
            340                 345                 350

Asp Gly Ile Tyr Trp Tyr Asn Asn Lys Phe
            355                 360

<210> SEQ ID NO 17
<211> LENGTH: 390
<212> TYPE: PRT
<213> ORGANISM: Oryza sativa

<400> SEQUENCE: 17

Met Gly Thr Ser Ser Arg Pro Thr Thr Val Lys Glu Gly Lys Lys Leu
1               5                   10                  15

Glu Ala Pro Arg Arg Ala Gly Ser His Ala Ala Val Lys Arg Ser Pro
            20                  25                  30

Val Asp Lys Pro Pro Phe Thr Leu Gly Asp Ile Arg Lys Ala Ile Pro
        35                  40                  45

Pro His Cys Phe His Arg Ser Val Ile Lys Ser Phe Ser Tyr Leu Leu
    50                  55                  60

His Asp Leu Ala Ile Ala Ala Gly Leu Leu Tyr Phe Ala Leu Val Val
65                  70                  75                  80

Ile Pro Ala Leu Pro Gly Val Leu Arg Leu Val Ala Trp Pro Phe Tyr
                85                  90                  95

Trp Ala Ala Gln Gly Cys Phe Leu Phe Gly Val Trp Ile Ile Ala His
            100                 105                 110

Glu Cys Gly His His Ala Phe Ser Gly His Ala Leu Leu Asp Asp Thr
        115                 120                 125

Leu Gly Leu Val Leu His Ser Trp Leu Leu Ala Pro Tyr Phe Ser Trp
    130                 135                 140

Lys Tyr Thr His Gln Arg His His Ser Asn Thr Ser Ser Gln Glu Arg
145                 150                 155                 160

Asp Glu Val Phe Val Pro Arg Phe Lys Ser Asp Leu Pro Trp Tyr Ser
                165                 170                 175

Pro Tyr Val Tyr Lys Tyr Asn Asn Pro Val Ala Arg Leu Leu Leu Leu
            180                 185                 190

Val Val Gln Leu Thr Val Gly Trp Pro Met Tyr Leu Val Phe Asn Thr
        195                 200                 205

Trp Gly Arg Gln Tyr Pro Arg Phe Ala Ser His Phe Asp Pro Ser Gly
    210                 215                 220

Pro Ile Tyr Lys Gly Arg Glu Arg Val Phe Ile Ala Ile Ser Asp Ile
225                 230                 235                 240

Gly Met Leu Ala Val Ser Leu Ala Leu Tyr Arg Leu Ala Glu Gly Tyr
                245                 250                 255
```

```
Gly Phe Trp Trp Val Val Arg Val Tyr Gly Val Pro Leu Leu Val Val
                260                 265                 270

Asn Ala Trp Leu Val Val Val Thr Tyr Leu His His Thr His Arg Ala
            275                 280                 285

Ile Pro His Tyr Asp Ser Ser Glu Trp Asp Trp Leu Arg Gly Ala Leu
        290                 295                 300

Ala Thr Val Asp Arg Asp Tyr Ser Phe Leu Asn Arg Val Phe His Asn
305                 310                 315                 320

Ile Thr Asp Thr His Val Val His His Leu Phe Pro Thr Ile Pro His
                325                 330                 335

Tyr His Ala Val Glu Ala Thr Lys Ala Ile Arg Pro Ile Leu Gly Glu
            340                 345                 350

Tyr Tyr Gln Phe Asp Pro Thr Pro Ile Val Lys Ala Ile Trp Arg Glu
        355                 360                 365

Ala Lys Glu Cys Ile Tyr Ile Gln Ser Glu Asp His Lys Gly Val Phe
370                 375                 380

Trp Tyr Ser Asn Lys Phe
385                 390

<210> SEQ ID NO 18
<211> LENGTH: 223
<212> TYPE: PRT
<213> ORGANISM: Oryza sativa

<400> SEQUENCE: 18

Met Ala Gly Gly Arg Arg Trp Gly Gly Trp Arg Glu Gln Glu Pro Pro
1               5                   10                  15

Arg Arg Ala Gly Ser Ser Ala Ala Val Gln Arg Phe His Arg Ser Val
            20                  25                  30

Ile Lys Ser Phe Ser Tyr Leu Leu Arg Asp Val Ala Ile Ala Ala Gly
        35                  40                  45

Leu Leu Asn Phe Ala Leu Val Gly Ile Pro Val Leu Pro Ala Gly Val
    50                  55                  60

Leu Arg Pro Pro Arg Arg Leu Ala Val Leu Leu Gly Arg Ala Gly Leu
65                  70                  75                  80

Leu Pro Val Arg Gly Val Asp His Arg Ala Arg Val Arg Ala Pro Arg
                85                  90                  95

Ala Pro Arg Arg His Pro Arg Ser Gly Pro Ala Leu Val Ala Ser Gly
            100                 105                 110

Thr Ile Leu Leu Val Glu Ile Gln Pro Pro Ala Ala Pro Leu Gln His
        115                 120                 125

Gln Leu Thr Gly Ala Arg Arg Gly Val Arg Pro Gln Val Gln Val Arg
    130                 135                 140

Ser Ala Val Glu Leu Pro Val Arg Val Gln Val Gln Gln Arg Pro Val
145                 150                 155                 160

Ala Arg Leu Leu Leu Leu Gly Met Gln Leu Thr Val Gly Trp Pro Met
                165                 170                 175

Tyr Leu Val Phe Asn Thr Trp Gly Arg Trp Tyr Pro Arg Phe Ala Ser
            180                 185                 190

His Phe Asp Pro Ser Gly Ala Ile Tyr Met Arg Arg Glu Arg Val Phe
        195                 200                 205

Ile Ala Ile Ser Asp Ile Gly Met Leu Ala Val Ser Leu Ala Leu
    210                 215                 220
```

```
<210> SEQ ID NO 19
<211> LENGTH: 1267
<212> TYPE: DNA
<213> ORGANISM: Oryza sativa

<400> SEQUENCE: 19
acggtggtgg aggggaagaa acaggagcta ctactccgcc gttccggcag cagcgcagcc    60
atgcagcgct caccggtgga caaaccgccg ttcacgctgg ggacataaa gaaggccatc    120 ccgccgcact gcttccaccg ctccgtgatc aagtcattct cctacctgct ccacgacctt    180
gccatcgccg ctggcctcct ctactttgct ctggtcggca tccctgccct cccaagcatc    240
ctccgcctcg tcgcctggcc gctctactgg gccgcgcagg gcagtgtact caccggcgtg    300
tgggtcatcg ggcacgagtg tggccaccac gccttctcgg actacttgct cctcgacaac    360
ctcgtgggcc tagtgctcca ctcggcgctt ctcacgccct tcttctcgtg gaagtacagc    420
caccggcggc accacgccaa caccggctcc atggagaaag acgaggtgta cgtcgcgaag    480
aagaagtccg cgctgccgtg gtacacccccg tacgtgttcg gcaaccccgt cgggcggctg    540
gtgtacatcg ccctgcagct caccctcgcg tggccactct acctcgcgtt caacctgtcc    600
gggcagccgt acccacgcct cgtcacctgc cactacgacc cctacagccc gctgttcagc    660
gaccaggagc gcgtccaagt cctcgtctcc gacgccgcca tcctggccgt gctgctcgcg    720
ctgcacaggt tgacggcggc gtacgggctc tggtgggtgg tgcgcgtgta cggcgtgccg    780
gtgatgatcg tgggcgcgct gttcgtgctc atcacgtacc tgcaccacac ccaccgggcg    840
ctcccgcact acgactccag cgagtgggag tggctgcgtg gctcgctcgc caccgtcgac    900
cgcgactacg gcgtcctcaa ccgcgtgctg cacaacgtca cggacacgca cgtcctccac    960
cacctcttcc ccagcatgcc acactaccac gccatggagg ccaccagggc agcgaggccc    1020
gtcctcggtg agtactacaa gtttgaccgc acgcccatca tcgaggcaac atggcgtgag    1080
gccaaggagt gcatgtacgt tgagcccagg gagcgcgatg gtatctactg gtacaacaac    1140 aagtttttagc tacagacagg ggatgagatt aagatatgat tataagtttt atatacttgg    1200
gtatgtcact gcttctgaat aaatatggtg ctggtctcac aataattaat taaggggacc    1260
ggccaac                                                                1267

<210> SEQ ID NO 20
<211> LENGTH: 1491
<212> TYPE: DNA
<213> ORGANISM: Oryza sativa

<400> SEQUENCE: 20
cctcctctcc tcctccctg cacagaccac tcgtttcctc cacaaagagg gagggaacaa    60
gggaagggtg tcgcccgccc cccaccccga tctgcctccg ccgctccgct cctccgcgcc    120
tgcgaaatct accaacgcta actcagcaag atgggtgccg gcggcaggat gacggagaag    180
gagcgggagg agcagcagaa gctgctcggc cgcgccggca atggcgcggc cgtgcagcgg    240
tcgccgacgg acaagccgcc gttcacgctg gggcagatca agaaggccat cccgcctcac    300
tgcttccagc gctcggtgat caagtccttc tcctacgtgg tccatgacct cgtgatcgtc    360
gccgcgctgc tctacttcgc gctggtcatg atccccgtgc tgccgagcgg gatggagttc    420
gcggcatggc cgctctactg gatcgcgcag ggctgcgtgc tcaccggcgt gtgggtcatc    480
gcgcacgagt gcggccacca tgccttctcc gactactcgg tgctcgacga catcgtcggc    540
ctcgtgctgc actcgtcgct gctcgtcccc tacttctcgt ggaagtacag ccaccgcgc    600
```

| | |
|---|---|
| caccactcca acaccgggtc gctggagcgc gacgaggtgt tcgtcccgaa gcagaagtcg | 660 |
| gcgatggcgt ggtacacccc gtacgtgtac cacaacccga tcggccggct ggtgcacatc | 720 |
| ttcgtgcagc tcaccctcgg gtggccgctg tacctggcgt tcaacgtgtc cggccgcccg | 780 |
| tacccgcgct tcgcgtgcca cttcgacccc tacggcccga tctacaacga ccgggagcgc | 840 |
| gtccagatct tcatctccga cgtcggcgtc gtgtccgcgg ggctcgccct gttcaagctg | 900 |
| tcgtcggcgt tcgggttctg gtgggtggtg cgcgtctacg gcgtgccgct gctgatcgtg | 960 |
| aacgcgtggc tggtgctcat cacctacctg cagcacaccc accecggcgct gccgcactac | 1020 |
| gactcgagcg agtgggactg gctccgcggc gcgctggcca ccgtggaccg cgactacggc | 1080 |
| atcctcaaca aggtgttcca caacatcacg gacacgcacg tcgcgcacca cctcttctcc | 1140 |
| accatgccgc actaccacgc catggaggcc actaaggcga tccgcccat cctcggcgag | 1200 |
| tactaccagt tcgacccgac gcccgtcgcc aaggcgacat ggcgcgaggc caaggagtgc | 1260 |
| atctacgtcg agcctgagga caacaagggc gtcttctggt acaacaacaa gttctaactg | 1320 |
| ctgctgctgt gaaatcagca tcacacatcc atagccaagc agcaaacaaa tttgaagaag | 1380 |
| aagattacaa gggaagagaa gatagtgtct tcggaaatcg tcgtagcaag tatccatcca | 1440 |
| tccatccaac ccatgaacaa tcgtctatct atccatgcat ctatctatgg t | 1491 |

<210> SEQ ID NO 21
<211> LENGTH: 1361
<212> TYPE: DNA
<213> ORGANISM: Oryza sativa

<400> SEQUENCE: 21

| | |
|---|---|
| ttgatgaacg tgttgactga ttgcttcgtg taattgcggt cagcagcagt acgtatgggt | 60 |
| accagcagcc ggccgacgac ggtgaaggag gggaagaaac tagaggcgcc ccgccgtgcc | 120 |
| ggcagccatg cagccgtgaa gcgctctccg gtggacaagc cgccgttcac gctgggcgac | 180 |
| atcagaaagg ccatcccacc gcactgcttc caccgctccg tgatcaagtc attctcctac | 240 |
| ctgctccacg accttgccat gccgcgggc ctcctctact ttgctctggt cgtcatccct | 300 |
| gccctcccag gcgtcctccg cctcgtcgcc tggccgttct actgggccgc gcaggggtgc | 360 |
| ttcctgttcg gggtgtggat catcgcgcac gagtgcgggc accacgcgtt ctcgggccac | 420 |
| gcactcctcg acgacaccct cggcctggtc ctgcactcat ggctcctagc gccatacttc | 480 |
| tcgtggaaat acacccacca acggcaccac tccaacacca gctcacagga gcgcgacgag | 540 |
| gtgttcgtcc ccaggttcaa gtccgacctg ccgtggtact ccccatacgt gtacaagtac | 600 |
| aacaaccccg tcgctcggct gctgctcctc gtcgtgcagc tcaccgtcgg gtggccgatg | 660 |
| tatttggtgt tcaacacctg gggtcgccag tacccaaggt tcgccagcca cttcgatccc | 720 |
| tctgggccca tctacaaggg gcgggagcgc gtcttcatcg ccatctcgga catcggcatg | 780 |
| ctggccgtgt cgctcgcgct gtacaggctt gcggagggtt acgggttttg gtgggtggtg | 840 |
| cgcgtctacg gcgtgccgct gcttgtcgtc aacgcgtggc ttgtggtcgt cacgtacctg | 900 |
| catcacactc accgggcgat cccacactac gactccagcg agtgggactg gttgcgcggg | 960 |
| gcgctcgcca ccgtggaccg cgactacagc ttccttaacc gagtgtttca caacatcacg | 1020 |
| gacacacacg tcgtgcacca cctgttccct accatcccgc actaccacgc tgtggaggcg | 1080 |
| accaaggcga tccgccctat cctcggcgag tactaccagt tcgatcccac acccatcgtc | 1140 |
| aaggcgatat ggcgcgaggc taaggagtgc atctacatcc agtccgagga ccacaagggc | 1200 |
| gtcttctggt acagcaacaa gttctagtac ctgtagcagc ggcaagcggg cgtataggaa | 1260 |

```
gggctgacag aattagccat gtcggtcttg cctcatcgct tcatctaaac ccataatcta   1320
cttgaagtct tgaattaatt gtaaactcaa atgaaattcc c                      1361

<210> SEQ ID NO 22
<211> LENGTH: 1173
<212> TYPE: DNA
<213> ORGANISM: Oryza sativa

<400> SEQUENCE: 22
atgggtacca gcagccggcc gacgacggtg aaggagggga agaaactaga ggcgccccgc    60
cgtgccggca gccatgcagc cgtgaagcgc tctccggtgg acaagccgcc gttcacgctg   120
ggcgacatca gaaaggccat cccaccgcac tgcttccacc gctccgtgat caagtcattc   180
tcctacctgc tccacgacct tgccattgcc gcgggcctcc tctactttgc tctggtcgtc   240
atccctgccc tcccaggcgt cctccgcctc gtcgcctggc cgttctactg ggccgcgcag   300
gggtgcttcc tgttcggggt gtggatcatc gcgcacgagt gcgggcacca cgcgttctcg   360
ggccacgcac tcctcgacga caccctcggc ctggtcctgc actcatggct cctagcgcca   420
tacttctcgt ggaaatacac ccaccaacgg caccactcca acaccagctc acaggagcgc   480
gacgaggtgt tcgtccccag gttcaagtcc gacctgccgt ggtactcccc atacgtgtac   540
aagtacaaca ccccgtcgc tcggctgctg ctcctcgtcg tgcagctcac cgtcgggtgg   600
ccgatgtatt tggtgttcaa cacctggggt cgccagtacc caaggttcgc cagccacttc   660
gatccctctg ggcccatcta caaggggcgg gagcgcgtct tcatcgccat ctcggacatc   720
ggcatgctgg ccgtgtcgct cgcgctgtac aggcttgcgg agggttacgg gttttggtgg   780
gtggtgcgcg tctacggcgt gccgctgctt gtcgtcaacg cgtggcttgt ggtcgtcacg   840
tacctgcatc acactcaccg ggcgatccca cactacgact ccagcgagtg ggactggttg   900
cgcggggcgc tcgccaccgt ggaccgcgac tacagcttcc ttaaccgagt gtttcacaac   960
atcacggaca cacacgtcgt gcaccacctg ttccctacca tcccgcacta ccacgctgtg  1020
gaggcgacca aggcgatccg ccctatcctc ggcgagtact accagttcga tcccacaccc  1080
atcgtcaagg cgatatggcg cgaggctaag gagtgcatct acatccagtc cgaggaccac  1140
aagggcgtct tctggtacag caacaagttc tag                              1173

<210> SEQ ID NO 23
<211> LENGTH: 672
<212> TYPE: DNA
<213> ORGANISM: Oryza sativa

<400> SEQUENCE: 23
atggcgggcg gacggcggtg gggcggatgg cgtgaacagg agccgcctcg ccgtgccggc    60
agcagtgcag ccgtgcagcg cttccaccgc tccgtgatca agtcattctc ctacctgctc   120
cgtgacgtag ccattgccgc gggcctcctc aactttgcgc tggtcggcat ccctgtcctc   180
cctgcaggcg tcctccggcc gcctcgtcgc ctggccgttc tactgggccg cgcagggctg   240
cttcctgttc gtggtgtgga tcatcgcgca cgagtgcggg caccacgcgc tccaagacga   300
caccctcggt ctggtcctgc acttgtggct tctggcacca tacttctcgt ggaaatacag   360
ccaccagcgg caccactcca acaccagctc acaggagcgc gacgaggtgt tcgtccccag   420
gttcaagtcc gatctgccgt ggaactcccc gtacgtgtac aagtacaaca acggcccgtc   480
gccccggcta ctgctcctcg gcatgcagct cactgtcggg tggccgatgt atttggtgttc   540 aacacctggg gtcgctggta cccgcggttc gccagccact tcgatccctc cggagccatc   600
```

```
tacatgaggc gggagcgcgt cttcatcgcc atctcggaca tcggcatgct ggccgtgtcg      660
ctcgcgctgt aa                                                          672

<210> SEQ ID NO 24
<211> LENGTH: 1167
<212> TYPE: DNA
<213> ORGANISM: Oryza sativa

<400> SEQUENCE: 24
atgggtgccg gcggcaggat gacggagaag gagcgggagg agcagcagaa gctgctcggc       60
cgcgccggca atggcgcggc cgtgcagcgg tcgccgacgg acaagccgcc gttcacgctg      120
gggcagatca agaaggccat cccgcctcac tgcttccagc gctcggtgat caagtccttc      180
tcctacgtgg tccatgacct cgtgatcgtc gccgcgctgc tctacttcgc gctggtcatg      240
atccccgtgc tgccgagcgg gatggagttc gcggcatggc cgctctactg gatcgcgcag      300
ggctgcgtgc tcaccggcgt gtgggtcatc gcgcacgagt gcggccacca tgccttctcc      360
gactactcgg tgctcgacga catcgtcggc ctcgtgctgc actcgtcgct gctcgtcccc      420
tacttctcgt ggaagtacag ccaccggcgc caccactcca acaccgggtc gctggagcgc      480
gacgaggtgt tcgtcccgaa gcagaagtcg gcgatggcgt ggtacacccc gtacgtgtac      540
cacaacccga tcggcggct ggtgcacatc ttcgtgcagc tcaccctcgg gtggccgctg      600
tacctggcgt tcaacgtgtc cggccgcccg tacccgcgct tcgcgtgcca cttcgacccc      660
tacggcccga tctacaacga ccgggagcgc gtccagatct tcatctccga cgtcggcgtc      720
gtgtccgcgg ggctcgcgct gttcaagctg tcgtcggcgt tcgggttctg gtgggtggtg      780
cgcgtctacg gcgtgccgct gctgatcgtg aacgcgtggc tggtgctcat cacctacctg      840
cagcacaccc accggcgct gccgcactac gactcgagcg agtgggactg gctccgcggc      900
gcgctggcca ccgtggaccg cgactacggc atcctcaaca aggtgttcca caacatcacg      960
gacacgcacg tcgcgcacca cctcttctcc accatgccgc actaccacgc catggaggcc     1020
actaaggcga tccgccccat cctcggcgag tactaccagt tcgacccgac gccgtcgcc      1080 aaggcgacat ggcgcgaggc caaggagtgc atctacgtcg agcctgagga caacaagggc     1140
gtcttctggt acaacaacaa gttctaa                                         1167

<210> SEQ ID NO 25
<211> LENGTH: 1089
<212> TYPE: DNA
<213> ORGANISM: Oryza sativa

<400> SEQUENCE: 25
atgcagcgct caccggtgga caaaccgccg ttcacgctgg ggacataaa gaaggccatc        60 ccgccgcact gcttccaccg ctccgtgatc aagtcattct cctacctgct ccacgacctt      120
gccatcgccg ctggcctcct ctactttgct ctggtcggca tccctgccct cccaagcatc      180
ctccgcctcg tcgcctggcc gctctactgg gccgcgcagg gcagtgtact caccggcgtg      240
tgggtcatcg ggcacgagtg tggccaccac gccttctcgg actacttgct cctcgacaac      300
ctcgtgggcc tagtgctcca ctcggcgctt ctcacgccct tcttctcgtg gaagtacagc      360
caccggcggc accacgccaa caccggctcc atggagaaag acgaggtgta cgtcgcgaag      420
aagaagtccg cgctgccgtg gtacaccccg tacgtgttcg caacccgt cgggcggctg      480 gtgtacatcg ccctgcagct cacccctcgcg tggccactct acctcgcgtt caacctgtcc      540
gggcagccgt acccacgcct cgtcacctgc cactacgacc cctacagccc gctgttcagc      600
```

```
gaccaggagc gcgtccaagt cctcgtctcc gacgccgcca tcctggccgt gctgctcgcg    660
ctgcacaggc tgacggcggc gtacgggctc tggtgggtgg tgcgcgtgta cggcgtgccg    720
gtgatgatcg tgggcgcgct gttcgtgctc atcacgtacc tgcaccacac ccaccgggcg    780
ctcccgcact acgactccag cgagtgggag tggctgcgtg gctcgctcgc caccgtcgac    840
cgcgactacg gcgtcctcaa ccgcgtgctg cacaacgtca cggacacgca cgtcctccac    900
cacctcttcc ccagcatgcc acactaccac gccatggagg ccaccagggc agcgaggccc    960
gtcctcggtg agtactacaa gtttgaccgc acgcccatca tcgaggcaac atggcgtgag   1020
gccaaggagt gcatgtacgt tgagcccagg gagcgcgatg gtatctactg gtacaacaac   1080
aagttttag                                                            1089
```

```
<210> SEQ ID NO 26
<211> LENGTH: 6
<212> TYPE: PRT
<213> ORGANISM: Artificial
<220> FEATURE:
<223> OTHER INFORMATION: FatB consensus sequence

<400> SEQUENCE: 26

Asn Gln His Val Asn Asn
1               5

<210> SEQ ID NO 27
<211> LENGTH: 21
<212> TYPE: PRT
<213> ORGANISM: Artificial
<220> FEATURE:
<223> OTHER INFORMATION: Fad2 consensus sequence

<400> SEQUENCE: 27

Phe Ser Tyr Val Val His Asp Leu Val Ile Val Ala Ala Leu Leu Phe
1               5                   10                  15

Ala Leu Val Met Ile
            20

<210> SEQ ID NO 28
<211> LENGTH: 19
<212> TYPE: PRT
<213> ORGANISM: Artificial
<220> FEATURE:
<223> OTHER INFORMATION: Fad2 consensus sequence

<400> SEQUENCE: 28

Ala Trp Pro Leu Tyr Ile Ala Gln Gly Cys Val Leu Thr Gly Val Trp
1               5                   10                  15

Val Ile Ala

<210> SEQ ID NO 29
<211> LENGTH: 21
<212> TYPE: PRT
<213> ORGANISM: Artificial
<220> FEATURE:
<223> OTHER INFORMATION: Fad2 consensus sequence

<400> SEQUENCE: 29

Ile Ser Asp Val Gly Val Ser Ala Gly Leu Ala Leu Phe Lys Leu Ser
1               5                   10                  15

Ser Ala Phe Gly Phe
            20
```

```
<210> SEQ ID NO 30
<211> LENGTH: 23
<212> TYPE: PRT
<213> ORGANISM: Artificial
<220> FEATURE:
<223> OTHER INFORMATION: Fad2 consensus sequence

<400> SEQUENCE: 30

Val Val Arg Val Tyr Gly Val Pro Leu Leu Ile Val Asn Ala Trp Leu
1               5                   10                  15

Val Leu Ile Thr Tyr Leu Gln
            20

<210> SEQ ID NO 31
<211> LENGTH: 6
<212> TYPE: PRT
<213> ORGANISM: Artificial
<220> FEATURE:
<223> OTHER INFORMATION: Fad2 consensus sequence

<400> SEQUENCE: 31

His Glu Cys Gly His His
1               5

<210> SEQ ID NO 32
<211> LENGTH: 6
<212> TYPE: PRT
<213> ORGANISM: Artificial
<220> FEATURE:
<223> OTHER INFORMATION: Fad2 consensus sequence

<400> SEQUENCE: 32

His Arg Arg His His Ala
1               5

<210> SEQ ID NO 33
<211> LENGTH: 5
<212> TYPE: PRT
<213> ORGANISM: Artificial
<220> FEATURE:
<223> OTHER INFORMATION: Fad2 consensus sequence

<400> SEQUENCE: 33

His Val Ala His His
1               5

<210> SEQ ID NO 34
<211> LENGTH: 20
<212> TYPE: DNA
<213> ORGANISM: Artificial
<220> FEATURE:
<223> OTHER INFORMATION: Oligonucleotide primer

<400> SEQUENCE: 34
cgctgctacc aaacaattca                                          20

<210> SEQ ID NO 35
<211> LENGTH: 19
<212> TYPE: DNA
<213> ORGANISM: Artificial
<220> FEATURE:
<223> OTHER INFORMATION: Oligonucleotide primer

<400> SEQUENCE: 35
ttctgtgttg ccatcatcg                                           19
```

```
<210> SEQ ID NO 36
<211> LENGTH: 24
<212> TYPE: DNA
<213> ORGANISM: Artificial
<220> FEATURE:
<223> OTHER INFORMATION: Oligonucleotide primer

<400> SEQUENCE: 36
caggaaataa agttggtgat gatg                                          24

<210> SEQ ID NO 37
<211> LENGTH: 24
<212> TYPE: DNA
<213> ORGANISM: Artificial
<220> FEATURE:
<223> OTHER INFORMATION: Oligonucleotide primer

<400> SEQUENCE: 37
cttcacaata tcagctcctg actc                                          24

<210> SEQ ID NO 38
<211> LENGTH: 24
<212> TYPE: DNA
<213> ORGANISM: Artificial
<220> FEATURE:
<223> OTHER INFORMATION: Oligonucleotide primer

<400> SEQUENCE: 38
caggaaataa agttggtgat gatg                                          24

<210> SEQ ID NO 39
<211> LENGTH: 21
<212> TYPE: DNA
<213> ORGANISM: Artificial
<220> FEATURE:
<223> OTHER INFORMATION: Oligonucleotide primer

<400> SEQUENCE: 39
cttcacaatg tcagccttca c                                             21

<210> SEQ ID NO 40
<211> LENGTH: 19
<212> TYPE: DNA
<213> ORGANISM: Artificial
<220> FEATURE:
<223> OTHER INFORMATION: Oligonucleotide primer

<400> SEQUENCE: 40
acaggcctga ctccacgat                                                19

<210> SEQ ID NO 41
<211> LENGTH: 20
<212> TYPE: DNA
<213> ORGANISM: Artificial
<220> FEATURE:
<223> OTHER INFORMATION: Oligonucleotide primer

<400> SEQUENCE: 41
gtccagagtg cttgttgcag                                               20

<210> SEQ ID NO 42
<211> LENGTH: 20
<212> TYPE: DNA
<213> ORGANISM: Artificial
<220> FEATURE:
<223> OTHER INFORMATION: Oligonucleotide primer
```

```
<400> SEQUENCE: 42
tacccactcc ctccttgagc                                              20

<210> SEQ ID NO 43
<211> LENGTH: 20
<212> TYPE: DNA
<213> ORGANISM: Artificial
<220> FEATURE:
<223> OTHER INFORMATION: Oligonucleotide primer

<400> SEQUENCE: 43
aggcactgtt ggtgatctcg                                              20

<210> SEQ ID NO 44
<211> LENGTH: 20
<212> TYPE: DNA
<213> ORGANISM: Artificial
<220> FEATURE:
<223> OTHER INFORMATION: Oligonucleotide primer

<400> SEQUENCE: 44
cacaaagagg gagggaacaa                                              20

<210> SEQ ID NO 45
<211> LENGTH: 20
<212> TYPE: DNA
<213> ORGANISM: Artificial
<220> FEATURE:
<223> OTHER INFORMATION: Oligonucleotide primer

<400> SEQUENCE: 45
gaaggacttg atcaccgagc                                              20

<210> SEQ ID NO 46
<211> LENGTH: 20
<212> TYPE: DNA
<213> ORGANISM: Artificial
<220> FEATURE:
<223> OTHER INFORMATION: Oligonucleotide primer

<400> SEQUENCE: 46
cacaacatca cggacacaca                                              20

<210> SEQ ID NO 47
<211> LENGTH: 20
<212> TYPE: DNA
<213> ORGANISM: Artificial
<220> FEATURE:
<223> OTHER INFORMATION: Oligonucleotide primer

<400> SEQUENCE: 47
gcaagaccga catggctaat                                              20

<210> SEQ ID NO 48
<211> LENGTH: 19
<212> TYPE: DNA
<213> ORGANISM: Artificial
<220> FEATURE:
<223> OTHER INFORMATION: Oligonucleotide primer

<400> SEQUENCE: 48
acgtcctcca ccacctctt                                               19
```

```
<210> SEQ ID NO 49
<211> LENGTH: 22
<212> TYPE: DNA
<213> ORGANISM: Artificial
<220> FEATURE:
<223> OTHER INFORMATION: Oligonucleotide primer

<400> SEQUENCE: 49
cagaagcagt gacataccca ag                                             22

<210> SEQ ID NO 50
<211> LENGTH: 20
<212> TYPE: DNA
<213> ORGANISM: Artificial
<220> FEATURE:
<223> OTHER INFORMATION: Oligonucleotide primer

<400> SEQUENCE: 50
tacccactcc ctccttgagc                                                20

<210> SEQ ID NO 51
<211> LENGTH: 20
<212> TYPE: DNA
<213> ORGANISM: Artificial
<220> FEATURE:
<223> OTHER INFORMATION: Oligonucleotide primer

<400> SEQUENCE: 51
aggcactgtt ggtgatctcg                                                20

<210> SEQ ID NO 52
<211> LENGTH: 33
<212> TYPE: DNA
<213> ORGANISM: Artificial
<220> FEATURE:
<223> OTHER INFORMATION: Oligonucleotide primer

<400> SEQUENCE: 52
aaaggatcct ctagagggag gagcagcaga agc                                 33

<210> SEQ ID NO 53
<211> LENGTH: 35
<212> TYPE: DNA
<213> ORGANISM: Artificial
<220> FEATURE:
<223> OTHER INFORMATION: Oligonucleotide primer

<400> SEQUENCE: 53
aaaactagtg aattctacac gtacggggtg tacca                               35

<210> SEQ ID NO 54
<211> LENGTH: 24
<212> TYPE: DNA
<213> ORGANISM: Artificial
<220> FEATURE:
<223> OTHER INFORMATION: Oligonucleotide primer

<400> SEQUENCE: 54
agtcatggct ggttctcttg cggc                                           24

<210> SEQ ID NO 55
<211> LENGTH: 24
<212> TYPE: DNA
<213> ORGANISM: Artificial
<220> FEATURE:
<223> OTHER INFORMATION: Oligonucleotide primer
```

<400> SEQUENCE: 55
accatcacct aagagaccag cagt                                                              24

<210> SEQ ID NO 56
<211> LENGTH: 16
<212> TYPE: PRT
<213> ORGANISM: Oryza sativa

<400> SEQUENCE: 56

Cys Gly Met Asn Lys Asn Thr Arg Arg Leu Ser Lys Met Pro Asp Glu
1               5                   10                  15

<210> SEQ ID NO 57
<211> LENGTH: 10
<212> TYPE: PRT
<213> ORGANISM: Oryza sativa

<400> SEQUENCE: 57

Thr Arg Arg Leu Ser Lys Met Pro Asp Glu
1               5                   10

<210> SEQ ID NO 58
<211> LENGTH: 17
<212> TYPE: PRT
<213> ORGANISM: Oryza sativa

<400> SEQUENCE: 58

Cys Gly Glu Lys Gln Trp Thr Leu Leu Asp Trp Lys Pro Lys Lys Pro
1               5                   10                  15

Asp

<210> SEQ ID NO 59
<211> LENGTH: 16
<212> TYPE: PRT
<213> ORGANISM: Oryza sativa

<400> SEQUENCE: 59

Cys Gly Ala Gln Gly Glu Gly Asn Met Gly Phe Phe Pro Ala Glu Ser
1               5                   10                  15

<210> SEQ ID NO 60
<211> LENGTH: 21
<212> TYPE: DNA
<213> ORGANISM: Artificial
<220> FEATURE:
<223> OTHER INFORMATION: Oligonucleotide primer

<400> SEQUENCE: 60
gtgccggcgg caggatgacg g                                                                  21

<210> SEQ ID NO 61
<211> LENGTH: 21
<212> TYPE: DNA
<213> ORGANISM: Artificial
<220> FEATURE:
<223> OTHER INFORMATION: Oligonucleotide primer

<400> SEQUENCE: 61
gccgacgatg tcgtcgagca c                                                                  21

<210> SEQ ID NO 62
<211> LENGTH: 20
<212> TYPE: DNA
<213> ORGANISM: Artificial

```
<220> FEATURE:
<223> OTHER INFORMATION: Oligonucleotide primer

<400> SEQUENCE: 62
tgccttctcc gactactcgg                                        20

<210> SEQ ID NO 63
<211> LENGTH: 21
<212> TYPE: DNA
<213> ORGANISM: Artificial
<220> FEATURE:
<223> OTHER INFORMATION: Oligonucleotide primer

<400> SEQUENCE: 63
cctcgcgcca tgtcgccttg g                                      21

<210> SEQ ID NO 64
<211> LENGTH: 19
<212> TYPE: RNA
<213> ORGANISM: Artificial
<220> FEATURE:
<223> OTHER INFORMATION: RNAi molecule

<400> SEQUENCE: 64
ggagcgggag gagcagcag                                         19

<210> SEQ ID NO 65
<211> LENGTH: 19
<212> TYPE: RNA
<213> ORGANISM: Artificial
<220> FEATURE:
<223> OTHER INFORMATION: RNAi molecule

<400> SEQUENCE: 65
gcugcucggc cgcgccggc                                         19

<210> SEQ ID NO 66
<211> LENGTH: 19
<212> TYPE: RNA
<213> ORGANISM: Artificial
<220> FEATURE:
<223> OTHER INFORMATION: RNAi molecule

<400> SEQUENCE: 66
uggcgcggcc gugcagcgg                                         19

<210> SEQ ID NO 67
<211> LENGTH: 19
<212> TYPE: RNA
<213> ORGANISM: Artificial
<220> FEATURE:
<223> OTHER INFORMATION: RNAi molecule

<400> SEQUENCE: 67
gccgccguuc acgcugggg                                         19

<210> SEQ ID NO 68
<211> LENGTH: 19
<212> TYPE: RNA
<213> ORGANISM: Artificial
<220> FEATURE:
<223> OTHER INFORMATION: RNAi molecule

<400> SEQUENCE: 68
gaaggccauc ccgccucac                                         19
```

```
<210> SEQ ID NO 69
<211> LENGTH: 19
<212> TYPE: RNA
<213> ORGANISM: Artificial
<220> FEATURE:
<223> OTHER INFORMATION: RNAi molecule

<400> SEQUENCE: 69
ggccaucccg ccucacugc                                                19

<210> SEQ ID NO 70
<211> LENGTH: 19
<212> TYPE: RNA
<213> ORGANISM: Artificial
<220> FEATURE:
<223> OTHER INFORMATION: RNAi molecule

<400> SEQUENCE: 70
guccuucucc uacgugguc                                                19

<210> SEQ ID NO 71
<211> LENGTH: 19
<212> TYPE: RNA
<213> ORGANISM: Artificial
<220> FEATURE:
<223> OTHER INFORMATION: RNAi molecule

<400> SEQUENCE: 71
guacagccac cggcgccac                                                19

<210> SEQ ID NO 72
<211> LENGTH: 19
<212> TYPE: RNA
<213> ORGANISM: Artificial
<220> FEATURE:
<223> OTHER INFORMATION: RNAi molecule

<400> SEQUENCE: 72
caccgggucg cuggagcgc                                                19

<210> SEQ ID NO 73
<211> LENGTH: 19
<212> TYPE: RNA
<213> ORGANISM: Artificial
<220> FEATURE:
<223> OTHER INFORMATION: RNAi molecule

<400> SEQUENCE: 73
gcagaagucg gcgauggcg                                                19

<210> SEQ ID NO 74
<211> LENGTH: 19
<212> TYPE: RNA
<213> ORGANISM: Artificial
<220> FEATURE:
<223> OTHER INFORMATION: RNAi molecule

<400> SEQUENCE: 74
gcuccaagaa ugcugcugu                                                19

<210> SEQ ID NO 75
<211> LENGTH: 19
<212> TYPE: RNA
<213> ORGANISM: Artificial
<220> FEATURE:
<223> OTHER INFORMATION: RNAi molecule
```

```
<400> SEQUENCE: 75
gaaugcugcu guuaccggc                                                19

<210> SEQ ID NO 76
<211> LENGTH: 19
<212> TYPE: RNA
<213> ORGANISM: Artificial
<220> FEATURE:
<223> OTHER INFORMATION: RNAi molecule

<400> SEQUENCE: 76
ugcugcuguu accggcgaa                                                19

<210> SEQ ID NO 77
<211> LENGTH: 19
<212> TYPE: RNA
<213> ORGANISM: Artificial
<220> FEATURE:
<223> OTHER INFORMATION: RNAi molecule

<400> SEQUENCE: 77
uugccggaga auuugagug                                                19

<210> SEQ ID NO 78
<211> LENGTH: 19
<212> TYPE: RNA
<213> ORGANISM: Artificial
<220> FEATURE:
<223> OTHER INFORMATION: RNAi molecule

<400> SEQUENCE: 78
uuugaguguc cguggcauu                                                19

<210> SEQ ID NO 79
<211> LENGTH: 19
<212> TYPE: RNA
<213> ORGANISM: Artificial
<220> FEATURE:
<223> OTHER INFORMATION: RNAi molecule

<400> SEQUENCE: 79
agccuacccc accuccugc                                                19

<210> SEQ ID NO 80
<211> LENGTH: 19
<212> TYPE: RNA
<213> ORGANISM: Artificial
<220> FEATURE:
<223> OTHER INFORMATION: RNAi molecule

<400> SEQUENCE: 80
cccaccuccu gcagccaug                                                19

<210> SEQ ID NO 81
<211> LENGTH: 19
<212> TYPE: RNA
<213> ORGANISM: Artificial
<220> FEATURE:
<223> OTHER INFORMATION: RNAi molecule

<400> SEQUENCE: 81
guaaaggcac aggcucaaa                                                19
```

```
<210> SEQ ID NO 82
<211> LENGTH: 19
<212> TYPE: RNA
<213> ORGANISM: Artificial
<220> FEATURE:
<223> OTHER INFORMATION: RNAi molecule

<400> SEQUENCE: 82
aggcacaggc ucaaacccu                                                    19

<210> SEQ ID NO 83
<211> LENGTH: 19
<212> TYPE: RNA
<213> ORGANISM: Artificial
<220> FEATURE:
<223> OTHER INFORMATION: RNAi molecule

<400> SEQUENCE: 83
acccuuccca agguuaaug                                                    19
```

METHOD OF PREPARING FOOD USING RICE OIL

This application is a divisional of U.S. Ser. No. 12/309,276, a §371 national stage of PCT International Application No. PCT/AU2007/000977, filed Jul. 13, 2007, and claims priority of Australian Patent Application No. 2006903810, filed Jul. 14, 2006, the contents of all of which are hereby incorporated by reference into this application.

FIELD OF THE INVENTION

The present invention relates to rice oil, rice bran and rice seeds which have altered levels of oleic acid, palmitic acid and/or linoleic acid. The present invention also provides methods for genetically modifying rice plants such that rice oil, rice bran and rice seeds produced therefrom have altered levels of oleic acid, palmitic acid and/or linoleic acid.

BACKGROUND OF THE INVENTION

Plant oils are an important source of dietary fat for humans, representing about 25% of caloric intake in developed countries (Broun et al., 1999). The current world production of plant oils is about 110 million tones per year, of which 86% is used for human consumption. Almost all of these oils are obtained from oilseed crops such as soybean, canola, sunflower, cottonseed and groundnut, or plantation trees such as palm, olive and coconut (Gunstone, 2001; Oil World Annual, 2004). The growing scientific understanding and community recognition of the impact of the individual fatty acid components of food oils on various aspects of human health is motivating the development of modified vegetable oils that have improved nutritional value while retaining the required functionality for various food applications. These modifications require knowledge about the metabolic pathways for plant fatty acid synthesis and genes encoding the enzymes for these pathways (Liu et al., 2002a; Thelen and Ohlrogge, 2002).

Considerable attention is being given to the nutritional impact of various fats and oils, in particular the influence of the constituents of fats and oils on cardiovascular disease, cancer and various inflammatory conditions. High levels of cholesterol and saturated fatty acids in the diet are thought to increase the risk of heart disease and this has led to nutritional advice to reduce the consumption of cholesterol-rich saturated animal fats in favour of cholesterol-free unsaturated plant oils (Liu et al., 2002a). While dietary intake of cholesterol present in animal fats can significantly increase the levels of total cholesterol in the blood, it has also been found that the fatty acids that comprise the fats and oils can themselves have significant effects on blood serum cholesterol levels. Of particular interest is the effect of dietary fatty acids on the undesirable low density lipoprotein (LDL) and desirable high density lipoprotein (HDL) forms of cholesterol in the blood. In general, saturated fatty acids, particularly myristic acid (14:0) and palmitic acid (16:0), the principal saturates present in plant oils, have the undesirable property of raising serum LDL-cholesterol levels and consequently increasing the risk of cardiovascular disease (Zock et al., 1994; Hu et al., 1997). However, it has become well established that stearic acid (18:0), the other main saturate present in plant oils, does not raise LDL-cholesterol, and may actually lower total cholesterol (Bonanome and Grundy, 1988; Dougherty et al., 1995). Stearic acid is therefore generally considered to be at least neutral with respect to risk of cardiovascular disease (Tholstrup, et al, 1994). On the other hand, unsaturated fatty acids, such as the monounsaturate oleic acid (18:1) and the polyunsaturates linoleic acid (18:2) and α-linolenic acid (ALA, 18:3), have the beneficial property of lowering LDL-cholesterol (Mensink and Katan, 1989; Roche and Gibney, 2000), thus reducing the risk of cardiovascular disease.

Although nutritionally desirable, highly unsaturated oils are too unstable for use in many food applications, particularly for commercial deep-frying where they are exposed to high temperatures and oxidative conditions for long periods of time. Under such conditions, the oxidative breakdown of the numerous carbon double bonds present in unsaturated oils results in the development of short-chain aldehyde, hydroperoxide and keto derivatives, imparting undesirable flavours and reducing the frying performance of the oil by raising the level of polar compounds (Chang et al., 1978; Williams et al., 1999).

Oil processors and food manufacturers have traditionally relied on hydrogenation to reduce the level of unsaturated fatty acids in oils, thereby increasing their oxidative stability in frying applications and also providing solid fats for use in margarine and shortenings. Hydrogenation is a chemical process that reduces the degree of unsaturation of oils by converting carbon double bonds into carbon single bonds. Complete hydrogenation produces a fully saturated fat. However, the process of partial hydrogenation results in increased levels of both saturated fatty acids and monounsaturated fatty acids. Some of the monounsaturates formed during partial hydrogenation are in the trans isomer form (such as elaidic acid, a trans isomer of oleic acid) rather than the naturally occurring cis isomer (Sebedio et at, 1994; Fernandez San Juan, 1995). In contrast to cis-unsaturated fatty acids, trans-fatty acids are now known to be as potent as palmitic acid in raising serum LDL cholesterol levels (Mensink and Katan, 1990; Noakes and Clifton, 1998) and lowering serum HDL cholesterol (Zock and Katan, 1992), and thus contribute to increased risk of cardiovascular disease (Ascherio and Willett, 1997). As a result of increased awareness of the anti-nutritional effects of trans-fatty acids, there is now a growing trend away from the use of hydrogenated oils in the food industry, in favour of fats and oils that are both nutritionally beneficial and can provide the required functionality without hydrogenation, in particular those that are rich in either oleic acid where liquid oils are required or stearic acid where a solid or semi-solid fat is preferred.

Plant oils are composed almost entirely of triacylglycerols (TAG) molecules, which consist of three fatty acid (acyl) chains esterified to a glycerol backbone and are deposited in specialised oil body structures called oleosomes (Stymne and Stobart, 1987). These storage lipids serve as an energy source for the germinating seedling until it is able to photosynthesise. Edible plant oils in common use are generally comprised of five main fatty acids—the saturated palmitic and stearic acids, the monounsaturated oleic acid, and the polyunsaturated linoleic and α-linolenic acids. In addition to fatty acids, plant oils also contain some important minor components such as tocopherols, phytosterols, terpenes and mixed isoprenoids. These minor constituents are of increasing interest because some have been shown to exert beneficial effects on skin health, aging, eyesight and blood cholesterol or preventing breast cancer or cardiovascular disease (Theriault et al., 1999; Moghadasian and Frohlich, 1999).

Fatty Acid and TAG Synthesis in Seeds

A diagrammatic overview of the metabolic pathways for fatty acids synthesis in developing seeds is shown in FIG. 1. The initial stages of fatty acid synthesis occur in the plastid compartments of the cell, where synthesis of fatty acid carbon chains is initiated with a C2 molecule and extended through a stepwise condensation process whereby additional C2 carbon units are donated from malonyl-ACP to the elongating acyl chains. The first step in this sequence involves acetyl-CoA condensing with malonyl-ACP and is catalysed by the β-ketoacyl synthase III (KASIII) enzyme. The subsequent condensation rounds are catalysed by β-ketoacyl synthase I (KASI) and result in the eventual formation of a saturated C16 acyl chain joined to acyl carrier protein (ACP), palmitoyl-ACP. The final elongation within the plastid is catalysed by β-ketoacyl synthase II (KASII) to form the saturated C18 acyl chain, stearoyl-ACP. When desaturation occurs, the first double bond is introduced into the Δ9 position of the C18 chain by a soluble enzyme in the plastid, stearoyl-ACP Δ9-desaturase, to yield the monounsaturated C18:1 oleoyl-ACP.

Fatty acids thus synthesised are either retained in the plastid for further modification and incorporation into plastidic lipids, or are released from their ACPs by acyl-thioesterases to produce free fatty acids which are exported into the cytosol for further modification and eventual incorporation into TAG molecules. Higher plants have been found to have at least two types of acyl-thioesterase, FatA with substrate specificity towards oleoyl-ACP, an unsaturated acyl-ACP, and FatB with preference for saturated acyl-ACPs (Jones et al., 1995; Voelker et al., 1996).

On exiting the plastids, free fatty acids become esterified to Co-enzyme A (CoA) and are then available for transfer to glycerol 3-phosphate (G-3-P) backbones to form lysophosphatidic acid (LPA), phosphatidic acid (PA) and phosphatidyl-choline (PC). Additionally, in some plants, notably the *Brassica* species, oleic acid esterified to CoA is able to be elongated to form eicosenoic acid (C20:1) and erucic acid (C22:1). Oleic acid esterified to PC is available for further modification before incorporation into TAG. In edible oils, the principal modifications on PC are the sequential desaturations of oleic acid to form linoleic and α-linolenic acids by the microsomal Δ12-desaturase (Fad2) and Δ15-desaturase (Fad3) enzymes respectively.

Modification of Existing Fatty Acid Biosynthetic Enzymes

Gene inactivation approaches such as post transcriptional gene silencing (PTGS) have been successfully applied to inactivate fatty acid biosynthetic genes and develop nutritionally improved plant oils in oilseed crops. For example, soybean lines with 80% oleic acid in their seed oil were created by cosuppression of the Fad2 encoded microsomal Δ12-desaturase (Kinney, 1996). This reduced the level of Δ12-desaturation and resulted in accumulation of high amounts of oleic acid. Using a similar approach, cosuppression-based silencing of the Fad2 gene was used to raise oleic acid levels in *Brassica napus* and *B. juncea* (Stoutjesdijk et al., 2000). Likewise, transgenic expression in cottonseed of a mutant allele of the Fad2 gene obtained from rapeseed was found to be able to suppress the expression of the endogenous cotton Fad2 gene and resulted in elevated oleic acid content in about half of the primary transgenic cotton lines (Chapman et al., 2001). In another variation, transgenic expression in soybean of a Fad2 gene terminated by a self-cleaving ribozyme was able to inactivate the endogenous Fad2 gene resulting in increased oleic acid levels (Buhr et al., 2002). RNAi-mediated gene silencing techniques have also been employed to develop oilseeds with nutritionally-improved fatty acid composition. In cottonseed, transgenic expression of a hairpin RNA (hpRNA) gene silencing construct targeted against ghFad2-1, a seed-specific member of cotton Fad2 gene family, resulted in the increase of oleic acid from normal levels of 15% up to 77% of total fatty acids in the oil (Liu et al., 2002b). This increase was mainly at the expense of linoleic acid which was reduced from normal levels of 60% down to as low as 4%.

Fatty Acids in Cereals

In contrast to the considerable work done on fatty acid biosynthesis and modification in oilseeds, oil modification in cereals is relatively unexplored. This is probably due to the much lower levels of oils (about 1.5-6% by weight) in cereal grains and consequently the perceived lower importance of oils from cereals in the human diet.

Rice (*Oryza sativa* L.) is the most important cereal crop in the developing world and is grown widely, particularly in Asia which produces about 90% of the world total. The vast majority of rice in the world is eaten as "white rice" which is essentially the endosperm of the rice grain, having been produced by milling of harvested grain to remove the outer bran layer and germ (embryo and scutellum). This is done primarily because "brown rice" does not keep well on storage, particularly under hot tropical conditions.

The oil content of cereal grains such as rice (4%) is quite low relative to oilseeds where oil can make up to 60% of the weight of the grain (Ohlrogge and Jaworski, 1997). However, lipids may still comprise up to 37% of the dry weight of the cereal embryo (Choudhury and Juliano 1980). Most of the lipid content in the rice grain is found in the outer bran layer (Resurreccion et al, 1979) but some is also present in the endosperm, at least some associated with the starch (Tables 1 and 2). The main fatty acids in rice oil are palmitic (16:0) (about 20% of total fatty acids in the TAG), oleic (18:1) (about 40%), and linoleic acids (18:2) (about 34%) (Radcliffe et at, 1997). There is a range of levels naturally occurring in different rice cultivars, for example for oleic acid, from 37.9% to 47.5% and for linoleic (18:2), from 38.2% to 30.4% (Taira et al., 1988).

TABLE 1

Typical fatty acid composition (wt % of total fatty acids) for selected fatty acids of various plant oils.

| Plant | 16:0 | 18:1 | 18:2 |
|---|---|---|---|
| Barley | 18 | 22 | 54 |
| Soybean | 11 | 23 | 51 |
| Peanut | 8 | 50 | 36 |
| Canola | 4 | 63 | 20 |
| Olive | 15 | 75 | 9 |
| Rice bran | 22 | 38 | 34 |

While the FatB gene has been shown to have a high affinity to catalysing the production of free palmitic acid which is subsequently converted to palmitoyl-CoA in oilseed plants and dicot plants, no information is reported on the role of FatB in rice or other cereals.

TABLE 2

Fatty acid composition (wt % of total fatty acids) for selected fatty acids of plant lipids associated with starch.

| Plant | 16:0 | 18:1 | 18:2 |
|---|---|---|---|
| Wheat | 35-44 | 6-14 | 42-52 |
| Barley | 55 | 4 | 36 |
| Rye | 23 | 41 | 35 |
| Oat | 40 | 22 | 35 |
| Maize | 37 | 11 | 46 |
| Maize- High amylose | 36 | 20 | 38 |
| Maize- waxy | 36 | 23 | 36 |
| Millet | 36 | 28 | 29 |
| Rice | 37-48 | 9-18 | 29-46 |

Data adapted from: Morrison (1988).

Some of the fatty acid desaturases have been characterized in rice but not Fad2. Akagai et al, (1995) published the nucleotide sequence of a gene on rice chromosome 4 encoding stearoyl-acyl carrier protein desaturase from developing seeds. The gene product participates in the production of oleoyl ACP from stearoyl ACP. Kodama et al. (1997) reported the structure, chromosomal location and expression of Fad3 in rice.

The proportion of linolenic acid (18:3) in rice seed oil has been increased ten-fold by using soybean Fad3 expression (Anal et al., 2003). More recently, there have been reports of the production of conjugated linoleic acid in rice by introduction of a linoleate isomerase gene from bacteria (Kohno-Murase et al., 2006); conjugated linoleic acid is reported to have anti-carcinogenic activity. In a similar vein, in vitro modification of rice bran oil to incorporate capric acid, which may improve dietary lipid utilisation in some diseases, using immobilized microbial enzymes has also been reported (Jennings and Akoh, 2000). In maize, Fad2 and FA-6 desaturase genes have been sequenced and mapped to chromosomes (Mikkilinen and Rocheford, 2003). The Fad2 and Fad6 clones could not be mapped to any QTLs for oleic/linoliec acid ratios in the maize grain. There are no published reports of other Fad2 or FatB genes characterized from rice, maize or wheat.

Storage of Rice

Storage of rice for prolonged times at high temperatures impairs grain quality due to hydrolytic and oxidative deterioration of bran oil. Dehulling the outer husk during harvest to produce brown rice disturbs the outer bran layers, which allows the oil to diffuse to the outer layers. Endogenous and microbial lipases then catalyse the hydrolysis of triglycerides to free fatty acids (FFA) which are then oxidised to produce an off-flavour (Yasumatsu et al., 1966, Tsuzuki et al., 2004, Thou et al., 2002 Champagne and Grimm, 1995).

Hexanal is the major component increased in the headspace of raw and cooked brown rice stored at high temperatures (Boggs et al., 1964, Shibuya et al., 1974, Tsugita et al., 1983). However, hexanal itself is not the main cause of the 'off' smell; the unattractive smell and flavour of deteriorated rice is probably due to a mixture of the volatiles that are increased after storage. These include alkanals, alkenals, aromatic aldehydes, ketones, 2-pentylfuran, 4-vinylphenol and others (Tsugita et al., 1983). Nevertheless, hexanal levels during storage have been shown to be associated with the oxidation of linoleic acid (18:2) in brown rice and therefore are a good indicator of oxidative deterioration (Shin et al., 1986).

The production of hexanal from linoleic acid can be catalysed by the enzyme lipoxygenase (LOX) (St Angelo et al., 1980). Suzuki et al. (1999) identified rice varieties lacking Lox3 and found that on storage of the mutant grain at 35° C. for 8 weeks, less hexanal was formed in the headspace vapour, both for raw and cooked brown rice grain. They also found that mutant rice formed less pentanal and pentanol.

The nutrient-rich outer rice bran layer obtained through polishing the outer layers of the rice grain is an excellent food source, containing antioxidant compounds such as tocotrienols and gamma-oryzanol which is also a phytoestrogen (Rukmini and Raghuram, 1991). The bioactive compounds present in rice bran oil have been found to lower cholesterol in humans (Most et al., 2005). These bioactive components have also been shown to improve lipid profiles in rats fed a high cholesterol diet (Ha et al., 2005). Another important component found primarily in the bran is vitamin A precursors. However, these nutritional and health benefits are lost through the polishing of rice and the consumption of white rice.

There is still a need for cereal, such as rice, varieties that produce grain with an improved oil composition for health benefits, which at the same time is more stable on storage, allowing greater use of, for example, brown rice in the human diet.

SUMMARY OF THE INVENTION

In one aspect, the present invention provides rice oil having a fatty acid composition comprising greater than about 48% oleic acid, less than about 17% palmitic acid, less than about 30% linoleic acid and/or any combination thereof.

In an embodiment, the ratio of oleic acid to linoleic acid is greater than 1.5:1, preferably greater than 2:1, more preferably greater than 3:1, and even more preferably greater than 4:1.

In another embodiment, the rice oil has a fatty acid composition comprising greater than about 48% oleic acid, less than about 17% palmitic acid, and less than about 30% linoleic acid.

In a further embodiment, the rice oil has a fatty acid composition comprising greater than about 40% oleic acid, preferably greater than about 50% oleic acid, and even more preferably greater than about 60% oleic acid. In an embodiment, the fatty acid composition of the rice oil is in the range 48-80% oleic acid, 6-16% palmitic acid and 10-25% linoleic acid.

In yet another embodiment, the rice oil has a fatty acid composition comprising less than about 16% palmitic acid, preferably less than about 15% palmitic acid, more preferably less than about 14% palmitic acid, more preferably less than about 13% palmitic acid, and even more preferably less than about 12% palmitic acid.

In another embodiment, the rice oil has a fatty acid composition comprising less than about 25% linoleic acid, preferably less than about 20% linoleic acid, even more preferably less than about 15% linoleic acid.

In another aspect the present invention provides rice bran having a fatty acid composition comprising greater than about 48% oleic acid, less than about 17% palmitic acid, less than about 30% linoleic acid and/or any combination thereof.

In an embodiment, the ratio of oleic acid to linoleic acid is greater than 1.5:1, preferably greater than 2:1, more preferably greater than 3:1, and even more preferably greater than 4:1.

In another embodiment, the rice bran has a fatty acid composition comprising greater than about 48% oleic acid, less than about 17% palmitic acid, and less than about 30% linoleic acid.

In a further embodiment, the rice bran has a fatty acid composition comprising greater than about 40% oleic acid, preferably greater than about 50% oleic acid, and even more preferably greater than about 60% oleic acid. In an embodiment, the fatty acid composition of the rice bran is in the range 48-80% oleic acid, 6-16% palmitic acid and 10-25% linoleic acid.

In yet another embodiment, the rice bran has a fatty acid composition comprising less than about 16% palmitic acid, preferably less than about 15% palmitic acid, more preferably less than about 14% palmitic acid, more preferably less than about 13% palmitic acid, and even more preferably less than about 12% palmitic acid.

In another embodiment, the rice bran has a fatty acid composition comprising less than about 25% linoleic acid, preferably less than about 20% linoleic acid, even more preferably less than about 15% linoleic acid.

In a further aspect, the present invention provides a rice seed having a fatty acid composition comprising greater than about 48% oleic acid, less than about 17% palmitic acid, leas than about 30% linoleic acid and/or any combination thereof.

In an embodiment, the ratio of oleic acid to linoleic acid is greater than 1.5:1, preferably greater than 2:1, more preferably greater than 3:1, and even more preferably greater than 4:1.

In another embodiment, the rice seed has a fatty acid composition comprising greater than about 48% oleic acid, less than about 17% palmitic acid, and less than about 30% linoleic acid.

In a further embodiment, the rice seed has a fatty acid composition (i.e. of the oil inside the seed) comprising greater than about 40% oleic acid, preferably greater than about 50% oleic acid, and even more preferably greater than about 60% oleic acid.

In an embodiment, the fatty acid composition of the rice seed is in the range 48-80% oleic acid, 6-16% palmitic acid and 10-25% linoleic acid.

In yet another embodiment, the rice seed has a fatty acid composition comprising less than about 16% palmitic acid, preferably less than about 15% palmitic acid, more preferably less than about 14% palmitic acid, more preferably less than about 13% palmitic acid, and even more preferably less than about 12% palmitic acid.

In another embodiment, the rice seed has a fatty acid composition comprising less than about 25% linoleic acid, preferably less than about 20% linoleic acid, even more preferably less than about 15% linoleic acid.

In any of the embodiments described above for rice bran or rice seed, the fatty acid composition is typically determined by extraction of the oil and analysis by FAME/GC as described in Example 1. Compositions for individual fatty acids are expressed as percent (w/w) of the total fatty acids in the oil.

In a further aspect, provided is a rice plant which produces rice oil of the invention, rice bran of the invention, and/or a rice seed of the invention.

In another aspect, the present invention provides an isolated polynucleotide which, when present in a cell of a rice plant, down-regulates the level of activity of a Fad2 and/or FatB polypeptide in the cell when compared to a cell that lacks said polynucleotide.

Preferably, the polynucleotide is operably linked to a promoter capable of directing expression of the polynucleotide in a cell of a rice plant.

In an embodiment, the polynucleotide down-regulates mRNA levels expressed from at least one Fad2 and/or FatB gene.

Examples of suitable polynucleotides include, but are not limited to, a polynucleotide selected from: an antisense polynucleotide, a sense polynucleotide, a catalytic polynucleotide, a microRNA, a polynucleotide which encodes a polypeptide which binds a Fad2 or FatB polypeptide and a double stranded RNA.

In an embodiment, the polynucleotide is an antisense polynucleotide which hybridises under physiological conditions to a polynucleotide comprising any one or more of the sequence of nucleotides provided as SEQ NOs 5 to 8, 11 to 14 or 19 to 25.

In a further embodiment, the polynucleotide is a catalytic polynucleotide capable of cleaving a polynucleotide comprising any one or more of the sequence of nucleotides provided as SEQ ID NOs 5 to 8, 11 to 14 or 19 to 25.

In another embodiment, the polynucleotide is a double stranded RNA (dsRNA) molecule comprising an oligonucleotide which comprises at least 19 contiguous nucleotides of any one or more of the sequence of nucleotides provided as SEQ ID NOs 5 to 8, 11 to 14 or 19 to 25, wherein the portion of the molecule that is double stranded is at least 19 basepairs in length and comprises said oligonucleotide.

Preferably, the dsRNA is expressed from a single promoter, wherein the strands of the double stranded portion are linked by a single stranded portion. Examples of the construction of vectors to produce such dsRNA molecules is provided in Example 5.

In a preferred embodiment, the polynucleotide, or a strand thereof, is capable of hybridising to a polynucleotide comprising any one or more of the sequence of nucleotides provided as SEQ ID NOs 5 to 8, 11 to 14 or 19 to 25 under stringent conditions.

In a further aspect, the present invention provides a method of identifying a polynucleotide which, when present in a cell of a rice plant, down-regulates the level of activity of a Fad2 and/or FatB polypeptide in the cell when compared to a cell that lacks said polynucleotide, the method comprising
  i) determining the ability of a candidate polynucleotide to down-regulate the level of activity of a Fad2 and/or FatB polypeptide in a cell, and
  ii) selecting a polynucleotide which down-regulated the level of activity of a Fad2 and/or FatB polypeptide in the cell.

Step i) can rely on, for example, analysing the amount or enzymatic activity of a Fad2 and/or FatB polypeptide, or the amount of mRNA encoding a Fad2 and/or FatB polypeptide in the cell. Alternatively, step i) may comprise analysing the fatty acid content of the cell, or a seed or plant comprising said cell. Preferably, step i) comprises the introduction of the candidate polynucleotide or a chimeric DNA including a promoter operably linked to the candidate polynucleotide into a plant cell, more preferably into a rice cell, and even more preferably comprises the step of regenerating a transgenic plant from the plant cell and the production of seed from the transgenic plant. The candidate gene may be one of a collection of candidate genes, at least 2 or 3 in number. The invention therefore provides for the use of the polynucleotides of the invention in a screening method.

The polynucleotide can be, but not limited to, an antisense polynucleotide, a sense polynucleotide, a catalytic polynucleotide, a microRNA, a polynucleotide which encodes a polypeptide which binds a Fad2 or FatB polypeptide and a double stranded RNA.

In an embodiment, the antisense polynucleotide hybridises under physiological conditions to a polynucleotide comprising any one or more of the sequence of nucleotides provided as SEQ ID NOs 5 to 8, 11 to 14 or 19 to 25.

In another embodiment, the catalytic polynucleotide is capable of cleaving a polynucleotide comprising any one or more of the sequence of nucleotides provided as SEQ ID NOs 5 to 8, 11 to 14 or 19 to 25.

In a further embodiment, the double stranded RNA (dsRNA) molecule comprises an oligonucleotide which comprises at least 19 contiguous nucleotides of any one or more of the sequence of nucleotides provided as SEQ ID NOs 5 to 8, 11 to 14 or 19 to 25, wherein the portion of the molecule that is double stranded is at least 19 basepairs in length and comprises said oligonucleotide.

Also provided is an isolated polynucleotide identified using a method of the invention.

In a further aspect the present invention provides a vector comprising or encoding a polynucleotide of the invention.

Preferably, the polynucleotide, or sequence encoding the polynucleotide, is operably linked to a promoter. Preferably, the promoter confers expression of the polynucleotide preferentially in the embryo, endosperm, bran layer and/or seed of a rice plant relative to at least one other tissue or organ of said plant.

Also provided is a cell comprising the vector of the invention, and/or the polynucleotide of the invention.

In an embodiment, the polynucleotide or vector was introduced into the cell or a progenitor of the cell.

In a further embodiment, the cell is a rice cell or an *Agrobacterium* cell.

Preferably, the polynucleotide is integrated into the genome of the cell.

In another aspect, the present invention provides a rice plant comprising a cell of the invention.

In yet another aspect, the present invention provides a method of producing the cell of the invention, the method comprising the step of introducing the polynucleotide of the invention, or a vector of the invention, into a cell.

Preferably the method further comprises the step of regenerating a transgenic plant from the cell.

Also provided is the use of the polynucleotide of the invention or a vector of the invention to produce a recombinant cell.

In yet another aspect, the present invention provides a genetically modified rice plant, wherein the plant has decreased expression of a polypeptide having Fad2 and/or FatB activity relative to a corresponding non-modified plant.

Preferably, the plant has been transformed such that it comprises a polynucleotide of the invention, or a progeny plant thereof which comprises said polynucleotide.

In a further aspect the present invention provides a method of producing rice oil of the invention, rice bran of the invention and/or rice seed of the invention, the method comprising exposing a rice plant to an antagonist of a Fad2 or FatB polypeptide.

In another aspect, the present invention provides a method of obtaining a genetically modified rice plant which can be used to produce brown rice seed with an increased storage life when compared to unmodified brown rice seed, the method comprising genetically manipulating the plant such that the activity and/or level of production of a Fad2 and/or FatB polypeptide is reduced in the rice seed when compared to a corresponding plant which produces unmodified brown rice seed.

Preferably, the activity and/or level of production of a Fad2 and/or FatB polypeptide is only reduced in the seed of the plant.

In an embodiment, the activity and/or level of production of a Fad2 polypeptide is reduced.

In a further embodiment, the transgenic plant comprises a polynucleotide of the invention or a vector of the invention.

In a further aspect, the present invention provides a genetically modified rice plant produced using a method of the invention, or progeny thereof.

In a further aspect, the present invention provides a method of selecting a rice plant which can be used to produce rice oil of the invention, rice bran according to the invention and/or rice seed of the invention, the method comprising;

i) screening a mutagenized population of rice seeds or rice plants, and ii) selecting a seed or plant which is capable of, producing rice oil of the invention, rice bran of the invention and/or rice seed of the invention.

In one embodiment, step i) comprises analysing a mutagenized seed and/or plant for a polypeptide which has Fad2 or FatB activity.

In another embodiment, step i) comprises analysing the sequence and/or expression levels of a Fad2 or FatB gene of the mutagenized seed and/or plant.

In a further embodiment, step i) comprises analysing the fatty acid composition of the oil, bran and/or seed of the mutagenized seed and/or plant.

In a further aspect, the present invention provides a method of selecting a rice plant which can be used to produce rice oil of the invention, rice bran of the invention and/or rice seed of the invention, the method comprising i) analysing the fatty acid content of said rice oil, rice bran and/or seed obtained from a candidate rice plant, and ii) selecting a rice plant which can be used to produce rice oil of the invention, rice bran of the invention and/or rice seed of the invention.

In yet a further aspect, the present invention provides a method of selecting a rice plant which can be used to produce rice oil of the invention, rice bran of the invention and/or rice seed of the invention, the method comprising i) analysing a sample from a candidate plant for a polypeptide which has Fad2 or FatB activity, and ii) selecting a rice plant which can be used to produce rice oil of the invention, rice bran of the invention and/or rice seed of the invention based on the sequence, level of production and/or activity of said polypeptide.

In another aspect, the present invention provides a method of selecting a rice plant which can be used to produce rice oil of the invention, rice bran of the invention and/or rice seed of the invention, the method comprising i) analysing the sequence and/or expression levels of a Fad2 or FatB gene of a candidate plant, and ii) selecting a rice plant which can be used to produce rice oil of the invention rice bran of the invention and/or rice seed of the invention based on the sequence and/or expression levels of said gene.

In yet another aspect the present invention provides a method of identifying a rice plant which can be used to produce rice oil of the invention, rice bran of the invention and/or rice seed of the invention, the method comprising detecting a nucleic acid molecule of the plant, wherein the nucleic acid molecule is linked to, and/or comprises at least a part of a Fad2 gene and/or FatB gene in the plant.

In a further aspect, the present invention provides a method of identifying a rice plant which can be used to produce brown rice seed with an increased storage life, the method comprising detecting a nucleic acid molecule of the plant, wherein the nucleic acid molecule is linked to, and/or comprises at least a part of, a Fad2 gene and/or FatB gene in the plant.

In an embodiment, the above two methods comprise:

i) hybridising a second nucleic acid molecule to said nucleic acid molecule which is obtained from said plant, ii) optionally hybridising at least one other nucleic acid molecule to said nucleic acid molecule which is obtained from said plant; and iii) detecting a product of said hybridising step(s) or the absence of a product from said hybridising step(s).

In an embodiment, the second nucleic acid molecule is used as a primer to reverse transcribe or replicate at least a portion of the nucleic acid molecule.

The nucleic acid can be detected using any technique such as, but not limited to, restriction fragment length polymorphism analysis, amplification fragment length polymorphism analysis, microsatellite amplification and/or nucleic acid sequencing.

In an embodiment, the method comprises nucleic acid amplification. In another embodiment, the method analyses expression levels of the gene.

Also provided is a method of obtaining a rice plant or seed, the method comprising;

i) crossing a first parental rice plant which comprises a Fad2 allele which confers an increased proportion of oleic acid in oil of the grain of the plant with a second parental rice plant which comprises a FatB allele which confers a decreased proportion of palmitic acid in oil of the grain of the plant;
ii) screening progeny plants or grain from the cross for the presence of both alleles; and
iv) selecting a progeny plant or grain comprising both alleles and having an increased proportion of oleic acid and a decreased proportion of palmitic acid in oil of the grain of the plant.

In another aspect, the present invention provides a method of introducing a Fad2 allele into a rice plant, the method comprising
i) crossing a first parental rice plant with a second parental rice plant, wherein the second plant comprises said allele, and
ii) backcrossing the progeny of the cross of step i) with plants of the same genotype as the first parent plant for a sufficient number of times to produce a plant with a majority of the genotype of the first parent but comprising said allele
iii) selecting a plant with the majority of the genotype of the first plant and comprising said allele;
wherein said allele confers an increased proportion of oleic acid in oil, bran and/or seed of the plant In yet another aspect, the present invention provides a method of introducing a FatB allele into a rice plant, the method comprising
i) crossing a first parental rice plant with a second parental rice plant, wherein the second plant comprises said allele, and
ii) backcrossing the progeny of the cross of step i) with plants of the same genotype as the first parent plant for a sufficient number of times to produce a plant with a majority of the genotype of the first parent but comprising said allele
iii) selecting a plant with the majority of the genotype of the first plant and comprising said allele;
wherein said allele confers a decreased proportion of palmitic acid in oil, bran and/or seed of the plant.

Further, provided is a method of increasing the proportion of oleic acid in oil, bran and/or seed of a rice plant, the method comprising genetically manipulating said plant such that the production of a Fad2 polypeptide is decreased when compared to a wild-type plant, wherein the polypeptide has $\Delta 12$ desaturase activity.

In yet another aspect, the present invention provides a method of decreasing the proportion of palmitic acid in oil, bran and/or seed of a rice plant, the method comprising genetically manipulating said plant such that the production of a FatB polypeptide is decreased when compared to a wild-type plant, wherein the polypeptide has (FatB) activity.

Also provided is a rice plant obtained using a method of the invention, or progeny plant thereof.

In a further aspect, the present invention provides rice oil obtained from a plant of the invention.

In a further aspect, the present invention provides rice bran obtained from a plant of the invention.

In a further aspect, the present invention provides rice seed obtained from a plant of the invention.

Further, provided is a method of producing seed, the method comprising;
a) growing a plant of the invention, and
b) harvesting the seed.

In yet another aspect, the present invention provides a food product comprising rice oil of the invention, rice bran of the invention and/or rice seed of the invention.

In another aspect, the present invention provides a method of preparing food, the method comprising cooking an edible substance in rice oil of the invention.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1—Principal fatty acid biosynthetic pathways in plastid and cytosol of higher plants.

FIGS. 2(A)-(B)—Alignment of rice FatB proteins. ProteinFA1B2=SEQ ID NO:1, proteinFATB3=SEQ ID NO:2, proteinFATB1=SEQ ID NO:3 and proteinFATB4=SEQ ID NO:4.

Figure 3:
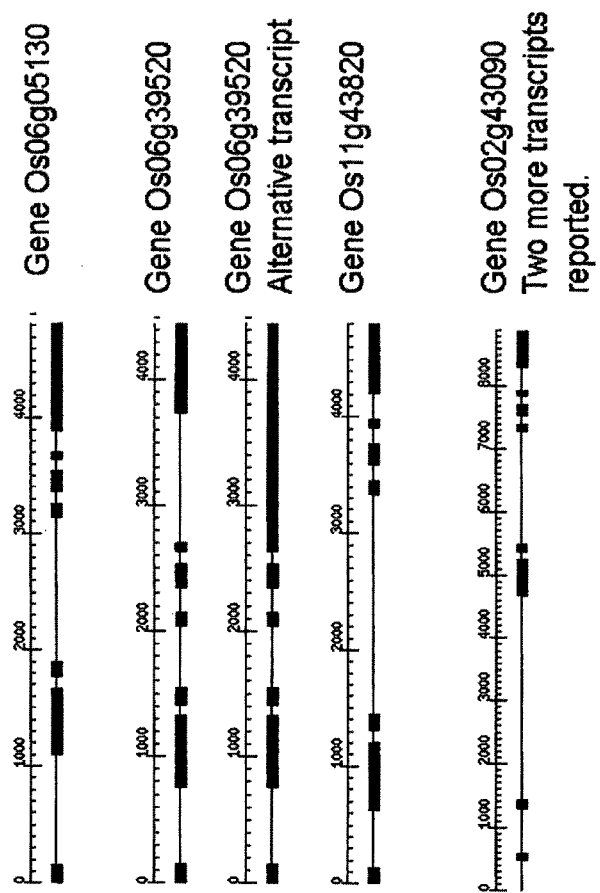

FIG. 3—Rice FatB gene structures. LOC_Os02g4=SEQ ID NO:5, LOC_Os11g4=SEQ ID NO:6, LOC_Os06g0=SEQ ID NO:7 and LOC_Os06g3=SEQ ID NO:8.

FIGS. 4(A)-(L)—Alignment of FatB gene sequences by ClustalW. Default parameters were used and note that the 'genes' are of different lengths.

FIGS. 5(A)-(C)—The exon-intron structures of the FatB gene corresponding to LOC_Os6g05130. The top line corresponds to the start of the coding sequence in mRNA (SEQ ID NO:9) and the second line of the pair corresponds to the gene (SEQ ID NO:10).

Figure 6A:
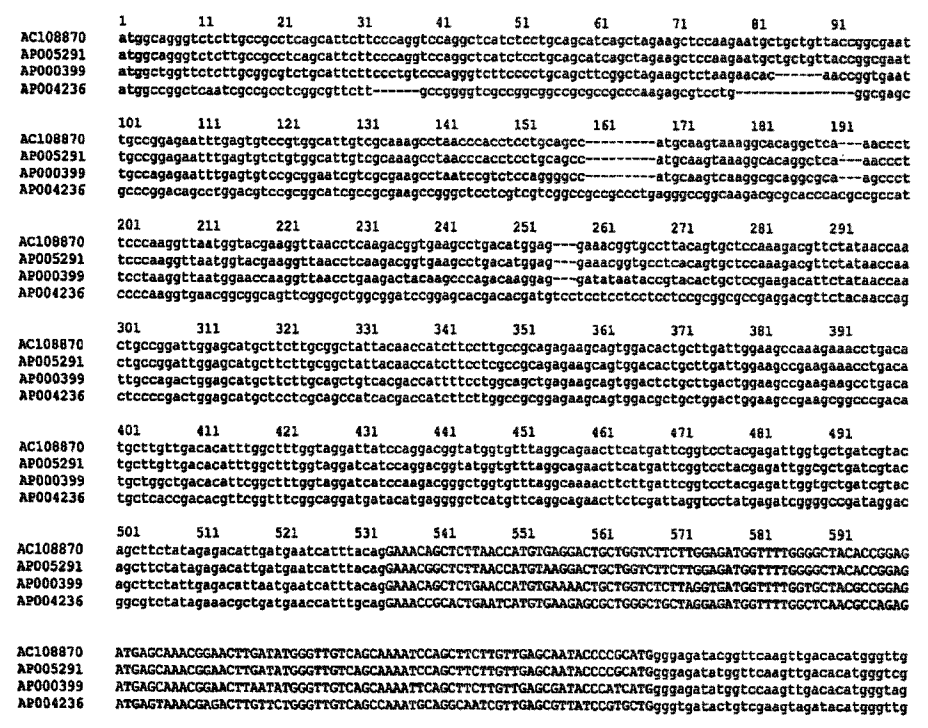
Figure 6B:
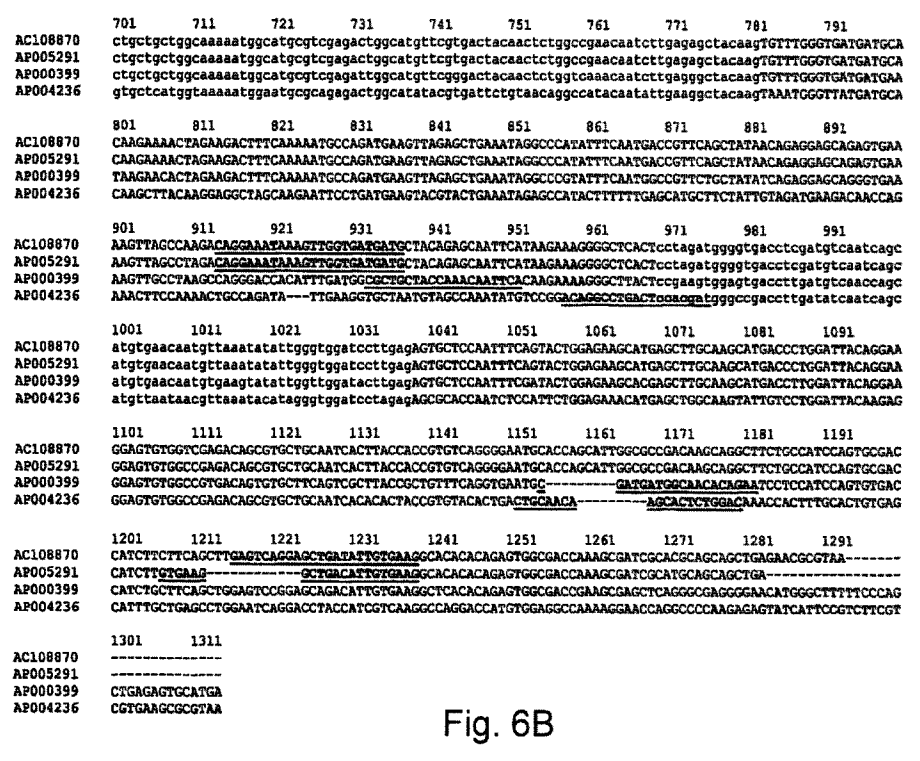

FIGS. 6(A)-(B)—Alignment of coding sequence of four FatB isoforms showing consecutive exons in alternating lower case and upper case respectively and location of primers (underlined) used to distinguish the isoforms by RT-PCR. The initiating codon (start position 1) is in bold. ACI08870=SEQ ID NO:1 I, AP005291=SEQ ID NO:12, AP000399=SEQ ID NO:13 and AP004236=SEQ ID NO: 14.

Figure 8A:
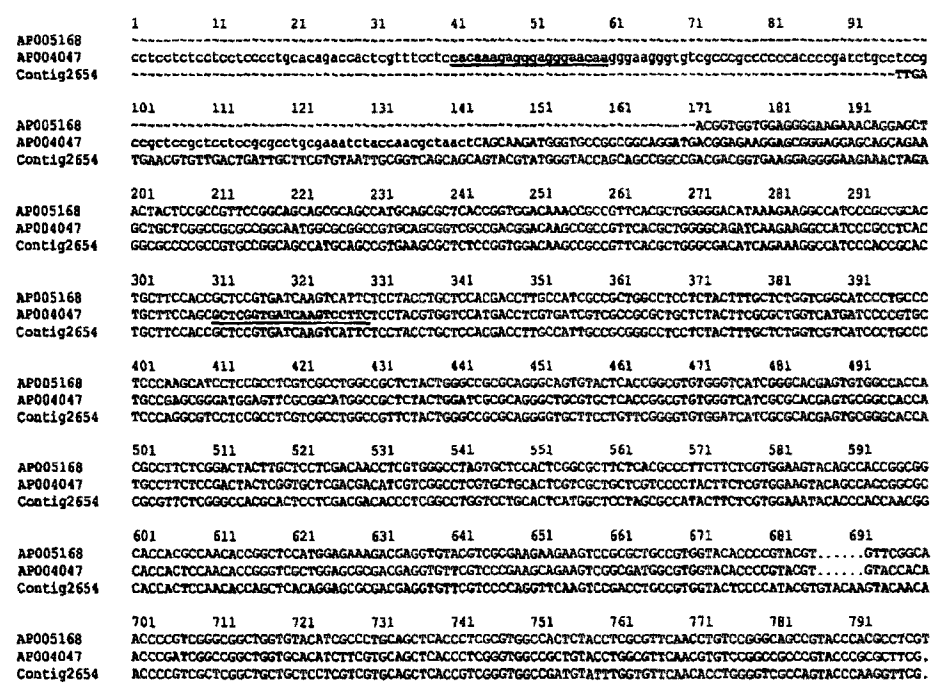
Figure 8B:
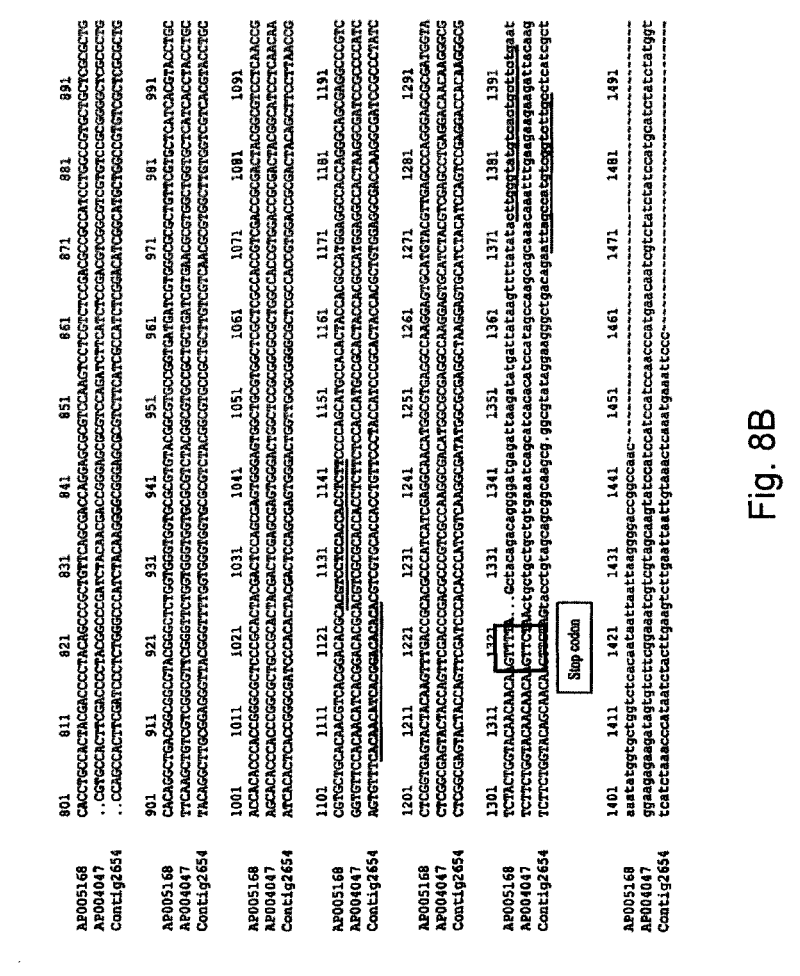

FIGS. 7(A)-(B) Clustal W alignment of deduced polypeptide sequence of Fad2 isoforms. Note that line F_1 corresponds to Os02g48S60, F_2 corresponds to Os07g23410, F_3 to Os07g23430 and O_4 to Os07g23390. The program ClustalW (Fast) with default parameters was used. ProteinF_1=SEQ ID NO:15, ProteinF_3=SEQ ID NO:16, ProteinF_2=SEQ ID NO:17 and ProteinF_4=SEQ ID NO:18, FIGS. 8(A)-(B)—Alignment of Fad2 sequences showing location of 5' UTR in isoform AP004047 (lowercase) and location of primers used for amplification by RT-PCR (underlined). The location of the stop codon is indicated by a box and untranslated regions downstream of the stop codon are in lower case. AP005168=SEQ ID NO:19, AP004047=SEQ ID NO:20 and Contig2654=SEQ ID NO:21.

Figure 9:
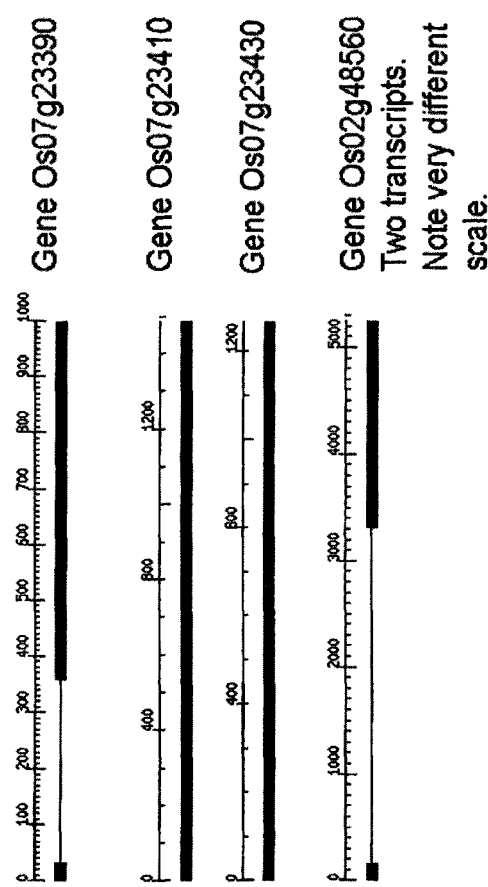

FIG. 9—Rice Fad2 gene structures.

FIGS. 10(A)-(D)—Alignment of the nucleotide sequences of the protein coding regions for rice Fad2 genes. Line 0_2 corresponds to Os07g23410, 0_4 to Os07g23390, 0_1 to Os02g48560 and 0_3 to Os07g23410. The program ClustalW with default parameters was used. CdsFAD20_2=SEQ ID NO:22, CdsFAD20_4=SEQ ID NO:23, CdsFAD20_1=SEQ ID NO:24 and CdsFAD20_3=SEQ ID NO:25.

Figure 11:
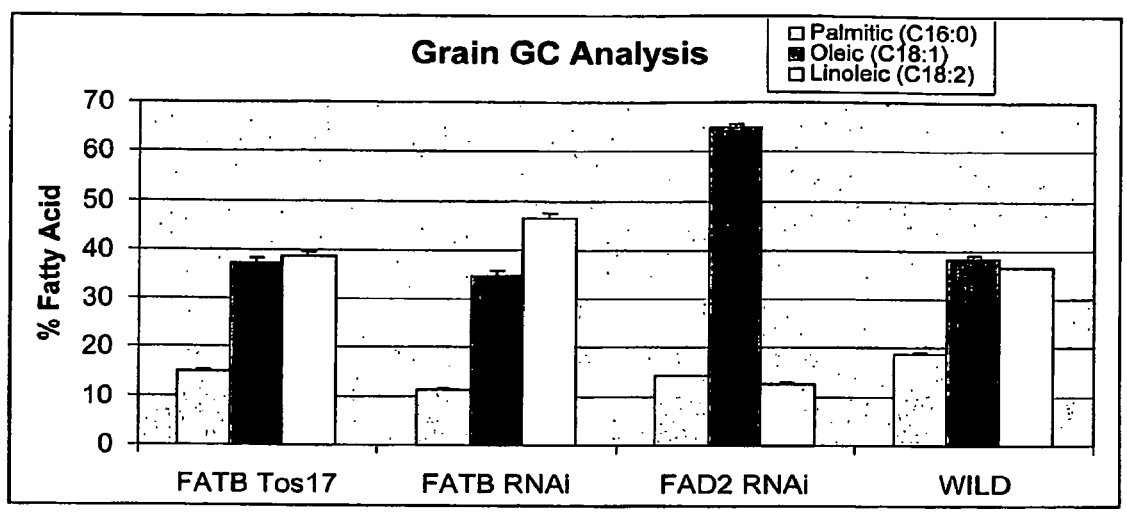

FIG. 11—Graphical representation of the relative percentages of palmitic, oleic and linoleic acid as determined by GC analysis of total oil fraction from grains of indicated genotypes.

Figure 12:
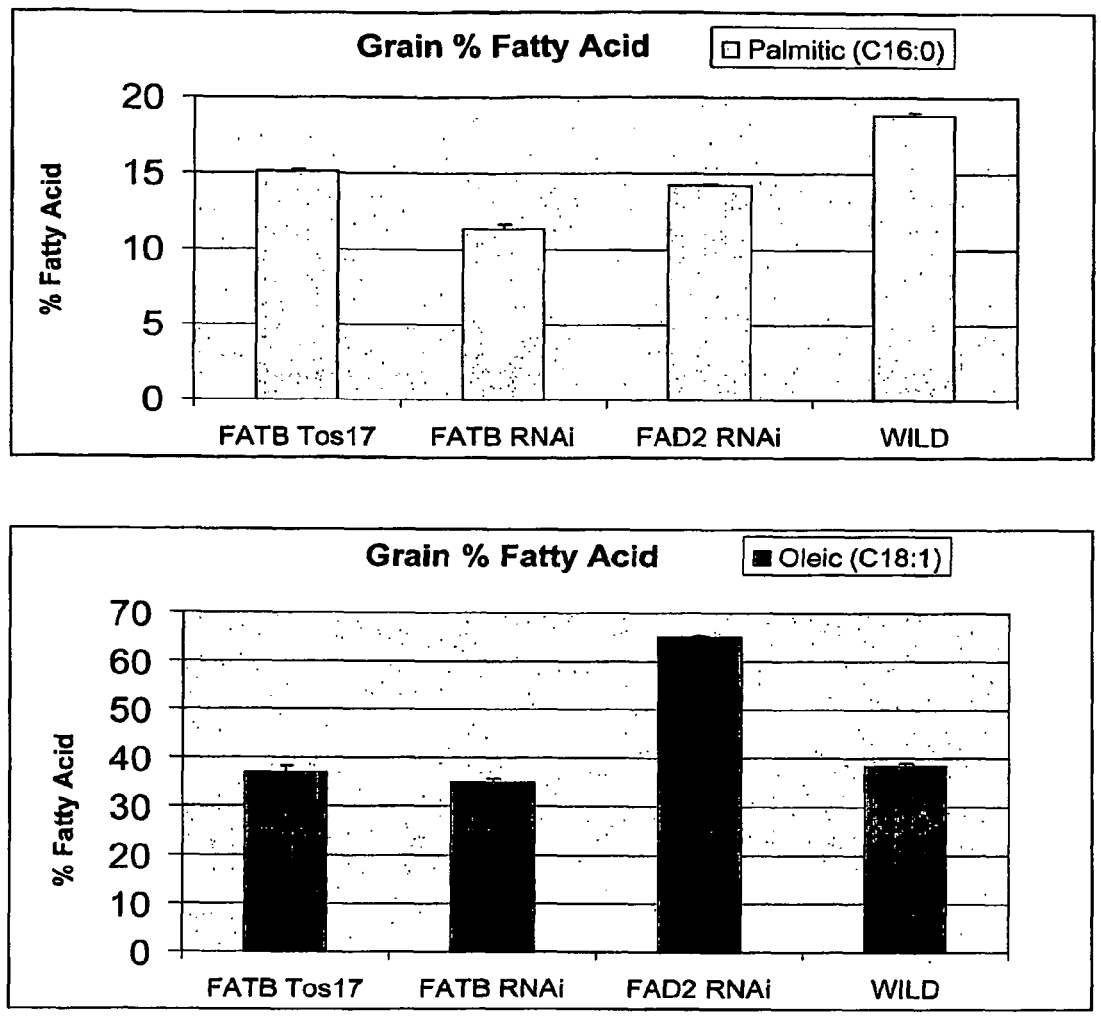

FIG. 12—Graphical representation of the relative percentages of palmitic and oleic acid in a GC total lipid analysis from grains of the genotypes indicated.

Figure 13:
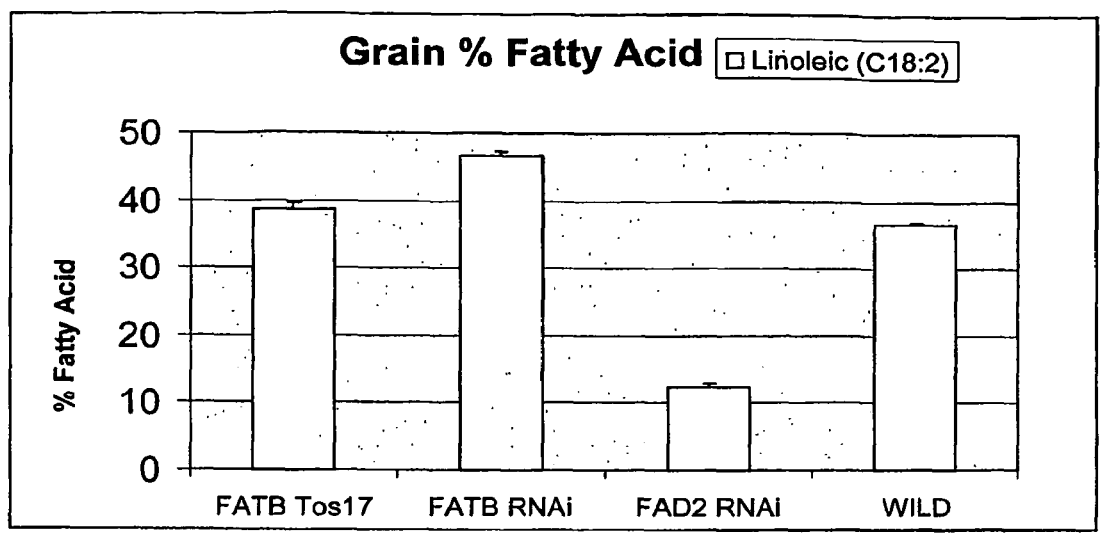

FIG. 13—Graphical representation of the relative percentages of linoleic and oleic acid in a GC total lipid analysis from grains of the genotypes indicated.

Figure 14:
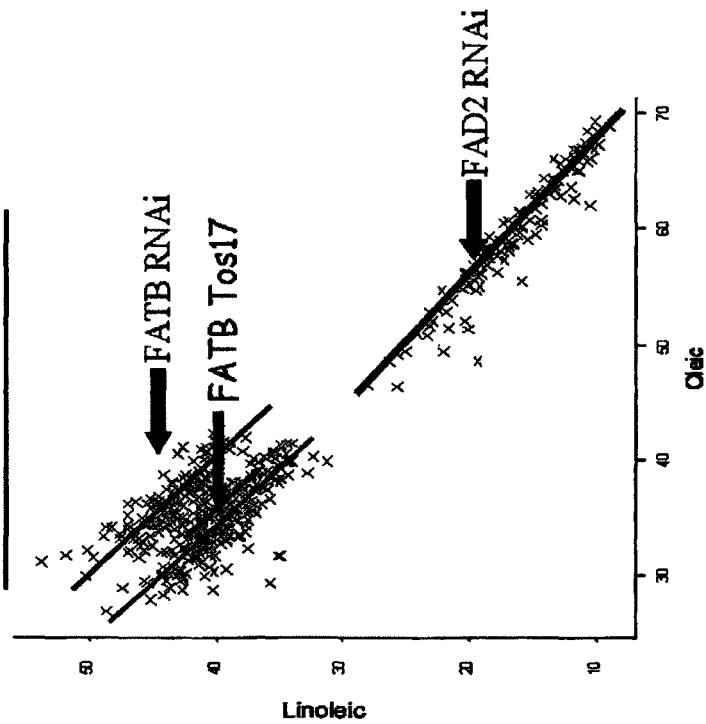

FIG. 14—Scatterplot showing the percentage of linoleic versus oleic acid in the grain of rice plants of the indicated genotypes. Note that the relationship (reflected in the slope of the line) between the amounts of these two fatty acids is essentially the same in all of the lines analysed but the pool size capacity appears to be different (as reflected in the displacements of the different lines along the space analysed.

Figure 15:
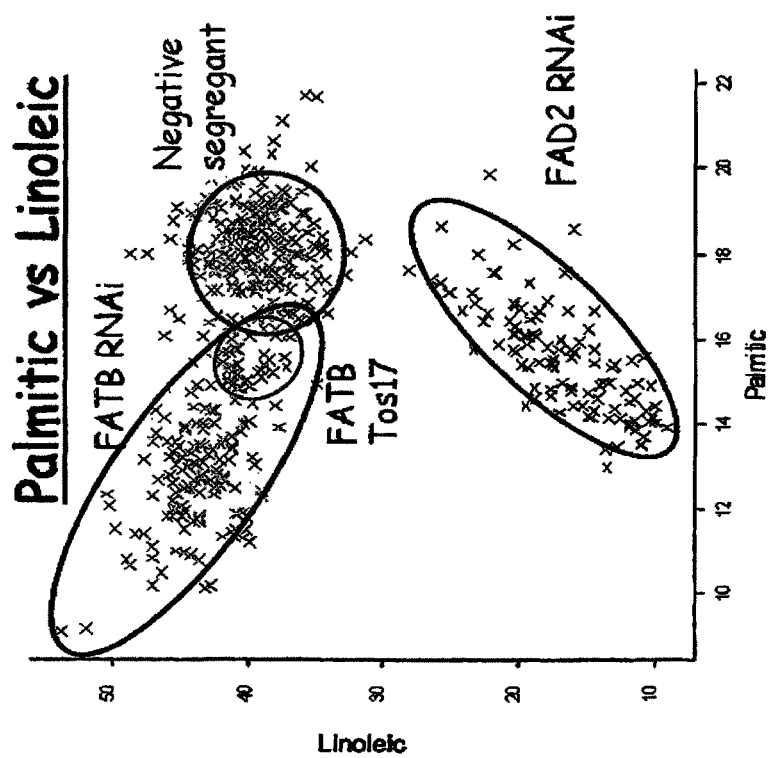

FIG. 15—Scatterplot of the percentage of linoleic versus palmitic acid among different genotypes. Note the different slopes of the lines affected in FatB compared to those affected in Fad2. This suggests the relationship between these components is different in the different genotypes, probably reflecting the differences in the steps affected.

Figure 16:
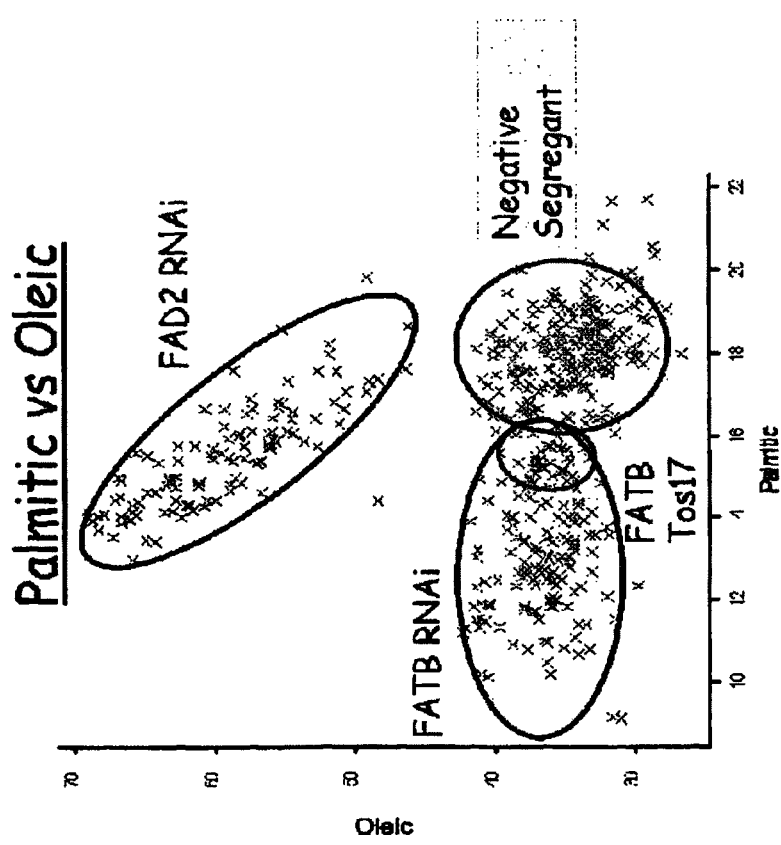

FIG. 16—Scatterplot of the percentage of oleic versus palmitic acid for various genotypes. Note the differences in slopes.

Figure 17:
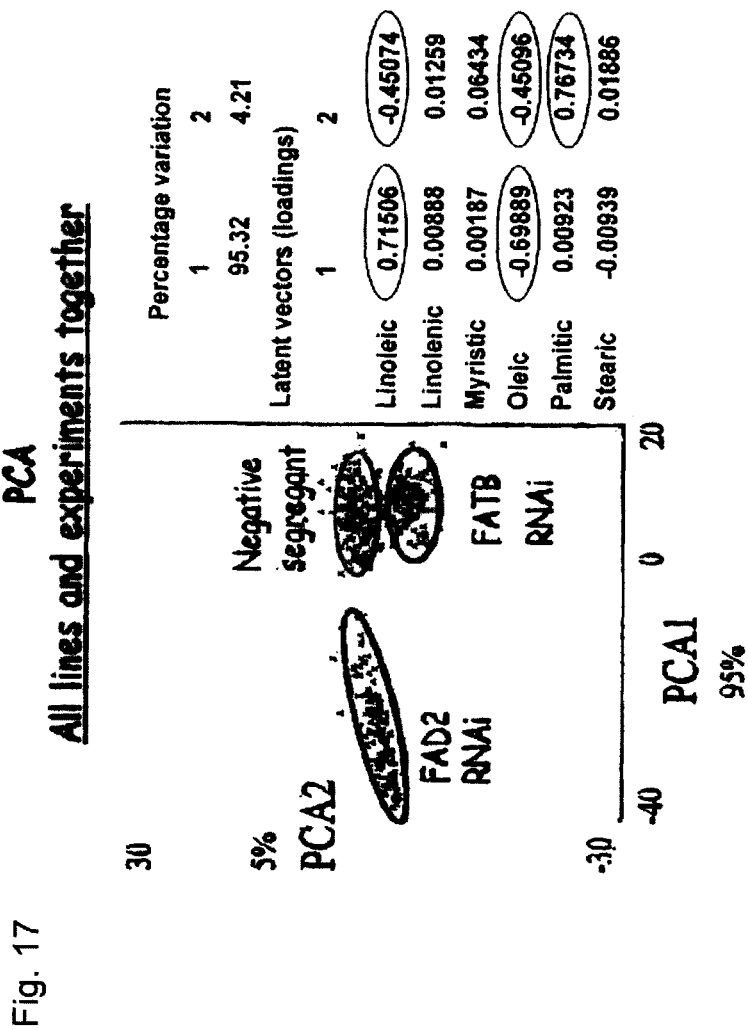

FIG. 17—Graphical representation of Principal Component Analysis of variation in oil composition for Fad2 RNAi plants and FatB RNAi plants. The results show that Principal Component 2 is Linoleic versus Oleic and Principal Component 2 is Palmitic versus Linoleic plus Oleic.

Figure 18:
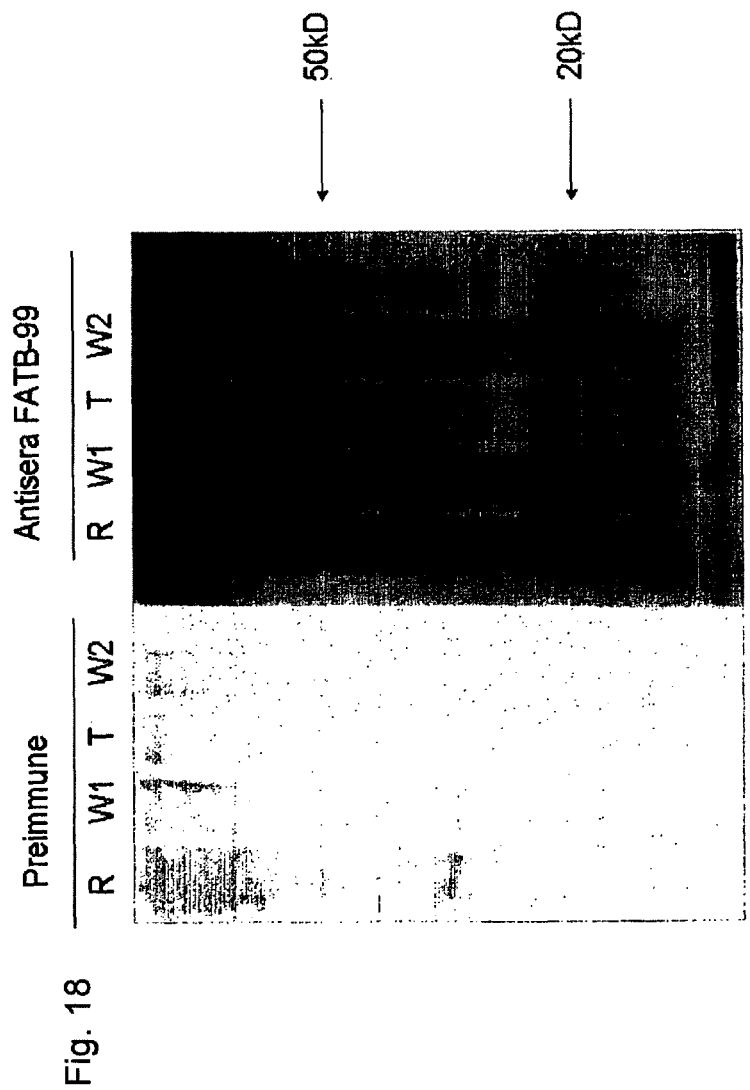

FIG. 18—Western blot showing the reaction of antisera raised against peptide. FatB-99 against total leaf protein extracts analysed by SDS-PAGE. A peptide of approx 20 kDa is missing in the Tos-17 line. The reaction with preimmune sera is indicated. R refers to FatB RNAi lines and T is the Tos-17 line. W and W2 are wildtype.

KEY TO SEQUENCE LISTING

SEQ ID NO:1—Rice FatB2 protein.
SEQ ID NO:2—Rice FatB3 protein.
SEQ ID NO:3—Rice FatB1 protein.
SEQ ID NO:4—Rice FatB4 protein.
SEQ ID NO:5—Rice FatB3 gene.
SEQ ID NO:6—Rice FatB2 gene.
SEQ ID NO:7—Rice FatB1 gene.
SEQ ID NO:8—Rice FatB4 gene.
SEQ ID NO:9—cDNA encoding rice FatB1 protein.
SEQ ID NO:10—Gene encoding rice FatB1 protein (partial sequence only, see FIG. 5—includes all exon sequences and some flanking and intron sequence).
SEQ ID NO: 11—Open reading frame encoding rice FatB2 protein.
SEQ ID NO:12—Open reading frame encoding rice FatB3 protein.
SEQ ID NO: 13—Open reading frame encoding rice FatB1 protein.
SEQ ID NO:14—Open reading frame encoding rice FatB4 protein.
SEQ ID NO:15—Rice Fad2 isoform 1.
SEQ ID NO:16—Rice Fad2 isoform 3.
SEQ ID NO:17—Rice Fad2 isoform 2.
SEQ ID NO:18—Rice Fad2 isoform 4.
SEQ ID NO:19—Rice Fad2-3 cDNA.
SEQ ID NO:20—Rice Fad2-1 cDNA.
SEQ ID NO:21—Rice Fad2-2 cDNA.
SEQ ID NO:22—Open reading frame encoding rice Fad2-2.
SEQ ID NO:23—Open reading frame encoding rice Fad2-4.
SEQ ID NO:24—Open reading frame encoding rice Fad2-1.
SEQ ID NO:25—Open reading frame encoding rice Fad2-3.

SEQ ID NO:26—FatB consensus sequence.
SEQ ID NOs 27 to 33—Fad2 consensus sequences.
SEQ ID NOs 34 to 55 and 60 to 63—Oligonucleotide
SEQ ID NOs 56 to 59—Antigenic rice FatB peptides.
SEQ ID NOs 64 to 83—Sequence of one strand of molecules that can be used for RNAi.

DETAILED DESCRIPTION OF THE INVENTION

General Techniques

Unless specifically defined otherwise, all technical and scientific terms used herein shall be taken to have the same meaning as commonly understood by one of ordinary skill in the art (e.g., in cell culture, plant molecular biology, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and S. D. Flames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

SELECTED DEFINITIONS

As used herein, the term "Fad2 polypeptide" refers to a protein which performs a desaturase reaction converting oleic acid to linoleic acid. Thus, the term "Fad2 activity" refers to the conversion of oleic acid to linoleic acid. These fatty acids may be in an esterified form, such as, for example, as part of a phospholipid. Examples of rice Fad2 polypeptides include proteins comprising an amino acid sequence provided in FIG. 7 and SEQ ID NOs 15 to 18, as well as variants and/or mutants thereof. Such variants and/or mutants may be at least 80% identical, more preferably at least 90% identical, more preferably at least 95% identical, and even more preferably at least 99% identical to any one of the polypeptides provided in FIG. 7 and SEQ ID NOs 15 to 18.

A "Fad2 polynucleotide" or "Fad2 gene" encodes a Fad2 polypeptide. Examples of Fad2 polynucleotides include nucleic acids comprising a nucleotide sequence provided in FIG. 8 or 10 and SEQ ID NOs 19 to 25, as well as allelic variants and/or mutants thereof. Examples of Fad2 genes include nucleic acids comprising a nucleotide sequence provided in FIG. 8 and SEQ ID NOs 19 to 21, as well as allelic variants and/or mutants thereof. Such allelic variants and/or mutants may be at least 80% identical, more preferably at least 90% identical, more preferably at least 95% identical, and even more preferably at least 99% identical to any one of the polynucleotides provided in FIG. 8 and/or 10, and/or SEQ ID NOs 19 to 25.

As used herein, the term "FatB polypeptide" refers to a protein which hydrolyses palmitoyl-ACP to produce free palmitic acid. Thus, the term "FatB activity" refers to the hydrolysis of palmitoyl-ACP to produce free palmitic acid. Examples of rice FatB polypeptides include proteins comprising an amino acid sequence provided FIG. 2 SEQ ID NOs 1 to 4, as well as variants and/or mutants thereof. Such variants and/or mutants may be at least 80% identical, more preferably at least 90% identical, more preferably at least 95% identical, and even more preferably at least 99% identical to any one of the polypeptides provided in FIG. 2 and SEQ ID NOs 1 to 4.

A "FatB polynucleotide" or "FatB gene" encodes a FatB polypeptide. Examples of FatB polynucleotides include nucleic acids comprising a nucleotide sequence provided in FIGS. 4 and 6 and SEQ ID NOs 5 to 8 and 11 to 14, as well as allelic variants and/or mutants thereof. Examples of FatB genes include nucleic acids comprising a nucleotide sequence provided in FIG. 4 and SEQ ID NOs 5 to 8, as well as allelic variants and/or mutants thereof. Such allelic variants and/or mutants may be at least 80% identical, more preferably at least 90% identical, more preferably at least 95% identical, and even more preferably at least 99% identical to any one of the polynucleotides provided in FIG. 4 and/or 6, and/or SEQ ID NOs 5 to 8 and 11 to 14.

As used herein, the term "rice" refers to any species of the Genus *Oryza*, including progenitors thereof, as well as progeny thereof produced by crosses with other species. It is preferred that the plant is of a *Oryza* species which is commercially cultivated such as, for example, a strain or cultivar or variety of *Oryza* saliva or suitable for commercial production of grain.

As used herein, the term "rice oil" refers to a composition obtained from the seed/grain, or a portion thereof such as the bran layer, of a rice plant which comprises at least 60% (w/w) lipid. Rice oil is typically a liquid at room temperature. Preferably, the lipid comprises fatty acids that are at least 6 carbons in length. The fatty acids are typically in an esterified form, such as for example as triacylglycerols, phospholipid. Rice oil of the invention comprises oleic acid. Rice oil of the invention may also comprise at least some other fatty acids such as palmitic acid, linoleic acid, myristic acid, stearic acid and/or linolenic acid. The fatty acids may be free fatty acids and/or be found as triacylglycerols (TAGs). In an embodiment, at least 50%, more preferably at least 70%, more preferably at least 80% of the fatty acids in rice oil of the invention be found as TAGs. Rice oil of the invention can form part of the rice grain/seed or portion thereof such as the aleurone layer or embryo/scutellum, which together are referred to as "rice bran". Alternatively, rice oil of the invention has been extracted from rice grain/seed or rice bran. An example of such an extraction procedure is provided in Example 1. Thus, in an embodiment, "rice oil" of the invention is "substantially purified" or "purified" rice oil that has been separated from one or more other lipids, nucleic acids, polypeptides, or other contaminating molecules with which it is associated in its native state. It is preferred that the substantially purified rice oil is at least 60% free, more preferably at least 75% free, and more preferably at least 90% free from other components with which it is naturally associated. In a preferred embodiment, upon extraction the ratio of oleic acid to linoleic acid, palmitic acid to oleic acid and/or palmitic acid to linoleic acid has not been significantly altered (for example, no greater than a 5% alteration) when compared to the ratio in the intact seed/grain or bran. In a further embodiment, the rice oil has not been exposed to a procedure, such as hydrogenation, which may alter the ratio of oleic acid to linoleic acid, palmitic acid to oleic acid and/or palmitic acid to linoleic acid when compared to the ratio in the intact seed/grain or bran. Rice oil of the invention may further comprise non-fatty acid molecules such as, but not limited to, γ-oryzanols and sterols.

Rice oil may be extracted from rice seed or bran by any method known in the art. This typically involves extraction with nonpolar solvents such as diethyl ether, petroleum ether, chloroform/methanol or butanol mixtures. Lipids associated with the starch in the grain may be extracted with water-saturated butanol. The rice oil may be "de-gummed" by methods known in the art to remove polysaccharides or treated in other ways to remove contaminants or improve purity, stability or colour. The triacylglycerols and other esters in the oil may be hydrolysed to release free fatty acids, or the oil hydrogenated or treated chemically or enzymatically as known in the art.

Rice oil after extraction from rice seed or bran typically comprises the group of lipids called γ-oryzanols. As used herein, "comprises γ-oryzanol" refers to the presence of at least 0.1% (w/w) γ-oryzanol compounds in the oil. The levels of γ-oryzanol in rice oil after extraction and before removal from the TAG is typically 1.5-3.5% (w/w). The compounds are typically a mixture of steryl and other triterpenyl esters of ferulic acid (4-hydroxy-3-methoxy cinnamic acid). Cycloartenyl ferulate, 24-methylene cycloartanyl fendate and campesteryl ferulate are the predominant ferulates in oryzanol, with lower levels of β-sitosteryl ferulate and stigmasteryl ferulate. The presence of γ-oryzanols is thought to help protect consumers of rice oil against chronic diseases such as heart disease and cancer and therefore the presence of γ-oryzanol is advantageous.

As used herein, the term "rice bran" refers to the layer (aleurone layer) between the inner white rice grain and the outer hull of a rice seed/grain as well as the embryo/scutellum of the grain. The rice bran is the primary by product of the polishing of brown rice to produce white rice.

As used herein, the term "increased storage life" refers to a method of the invention producing a seed/grain, which upon harvesting, can be stored as brown rice for an enhanced period of time when compared to, for example, brown rice harvested from a wild type (non-genetically modified) rice plant. As described herein, one measure for "increased storage life" of brown rice is hexanal production following storage for at least 8 weeks at 40° C. (see Example 8).

The term "plant" includes whole plants, vegetative structures (for example, leaves, stems), roots, floral organs/structures, seed (including embryo, endosperm, and seed coat), plant tissue (for example, vascular tissue, ground tissue, and the like), cells and progeny of the same.

A "transgenic plant", "genetically modified plant" or variations thereof refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

The terms "seed" and "grain" are used interchangeably herein. "Grain" generally refers to mature, harvested grain but can also refer to grain after imbibition or germination, according to the context. Mature grain commonly has a moisture content of less than about 18-20%.

As used herein, the term "corresponding non-modified plant" refers to a wild-type plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein. Wild-type rice varieties that are suitable as a reference standard include Nipponbare.

"Nucleic acid molecule" refers to a oligonucleotide, polynucleotide or any fragment thereof. It may be DNA or RNA of genomic or synthetic origin, double-stranded or single-stranded, and combined with carbohydrate, lipids, protein, or other materials to perform a particular activity defined herein. The terms "nucleic acid molecule" and "polynucleotide" are used herein interchangeably.

The % identity of a polynucleotide is determined by GAP (Needleman and Wunsch, 1970) analysis (GCG program) with a gap creation penalty-5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

"Oligonucleotides" can be RNA, DNA, or derivatives of either. Although the terms polynucleotide and oligonucleotide have overlapping meaning, oligonucleotide are typically relatively short single stranded molecules. The minimum size of such oligonucleotides is the size required for the formation of a stable hybrid between an oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

As used herein, the term "nucleic acid amplification" refers to any in vitro method for increasing the number of copies of a nucleic acid molecule with the use of a DNA polymerase. Nucleic acid amplification results in the incorporation of nucleotides into a DNA molecule or primer thereby forming a new DNA molecule complementary to a DNA template. The newly formed DNA molecule can be used a template to synthesize additional DNA molecules.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, the term "gene" is to be taken in its broadest context and includes the deoxyribonucleotide sequences comprising the protein coding region of a structural gene and including sequences located adjacent to the coding region on both the 5' and 3' ends for a distance of at least about 2 kb on either end and which are involved in expression of the gene. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, the term "genetically linked" or similar refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the embodiment where the marker locus comprises a polymorphism that is responsible for the trait of interest (in other words the marker locus is directly "linked" or "perfectly linked" to the phenotype). In another embodiment, the marker locus and a second locus are different, yet sufficiently close on a chromosome that they will be inherited together in more than 50% of meioses. The percent of recombination observed between genetically linked loci per generation (centimorgans (cM)), will be less than 50. In particular embodiments of the invention, genetically linked loci may be 45, 35, 25, 15, 10, 5, 4, 3, 2, or I or less cM apart on a chromosome. Preferably, the markers are less than 5 cM apart and most preferably about 0 cM apart.

An "allele" refers to one specific form of a genetic sequence (such as a gene) within a cell, an individual plant or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations".

A "polymorphism" as used herein denotes a variation in the nucleotide sequence between alleles of the loci of the invention, of different species, cultivars, strains or individuals of a plant. A "polymorphic position" is a preselected nucleotide position within the sequence of the gene. In some cases, genetic polymorphisms are reflected by an amino acid sequence variation, and thus a polymorphic position can result in location of a polymorphism in the amino acid sequence at a predetermined position in the sequence of a polypeptide. In other instances, the polymorphic region may be in a non-polypeptide encoding region of the gene, for example in the promoter region such may influence expression levels of the gene. Typical polymorphisms are deletions, insertions or substitutions. These can involve a single nucleotide (single nucleotide polymorphism or SNP) or two or more nucleotides.

The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

Antisense Polynucleotides

The term "antisense polynucleotide" shall be taken to mean a DNA or RNA, or combination thereof, molecule that is complementary to at least a portion of a specific mRNA molecule encoding a FatB or Fad2 polypeptide and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque, 1995 and Senior, 1998. Bourque, 1995 lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior (1998) states that antisense methods are now a very well established technique for manipulating gene expression.

An antisense polynucleotide of the invention will hybridize to a target polynucleotide under physiological conditions. As used herein, the term "an antisense polynucleotide which hybridises under physiological conditions" means that the polynucleotide (which is fully or partially single stranded) is at least capable of forming a double stranded polynucleotide with mRNA encoding a protein, such as those provided in FIG. 2 or 7 or SEQ ID NOs 1 to 4 or 15 to 18 under normal conditions in a cell, preferably a rice cell.

Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are the hammerhead ribozyme (Haseloff and Gerlach, 1988; Perriman et al., 1992) and the hairpin ribozyme (Shippy et al., 1999).

The ribozymes of this invention and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for 17 RNA polymerase or SP6 RNA polymerase. Accordingly, also provided by this invention is a nucleic acid molecule, i.e., DNA or cDNA, coding for a catalytic polynucleotide of the invention. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, catalytic polynucleotides of the invention should also be capable of hybridizing a target nucleic acid molecule (for example an mRNA encoding any polypeptide provided in FIG. 2 or 7 or SEQ ID NOs 1 to 4 or 15 to 18) under "physiological conditions", namely those conditions within a cell (especially conditions in a plant cell such as a rice cell).

RNA Interference

RNA interference (RNAi) is particularly useful for specifically inhibiting the production of a particular protein. Although not wishing to be limited by theory. Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof in this case an mRNA encoding a polypeptide according to the invention. Conveniently, the dsRNA can be produced from a single promoter in a recombinant vector or host cell, where the sense and antisense sequences are linked by an unrelated sequence which enables the sense and antisense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ('siRNA') molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the plant (preferably rice) in which it is to be introduced, e.g., as determined by standard BLAST search.

Examples of dsRNA molecules of the invention are provided in Example 5. Further examples include those which comprise a sequence as provided in one or more of SEQ ID NOs 64 to 73 (for Fad2) and SEQ ID NOs 74 to 83 (for FatB).

microRNA

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al., 2005; Almeida and Allshire, 2005).

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 9720936 and EP 0465572 for methods of implementing co-suppression approaches.

Nucleic Acid Hybridization

In an embodiment, polynucleotides of the invention, or a strand thereof, hybridize under physiological conditions to a polynucleotide comprising any one or more of the sequence of nucleotides provided as SEQ ID NOs 5 to 8, 11 to 14 or 19 to 25. In a further embodiment, polynucleotides of the invention, or a strand thereof, also hybridize to a polynucleotide comprising any one or more of the sequence of nucleotides provided as SEQ ID NOs 5 to 8, 11 to 14 or 19 to 25 under stringent conditions.

As used herein, the phrase "stringent conditions" refers to conditions under which a polynucleotide, probe, primer and/or oligonucleotide will hybridize to its target sequence(s), but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al (supra), Current Protocols In Molecular Biology, John Wiley & Sons, N.Y. (1989), 6.3.1-6.3.6, as well as the Examples described herein. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. In another embodiment, a nucleic acid sequence that is hybridizable to the nucleic acid molecule comprising the nucleotide sequence of SEQ ID NOs 5 to 8, 11 to 14 or 19 to 25, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art, see, e.g., Ausubel et al. (supra), and Kriegler, 1990; Gene Transfer And Expression, A Laboratory Manual, Stockton Press, NY. In yet another embodiment, a nucleic acid that is hybridizable to the nucleic acid molecule comprising the nucleotide sequences SEQ ID NOs 5 to 8, 11 to 14 or 19 to 25, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art, see, e.g., Ausubel et al. (supra) and Kriegler, 1990, Gene Transfer And Expression, A Laboratory Manual, Stockton Press, NY, as well as the Examples provided herein.

Nucleic Acid Constructs, Vectors and Host Cells

The present invention includes the production of genetically modified rice plants, wherein the plant has decreased expression of a polypeptide having Fad2 and/or FatB activity relative to a corresponding non-modified plant.

Nucleic acid constructs useful for producing the above-mentioned transgenic plants can readily be produced using standard techniques.

When inserting a region encoding an mRNA the construct may comprise intron sequences. These intron sequences may aid expression of the transgene in the plant. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not. However, in a preferred embodiment, any polypeptide encoding region is provided as a single open reading frame. As the skilled addressee would be aware, such open reading frames can be obtained by reverse transcribing mRNA encoding the polypeptide.

To ensure appropriate expression of the gene encoding an mRNA of interest, the nucleic acid construct typically comprises one or more regulatory elements such as promoters, enhancers, as well as transcription termination or polyadenylation sequences. Such elements are well known in the art.

The transcriptional initiation region comprising the regulatory element(s) may provide for regulated or constitutive expression in the plant. Preferably, expression at least occurs in cells of the embryo, endosperm, bran layer developing seed and/or mature seed (grain). In an alternate embodiment, the regulatory elements may be promoters not specific for seed cells (such as ubiquitin promoter or CaMV35S or enhanced 35S promoters).

Examples of seed specific promoters useful for the present invention include, but are not limited to, the wheat low molecular weight glutenin promoter (Colot et al., 1987), the promoter expressing α-amylase in wheat seeds (Stefanov et al., 1991), and the hordein promoter (Brandt et al., 1985).

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants; see, e.g., PCT publication WO 8402913. All of these promoters have been used to create various types of plant-expressible recombinant DNA vectors.

The promoter may be modulated by factors such as temperature, light or stress. Ordinarily, the regulatory elements will be provided 5' of the genetic sequence to be expressed. The construct may also contain other elements that enhance transcription such as the nos 3' or the ocs 3' polyadenylation regions or transcription terminators.

The 5' non-translated leader sequence can be derived from the promoter selected to express the heterologous gene sequence of the polynucleotide of the present invention, and can be specifically modified if desired so as to increase translation of mRNA. For a review of optimizing expression of transgenes, see Koziel et al. (1996). The 5 non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. No. 5,362,865 and U.S. Pat. No. 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' translated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Typically, the nucleic acid construct comprises a selectable marker. Selectable markers aid in the identification and screening of plants or cells that have been transformed with the exogenous nucleic acid molecule. The selectable marker gene may provide antibiotic or herbicide resistance to the rice cells, or allow the utilization of substrates such as mannose. The selectable marker preferably confers hygromycin resistance to the rice cells.

Preferably, the nucleic acid construct is stably incorporated into the genome of the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al. Cloning Vectors: A Laboratory Manual, 1985, supp. 1987; Weissbach and Weissbach, Methods for Plant Molecular Biology, Academic Press, 1989; and Gelvin et al, Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably cells of a cereal plant, and even more preferably a rice cell.

Transgenic Plants

Transgenic rice (also referred to herein as genetically modified rice) can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every polynucleotide that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. No. 5,472,869, 5,384,253, WO 92/09696 and WO 93/21335); and the gene gun (see, for example, U.S. Pat. No. 4,945,050 and U.S. Pat. No. 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of Agrobacterium infection are required. An illustrative embodiment of a method for delivering DNA into Zea mays cells by acceleration is a biolistics α-particle delivery system, that can be used to propel particles coated with DNA through a screen, such as a stainless steel or Nytex screen, onto a filter surface covered with corn cells cultured in suspension. A particle delivery system suitable for use with the present invention is the helium acceleration PDS-1000/He gun is available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. No. 5,451,513, U.S. Pat. No. 5,545,818, U.S. Pat. No. 5,877,402, U.S. Pat. No. 5,932,479, and WO 99/05265.

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

Agrobacterium-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. No. 5,177,010, U.S. Pat. No. 5,104,310, U.S. Pat. No. 5,004,863, U.S. Pat. No. 5,159,135). Further, the integration of the T-DNA is a relatively precise process resulting in few rearrangements. The region of DNA to be transferred is defined by the border sequences, and intervening DNA is usually inserted into the plant genome.

Modern *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyarna et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transformation of cereal plants such as rice for introducing genetic variation into the plant by introduction of an exogenous nucleic acid and for regeneration of plants from protoplasts or immature plant embryos are well known in the art, see for example, Canadian Patent Application No. 2,092, 588, Australian Patent Application No 61781/94, Australian Patent No 667939, U.S. Pat. No. 6,100,447, International Patent Application PCT/US97/10621, U.S. Pat. No. 5,589, 617, U.S. Pat. No. 6,541,257, and other methods are set out in Patent specification WO99/14314. Preferably, transgenic rice plants are produced by *Agrobacterium tumefaciens* mediated transformation procedures. An example of *Agrobacterium* mediated transformation of rice is provided herein in Example 5. Vectors carrying the desired nucleic acid construct may be introduced into regenerable rice cells of tissue cultured plants or explants, or suitable plant systems such as protoplasts.

The regenerable rice cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis for the desired genotype allows rapid selection of plants carrying the desired trait, which may be nurtured to maturity in the greenhouse or field for subsequent further backcrossing to the recurrent parent.

Any molecular biological technique known in the art which is capable of detecting a Fad2 or FatB gene can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DOGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of (for example) a Fad2 or FatB gene which confer the desired phenotype. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al. (2001).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (Ed. M. J. McPherson and S. G Moller (2000) BIOS Scientific Publishers Ltd, Oxford). PCR can be performed on cDNA obtained from reverse transcribing mRNA isolated from plant cells. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. (supra) and Sambrook et at (supra). Sequencing can be carried out by any suitable method, for example, dideoxy sequencing, chemical sequencing or variations thereof. Direct sequencing has the advantage of determining variation in any base pair of a particular sequence.

Hybridization based detection systems include, but are not limited to, the TaqMan assay and molecular beacons. The TaqMan assay (U.S. Pat. No. 5,962,233) uses allele specific (ASO) probes with a donor dye on one end and an acceptor dye on the other end such that the dye pair interact via fluorescence resonance energy transfer (FRET). A target sequence is amplified by PCR modified to include the addition of the labeled ASO probe. The PCR conditions are adjusted so that a single nucleotide difference will effect binding of the probe. Due to the 5 nuclease activity of the Taq polymerase enzyme, a perfectly complementary probe is cleaved during PCR while a probe with a single mismatched base is not cleaved. Cleavage of the probe dissociates the donor dye from the quenching acceptor dye, greatly increasing the donor fluorescence.

An alternative to the TaqMan assay is the molecular beacon assay (U.S. Pat. No. 5,925,517). In the molecular beacon assay, the ASO probes contain complementary sequences flanking the target specific species so that a hairpin structure is formed. The loop of the hairpin is complimentary to the target sequence while each arm of the hairpin contains either donor or acceptor dyes. When not hybridized to a donor sequence, the hairpin structure brings the donor and acceptor dye close together thereby extinguishing the donor fluorescence. When hybridized to the specific target sequence, however, the donor and acceptor dyes are separated with an increase in fluorescence of up to 900 fold. Molecular beacons can be used in conjunction with amplification of the target sequence by PCR and provide a method for real time detection of the presence of target sequences or can be used after amplification.

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TELLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005) and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Mutagenesis Procedures

Techniques for generating mutant rice plant lines are known in the art. Examples of mutagens that can be used for generating mutant rice plants include irradiation and chemical mutagenesis. Mutants may also be produced by techniques such as T-DNA insertion and transposon-induced mutagenesis. The mutagenesis procedure may be performed on any parental cell of a rice plant, for example a seed or a parental cell in tissue culture.

Chemical mutagens are classifiable by chemical properties, e.g., alkylating agents, cross-linking agents, etc. Useful chemical mutagens include, but are not limited to, N-ethyl-N-nitrosourea (ENU); N-methyl-N-nitrosourea (MNU); procarbazine hydrochloride; chlorambucil; cyclophosphamide; methyl methanesulfonate (MMS); ethyl methanesulfonate (EMS); diethyl sulfate; acrylamide monomer, triethylene melamine (TEM); melphalan; nitrogen mustard; vincristine; dimethylnitrosamine; N-methyl-N'-nitro-Nitrosoguani-dine (MNNG); 7,12 dimethylbenzanthracene (DMBA); ethylene oxide; hexamethylphosphoramide; and bisulfan.

An example of suitable irradiation to induce mutations is by gamma radiation, such as that supplied by a Cesium 137 source. The gamma radiation preferably is supplied to the plant cells in a dosage of approximately 60 to 200 Krad., and most preferably in a dosage of approximately 60 to 90 Krad.

Plants are typically exposed to a mutagen for a sufficient duration to accomplish the desired genetic modification but insufficient to completely destroy the viability of the cells and their ability to be regenerated into a plant.

Antibodies

Monoclonal or polyclonal antibodies which bind specifically to FatB or Fad2 polypeptides can be useful for some of the methods of the invention.

The term "binds specifically" refers to the ability of the antibody to bind to a FatB or Fad2 polypeptide but not other proteins of rice, especially proteins of rice seeds.

As used herein, the term "epitope" refers to a region of a FatB or Fad2 polypeptide which is bound by the antibody. An epitope can be administered to an animal to generate antibodies against the epitope, however, antibodies useful for the methods described herein preferably specifically bind the epitope region in the context of the entire polypeptide.

If polyclonal antibodies are desired, a selected mammal (e.g., mouse, rabbit, goat, horse, etc.) is immunised with an immunogenic polypeptide such as those provided in FIG. 2 or 7 or SEQ NOs 1 to 4 or 15 to 18. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides peptides of the invention or fragments thereof haptenised to another peptide for use as immunogens in animals.

Monoclonal antibodies directed against polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

Antibodies may be bound to a solid support and/or packaged into kits in a suitable container along with suitable reagents, controls, instructions and the like.

Preferably, the antibodies are delectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like. Preferably, the detectable label allows for direct measurement in a plate luminometer, e.g., biotin. Such labeled antibodies can be used in techniques known in the art to detect polypeptides of the invention.

EXAMPLES

Example 1

Materials and Methods

Extraction of Oil with Sodium Methoxide

For fatty acid and other analyses, total lipid was extracted from rice grains as follows unless stated otherwise. In some cases, samples each consisting of a half grain were used for the extraction, with the second half-grain containing the embryo being used for embryo rescue. The technique can also be used with other cereals.

A single developing seed or half-seed was squashed between filter papers and placed in a tube. 2 ml 0.5M sodium methoxide was added, the tube sealed tightly and then incubated at 80° C. for 10 min. After the tube was cooled, 0.1 ml glacial acetic acid was added followed by 2 ml of distilled water and 2 ml of petroleum spirit. The mixtures were vortexed for 10 sec and, after the phases had separated, the upper petroleum layer was transferred to a small test tube. Approximately 1 g of potassium bicarbonate/sodium sulphate mixture was added to the test tubes and the mixture vortexed. The sample solutions were transferred to autosampler vials and stored in a freezer at −20° C. until GC analysis was performed as described by Soutjesdic et al. (2002).

Extraction of Lipids from Tissues with High Water Content (Bligh-Dyer Method)

This method was adapted from Bligh and Dyer (1959). 1.5 ml of $CHCl_3$/MeOH (1:2) was added to a tissue sample in 0.4 ml of buffer and the sample vortexed vigorously. A further 0.5 ml of $CHCl_3$ was added and the sample vortexed again. 0.5 ml of $H_2O$ was added and the sample vortexed again. The tube was centrifuged briefly at 3000 rpm to separate phases; a white precipitate appeared at the interface. The organic (lower) phase was transferred to a new tube and concentrated under vacuum. If acidic lipids were to be extracted, 0.5 ml of 1% $HClO_4$ was added instead of 0.5 ml of $H_2O$. The volumes in the above procedure could be modified as long as the ratios of $CHCl_3$/MeOH/$H_2O$ were maintained.

Preparation of Fatty Acid Methyl Esters (FAME) for Quantitative Determination of Fatty Acid Content To prepare FAME directly from grain, 10-15 seed were weighed accurately and transferred to a glass tube. An internal standard of 10 µl of 1 mg/ml 17:0-methyl ester was added to each seed sample. 0.75 ml 1 N methanolic-HCl (Supelco) was added to each tube which was capped tightly and refluxed at 80° C. for at least 2-3 hrs or overnight Samples were cooled, 0.5 ml NaCl (0.9% w/v) added followed by 300 µl hexane. The tubes were capped again and vortexed vigorously. The upper hexane phase (200-250 µl) was carefully transferred to an eppendorf tube. The sample was dried down completely under nitrogen. The dried FAME samples were dissolved in 20 µl of hexane and transferred to conical glass inserts in vials for GC analysis.

FA Analysis by Gas Chromatography

Fatty acid methyl esters were prepared by alkaline transmethylation as follows. Single seed samples were squashed between filter paper disks. The fatty acids in the lipid transferred to the filter paper disks were then methylated in 2 mL of 0.02 M sodium methoxide for 10 minutes at 80° C., followed by cooling for 30 minutes. 0.1 mL of glacial acetic acid was then added, followed in order by 2 mL of distilled water and 2 mL of hexane. After vortexing and phase separation, the upper hexane layer containing the fatty acid methyl esters was transferred to a microvial. Fatty acid methyl esters were analysed by gas-liquid chromatography as previously described (Stoutjesdijk et al., 2002).

Transformation of Rice

Rice (cv. Nipponbare) was transformed as follows.

i) Induction and Culture

Husks were removed from mature grain, which were then soaked in 70% EtOH for 30 sec to remove any outer layer of wax. The cleaned grains were washed 3 times with sterile $H_2O$ and soaked in a solution of 25% bleach (with 2 drops Tween-20 detergent added) for 20 minutes with shaking to surface sterilize them. Under aseptic conditions, the grains were rinsed briefly with 70% EtOH, washed thoroughly with sterile $H_2O$ 8-10 times and plated onto $N_6D$ medium. Plates were sealed with Micropore-tape and incubated under full light at 28° C. Calli were produced after 6-8 weeks and then transferred to NB media. They were sealed with paraffin paper and left in the at 28° C. with sub-culturing every 4 weeks onto fresh NB plates. Calli were not used for transformation after more then 5 subcultures.

ii) Transformation

Healthy looking calli were picked from subculture plates and transferred onto fresh NB plates at a density of 25-30 calli/plate. Two days later, a fresh culture was established of the *Agrobacterium* strain containing the construct to be used, and incubated at 28° C. The culture medium was NB medium supplemented with 100 µM acetosyringone. Calli were immersed in a suspension of the cells for 10 minutes. After draining off excess suspension, calli were placed on NB medium supplemented with 100 µM acetosyringone and incubated in the dark at 25° C. for 3 days (co-cultivation). After the co-cultivation step, calli were washed gently three times in a tube with sterile $H_2O$ containing 150 mg/ml Timetin. Calli were blotted dry on filter paper and plated well spaced onto NBCT plates (containing 100 µg/ml kanamycin if a kanamycin selectable marker gene was used or other selection agent as appropriate, 150 µg/ml Timentin and 200 µg/ml Claroforan). The plates were incubated in the dark for 3-4 weeks at 26-28° C. Resistant calli were observed after about 10 days and transferred to NBCT+selection plates and incubated in the dark for a further 14-21 days. Healthy call were transferred onto PRCT+selection plates and incubated in the dark for 8-12 days, then transferred onto RCT+selection plates and incubated in full light at 28° C. for 30 days. After this time, plantlets that had developed were transferred to ½MS medium in tissue culture pots and incubated under light for 10-14 days for further growth before transfer to soil.

iii) Media Composition and Components for Rice Tissue Culture

N6 macro-elements (20×) (g/l): $(NH_4)_2SO_4$, 9.3; $KNO_3$, 56.6; $KH_2PO_4$, 8; $MgSO_4.7H_2O$, 3.7; $CaCl_2.2H_2O$, 3.3.

N6 micro (1000×) (mg/100 ml): $MnSO_4.4H_2O$, 440; $ZnSO_4.7H_2O$, 150; $H_3BO_3$, 160; KI, 80.

N6 Vitamins (100×) (mg/100 ml): Glycine, 20; Thiamine-HCl, 10; Pyridoxine-HCl, 5; Nicotinic acid, 5.

B5 micro-elements (100×) (mg/1000 ml): $MnSO_4.4H_3O$, 1000; $Na_2MoO_4.2H_2O$, 25; $H_3BO_3$, 300; $ZnSO_4.7H_3O$, 200; $CuSO_4.5H_2O$, 3.87; $CoCl_2.6H_2O$, 2.5; KI, 75.

B5 vitamins (100×) and Gamborg's vitamin solution (1000×) from Sigma cell culture.

FeEDTA (200×) (g/200 ml): Ferric-sodium salt, 1.47.

2,4-D (1 mg/ml): Dissolve 100 mg of 2,4-dichloro-phenoxy-acetic acid in 1 ml absolute ethanol, add 3 ml of 1N KOH, adjust to pH 6 with 1N HCl.

BAP (1 mg/ml): 6-benzyl amino purine from Sigma cell culture.

NAA (1 mg/ml): Naphthalene acetic acid from Sigma cell culture.

ABA (2.5 mg/ml): Dissolve 250 mg of Abscisic acid in 2 ml of 1M NaOH, make up to 100 ml with sterile distilled water. Final background concentration to be 20 mM NaOH.

Hygromycin (50 mg/ml): Hygromycin solution from Roche.

Timetin (150 mg/ml): Dissolve 3100 mg of Timetin in 20.66 ml of sterile water. Final concentration to be 150 mg/ml.

Claforan (200 mg/ml): Dissolve 4 gm of Claforan in 20 ml of sterile water.

MS salts: Murashige-Skoog minimal organic medium.

N6D medium (amount per liter):

| | |
|---|---|
| N6 macro (10X) | 100 ml |
| N6 micro (1000X) | 1 ml |
| N6 vitamins (1000X) | 1 ml |
| MS iron/EDTA | 5 ml |
| Myoinositol | 100 mg |
| Casamino acid | 300 mg |
| Proline | 2.9 g |
| 2,4-D (1 mg/ml) | 2 ml |
| Sucrose | 30 g | pH adjusted to 5.8 with 1M KOH, add 3 g phytogel/liter, autoclave.

NB medium (amount per liter):

| | |
|---|---|
| N6 macro-elements (20X) | 50 ml |
| B5 micro-elements (100) | 10 ml |
| B5 vitamins (100X) | 10 ml |
| FeEDTA (200X) | 5 ml |
| 2,4-D (1 mg/ml) | 2 ml |
| Sucrose | 30 g |
| Proline | 500 mg |
| Glutamine | 500 mg |
| Casein enzymatic hydrolysate (CEH) | 300 mg |

NBO: NB media, plus 30 gll mannitol and 30 g/l sorbitol, added before pH adjustment.

NBCT+selection (Hygromycin-H30): NB media plus 30 mg/l hygromycin, Timetin 1S0 mg/ml, Claforan 200 mg/l. NBCT+selection (Hygromycin-HSO); NB media plus selection 50 mg/l hygromycin, 200 mg/l Claforan and Timetin 150 mg/ml.

PRCT+Selection: NB media with no 2,4-D, plus following added after autoclave: BAP, 2 mg/l; NAA, 1 mg/l; ABA, 5 mg/l; Claforan, 100 g/l; Timetin; 150 mg/ml+selection.

RCT+Selection: NB media with no 2,4-D, plus following added after autoclave: BAP; 3 mg/l; NAA, 0.5 mg/l; Timetin, 150 mg/ml; Claforan, 100 mg/l+selection.

½ MS media: MS salts and vitamin mixture, 2.21 g; Sucrose, 109 per liter, add 2.5 g phytogel/l. after autoclaving add 0.05 mg/l NAA and Timetin 150 mg/ml.

Example 2

Identification and Isolation of FutB Genes from Rice

FutB genes encode the enzyme palmitoyl-ACP thioesterase which have the activity preferentially transferring fatty acids that have a length of 16 carbons or less from acyl carrier protein to acyl-CoA and thus prevent further elongation of the fatty acid carbon chain. Putative rice FatB sequences were identified using homology based searches using the sequence for the Genbank accession Arabidopsis locus AtACPTE32 and Iris locus AF213480. The program used was Megablast available at NCBI (www.ncbi.nlm.nih.gov/). Default parameters used by NCBI were used and the databases used were both non-redundant (nr) and high throughput gene sequences (htgs) for rice, Oryza sativa. The most similar sequences from rice selected by the Megablast program were then translated and examined for the presence of the conserved sequence NQHVNN (SEQ ID NO:26) found in all FatB sequences. A further amino acid residue believed to be essential in Arabidopsis is cysteine 264 and along with asparagine 227 and histidine 229 (which are both present in the conserved sequence NQHVNN) comprise the proposed catalytic triad. The Chinese Rice Database (current Website address rise.genomics.org.cn/rice/index2.jsp) was also used to a limited extent and default parameters for BLAST searching were used with the Arabidopsis sequence and Iris sequences. The translated sequences are aligned in FIG. 2.

An overview of the structures of all the FatB genes is shown as in FIG. 3. The genes described correspond as follows to the protein sequences discussed—AC108870 corresponds to Os11g43820, AP005291 corresponds to Os02g43090, AP000399 corresponds to Os06g5130 and AP004236 corresponds to Os06g39520. Note the possibility of multiple transcripts from one gene as indicated on the diagram. FIG. 4 shows a CLUSTAL W (fast) alignment of the 'gene' sequences using default parameters-note that the 'genes' are of different lengths.

The genes comprise 6 exons. The structure of the gene described by Os06g5130 is shown in detail FIG. 5, FIG. 6 shows an alignment of the coding sequences of the FatB cDNAs indicating the different primers used for selective PCR amplification.

The sequence identity between the translated peptide sequence of Os06g5130 and Os06g39520 (corresponding to sequence ap000399 and ap004236 in FIG. 2) was 74% overall, and the identity at the nucleotide level over the entire coding sequence was 69%. In both cases the program BESTFIT with default parameters was used. The polypeptides deduced from Os02g43090 (one transcript). Os06g05130, Os06g39520 and Os011g43820 correspond to 298, 427, 423 and 425 amino acids respectively.

Activity of the encoded proteins was surmised from the high degree of sequence identity with known polypeptides shown to have this activity. Furthermore, the observed effect on palmitic acid levels of gene inactivating constructs based on these sequences was also consistent with this conclusion (see below).

Expression of the gene family was complex, with at least seven transcripts predicted from these four genes. On the basis of RT-PCR experiments that were performed and relative numbers of clones recovered from EST libraries, it appeared that RNA from Os06g5130 was relatively abundant in the grain, while Os11g43820 was expressed at a moderate levels in that tissue and the other genes were only expressed at a low level.

Example 3

Identification and Isolation of Fad2 Genes from Rice

Proteins encoded by Fad2 genes (Fatty acid desaturase 2) are responsible for the introduction of a double bond into 18:1 fatty acids—they are Δ12 desaturases. The Genbank sequence from the Arabiodopsis locus athd12aaa was used to search the or and htgs databases for Oryza sativa using Megablast at default settings. The most similar sequences retrieved from rice were translated and examined for the presence of conserved hydrophobic motifs FSYVVHDLVIVAALL-FALVMI (SEQ ID NO:27), AWPLYIAQGCVLTGVWVIA (SEQ ID NO:28), ISDVGVSAGLALFKLSSAFGF (SEQ ID NO:29), VVRVYGVPLLIVNAWLVLITYLQ (SEQ ID NO:30) and the histidine rice sequences HECGHH (SEQ ID NO:31), HRRHHA (SEQ ID NO:32) and HVAHH (SEQ ID NO:33). The translated amino acid sequences of the isoforms obtained are shown in FIG. 7.

FIG. 8 provides an alignment of Fad2 sequences showing location of 5' UTR in isoform AP004047 (lowercase) and location of primers used for amplification by RT-PCR (underlined). The location of the stop codon is indicated by a box and untranslated regions downstream of the stop codon are in lower case.

Four gene sequences are recovered as being highly similar from the rice genome when the nucleotide sequence encoding the protein with the amino acid sequence of AP004047 was used to search the rice genome using the program BLAST with the default parameters. The overall structure of these genes are shown in FIG. 9. The genes correspond to the protein sequences as follows. The protein sequence AP004047 (also called FAD2-1 herein) corresponded to the gene Os02g48560, the sequence AP0050168 (also called FAD2-2 herein) corresponded to Os07g23410, and the sequence contig2654 corresponded to Os07g23430. In addition there was a sequence that shared an intriguing extent of sequence identity but was clearly different to these sequences and may be a pseudo-gene. This sequence was Os07g23390.

Unlike the FatB genes, the Fad2 genes did not contain any introns. An alignment of all the protein coding sequences is shown in FIG. 10. The sequence identity over the entire coding region for Os02g48560 to Os07g23410 was 79%.

The molecular weight of the polypeptide encoded by Os02g48560 (ie AP004047) was 44.35 kDa before processing and contained 388 amino acids. The molecular weight of the polypeptide encoded by Os07g23410 was 44.9 kDa and contained 390 amino acids. These deduced polypeptides had 77% sequence identity as determined by the program BEST-FIT using default parameters. The deduced polypeptide from Os07g23430 had a molecular weight of 41 kDa (363 amino acids) and from Os07g23390 was 24 kDa (223 amino acids). An alignment of all the deduced polypeptide sequences is shown in FIG. 7.

The sequence corresponding to Os02g48560 was expressed in the grain and this observation was consistent with data from the relative frequencies of clones for this gene in EST libraries where cognate sequences were recovered from grain cDNA libraries. Sequences corresponding to two of the isoforms encoded on chromosome 7 (Os07g23430, 23410) have been recovered from a leaf EST library but the sequence corresponding to the other gene (Os07g23390) has not yet been reported; we concluded it may be expressed at low levels if at all.

In conclusion, the rice Fad2 gene family was also a complex gene family. The two transcripts deduced from Os02g48560 were indistinguishable by sequence. The sequence deduced from Os02g48560 was clearly expressed in the grain.

Example 4

Expression of FatB and Fad2 Genes in Rice

To determine which, if any, of the 4 putative FatB and 3 Fad2 genes identified in rice as described in Examples 2 and 3 might be expressed in developing rice grain, reverse transcription polymerase chain reaction (RT-PCR) assays were carried out. Since the genes were closely related in sequence, primers had to be designed that were specific for each of the genes, to assay transcripts for each gene specifically. Regions of sequence divergence were identified from the alignments (FIGS. 6 and 8) and several primer pairs were designed and tested. Primer sequences for detecting expression of the putative FatB genes are given in Tables 3 and 4. As an internal standard against which to compare expression levels, RT-PCR was also carried out on the RNA for expression oldie rice gene encoding alpha-tubulin, OsTubA1. This gene was known to be expressed in all actively dividing tissues and was not affected by the hormone ABA and so was suitable as a constitutively expressed control for leaf and grain analysis.

RNA was prepared from rice grains approx 15 days after flowering using the Qiagen RNeasy kit following protocols supplied by the manufacturer. DNAse treatment (DNA-free kit, Ambion) was then used to remove contaminating DNA from the RNA preparation. The RT-PCR mix contained 5 µl of 5× Qiagen OneStep RT-PCR buffer, 1 µl of dNTP mix (containing 10 mM of each dNTP), 15 pmol of each primer and approximately 20 pg of RNA to a final volume of 25 µl. The following RT-PCR cycling program was used for the RT-PCR amplifications: 30 min at 50° C. (reverse transcription), 15 min at 95° C. PCR activation), 30 cycles of (1 min at 94° C., 1 min at 57° C., 1 min at 72° C.) (PCR amplification), then a final extension of 10 min at 72° C.

TABLE 3

Primers designed to amplify and discriminate relative expression of the putative FatB transcripts using one-step RT-PCR.

| Gene Amplified | Genbank ID/ Chinese Contig no. ID | Primer name | Primer Sequence |
|---|---|---|---|
| FatB-1 | AP000399 | p0399F2 | CGCTGCTACCAAACAATTCA (SEQ ID NO: 34) |
|  |  | p0399R2 | TTCTGTGTTGCCATCATCG (SEQ ID NO: 35) |
| FatB-2 | AC108870 | p5291_F2 | CAGGAAATAAAGTTGGTGATGATG (SEQ ID NO: 36) |
|  |  | p8870R | CTTCACAATATCAGCTCCTGACTC (SEQ ID NO: 37) |

TABLE 3-continued

Primers designed to amplify and discriminate relative expression of the putative FatB transcripts using one-step RT-PCR.

| Gene Amplified | Genbank ID/ Chinese Contig no. ID | Primer name | Primer Sequence |
|---|---|---|---|
| FatB-3 | AP005291 | p5291_F2 | CAGGAAATAAAGTTGGTGATGATG (SEQ ID NO: 38) |
|  |  | p5291R | CTTCACAATGTCAGCCTTCAC (SEQ ID NO: 39) |
| FatB-4 | AP004236 | p4236F2 | ACAGGCCTGACTCCACGAT (SEQ ID NO: 40) |
|  |  | p4236R2 | GTCCAGAGTGCTTGTTGCAG (SEQ ID NO: 41) |
| OsTubA1 | AF182523 | OSTUBA1_F | TACCCACTCCCTCCTTGAGC (SEQ ID NO: 42) |
|  |  | OSTUBA1_R | AGGCACTGTTGGTGATCTCG (SEQ ID NO: 43) |

TABLE 4

Primers designed to amplify and discriminate relative expression of the putative Fad2 transcripts using one-step RT-PCR.

| Gene Amplified | Genbank ID/ Chinese Contig no. ID | Primer name | Primer Sequence |
|---|---|---|---|
| Fad2-1 | AP004047 | pFad2-1F | CACAAAGAGGGAGGGAACAA (SEQ ID NO: 44) |
|  |  | pFad2-1R | GAAGGACTTGATCACCGAGC (SEQ ID NO: 45) |
| Fad2-2 | Contig2654 | UTR_2654_F | CACAACATCACGGACACACA (SEQ ID NO: 46) |
|  |  | UTR_2654_R | GCAAGACCGACATGGCTAAT (SEQ ID NO: 47) |
| Fad2-3 | AP005168 | UTR_5168_F | ACGTCCTCCACCACCTCTT (SEQ ID NO: 48) |
|  |  | UTR_5168_R | CAGAAGCAGTGACATACCCAAG (SEQ ID NO: 49) |
| OsTubA1 | AF182523 | OSTUBA1_F | TACCCACTCCCTCCTTGAGC (SEQ ID NO: 50) |
|  |  | OSTUBA1_R | AGGCACTGTTGGTGATCTCG (SEQ ID NO: 51) |

Results from the RT-PCR experiments demonstrated that the sequence Fad2-1 gene (TIGR rice database identifier LOC_Os02g48560) was highly expressed in both grain and leaf relative to the genes encoding the other isoforms. The other two Fad2 genes (LOC_Os07g23410 and LOC_Os07g23430) appeared to be expressed at low levels and primarily in the leaf. The analysis of genes encoding the FatB isoforms showed that FatB-1 (Genbank identifier AP000399, Tigr LOC_Os06g05130) and FatB-2 (Genbank identifier AC108870, TIGR identifier Os11g43820) were more highly expressed in the grain than the other two genes. The Tos-17 transpositional insertion mutant had an insertion in the gene encoding AP000399.

In leaf tissue, FatB-1 (Genbank identifier AP000399, TIGR LOC_Os06g05130) and FatB-4 (AP004236, TIGR LOC_Os06g39520) were more highly expressed, referring to the relative abundance of mRNA transcripts from the genes. When compared to the abundance of the tubulin gene transcripts as a standard, which was a moderately abundant mRNA in wheat grain and was therefore expected to similarly abundant in rice grain, all the FatB and Fad2 mRNAs accumulated to low levels as determined by RT-PCR. However, this conclusion was based on the assumption that the primers, for each of the genes tested, hybridized to the target transcripts with similar efficiency to the tubulin primers/transcript.

This conclusion is corroborated by EST database searching. When the Fad2-1 (TIGR Os02g48560) sequence was used to search rice EST sequences, transcript sequences were present in panicle, root and whole plant cDNA libraries. In contrast, Fad2-2 (TIGR Os07g23410) and Fad2-3 (TIGR Os07g23430) sequences were present only in leaf, shoot or whole plant libraries. The sequence for Os07g23390, the Fad2-like gene considered to be a pseudogene, was not present in any of the EST libraries. Similarly, FatB-1 (TIGR Os06g05130) sequences were present in both leaf and panicle EST libraries, whereas FatB-2 sequences (TIGR Os11g43820) were present only in panicle or whole plant EST libraries and FatB-1 (TIGR Os06g39520) only in a leaf library. FatB-3 (AP005291, Os02g430900) sequences although expressed at a relatively low level to the others in both leaf and grain as judged by RT-PCR, were present in panicle and whole plant EST libraries. These searches used the BLAST program on the NCBI website (www.ncbi.nlm-.nih.gov/BLAST/Blast.cgi) using the EST database and limiting the search to sequences from rice.

Based on these data, Fad2-1 and FatB-2 were considered to be the genes that should be down-regulated for alteration of grain lipid. FatB-3 was also thought be important in this regard.

Example 5

Construction of Gene Silencing Constructs and Transformation of Rice

Creation of duplexRNA Construct for Inhibition of Fad2 Expression

A construct was designed to express a duplex RNA (hairpin RNA) in developing rice grain in order to reduce expression of Fad2-1. By targeting common regions of the three Fad2 gene sequences, the construct was designed so that it would be effective for all three of the identified Fad2 genes in rice grain in order to potentially maximize the effect on fatty acid composition. To improve silencing efficiency, the construct contained an intron between the sense and antisense portions of the inverted repeat sequences as described by Smith et al. (2000).

A 505 basepair fragment was amplified by PCR from the 5' end of the Fad2-1 gene using the oligonucleotides pFad2-F 5'AAAGGATCCTCTAGAGGGAGGAGCAGCAGAAGC-3' (SEQ ID NO:52) and pFad2-R 5'-AAAACTAGTGAAT-TCTACACGTACGGGGTGTACCA-3' (SEQ ID NO:53). The PCR product was ligated into pGEM-Teasy, transformed into *E. coli* and colonies containing the insert identified. The XbaI/EcoRI fragment from the plasmid designated pGEM-T-Fad2, containing the 505 bp Fad2 fragment, was then ligated in the sense direction into the vector ZLRint9_BC3895 (obtained from Zhongyi Li, CSIRO Plant Industry) containing the intron Rint9. A BamHI/SpeI fragment from pGEM-T-Fad2 was then ligated (in the antisense orientation) into the resultant plasmid so that an intron containing hairpin construct was formed. The BamHI/KpnI fragment containing the Fad2-1 intron containing hairpin was then inserted into the same restriction sites of the pBx17casNOT vector (Zhongyi Li, personal communication), containing the Bx17 seed specific promoter containing a Nos terminator/polyadenylation sequence so that the silencing gene would be expressed in developing seed in the order (promoter) sense-intron-antisense (terminator). The HindIII/NotI fragment containing the Bx17 promoter and Fad2-1 inverted repeat region was then inserted into the same restriction sites of the binary vector pWBvec8 (Wang et al., 1998) that combined a selectable maker gene conferring hygromycin resistance. This vector was then introduced into *Agrobacterium* and used for rice transformation as described in Example 1. The duplex RNA construct was designated dsRNA-Fad2-1.

Creation of duplexRNA Construct for Inhibition of FatB Expression

A 665-basepair fragment of the rice palmitoyl-ACP thioesterase FatB-1 gene (Tigr LOC_Os06g05130) was amplified by PCR using primers with the following sequences: Rte-s1, 5'-AGTCATGGCTGGTTCTCT-TGCGGC-3' (SEQ ID NO:54) and Rte-a1, 5'-ACCATCAC-CTAAGAGACCAGCAGT-3' (SEQ ID NO:55). This PCR fragment was used to make an inverted repeat construct with one copy of the fragment in the sense orientation and a second copy in the antisense orientation, separated by the intron sequence from the 5' UTR of the cotton microsomsal ω6-desaturase GhFad2-1 gene (Liu et al., 1999). The inverted repeat construct was subsequently inserted into the SacI site between the Ubi1 promoter and Nos terminator of pUbilcas-NOT (from Zhongyi Li based on sequence described in Li et al., 1997). The inverted repeat portion of rice FatB with the pUbil promoter was then inserted in the NotI site of the binary vector pWBVec8 and introduced into *Agrobacterium* as for the Fad2 construct described above. The duplex RNA construct was designated dsRNA-FatB-1.

Analysis of Fatty Acid Composition in Transformed Rice

Ten independent fertile transgenic plants obtained with dsRNA-Fad2-1 were tested for the presence of the dRNA gene by PCR using one primer corresponding to a site within the promoter region and a second primer for the end of the Fad2 sequence. Nine of the ten plants were found to be positive in the PCR reaction and therefore contained the Fad2 RNAi construct. Similarly, 23 fertile transgenic lines were tested for the FatB RNAi construct and 20 lines were found to be PCR positive.

To analyse the effect of the transgenes on fatty acid composition, total lipid was isolated from grain and leaf samples of the transformed rice plants. This was also done for a rice mutant line containing a Tos17 insertional sequence in the gene for FatB-1 (TIGR locus Os06g5130 corresponding to the protein identified by the Accession No. AP000399) to compare the effect of specifically inactivating this gene. Fatty acid composition was determined for each lipid extract by GC-FAME as described in Example 1. The data are presented in Tables 5 to 7 and some of that data is presented graphically in FIGS. 11 to 13. The proportion of each fatty acid was expressed as a percentage of the total fatty acid in the seed oil of the grain as determined by HPLC as described in Example 1.

The most striking and surprising aspect of the results was the extent of the change in grain oleic acid and linoleic acid composition in the Fad2 dsRNA plants. The proportion of oleic acid in some lines increased from 36% to at least 65% (w/w) and that of linoleic acid decreased from 37% to about 13% in the rice line most affected (Line 22A). Surprisingly, the proportion of palmitic acid in the Fad2 lines was also decreased, for example in Line 22A to less than 14% as compared to the control (18%).

In the FatB dsRNA lines, the reduction in the proportion of palmitic acid in the grain was correlated with an increase in the linoleic acid content while the proportions of oleic acid and linolenic acids were essentially unchanged. It was noted that the extent, of the decrease in the proportion of palmitic acid in both Fad2 and FatB transgenic lines was similar, but the extent of increase in the linoleic acid level in the FatB lines was much less than the extent of the decrease observed in the Fad2 lines. That is, the extent of the change in levels of linoleic was greater with the Fad2 construct.

An interesting insight into the FatB catalysed step of the pathway is provided by analysis of the Tos-17 insertional knockout of one isoform of FatB, FatB-1. In the Tos-17 mutant, the extent of the change in the proportions of palmitic acid and oleic acid was reduced compared to the FatB dsRNA lines. These results indicated that genes encoding the FatB isoforms differed in their function.

When the results of the proportions of linoleic acid versus oleic acid were plotted as a scatter plot (FIG. 14), it was clear that the relationship between these two fatty acids in the Fad2 knockouts was the same as in wildtype rice, although the proportion of linoleic acid was vastly reduced. In contrast, with the FatB knockout and

TABLE 5

GC analysis of fatty acid composition in rice grain of FatB and Fad2 mutants

| Grain- Mutant | Myristic (C14:0) | Palmitic (C16:0) | Stearic (C18:0) | Oleic (C18:1) | Linoleic (C18:2) | Linolenic (C18:3) |
|---|---|---|---|---|---|---|
| Wild type (WH12) | 0.70 | 18.83 | 1.64 | 38.41 | 36.42 | 1.29 |
| FatB Tos17 insertional mutant | 0.72 | 15.13 | 2.33 | 37.15 | 38.61 | 1.87 |
| FatB dsRNA transformed line | 0.58 | 11.43 | 1.81 | 34.92 | 46.60 | 1.91 |
| Fad2 dsRNA transformed line | 0.58 | 14.26 | 2.11 | 64.94 | 12.62 | 1.23 |
| Control for Tos17 | 0.85 | 17.91 | 2.60 | 33.23 | 39.84 | 1.76 |
| Control for FatB dsRNA | 1.03 | 18.86 | 1.84 | 34.08 | 39.63 | 1.75 |
| Control for Fad2 dsRNA | 1.02 | 17.47 | 2.38 | 36.03 | 37.42 | 1.50 |

TABLE 6

GC analysis of fatty acid composition in rice leaves of FatB and Fad2 mutants

| Leaf- mutant | Lauric (C12:0) | Myristic (C14:0) | Palmitic (C16:0) | Stearic (C18:0) | Oleic (C18:1) | Linoleic (C18:2) | Linolenic (C18:3) |
|---|---|---|---|---|---|---|---|
| Wild-type (WF2) | | 0.80 | 14.43 | 1.90 | 2.32 | 8.99 | 68.96 |
| FatB Tos17 insertional mutant | | 0.34 | 11.55 | 1.84 | 2.24 | 15.04 | 67.70 |
| FatB dsRNA transformed line | 0.56 | 1.01 | 14.39 | 2.09 | 2.07 | 13.21 | 64.56 |
| Fad2 dsRNA transformed line | | | | | | | |
| Control for Tos17 | | 0.39 | 10.52 | 1.80 | 2.30 | 15.61 | 67.65 |
| Control for FatB dsRNA | 0.72 | 1.15 | 13.30 | 2.03 | 4.04 | 24.62 | 52.28 |

TABLE 7

Relative amounts of grain fatty acids in mutant lines compared to corresponding control lines (% in mutant/% in corresponding control)

| | Myristic (C14:0) | Palmitic (C16:0) | Stearic (C18:0) | Oleic (C18:1) | Linoleic (C18:2) | Linolenic (C18:3) |
|---|---|---|---|---|---|---|
| Grain fatty acids | | | | | | |
| FatB Tos17 insertional mutant | 0.85 | 0.8451 * | 0.899 | 1.118 * | 0.9691 | 1.06 |
| FatB dsRNA transformed line | 0.57 * | 0.6060 * | 0.980 | 1.025 | 1.176 * | 1.09 |
| Fad2 dsRNA transformed line | 0.570 * | 0.8167 * | 0.887 * | 1.802 * | 0.3373 * | 0.822 * |
| Leaf fatty acids | | | | | | |
| FatB Tos17 insertional mutant | nd | 0.911 * | 0.977 | 1.03 | 1.037 | 0.9992 |
| FatB dsRNA transformed line | nd | 0.9247 | 0.969 | 1.95 * | 1.864 * | 0.8098 * |

* Statistically significant change shifted by a constant. This meant that there was more linoleic acid in the FatB knockout plants for a given amount of oleic acid than in wild-type or Fad2 knockout plants. This was consistent with the idea that knockout of FatB influenced the pathways controlling the amounts of oleic and linoleic acid but not the step directly linking oleic acid and linoleic acid which was controlled by Fad2.

The results of the proportion of linoleic acid versus palmitic were also plotted for all of the rice lines analysed. A positive linear relationship was observed for the Fad2 knockout lines, inverse of what was observed for linoleic versus oleic acid. For the FatB lines, however, a different relationship is observed (FIG. 15). A difference in the relationship between oleic and palmitin acid was also observed when the Fad2 dsRNA plants and FatB dsRNA plants were plotted as a scatter plot (FIG. 16). These results confirmed that the relationship between palmitic and linoleic acid (and oleic acid) was different for the two perturbations of the pathway.

Principal component analysis of the proportions of the various fatty acids under different perturbations of the pathway confirm that principal component 1 (which indicates the axes that contribute the greatest variation) was composed of the proportions of linoleic versus oleic whereas the principal component 2 (the second most important set of axes) was composed of proportions of linoleic and oleic acid versus palmitin acid). This is illustrated in FIG. 17.

to a lesser extent in the FatB Tos-17 line, although the relationship between linoleic acid and oleic was similar, it is We also concluded from the results presented in this Example that crossing the dsRNA Fad2 plants with the dsRNA FatB plants or Tos-17 FatB plants to combine the mutations would further increase the relative proportion of oleic acid and further decrease palmitin and linoleic acid levels.

Example 6

Production and Use of Antibodies

Antibodies were raised by synthesizing 15 or 16-mer peptides that were present in the deduced sequence of FatB. The peptides used to raise antibodies against FatB were:
FatB-U1 Ac-CGMNKNTRRLSKMPDE (SEQ ID NO:56). This corresponds to the translated sequence of FatB (Accession No. AP000399) from amino acid position number 259 and was also found in sequences translated from AP005291, ACI08870 and AC004236. However, the sequence was only identical between the four isoforms in the sequence TRRLSKMPDE (SEQ ID NO:57).
FatB-U2. Ac-CGEKQWTLLDWKPKKPD (SEQ ID NO:58). This sequence was found in the translated sequence of all four FatB isoforms.
FatB-99. Ac-CGAQGEGNMGFFPAES (SEQ ID NO:59). This sequence was found only in AP00399 and was at the very C terminus of the deduced polypeptide.

After synthesis the peptides were coupled to either Ovalbumin or Keyhole Limpet Haemocyanin protein (KLH) using the cross-linker MBS (maleimidobenzoic acid N-hydroxyl succinimide ester) using standard techniques. The cross-linked peptide was dialysed and lyophilized and injected into rabbits at two weekly intervals for two months with Friends incomplete adjuvant at a concentration of approx Antisera raised against FatB-99 detected a clear difference between FatB isoforms in that a polypeptide of 20 kDa present in wild-type rice was missing in the Tos-17 mutant line having an insertion in the gene corresponding to TIGR identifier Os06g5130, the product corresponds to FatB-1, the sequence is represented by accession No. AP000399 (FIG. 18). Although this was different to the expected size of approx 40 kDa, such a discrepancy had been noticed before with FatB isoforms Different size of FatB products have been observed in developing and mature *Cuphea wrightii* seeds showing five different FatB isoforms, longer size in mature seeds and shorter product in mature seeds (Leonard et al., 1997).

The antisera can be used to detect FatB protein in the transgenic or mutant plant samples and confirm the extent of gene inactivation.

Example 7

Identification of Mutants in Rice Fad2

PCR products spanning the active sites (essentially positions 330 to 1020 if the initiating ATG is taken as the start of the numbering in TIGR Loc_Os2g48560) of Fad2-1 (coding sequence corresponding to AP00 4047 in NCBI database, TIGR locus identifier LOC_Os02g48560) will be produced from rice DNA extracted from a large number of different rice accessions. The size of the products will be up to 800 bp depending on the primers used. Two sets of overlapping primer pairs may need to be used. One possible set of primers is:

Set A (SEQ ID NO: 60)
GTGCCGGCGGCAGGATGACGG (positions 5-20 in the alignment shown in FIG. 10)

(SEQ ID NO: 61)
GCCGACGATGTCGTCGAGCAC (reverse complement of positions 379-398 in the alignment shown in

FIG. 10)

Set 8

(SEQ ID NO: 62)
TGCCTTCTCCGACTACTCGG (positions 360-379 in FIG.

10)

(SEQ ID NO: 63)
CCTCGCGCCATGTCGCCTTGG (reverse complement of positions 1099-1118 in FIG. 10).

The annealed products will then be subjected to melting in a Rotorgene 6000 instrument (Corbett Life Science) or a comparable instrument where differences in melting of heteroduplexes can be sensitively detected by means of alteration of fluorescence of a dye LC Green. Hundreds and possibly thousands of rice lines can be screened daily by this technique.

The PCR products from samples showing an altered thermal profile will be sequenced and the mutations in Fad2 identified. Selected mutations which inactivate Fad2 can then be crossed into elite rice lines to produce rice lines with reduced Fad2 activity and therefore high oleic acid. If two or all of the Fad2 isoforms need to be eliminated then this can be achieved by identifying lines with the required mutations in different isoforms and combining the mutations in an elite rice line through marker assisted breeding. At least the Fad2-1 gene needs to be inactive for substantial increases in oleic acid content or decreased linoleic acid content. Inactivation of one or more of the additional Fad2 genes will further increase oleic acid content and decrease linoleic acid content Mutants having mutations in additional Fad2 genes may be identified in the same way as for Fad2-1, using specific primers for the additional Fad genes.

Example 8

Stability Analysis—Detection of Hexanal Production in Storage

Experiments are underway with FSA, Werribee to detect the production of hexanal on storage in wildtype rice. This involves GC using a sampler to detect the volatiles in the headspace of grain stored at high temperature (40° C.). Once the system is optimized (and also we have sufficient quantity of grain) we will undertake a comparison of the production of volatiles, particularly hexanal, upon storage of wildtype and Fad2 RNAi and FatB RNAi rice lines and suitable combinations of genotypes. This is an important quality issue in the rice industry for storage of grain and also of storage of bran. The production and detection of other volatiles, which could have a role in affecting grain quality, is also being investigated, both with FSA, Werribee and CSIRO Entomology.

Around 10 g of raw brown rice is required for headspace analysis. The brown rice is stored at 4° C. (control) and 35° C. for 8 weeks. The gas sample released from brown rice can be obtained in the headspace of a vial by either heating at 80° C. or by natural diffusion. The volatile components in the headspace can then be analysed by direct injection into a GC or GC-MS machine and analysis of the gas chromatographic profiles (Suzuki et al, 1999). Another method for analysis of volatiles in the headspace is through the trapping of volatiles onto a suitable matrix (eg 250 mg Tenax GR) as described by Nielsen et al. (2004) using nitrogen as a purge gas. The desorption of the aroma compounds is then done thermally and the trapped molecules are analysed by GC and identified using standards.

The expectation that storage of rice would be improved in rice lines with low linoleic acid is based on a number of observations. Suzuki et al. (1999). have presented data that the amount of free linoleic acid increases during storage and that the amount of volatile aldehydes such as pentanal, hexanal and pentanol increase three fold at 35 C. The correlation of hexanal and volatile aldehydes with odour has been noted by other authors as well. On the other hand, Zhou et al. (2002) found a reduction of total linoleic acid upon storage and related this to the decomposition of linoleic acid to other products, including volatiles responsible for off-odours. The differences in the results may be due to differences in the extraction and analytical methods.

The production of hexanal for linoleic acid in vitro has been demonstrated by Nielsen et al. (2004).

It will be appreciated by persons skilled in the art that numerous variations and/or modifications may be made to the invention as shown in the specific embodiments without departing from the spirit or scope of the invention as broadly described. The present embodiments are, therefore, to be considered as illustrative and not restrictive.

All publications discussed and/or referenced herein are incorporated herein in their entirety.

This application claims priority from AU 2006903810, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Akagi et al. (1995) Plant Physiol. 108, 845-846
Almeida and AlLshire (2005) TRENDS Cell Biol 15: 251-258.
Anal et al. (2003) Plant Cell Rep. 21, 988-992.
Ascherio and Willett (1997) Am. J. Clin. Nutr. 66: 10065-1010S.
Bligh and Dyer Canadian J. Biochem. (1959) 37: 911-917.
Boggs et al. (1964) J. Food Sci. 29:487-489.
Bonanome and Grundy (1988). N. Engl. Med. 318: 1244-1248.
Brandt et al. (1985) Carlsberg Res. Commun. 50: 333-345.
Broun et al., (1999) Annu. Rev. Nutr. 19: 197-216.
Buhr et al. (2002). Plant J. 30: 155-163.
Capecchi (1980) Cell 22:479-488.
Champagne et al. (1995) Cereal Chem 72:255-258.
Chang et al., (1978). J. Am. Oil Chem. Soc. 55: 718-727.
Chapman et al., (2001). J. Am. Oil Chem. Soc. 78: 941-947.
Choudry et al. (1980) Phytochemistry 19: 1063-1069.
Clapp (1993) Clin. Perinatol. 20:155-168.
Colot et al. (1987) EMBO J 6: 3559-3564.
Comai et al. (2004) Plant J 37: 778-786.
Curiel et al. (1992) Hum. Geo. Ther. 3:147-154.
Dougherty et al. (1995). Am. J. Clin. Nutr. 61:1120-1128.
Eglitis et al. (1988) Biotechniques 6:608-614.
Fenandez San Juan (1995). Alimentaria 33: 93-98.
Fujimura et al. (1985) Plant Tissue Culture Letters 2:74.
Graham et al. (1973) Virology 54:536-539.
Gunstone (2001) Inform 11: 1287-1289.
Ha (2005) Nutrition research 25, 597-606.
Haseloff and Gerlach (1988) Nature 334:585-591.
Henikoff et al. (2004) Plant Physiol 135: 630-636.
Hu et al. (1997). N. Engl. J. Med. 337: 1491-1499.
Jennings and Akoh (2000) Journal of Agricultural and Food Chemistry, 48:4439-4443.
Jones et al. (1995) Plant Cell 7: 359-371.
Kinney (1996) J. Food Lipids 3: 273-292.
Kodama et al. (1997) Plant Molecular Biology 33:493-502.
Kohno-Murase et al. (2006). Transgenic Research 15:95-100.
Koziel et al. (1996) Plant Mol. Biol. 32:393-405.
Langridge et al. (2001) Aust J Agric Res 52: 1043-1077.
Lemieux (2000) Current Genomics 1: 301-311.
Leonard et al. (1997) Plant Molecular Biology, Volume 34, Issue 4: 669-679.
Li et al. (1997) Molec Breeding 3:1-14.
Lu et al. (1993) J. Exp. Med. 178:2089-2096.
Liu et al. (1999) Aust. J. Plant Physiol. 26:101-106.
Liu et al. (2002a). J. Am. Coll. Nutr. 21: 205S-211S.
Liu et al. (2002b). Plant Physiol. 129: 1732-1743.
Mensink and Katan (1990). N. Engl. J. Med. 323: 439-445.
Mikkilineni and Rocheford (2003) Theor. Applied Genetics, 106, 1326-1332.
Millar and Waterhouse (2005) Funct Integr Genomics 5:129-135.
Moghadasian and Frohlich (1999) Am. J. Med. 107: 588-94.
Morrison (1988) 1 Cereal Sci 8:1-15.
Most et al. (2005) Am J Clin Nutr 81:64-8.
Needleman and Wunsch (1970) J. Mol. Biol. 48:443-453.
Nielsen et al. (2004) Journal of Agricultural and Food Chemistry 52:2315-2321.
Noakes and Clifton (1998) Am. J. Clin. Nutr. 98: 242-247.
Ohlrogge and Jaworski (1997) Annu Rev Plant Physiol Plant Mol Biol. 48:109-136.
Oil World Annual (2004) International Seed Testing Association (ISTA) Mielke GmbH, Hamburg, Germany
Pasquinelli et al. (2005) Curr Opin Genet Develop 15: 200-205.
Perriman et al. (1992) Gene 113: 157-16.
Radcliffe et al (1997) Biochem Arch 13: 87-95.
Resurreccion et al (1979) Journal of the Science of Food and Agriculture, 30: 475-481.
Roche and Gibney (2000) Am. J. Clin. Nutr. 71: 232S-237S.
Rukmini et al. (1991). Journal of The American College of Nutrition 10: 593-601.
Sebedio et al. (1994) Fett. Wiss. Technol. 96: 235-239.
Senior (1998) Biotech. Genet. Engin. Revs. 15:79-119.
Shibuya et al. (1974) Journal of the Japanese Society of Food Science and Technology 21: 597-603.
Shin et al. (1986) J. Food Sci. 51:460-463.
Shippy et al. (1999) Mol. Biotech. 12: 117-129.
Slade and Knauf (2005) Transgenic Res 14: 109-115.
Smith et al. (2000) Nature 407: 319-320.
St Angelo et al. (1980) J Lipids 1:45-49.
Stefanov et al. (1991) Acta Biologics Hungarica 42:323-330.
Stoutjesdijk et al., (2000). Biochem. Soc. Trans. 28: 938-940.
Stoutjesdijk et al. (2002) Plant Physiology 129: 1723-1731.
Stymne and Stobart (1987) Lipids, Vol. 9: 175-214.
Suzuki et al. (1999) T. Agric. Food Chem. 47: 1119-1124.
Taira et al. (1988) J. Agric. Food Chem. 34:542-545.
Thelen and Ohlrogge (2002) Metabolic Engineering 4: 12-21
Theriault et al. (1999). Clin. Biochem. 32: 309-19.
Tholstrup et al. (1994). Am. J. Clin. Nutr. 59: 371-377.
Toriyama et al. (1986) Theor. Appl. Genet. 205:34.

Tsugita et al (1983) Agricultural and Biological Chemistry 47: 543-549.
Tsuzuki et al (2004) Lipids 39:475-480.
Voelker et al. (1996). Plant J. 9: 229-241.
Wagner et al. (1992) Proc. Natl. Acad. Sci. USA 89:6099-6103.
Wang et al. (1998) ACTA Hort. 461:401-407.
Waterhouse et al. (1998) Proc. Natl. Acad. Sci. USA 95: 13959-13964.
Williams et al. (1999) J. Am. Coll. Cardiol. 33:1050-1055.
Yasumatsu et al. (1966) Agric. Biol. Chem. 30:483-486.
Zhou et al. (2002) Journal of Cereal Science 35:65-78.
Zock et al. (1994) Arterioscler Thromb. 14: 567-575

The invention claimed is:

1. A method of preparing food, the method comprising cooking an edible substance in rice oil from rice grain having a fatty acid composition comprising greater than 60% w/w oleic acid, less than 15% w/w palmitic acid and less than 25% w/w linoleic acid, wherein the rice oil has not been exposed to a procedure which alters the ratio of oleic acid to linoleic acid, palmitic acid to oleic acid, and/or palmitic acid to linoleic acid when compared to the ratio in the rice grain.

2. The method of claim 1, wherein in the rice oil the weight ratio of oleic acid to linoleic acid is greater than 3.0:1.

3. The method of claim 1, wherein the rice oil has a fatty acid composition comprising greater than 60% oleic acid, less than 12% palmitic acid, and/or less than 15% linoleic acid.

4. The method of claim 1, wherein the rice oil further comprises γ-oryzanol.

5. The method of claim 1, wherein the rice oil is substantially purified.

6. The method of claim 5, wherein the substantially purified rice oil is at least 75% free from other components with which it is naturally associated.

7. The method of claim 6, wherein the substantially purified rice oil is at least 90% free from other components with which it is naturally associated.

* * * * *